United States Patent
Oku et al.

[11] Patent Number: 5,994,368
[45] Date of Patent: Nov. 30, 1999

[54] PYRIDOPYRIMIDONES, QUINOLINES AND FUSED N-HETEROCYCLES AS BRADYKININ ANTAGONISTS

[75] Inventors: Teruo Oku; Hiroshi Kayakiri; Shigeki Satoh, all of Tsukuba; Yoshito Abe, Inashiki-gun; Yuki Sawada; Takayuki Inoue, both of Tsukuba; Hirokazu Tanaka, Takarazuka, all of Japan

[73] Assignee: Fujisawa Pharmaceutical Co., Ltd., Osaka, Japan

[21] Appl. No.: 08/809,416

[22] Filed: Apr. 25, 1997

[30] Foreign Application Priority Data

Oct. 27, 1994 [GB] United Kingdom .................. 9421684
Jun. 16, 1995 [GB] United Kingdom .................. 9512339

[51] Int. Cl.$^6$ ......................... A01N 43/42; C07D 215/16; C07D 215/38
[52] U.S. Cl. .......................... 514/312; 514/313; 514/314; 546/153; 546/159
[58] Field of Search ................................... 546/153, 159; 514/312, 313, 314

[56] References Cited

U.S. PATENT DOCUMENTS

| | | | |
|---|---|---|---|
| 5,212,182 | 5/1993 | Musser et al. | 514/314 |
| 5,563,162 | 10/1996 | Oku et al. | 514/311 |
| 5,574,042 | 11/1996 | Oku et al. | 514/300 |
| 5,708,173 | 1/1998 | Oku et al. | 546/153 |
| 5,750,699 | 5/1998 | Oku et al. | 546/121 |
| 5,795,889 | 8/1998 | Spada et al. | 514/233.5 |

FOREIGN PATENT DOCUMENTS

| | | |
|---|---|---|
| 0 224 086 | 11/1986 | European Pat. Off. . |
| 0 261 539 | 9/1987 | European Pat. Off. . |
| 0 578 521 | 6/1993 | European Pat. Off. . |
| 0 596 406 | 10/1993 | European Pat. Off. . |
| 0 622 361 | 4/1994 | European Pat. Off. . |

OTHER PUBLICATIONS

Kasai et al., Japan J. Pharmaacol . . . , vol. 58, No. 4, Apr. 1992 Kyoto, pp. 347–355.
Bando, T. et al, Arzneim. Forsch./Drug Res., vol. 44, No. 6, 1994 Heidelberg pp. 754–757.
Hermecz et al, J. Med. Chem., vol. 30, 1987 Washington, pp. 1543–1549.
Sharma, Gen. Pharmacol., vol. 24, No. 2 1993 Oxford, pp. 267–274.

*Primary Examiner*—Richard L. Raymond
*Assistant Examiner*—Tamthom N. Truong
*Attorney, Agent, or Firm*—Oblon, Spivak, McClelland, Maier & Neustadt, P.C.

[57] ABSTRACT

This invention relates to a compound of the formula:

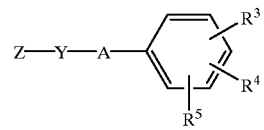

wherein
Z is a group of the formula:

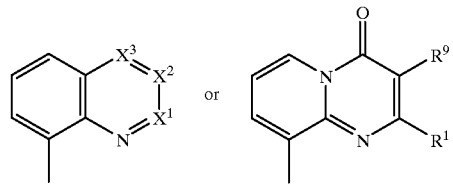

in which
$X^1$ is N or C—$R^1$,
$X^2$ is N or C—$R^9$,
$X^3$ is N or C—$R^2$,
$R^1$ is lower alkyl,
$R^2$ is hydrogen, lower alkyl, etc.,
$R^9$ is hydrogen or lower alkyl,
$R^3$ is halogen, etc.,
$R^4$ is halogen, etc.,
$R^5$ is a group of the formula:

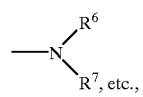

A is lower alkylene, and
Y is O, etc., and pharmaceutically acceptable salts thereof, to processes for preparation thereof, to a pharmaceutical composition comprising the same, and to methods to using the same therapeutically in the prevention and/or the treatment of bradykinin or its analogues mediated diseases in human being or animals.

6 Claims, No Drawings

PYRIDOPYRIMIDONES, QUINOLINES AND FUSED N-HETEROCYCLES AS BRADYKININ ANTAGONISTS

TECHNICAL FIELD

This invention relates to new heterocyclic compounds and pharmaceutically acceptable salts thereof.

More particularly, it relates to new heterocyclic compounds and pharmaceutically acceptable salts thereof which have activities as bradykinin antagonists, to processes for preparation thereof, to a pharmaceutical composition comprising the same, and to methods of using the same therapeutically in the prevention and/or the treatment of bradykinin or its analogues mediated diseases such as allergy, inflammation, autoimmune disease, shock, pain, or the like, in human being or animals.

One object of this invention is to provide new and useful heterocyclic compounds and pharmaceutically acceptable salts thereof which posses activities as bradykinin antagonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

Still further object of this invention is to provide a therapeutical method for the prevention and/or the treatment of bradykinin or its analogues mediated diseases such as allergy, inflammation, autoimmune disease, shock, pain, or the like, using said heterocyclic compounds and pharmaceutically acceptable salts thereof.

BACKGROUND ART

Some heterocyclic compounds have been known as described, for example in EP-A-224,086, EP-A-261,539, Chemical Abstracts 90:34849g (1979), or Chemical Abstracts 97:18948c (1982). However, it is not known that said compounds have activities as bradykinin antagonists.

Heterocyclic compounds having activities as bradykinin antagonists have been known as described in EP-A-596,406 and EP-A-622,361.

DISCLOSURE OF THE INVENTION

The object heterocyclic compounds of this invention are new and can be represented by the following general formula [I]:

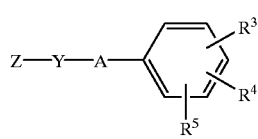

[I]

wherein

Z is a group of the formula:

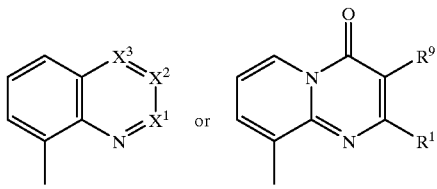

in which
X$^1$ is N or C—R$^1$,
X$^2$ is N or C—R$^9$,
X$^3$ is N or C—R$^2$,
R$^1$ is lower alkyl,
R$^2$ is hydrogen; lower alkyl; halogen; aryl; hydroxy(lower)alkyl; lower alkoxy(lower)alkyl; carboxy; esterified carboxy; carbamoyl optionally substituted with lower alkyl; cyclo(lower)alkoxy; lower alkoxy optionally substituted with a substituent selected from the group consisting of lower alkoxy, lower alkylamino, hydroxy, carboxy, esterified carboxy and carbamoyl optionally substituted with lower alkyl; halo(lower)alkoxy; lower alkylamino optionally substituted with a substituent selected from the group consisting of lower alkoxy, lower alkylamino and esterified carboxy; lower alkenylamino; or an N-containing heterocyclic-N-yl group optionally substituted with lower alkyl,
R$^9$ is hydrogen or lower alkyl,
R$^3$ is hydrogen, lower alkyl, lower alkoxy or halogen,
R$^4$ is lower alkyl, lower alkoxy or halogen,
R$^5$ is hydroxy; nitro; lower alkoxy optionally substituted with a substituent selected from the group consisting of amino, acylamino and lower alkoxy; piperazinyl substituted with acyl(lower)alkyl and oxo; or a group of the formula:

in which
R$^6$ is hydrogen or lower alkyl, and
R$^7$ is hydrogen; aryloxycarbonyl; aryl optionally substituted with a substituent selected from the group consisting of acyl-ar(lower)alkenyl, acyl-ar(lower)alkoxy, acyl-aryloxy(lower)alkyl and acyl-ar(lower)alkyl; heterocycliccarbonyl optionally substituted with acyl-ar(lower)alkenyl; acyl(lower)alkanoyl; hydroxy(lower)alkanoyl; acyloxy(lower)alkanoyl; carbamoyl optionally substituted with acyl(lower)alkyl; or a group of the formula:

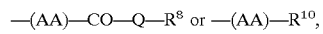

in which
R$^8$ is arylthio, aryloxy or arylamino, each of which is optionally substituted with substituent(s) selected from the group consisting of acyl, heterocyclic(lower)alkyl, heterocyclic(lower)alkenyl, nitro, amino and acylamino; heterocyclicthio or heterocyclicamino, each of which is optionally substituted with substituent(s) selected from the group consisting of acyl, acylamino, amino and lower alkoxy; halogen; tri(lower)alkylphosphonio; aryl substituted with substituent(s) selected from the group consisting of lower alkyl, lower alkoxy, acyl(lower)alkenyl, heterocyclic(lower)alkenyl, nitro, acyl, acyl(lower)alkoxy, guanidino, amino, acylamino, N-acyl-N-[heterocyclic(lower)-alkyl]amino and an N-containing heterocyclic-N-yl group substituted with oxo; or a heterocyclic group optionally substituted with substituent(s) selected from the group consisting of oxo, lower alkyl, lower alkoxy, nitro-aryl, acyl, acylamino, amino, N-acyl-N-(lower)alkylamino, lower alkylamino, halogen, heterocyclic(lower)alkyl, heterocyclic(lower)alkenyl and an N-containing heterocyclic-N-yl group substituted with oxo;

$R^{10}$ is hydrogen or acylbiphenyl, (AA) is amino acid residue, and

Q is lower alkylene, lower alkenylene or single bond,

A is lower alkylene, and

Y is O or N—$R^{11}$, in which $R^{11}$ is hydrogen or an N-protective group.

The object compound [I] or its salt can be prepared by processes as illustrated in the following reaction schemes.

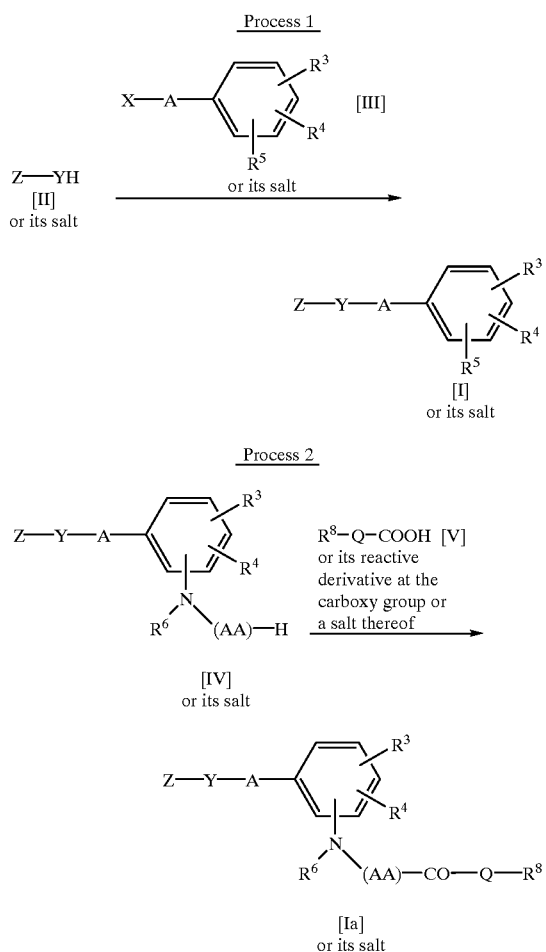

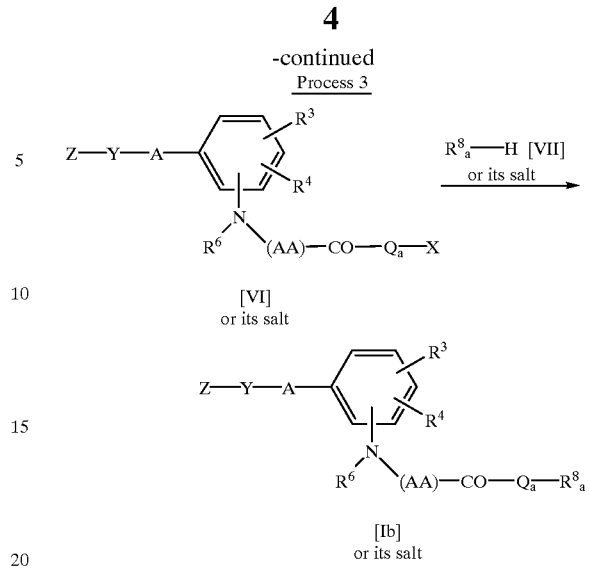

wherein $R_a^8$ is arylthio optionally substituted with substituent(s) selected from the group consisting of acyl, amino and acylamino; or heterocyclicthio optionally substituted with substituent(s) selected from the group consisting of acyl, acylamino, amino and lower alkoxy;

$Q_a$ is lower alkylene,

X is a leaving group, and $R^3$, $R^4$, $R^5$, $R^6$, $R^8$, A, Y, Z, (AA) and Q are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moiety, heterocyclic(lower)alkenyl moiety, acyl(lower)alkenyl moiety and ar(lower)alkenyl moiety in the various definitions is intended to mean a group having 2 to 6 carbon atoms.

Further, the term "lower" in ar(lower)alkenoyl moiety and heterocyclic(lower)alkenoyl moiety in the various definitions is intended to mean a group having 3 to 6 carbon atoms.

Suitable "lower alkyl" and lower alkyl moiety such as in the terms "heterocyclic(lower)alkyl", "acyl(lower)alkyl", "lower alkylthio", "N-acyl-N-(lower)alkylamino", "hydroxy(lower)alkyl", "lower alkoxy(lower)alkyl", "tri(lower)alkylphosphonio", "lower alkylamino", etc., may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "cyclo(lower)alkoxy" may be cyclo ($C_3$–$C_6$) alkoxy such as cyclopropyloxy, cyclobutyloxy, cyclopentyloxy, cyclohexyloxy or the like.

Suitable "lower alkoxy" and lower alkoxy moiety such as in the terms "acyl(lower)alkoxy", "lower alkoxy(lower)alkyl", etc., may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable "esterified carboxy" may be lower alkoxycarbonyl [e.g. methoxycarbonyl, ethoxycarbonyl, propoxycabonyl, butoxycarbonyl, isopropoxycarbonyl, tert-butoxycarbonyl, etc.], ar(lower)alkoxycarbonyl [e.g. benzyloxycarbonyl, etc.] or the like.

Suitable "halo(lower)alkoxy" may be chloromethoxy, trifluoromethoxy, trifluoroethoxy, trifluoropropoxy or the like.

Suitable lower alkenyl moiety such as in the terms "lower alkenylamino", "heterocyclic(lower)alkenyl", etc., may be a straight or branched one such as vinyl, allyl, 1-propenyl, isopropenyl, butenyl, isobutenyl, pentenyl, hexenyl or the like.

Suitable "halogen" may be fluorine, chlorine, bromine and iodine.

Suitable "acyl" and acyl moiety such as in the terms "acylamino", "acyl(lower)alkyl", "acyl(lower)alkoxy", "acyl-ar(lower)alkenylaroyl", "N-acyl-N-(lower)alkylamino", etc., may be lower alkanoyl [e.g. formyl, acetyl, propionyl, butyryl, isobutyryl, valeryl, isovaleryl, pivaloyl, hexanoyl, 3,3-dimethylbutyryl, etc.], halo(lower)alkyanoyl [e.g. chloroacetyl, trifluoroacetyl, bromoacetyl, bromobutyryl, heptafluorobutyryl, etc.], heterocyclic(lower)alkanoyl optionally substituted with lower alkyl [e.g. pyridylacetyl, methlpyridylcetyl, ethylpyridylacetyl, etc.], lower alkoxy(lower)alkanoyl [e.g. methoxyacetyl, methoxypropionyl, ethoxyacetyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], heterocycliccarbonyl optionally substituted with lower alkyl, lower alkoxy or lower alkylthio [e.g. pyridylcarbonyl, pyrazinylcarbonyl, isoquinolylcarbonyl, thiazolylcarbonyl, oxazolylcarbonyl, methylpyridylcarbonyl, methylpyrazolylcarbonyl, methoxypyridylcarbonyl, methylthiopyridylcarbonyl, etc.], carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], lower alkylamino(lower)alkylcarbamoyl [e.g. methylaminomethylcarbamoyl, methylaminoethylcarbamoyl, dimethylaminoethylcarbamoyl, etc.], N-[lower alkylamino(lower)alkyl]-N-(lower alkyl)carbamoyl [e.g. N-(methylaminoethyl)-N-methylcarbamoyl, N-(dimethylaminoethyl)-N-methylcarbamoyl, etc.], arylcarbamoyl optionally substituted with lower alkylcarbamoyl [e.g. phenylcarbamoyl, naphthylcarbamoyl, tolylcarbamoyl, methylcarbamoylphenylcarbamoyl, dimethylcarbamoylphenylcarbamoyl, etc.], heterocycliccarbamoyl optionally substituted with lower alkyl,lower alkoxy, lower alkylthio or oxo [e.g. pyridylcarbamoyl, or its oxide, pyrazinylcarbamoyl, isoquinolylcarbamoyl, thiazolylcarbamoyl, oxazolylcarbamoyl, methyloxazolylcarbamoyl, methylpyrazolylcarbamoyl, methylpyridylcarbamoyl, methoxypyridylcarbamoyl, methylthiopyridylcarbamoyl, etc.], ar(lower)alkylcarbamoyl [e.g. benzylcarbamoyl, phenethylcarbamoyl, etc.], heterocyclic(lower)alkylcarbamoyl [e.g. pyridylmethylcarbamoyl, pyrazinylmethycarbamoyl, pyrimidinylmethylcarbamoyl, etc.], lower alkylsulfonylcarbamoyl [e.g. methylsulfonylcarbamoyl, ethylsulfonylcarbamoyl, etc.], arylsulfonylcarbamoyl [e.g. phenylsulfonylcarbamoyl, tolylsulfonylcarbamoyl, etc.], ar(lower)alkenoyl substituted with lower alkylcarbamoyl [e.g. methylcarbamoylcinnamoyl, dimethylcarbamoylcinnamoyl, etc.], ar(lower)alkenoyl substituted with lower alkanoylamino [e.g. acetylaminocinnamoyl, etc.], heterocyclic(lower)alkenoyl substituted with lower alkylcarbamoyl [e.g. methylcarbamoylpyridylacryloyl, dimethylcarbamoylpyridylacryloyl, etc.], heterocyclic(lower)alkenoyl substituted with lower alkanoylamino [e.g. acetylaminopyridylacryloyl, etc.], lower alkylsulfonyl [e.g. methylsulfonyl, ethylsulfonyl, propylsulfonyl, isopropylsulfonyl, tert-butylsulfonyl, pentylsulfonyl, etc.], phthaloyl, or the like.

Suitable "aryl" and aryl moiety such as in the terms "aryloxycarbonyl", "arylthio", "aryloxy", "arylocarbamoyl", "aryloxy(lower)alkyl", "arylamino", "nitro-aryl", "ar(loweralkenoyl", etc., may be phenyl, naphthyl, phenyl or naphthyl substituted with lower alkyl [e.g. tolyl, xylyl, mesityl, cumenyl, di(tert-butyl)phenyl, methylnaphthyl, etc.] and the like, in which preferable one is phenyl, naphthyl and tolyl.

Suitable "aroyl" may be benzoyl, toluoyl, xyloyl, napthoyl or the like.

Suitable "ar(lower)alkyl" may be benzyl, phenethyl, phenylpropyl, napthylmethyl, benzhydryl, trityl or the like.

Suitable "ar(lower)alkoxy" may be benzyloxy, phenethyloxy, phenylpropoxy, napthylmethoxy or the like.

Suitable "ar(lower)alkenyl" may be phenylvinyl, naphthylvinyl, phenylpropenyl or the like.

Suitable lower alkanoyl moiety in the terms "acyl(lower)alkanoyl", "hydroxy(lower)alkanoyl" and "acyloxy(lower)alkanoyl" may be formyl, acetyl, propionyl, butyryl, isobutyryl, valeryl, hexanoyl or the like.

Suitable "heterocyclic group" and heterocyclic moiety such as in the terms "heterocyclic(lower)alkyl", "heterocyclic(lower)alkenyl", "heterocyclic(lower)alkanoyl", "heterocycliccarbonyl", "heterocycliccarbamoyl", "heterocyclic(lower)alkylcarbamoyl", "heterocyclic(lower)alkenoyl, "heterocyclicthio", "heterocyclicamino", etc., may be saturated or unsaturated, monocyclic or polycyclic heterocyclic group containing at least one hetero-atom such as an oxygen, sulfur and/or nitrogen atom such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl, tetrazolyl, dihydrotriazinyl, etc.;

saturated 3 to 8-membered, preferably 4 or 6-membered heteromonocyclic group containing 1 to 4 nitrogen atom(s), for example, azetidinyl, pyrrolidinyl, imidazolidinyl, piperidyl, pyrazolidinyl, piperazinyl, etc.;

unsaturated condensed 7 to 12-membered heterocyclic group containing 1 to 5 nitrogen atom(s), for example, indolyl, isoindolyl, indolizinyl, benzimidazolyl, quinlolyl, isoquinolyl, tetrahydroquinolyl, indazolyl, benzotriazolyl, imidazopyridyl, etc.;

unsaturated 3 to 8-membered, preferably 5 to 6-membered heteromonocyclic group containing an oxygen atom, for example, furyl, etc.;

unsaturated condensed 7 to 12-membered heterocyclic group containing 1 to 2 oxygen atom(s), for example, benzofuryl, piperonyl, etc.;

unsaturated 3 to 8-membered, preferably 5 to 6-membered heteromonocyclic group containing a sulfur atom, for example, thienyl, etc.;

unsaturated condensed 7 to 12-membered heterocyclic group containing 1 to 2 sulfur atom(s), for example, benzothienyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, etc.;

saturated 3 to 8-membered, preferably 5 to 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example thiazolyl, isothiazolyl, thiazolinyl, thiadiazolyl, etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated condensed 7 to 12-membered heterocyclic group containing 1 to 2 sulfur atom(s) and 1 to 3 nitrogen atom(s), for example, benzothiazolyl, benzothiadiazolyl, benzothiazinyl, benzothiazolinyl, etc., or the like.

Suitable "N-containing heterocyclic-N-yl group" may be morpholino, thiomorpholino, pyrrolidin-1-yl, piperidino, 1,2,3,6-tetrahydropyridin-1-yl, 1,2-dihydropyridin-1-yl, piperazin-1-yl, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutaminie, asparagine, lysine, arginine, histidine, ornithine, or the like, in which more preferable one is glycine, sarcosine, alanine, β-alanine and proline, and the most preferable one is glycine.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one are methylene and ethylene.

Suitable "lower alkenylene" may be a straight or branched $C_2$–$C_6$ alkenylene such a vinylene, methylvinylene, propenylene, 1,3-butadienylene or the like, in which the most preferable one is vinylene.

Suitable examples of Z may be a group of the formula:

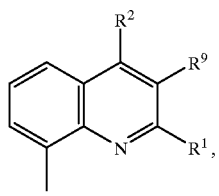

-continued

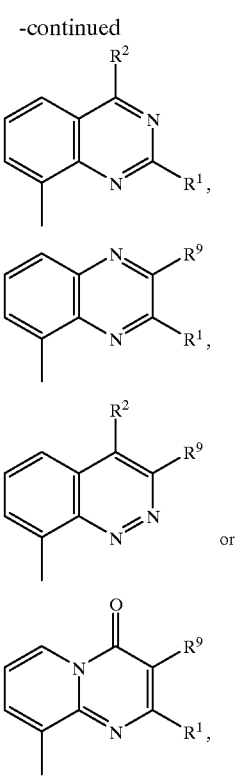

wherein $R^1$, $R^2$ and $R^9$ are each as defined above.

Suitable "N-protective group" may be ar(lower) alkoxycarbonyl [e.g. benzyloxycarbonyl, etc.], lower alkoxycarbonyl [e.g. tert-butoxycarbonyl, etc.] or the like.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] and [Ib] in the Processes 2 and 3, it is to be noted that these compounds are included within the scope of the compound [I], and accordingly the suitable examples of the salts of these compounds are to be referred to those as exemplified for the object compound [I].

Preferred embodiments of the object compound [I] are as follows:

a) a compound of the formula:

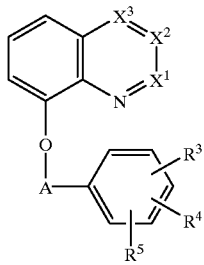

[I']

wherein
$X^1$ is N or C—$R^1$,
$X^2$ is N or C—$R^9$,
$X^3$ is N or C—$R^2$,
$R^1$ is lower alkyl,
$R^2$ is hydrogen; lower alkyl; aryl; hydroxy(lower)alkyl; lower alkoxy(lower)alkyl; carboxy; esterified carboxy; carbamoyl optionally substituted with lower alkyl; cyclo(lower)alkoxy; lower alkoxy optionally substituted with a substituent selected from the group consisting of lower alkoxy, lower alkylamino, hydroxy, carboxy, esterified carboxy and carbamoyl optionally substituted with lower alkyl; halo(lower)alkoxy; lower alkylamino optionally substituted with a substituent selected from the group consisting of lower alkoxy, lower alkylamino and esterified carboxy; lower alkenylamino; or an N-containing heterocyclic-N-yl group,
$R^3$ is hydrogen, lower alkyl, lower alkoxy or halogen,
$R^4$ is lower alkyl, lowered alkoxy or halogen,
$R^5$ is hydroxy; lower alkoxy optionally substituted with a substituent selected from the group consisting of amino, acylamino and lower alkoxy; piperazinyl substituted with acyl(lower)alkyl and oxo; or a group of the formula:

in which
$R^6$ is hydrogen or lower alkyl, and
$R^7$ is aryloxycarbonyl; acyl-ar(lower)alkenylaroyl; carbamoyl optionally substituted with acyl(lower)alkyl; or a group of the formula:

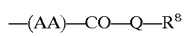

—(AA)—CO—Q—$R^8$ in which
$R^8$ is arylthio, aryloxy or arylamino, each of which is optionally substituted with substituent(s) selected from the group consisting of acyl, amino and acylamino; heterocycliothio or heterocyclicamino, each of which is optionally substituted with substituent(s) selected from the group consisting of acyl, acylamino, amino and lower alkoxy; halogen; tri(lower)alkylphosphonio; aryl substituted with substituent(s) selected from the group consisting of lower alkyl, lower alkoxy, nitro, acyl, acyl(lower)alkoxy, amino, acylamino and a N-containing heterocyclic-N-yl group substituted with oxo; or a heterocyclic group optionally substituted with substituent(s) selected from the group consisting of oxo, lower alkyl, lower alkoxy, nitro-aryl, acyl, acylamino, amino, N-acyl-N-(lower)alkylamino, lower alkyl, lower alkylamino, halogen, lower alkoxy, heterocyclic(lower)alkyl, heterocyclic(lower)alkenyl and an N-containing heterocyclic-N-yl group substituted with oxo;
(AA) is amino acid residue, and
Q is lower alkylene, lower alkenylene or single bond,
$R^9$ is hydrogen or lower alkyl, and
A is lower alkylene, and b) a compound of the formula:

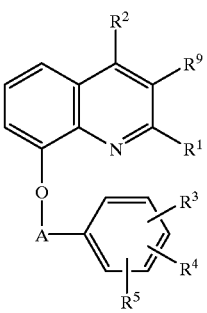

[I'']

wherein
$R^1$ is lower alkyl,
$R^2$ is hydrogen; cyclo(lower)alkoxy; lower alkoxy optionally substituted with a substituent selected from the group consisting of lower alkoxy, lower alkylamino, hydroxy, carboxy, esterified carboxy and carbamoyl optionally substituted with lower alkyl; halo(lower)alkoxy; lower alkylamino optionally substituted with a substituent selected from the group consisting of lower alkoxy, lower alkylamino and esterified carboxy; lower alkenylamino; or an N-containing heterocyclic-N-yl group,
$R^3$ is hydrogen, lower alkyl or halogen
$R^4$ is lower alkyl or halogen,
$R^5$ is hydroxy; lower alkoxy optionally substituted with a substituent selected from the group consisting of amino, acylamino and lower alkoxy; piperazinyl substituted with acyl(lower)alkyl and oxo; or a group of the formula:

in which
$R^6$ is hydrogen or lower alkyl, and
$R^7$ is aryloxycarbonyl; carbamoyl optionally substituted with acyl(lower)alkyl; or a group of the formula:

—(AA)—CO—Q—$R^8$ in which
$R^8$ is arylthio, aryloxy or arylamino, each of which is optionally substituted with substituent(s) selected from the group consisting of acyl, amino and acylamino; heterocyclicthio or heterocylicamino, each of which is optionally substituted with substituent(s) selected from the group consisting of acyl, acylamino, amino and lower alkoxy, halogen; tri(lower)alkylphosphonio; aryl substituted with substituent(s) selected from the group consisting of acyl, acyl(lower)alkoxy, amino and acylamino; or a heterocylic group optionally substituted with substituent(s) selected from the group consisting of nitro-aryl, acyl, acylamino, amino, N-acyl-N-(lower)alkylamino, lower alkyl, lower alkylamino, halogen, lower alkoxy, heterocyclic(lower)alkyl and an N-containing heterocyclic-N-yl group substituted with oxo;

(AA) is amino acid residue, and

Q is lower alkylene, lower alkenylene or single bond, $R^9$ is hydrogen or lower alkyl, and A is lower alkylene.

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carrier out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ia] or its salt can be prepared by reacting a compound [IV] or its salt with a compound [V] or its reactive derivative at the carboxy group or a salt thereof.

Suitable reactive derivative at the carboxy group of the compound [V] may include an acid halide, an acid anhydride, an activated amide, an activated ester, and the like. Suitable examples of the reactive derivatives may be an acid chloride; an acid azide; a mixed acid anhydride with an acid such as dialkylphosphoric acid, sulfuric acid, aliphatic carboxylic acid or aromatic carboxylic acid; a symmetrical acid anhydride; an activated amide with imidazole; or an activated ester [e.g. p-nitrophenyl ester, etc.]. These reactive derivatives can optionally be selected from them according to the kind of the compound [V] to be used.

Suitable salts of the compound [IV] can be referred to the organic or inorganic acid addition salts as exemplified for the compound [I].

Suitable salts of the compound [V] and its reactive derivative can be referred to the ones as exemplified for the compound [I].

The reaction is usually carried out in a conventional solvent, such a methylene chloride, chloroform, pyridine, dioxane, tetrahydrofuran, N,N-dimethylformamide, or the like. In case that the compound [V] is used in the free acid form or salt form, it is to carry out the reaction in the presence of a conventional condensing agent such a 1-ethyl-3-3-dimethylaminopropyl)carbodiimide, N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 3 the object compound [Ib] or its salt can be prepared by reacting a compound [VI] or its salt with a compound [VII] or its salt.

Suitable salts of the compound [VI] can be referred to the organic or inorganic acid addition salt as exemplified for the compound [I].

Suitable salts of the compound [VII] can be referred to the ones as exemplified for the compound [I].

This reaction can be carried out in substantially the same manner as Process 1, and therefore the reaction mode and reaction condition of this reaction are to be referred to those explained in Process 1.

The object compound [I] and the starting compounds can also be prepared by the methods of Examples and Preparations mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scop of this invention.

The object compound [I] and pharmaceutically acceptable salts thereof posses strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resporption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, emesis, hepatitis, pancreatitis, gastritis, esophagitis, food allergy, ulcer, irritable bowel syndrome, nephritis, angina, periodontitis, edema, hereditary angioneurotic edema, cerebral edema, low blood pressure, thrombosis, myocardial infarction, cerebral vasospasm, congestion, coagulation, gout, central nervous system injury, premature labor, arteriosclerosis (hyperlipidemia, hypercholesterolemia), postgastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

In order to illustrate the usefulness of the object compound [I], the pharmacological test data of some representative compounds of the compound [I] are shown in the following.

$^3$H-Bradykinin receptor binding (i) Test Method:

(a) Crude ileum membrane preparation

Male Hartly strain guinea pigs were sacrificed by decapitation. The ileum was removed and homogenized in buffer (50 mM trimethylaminoethanesulfonic acid (TES), 1 mM 1,10-phenanthroline pH 6.8). The homogenate was centrifuged (1000× g, 20 minutes) to remove tissue clumps and the supernatant was centrifuges (100,000× g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at -80° C. until use.

(b) $^3$H-Bradykinin binding to the membrane

The frozen crude membrane suspension was thawed. In binding assays, $^3$H-Bradykinin (0.06 mM) and drug (1×10$^{-6}$ M) were incubated with 50 μl of the membrane suspension at room temperature for 60 minutes in a final volume of 250 μl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 μM Bradykinin. The radioactivity retained on rinsed filters was determined by a liquid-scintillation counter.

| (ii) Test Results | |
|---|---|
| Test Compound (Example No.) | Inhibition % of $^3$H-Bradykinin binding (concentration: 1 × 10$^{-6}$ M) |
| 2-(14) | 96 |
| 10-(9) dihydrochloride | 99 |
| 25-(2) dihydrochloride | 96 |
| 34-(3) | 100 |
| 37-(5) hydrochloride | 100 |
| 73-(4) | 95 |
| 90-(2) | 98 |

The effects of the compound [I] on bradykinin-induced bronchoconstriction and carrageenin-induced paw edema were measured according to similar manners described in British Journal of Pharmacology, 102, 774–777 (1991).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal of hypoglossal administration. The pharmaceutical preparations may be capsules, tablets, dragees, gransules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

EXAMPLES

The following Preparations and Examples are given for the purpose of illustrating this invention.

Preparation 1

To a suspension of 4-formylbenzoic acid (1.00 g) in dry tetrahydrofuran (15 ml) was added methyl (triphenylphosphoranylidene)acetate (2.50 g) at ambient temperature under nitrogen atmosphere. The reaction mixture was stirred for 1 hour at the same temperature, poured into aqueous sodium bicarbonate solution, and washed with ethyl acetate. 1 N-hydrochloric acid was added to the aqueous layer until the layer was adjusted to pH 2. The aqueous layer was extracted with ethyl acetate. The organic layer was washed with water, dried over magnesium sulfate and evaporated in vacuo. The residue was crystallized from diisopropyl ether to give methyl 4-carboxycinnamate (1.21 g) as colorless powder.

mp: 243° C.

NMR (DMSO-D$_6$, δ): 3.74 (3 H, s), 6.76 (1 H, d, J=16 Hz), 7.73 (1 H, d, J=16 Hz), 7.85 (2 H, d, J=8 Hz), 7.96 (2 H, d, J=8 Hz).

Preparation 2

To a solution of methyl 4-carboxycinnamate (160 mg) in methylene chloride was added methylamine hydrochloride (58 mg) and 1-ethyl-3-(3-dimethylaminopropyl) carbodiimide (140 mg) at ambient temperature, and the mixture was stirred for 2 hours. To this suspension was added 1-hydroxybenzotriazole (137 mg) and dimethylformamide (2 ml), and the mixture was stirred for 14 hours at same temperature. The reaction mixture was poured into water, and extracted with dichloromethane. The organic layer was washed with aqueous sodium bicarbonate solution and water, dried over magnesium sulfate, and evaporated in vacuo. The residue was crystallized from diisopropyl ether to give methyl 4-(methylcarbamoyl)cinnamate (82 mg) as a colorless powder.

mp: 210° C.

NMR (DMSO-D$_6$, δ): 2.79 (3 H, d, J=5 Hz), 3.74 (3 H, s), 6.74 (1 H, d, J=16 Hz), 7.69 (1 H, d, J=16 Hz), 7.80 (2 H, d, J=8 Hz), 7.87 (2 H, d, J=8 Hz), 8.51 (1 H, q-like).

Preparation 3

To a solution of methyl 4-(methylcarbamoyl)cinnamate (75 mg) in methanol (3 ml) was added 1 N aqueous sodium hydroxide solution (0.5 ml) at 40° C. The mixture was stirred at same temperature for 3 hours. 1 N-Hydrochloric acid (0.5 ml) was added to the reaction mixture and evaporated in vacuo. Water was added to the residue, the mixture was filtered and the residue was washed with diethyl ether to give 4-(methylcarbamoyl)cinnamic acid (56 mg) as a colorless powder.

mp: >250° C.

NMR (DMSO-d$_6$, δ): 2.78 (3 H, d, J=5 Hz), 6.62 (1 H, d, J=16 Hz), 7.61 (1 H, d, J=16 Hz), 7.77 (2 H, d, J=8 Hz), 7.85 (2 H, d, J=8 Hz), 8.51 (1 H, q-like).

Preparation 4

A mixture of 2-acetylamino-5-formylpyridine (241 mg) and malonic acid (168 mg) in pyridine (0.12 ml) and ethanol (0.36 ml) was refluxed for 2 hours. After cooling the mixture, the precipitate was collected by filtration, and washed with ethyl acetate to give (E)-3-(6-acetylamino-3-pyridyl)acrylic acid (248 mg) as a colorless powder.

mp: 291–292° C.

NMR (DMSO-d$_6$, δ): 2.10 (3 H, s), 6.55 (1 H, J=16 Hz), 7.58 (1 H, d, J=16 Hz), 8.07–8.21 (2 H), 8.59 (1 H, br s).

Preparation 5

(E)-3-(6-Ethoxycarbonyl-3-pyridyl)acrylic acid (from ethyl 5-formyl-2-pyridinecarboxylate) was obtained according to a similar manner to that of Preparation 4.

mp: 201–202° C.

NMR (DMSO-$d_6$, δ): 1.33 (3 H, t, J=7 Hz), 4.36 (2 H, q, J=7 Hz), 6.80 (1 H, d, J=16 Hz), 7.69 (1 H, d, J=16 Hz), 8.07 (1 H, d, J=9 Hz), 8.33 (1 H, dd, J=9, 2 Hz), 9.00 (1 H, d, J=2 Hz).

Preparation 6

To a mixture of sodium hydride (40% in oil, 2.64 g) and N,N-dimethylformamide (100 ml) was added 8-hydroxy-2-methylquinoline (10 g) in an ice-water bath. The mixture was stirred for 30 minutes at the same temperature and then 2,6-dichloro-3-nitrobenzyl chloride (15.1 g) and tetrabutylammonium iodide (100 mg) were added therein. The reaction mixture was stirred at ambient temperature for 1 hour. To this mixture was added water (100 ml) in an ice-water bath. The precipitates were collected by vacuum filtration and washed with water (60 ml) to give 8-(2,6-dichloro-3-nitrobenzyloxy)-2-methylquinoline (20.36 g) as a powder.

NMR (CDCl$_3$, δ): 2.76 (3 H, s), 5.70 (2 H, s), 7.21–7.57 (5 H), 7.76 (1 H, d, J=8 Hz), 8.02 (1 H, d, J=8 Hz).

Preparation 7

The following compounds were obtained according to a similar manner to that of Preparation 6.

(1) 4-Chloro-8-(2,6-dichloro-3-nitrobenzyloxy)-2-methylquinoline

NMR (CDCl$_3$, δ): 2.70 (3 H, s), 5.67 (2 H, s), 7.23–7.92 (6 H).

(2) 8-(2,6-Dichloro-3-nitrobenzyloxy)-4-methoxy-2-methylquinoline

NMR (CDCl$_3$, δ): 2.70 (3 H, s), 4.02 (3 H, s), 5.68 (2 H, s), 6.67 (1 H, s), 7.25 (1 H, dd, J=8, 1 Hz), 7.34 (1 H, t, J=8 Hz), 7.50 (1 H, d, J=8 Hz), 7.75 (1 H, d, J=8 Hz), 7.84 (1 H, dd, J=8, 1 Hz).

Preparation 8

To a mixture of 8-(2,6-dichloro-3-nitrobenzyloxy)-2-methylquinoline (1.0 g), concentrated hydrochloric acid (5.2 ml) and methanol (5.2 ml)) was added iron powder (666 mg). The mixture was heated under reflux for 2 hours and stirred in an ice-water bath for 1 hour. The precipitate was collected by vacuum filtration and washed with 1 N hydrochloric acid and water to give 8-(3-amino-2,6-dichlorobenzyloxy)-2-methylquinoline dihydrochloride (635 mg) as a brownish powder.

NMR (DMSO-$d_6$, δ): 2.93 (3 H, s), 5.50 (2 H, s), 6.98 (1 H, d, J=8 Hz), 7.23 (1 H, d, J=8 Hz), 7.80–8.02 (4 H), 9.03 (1 H, d, J=8 Hz),

Preparation 9

To a mixture of 8-(3-amino-2,6-dichlorobenzyloxy)-2-methylquinoline dihydrochloride (4.06 g), 4-dimethylaminopyridine (120 mg), N-methylpyrrolidone (30 ml) and pyridine (10 ml) was added phthalimidoacetyl chloride (3.35 g) at ambient temperature. The mixture was stirred at 50° C. for 1.5 hours and cooled in an ice-water bath. Water (40 ml) was added therein and the mixture was stirred for 30 minutes in an ice water bath. The precipitate was collected by vacuum filtration and washed with water and ethyl acetate to give 8-[2,6-dichloro-3-(phthalimidoacetylamino)benzyloxy]-2-methylquinoline (4.45 g) as a yellowish powder.

NMR (CDCl$_3$, δ): 2.86 (3 H, s), 4.74 (2 H, s), 5.51 (2 H, s), 7.20–7.50 (5 H), 7.63–7.93 (4 H), 8.03 (1 H, d, J=8 Hz), 8.29 (1 H, d, J=8 Hz).

Preparation 10

To a mixture of 8-[2,6-dichloro-3-(phthalimidoacetylamino)benzyloxy]-2-methylquinoline (4.44 g) and N,N-dimethylformamide (44 ml) was added sodium hydride (60% in oil, 375 mg) in an ice-water bath. After stirring for 30 minutes in an ice-water bath, methyl iodide (0.6 ml) was added thereto and the mixture was stirred at ambient temperature for 1 hour. To this mixture was added water (88 ml) in an ice-water bath and the mixture was stirred at the same temperature for 1.5 hours. The precipitate was collected by vacuum filtration wand washed with water and methanol to give 8-[2,6-dichloro-3-[N-(phthalimidoacetyl)-N-methylamino]benzyloxy]-2-methylquinoline (3.99 g) as a yellow powder.

NMR (CDCl$_3$, δ): 2.76 (3 H, s), 3.23 (3 H, s), 4.08 (2 H, s), 5.68 (1 H, d, J=12 Hz), 5,75 (1 H, d, J=12 Hz), 7.24–7.59 (6 H), 7.66–7.91 (4 H), 8.03 (1 H, d, J=8 Hz).

Preparation 11

A mixture of 8-[2,6-dichloro-3-[N-(phthalimidoacetyl)-N-methylamino]benzyloxy]-2-methylquinoline (3.98 g), hydrazine monohydrate (0.72 ml) and ethanol (40 ml) was heated under reflux for 1 hour. The precipitate was removed by vacuum filtration and the filtrate was evaporated in vacuo. The residue was dissolved in dichloromethane and the precipitate was removed by vacuum filtration. The filtrate was evaporated in vacuo to give 8-[3-(N-glycl-N-methylamino)-2,6-dichlorobenzyloxy]-2-methylquinoline (2.99 g) as a yellow amorphous powder.

NMR (CDCl$_3$, δ): 2.76 (3 H, s), 2.96 (1 H, d, J=16 Hz), 3.10 (1 H, d, J=16 Hz), 3.21 (3 H, s), 5.66 (2 H, s), 7.20–7.50 (6 H), 8.02 (1 H, d, J=8 Hz).

Preparation 12

A mixture of 4-chloro-8-hydroxy-2-methylquinoline (9 g), 1,3-dimethyl-2-imidazolidinone (100 ml) and 28% solution of sodium methoxide in methanol (135 ml) was stirred at 150°0 C. for 4 hours. The reaction mixture was cooled to ambient temperature followed by partition into ethyl acetate and water. The organic layer was washed with water and brine, dried over magnesium sulfate and concentrated in vacuo. The crystalline residue was washed with n-hexane to give 8-hydroxy-4-methoxy-2-methylquinoline (5.57 g).

mp: 110.5–112° C.

NMR (CDCl$_3$, δ): 2.67 (3 H, s), 4.01 (3 H, s), 6.63 (1 H, s), 7.11 (1 H, d, J=8 Hz), 7.31 (1 H, t, J=8 Hz), 7.56 (1 H, d, J=8 Hz).

Preparation 13

The following compounds were obtained according to a similar manner to that of Preparation 12.

(1) 4-Ethoxy-8-hydroxy-2-methylquinoline mp: 85–86° C.

NMR (CDCl$_3$, δ): 1.56 (3 H, t, J=6 Hz), 2.66 (3 H, s), 4.23 (2 H, q, J=6 Hz), 6.60 (1 H, s), 7.10 (1 H, d, J=8 Hz), 7.31 (1 H, t, J=8 Hz), 7.60 (1 H, d, J=8 Hz).

(2) 8-Hydroxy-4-(2-methoxyethoxy)-2-methylquinoline

NMR (CDCl$_3$δ): 2.40 (3 H, s), 3.52 (3 H, s), 3.91 (2 H, t, J=6 Hz), 4.32 (2 H, t, J=6 Hz), 6.64 (1 H, s), 7.12 (1 H, d, J=8 Hz), 7.32 (1 H, t, J=8 Hz), 7.62 (1 H, d, J=8 Hz).

(3) 8-Hydroxy-2-methyl-4-(2-dimethylaminoethoxy)quinoline mp: 94–96° C.

NMR (CDCl$_3$, δ): 2.40 (6 H, s), 2.67 (3 H, s), 2.91 (2 H, t, J=6 Hz), 4.29 (2 H, t, J=6 Hz), 6.63 (1 H, s), 7.12 (1 H, d, J=8 Hz), 7.31 (1 H, t, J=8 Hz), 7.59 (1 H, d, J=8 Hz).

(4) 8-Hydroxy-4-isopropoxy-2-methylquinoline

NMR (CDCl$_3$, δ): 1.48 (6 H, d, J=7.5 Hz), 2.64 (3 H, s), 4.75–4.86 (1 H, m), 6.60 (1 H, s), 7.10 (1 H, d, J=8 Hz), 7.29 (1 H, t, J=8 Hz), 7.59 (1 H, d, J=8 Hz).

(5) 4-Cyclopentyloxy-8-hydroxy-2-methylquinoline

NMR (CDCl$_3$, δ): 1.56–2.07 (8 H, m), 2.66 (3 H, s), 4.94–5.02 (1 H, m), 6.60 (1 H, s), 7.10 (1 H, d, J=8 Hz), 7.29 (1 H, t, J=8 Hz), 7.55 (1 H, d, J=8 Hz).

Preparation 14

A mixture of 4-chloro-8-(2,6-dichloro-3-nitrobenzyloxy)-2-methylquinoline (200 mg) and N,N-dimethylformamide (3 ml) was heated under reflux for 18 hours. The reaction mixture was partitioned into ethyl acetate and saturated aqueous solution of sodium bicarbonate. The organic layer was washed with water, dried over magnesium sulfate and evaporated in vacuo. The residue was purified by preparative thin-layer chromatography (dichloromethane-methanol) to give 8-hydroxy-2-methyl-4-dimethylaminoquinoline (26 mg) as a brownish powder.

NMR (CDCl$_3$, δ): 2.62 (3 H, s), 3.03 (6 H, s), 5.29 (1 H, br s), 6.63 (1 H, s), 7.07 (1 H, d, J=8 Hz), 7.28 (1 H, t, J=8 Hz), 7.46 (1 H, d, J=8 Hz).

Preparation 15

(1) To a suspension of 8-(2,6-dichloro-3-nitrobenzyloxy)-4-methoxy-2-methylquinoline (1.75 g) in methanol (17 ml) was added tin (II) chloride (3.37 g) at ambient temperature. The mixture was refluxed for 1 hour. After cooling, the mixture was adjusted to pH 10 with 1 N sodium hydroxide solution. To this mixture was added dichloromethane (50 ml) and the precipitate was removed by filtration. The filtrate was extracted with dichloromethane twice. The organic layer was washed with water and brine. After dried over magnesium sulfate, the solvent was removed in vacuo to give 8-(3-amino-2,6-dichlorobenzyloxy)-4-methoxy-2-methylquinoline (1.16 g) as a colorless powder.

mp: >250° C.

NMR (DMSO-d$_6$, δ): 2.58 (3 H, s), 4.00 (3 H, s), 5.31 (2 H, s), 5.68 (2 H, br s), 6.90 (1 H, d, J=8 Hz), 7.23 (1 H, d, J=8 Hz), 7.31–7.46 (2 H), 7.68 (1 H, dd, J=8, 2 Hz).

(2) 8-[2,6-Dichloro-3-(phthalimidoacetylamino)benzyloxy]-4-methoxy-2-methylquinoline was obtained according to a similar manner to that of Preparation 9.

mp: 184–185° C.

NMR (CDCl$_3$, δ): 2.62 (3 H, s), 4.27 (3 H, s), 4.78–5.02 (2 H), 5.10–5.79 (2 H), 6.60 (1 H, br d, J=9 Hz), 7.19–7.38 (2 H), 7.58 (1 H, t, J=9 Hz), 7.70–7.99 (7 H).

(3) 8-[2,6-Dichloro-3-[N-(phthalimidoacetyl)-N-methylamino]benzyloxy]-4-methoxy-2-methylquinoline was obtained according to a similar manner to that of Preparation 10.

mp: 209–210° C.

NMR (CDCl$_3$, δ): 2.70 (3 H, s), 3.22 (2 H, s), 3.99 (3 H, s), 4.02 (2 H, s), 5.65 (1 H, d, J=10 Hz), 5.72 (1 H, d, J=10 Hz), 6.63 (1 H, s), 7.21–7.40 (2 H), 7.46 (1 H, d, J=9 Hz), 7.53 (1 H, d, J=9 Hz), 7.68–7.91 (5 H).

(4) 8-[3-(N-Glycyl-N-methylamino)-2,6-dichlorobenzyloxy]-4-methoxy-2-methylquinoline was obtained according to a similar manner to that of Preparation 11.

NMR (CDCl$_3$, δ): 2.70 (3 H, s), 2.95 (1 H, d, J=17 Hz), 3.10 (1 H, d, J=17 Hz), 3.21 (3 H, s), 4.01 (3 H, s), 5.62 (2 H, s), 7.18–7.29 (2 H), 7.33 (1 H, t, J=8 Hz), 7.46 (1 H, d, J=9 Hz), 7.32 (1 H, d, J=8 Hz).

Preparation 16

A mixture of 4-chloro-8-hydroxy-2-methylquinoline (500 mg), N,N-dimethylethylenediamine (341 mg) and phenol (486 mg) was heated at 125° C. for 18 hours. After cooling the reaction mixture, acetone (5 ml) was added thereto. The precipitates were collected by filtration and recrystallized from acetonitrile to give 4-(2-dimethylaminoethylamino)-8-hydroxy-2-methylquinoline hydrochloride (415 mg)) as brown crystals.

mp: 248–250° C.

NMR (DMSO-d$_6$, δ): 2.45 (6 H, s), 2.63 (3 H, s), 3.81–2.92 (2 H, m), 3.58–3.70 (2 H, m), 6.72 (1 H, s), 7.22 (1 H, d, J=8 Hz), 7.39 (1 H, t, J=8 Hz), 7.83 (1 H, d, J=8 Hz), 8.43 (1 H, br s).

Preparation 17

The following compounds were obtained according to a similar manner to that of Preparation 16.

(1) 4-Ethoxycarbonylmethylamino-8-hydroxy-2-methylquinoline (from 4-chloro-8-hydroxy-2-methylquinoline and ethyl aminoacetate hydrochloride)

mp: 227–229° C.

NMR (DMSO-d$_6$, δ): 1.23 (3 H, t, J=7 Hz), 2.59 (3 H, s), 4.18 (2 H, q, J=7 Hz), 4.29 (2 H, br d, J=6 Hz), 6.50 (1 H, s), 7.15 (1 H, d, J=7.5 Hz), 7.36 (1 H, t, J=7.5 Hz), 7.69 (1 H, d, J=7.5 Hz), 8.35 (1 H, br s).

(2) 4-Allylamino-8-hydroxy-2-methylquinoline (from 4-chloro-8-hydroxy-2-methylquinoline and allylamine)

mp: 263–264° C.

NMR (DMSO-d$_6$, δ): 2.66 (3 H, s), 4.11–4.09 (2 H, m), 5.18–5.30 (2 H, m), 5.88–6.02 (1 H, m), 6.67 (1 H, s), 7.38 (1 H, d, J=7.5 Hz), 7.47 (1 H, t, J=7.5 Hz), 7.91 (1 H, d, J=7.5 Hz), 9.29 (1 H, br t, J=6 Hz).

(3) 8-Hydroxy-4-(2-methoxyethylamino)-2-methylquinoline hydrochloride (from 4-chloro-8-hydroxy-2-methylquinoline and 2-methoxyethylamine)

mp: 235.8–239° C.

NMR (DMSO-d$_6$, δ): 2.65 (3 H, s), 3.29 (3 H, s), 3.59–3.61 (4 H, m), 6.79 (1 H, s), 7.31 (1 H, d, J=8 Hz), 7.43 (1 H, t, J=8 Hz), 7.89 (1 H, d, J=8 Hz), 8.90 (1 H, br s).

(4) 4-[Bis(2-methoxyethyl)amino]-8-hydroxy-2-methylquinoline (from 4-chloro-8-hydroxy-2-methylquinoline and bis(2-methoxyethyl)amino)

NMR (CDCl$_3$, δ): 2.63 (3 H, br s), 3.29 (6 H, s), 3.50–3.80 (8 H, m), 6.85 (1 H, br s), 7.06 (1 H, d, J=8 Hz), 7.29 (1 H, br t, J=8 Hz), 7.49 (1 H, br d, J=8 Hz).

(5) 8-Hydroxy-2-methyl-4-(piperidino)quinoline (from 4-chloro-8-hydroxy-2-methylquinoline and piperidine)

NMR (CDCl$_3$, δ): 1.63–1.74 ( 2 H, m), 1.79–1.89 (4 H, m), 2.64 (3 H, s), 3.15–3.22 (4 H, m), 6.70 (1 H, s), 7.06 (1 H, d, J=8 Hz), 7.28 (1 H, t, J=8 Hz), 7.39 (1 H, d, J=8 Hz).

(6) 8-Hydroxy-2-methyl-4-(morpholino)quinoline (from 4-chloro-8-hydroxy-2-methylquinoline and morpholine)

NMR (CDCl$_3$, δ): 2.66 (3 H, s), 3.24 (4 H, t, J=5 Hz), 3.98 (4 H, t, J=5 Hz), 6.74 (1 H, s), 7.09 (1 H, d, J=7.5 Hz), 7.31 (1 H, t, J=7.5 Hz), 7.39 (1 H, d, J=7.5 Hz).

Preparation 18

(1) To a solution of 2,6-dichloro-3-nitrobenzyl alcohol (5.0 g) in N,N-dimethylformamide (25 ml) were added imidazole (1.69 g) and tert-butyldiphenylsilyl chloride (6.0 ml) at ambient temperature with stirring. After 8 hours, the mixture was diluted with water (25 ml) and was extracted with ethyl acetate twice. The organic layer was washed with water and brine, dried over magnesium sulfate. The solvent was removed in vacuo to give 1-(tert-butyldiphenylsilyloxy-methyl)-2,6-dichloro-3-nitrobenzene (11.5 g) as an oil.

NMR (CDCl$_3$, δ): 1.05 (9H, s), 4.96 (2H, s), 7.27–7.51 (7H, m), 7.58–7.81 (5H, m), (2) To a stirred mixture of 1-(tert-butyldiphenylsilyloxymethyl)-2,6-dichloro-3-nitrobenzene (433 mg), ferric chloride hexahydrate (17.5 mg) and activated carbon (17.5 mg) in a mixture of methanol (2.78 ml) and water (0.69 ml) was added hydrazine monohydrate (0.135 ml) dropwise at 60–70° C. After the addition was finished, the mixture was refluxed for half an hour. The mixture was allowed to cool and filtered. The filtrate was concentrated in vacuo. The residue was extracted with dichloromethane and the organic phase was dried over anhydrous magnesium sulfate. After being filtered, the filtrate was concentrated in vacuo and the resulting residue was washed with n-hexane to give 3-amino-1-(tert-butyldiphenylsilyoxymethyl)-2,6-dichlorobenzene (348 mg) as a white mass.

NMR (CDCl$_3$, δ): 1.05 (9H, 2), 4.07 (2H, br s), 4.87 (2H, s), 6.66 (1H, d, J=9 Hz), 7.08 (1H, d, J=9 Hz), 7.30–7.50 (6H, m), 7.70–7.84 (4H, m).

(3) 1-(tert-Butyldiphenylsilyoxymethyl)-2,6-dichloro-3-(phthalimidoacetylamino) benzene was obtained according to a similar manner to that of Preparation 9.

mp: 198.1° C.

NMR (CDCl$_3$, δ): 1.04 (9H, s), 4.57 (2H, s), 4.90 (2H, s), 7.25–7.50 (7H, m), 7.55–7.83 (6H, m), 7.85–8.07 (2H, m), 8.00 (1H, br s), 8.25 (1H, d, J=8 Hz).

(4) 1-(tert-Butyldiphenylsilyoxymethyl)-2,6-dichloro-3-[N-methyl-N-(phthalimidoacetyl)amino]benzene was obtained according to a similar manner to that of Preparation 10.

mp: 167–172° C.

NMR (CDCl$_3$, δ): 1.06 (9H, s), 3.20 (3H, s), 4.04 (2H, s), 4.98 (2H, s), 7.31–7.51 (9H, m), 7.65–7.79 (6H, m), 7.80–7.92 (2H, m).

(5) 3-(N-Glycyl-N-methylamino)-1-(tert-butyldiphenylsilyloxymethyl)-2,6-dichlorobenzene was obtained according to a similar manner to that of Preparation 11.

NMR (CDCl$_3$, δ): 1.05 (9H, s), 2.94 (1H, d, J=17 Hz), 3.09 (1H, d, J=17 Hz), 3.20 (3H, s), 4.93 (2H, s), 7.18 (1H, d, J=8 Hz), 7.35–7.49 (7H, m), 7.69–7.77 (4H, m).

(6) 1-(tert-Butyldiphenylsilyloxymethyl)-2,6-dichloro-3-[N-methyl-N-[4-(methylcarbamoyl) cinnamoylglycyl]amino]-benzene was obtained by reacting 3-(N-glycyl-N-methylamino)-1-(tert-butyldiphenylsilyloxymethyl)-2,6-dichlorobenzene with 4-(methylcarbamoyl) cinnamic acid according to a similar manner to that of Example 1.

mp: 219–222° C.

NMR (CDCl$_3$, δ): 1.05 (9H, s), 3.02 (3H, d, J=5 Hz), 3.21 (3H, s), 3.56 (1H, dd, J=17.4 Hz), 3.93 (1H, dd, J=17, 5 Hz), 4.91 (1H, d, J=10 Hz), 4.98 (1H, d, J=10 Hz), 6.15 (1H, br d, J=5 Hz), 6.51 (1H, d, J=15 Hz), 6.63 (1H, br s), 7.19–7.28 (2H, m), 7.32–7.48 (6H, m), 7.50–7.60 (3H, m), 7.68–7.78 (6H, m).

(7) To a suspension of 1-(tert-butyldiphenylsilyloxymethyl)-2,6-dichloro-3-[N-methyl-N-[4-(methylcarbamoyl)-cinnamoylglycyl]amino]benzene (17.6 g) in tetrahydrofuran (138 ml) was added 1M tetrabutylammonium fluoride in tetrahydrofuran (38.4 ml) at ambient temperature. The reaction mixture was stirred for 1 hour. The mixture was concentrated and diluted with dichloromethane. The organic layer was washed with 1N hydrochloric acid, saturated sodium bicarbonate solution and water, dried over magnesium sulfate and evaporated in vacuo to give 2,6-dichloro-1-hydroxymethyl-3-[N-methyl-N-[4-(methylcarbamoyl)cinnamoylglycyl]amino]-benzene (8.14 g).

mp: 207–211° C.

NMR (CDCl$_3$, δ): 2.79 (3H, d, J=5 Hz), 3.11 (3H, s), 3.47 (1H, dd, J=17, 4 Hz), 3.77 (1H, dd, J=17, 5 Hz), 4.74 (1H, d, J=5 Hz), 5.34 (1H, t, J=5 Hz), 6.87 (1H, d, J=15 Hz), 7.40 (1H, d, J=15 Hz), 7.59–7.68 (4H, m), 7.85 (2H, d, J=8 Hz), 8.29 (1H, t, J=5 Hz), 8.48 (1H, d, J=5 Hz).

(8) To a mixture of 2,6-dichloro-1-hydroxymethyl-3-[N-methyl-N-[4-(methylcarbamoyl)cinnamoylglycyl]amino] benzene (8.10 g) in dichloromethane (81 ml) was added triphenylphosphine (5.66 g) and carbon tetrabromide (8.95 g) at 0° C. After 15 minutes the reaction mixture was stirred at ambient temperature for 3 hours. To the mixture was added triphenylphosphine (1.42 g) and carbon tetrabromide (2.39 g) and stirred for another 2 hours. The reaction mixture was washed with saturated sodium hydrogen carbonate, water and brine. After dried over anhydrous magnesium sulfate, the mixture was filtered and evaporated in vacuo. The residue was purified by flash column chromatography eluting with dichloromethane:ethyl acetate (1:1, V/V) followed by crystallizing from ethyl acetate to give 2,6-dichloro-3-[N-methyl-N-[4-(methylcarbamoyl) cinnamoylglycyl]amino]benzyl bromide (6.40 g) as pale yellow crystals.

mp: 211.6–216.5° C.

NMR (CDCl$_3$, δ): 3.02 (3H, d, J=5 Hz), 3.27 (3H, s), 3.62 (1H, dd, J=17, 4 Hz), 3.92 (1H, dd, J=17, 5 Hz), 4.78 (1.2H, s), 4.90 (0.8 H, s), 6.15 (1H, br d, J=5 Hz), 6.51 (1H, d, J=15 Hz), 6.67 (1H, br t, J=5 Hz), 7.29 (1H, overlapped with H$_2$O), 7.45–7.62 (4H, m), 7.76 (2H, d, J=8 Hz).

Preparation 19

(1) 3-[N-[(E)-3-(6-Acetamidopyridin-3-yl)acryloylglycyl]-N-methylamino]-1-[tert-butyldiphenylsilyloxymethyl]-2,6-dichlorobenzene was obtained by reacting 3-(N-glycyl-N-methylamino)-1-(tert-butyldiphenylsilyloxymethyl)-2,6-dichlorobenzene with (E)-3-(6-acetamidopyridin-3-yl) acrylic acid according to a similar manner to that of Preparation 18-(6).

mp: 194–196° C.

NMR (CDCl$_3$, δ): 1.06 (9H, s), 2.22 (3H, s), 3.23 (3H, s), 3.57 (1H, dd, J=17, 4 Hz), 3.94 (1H, dd, J=17, 5 Hz), 4.92 (1H, d, J=10 Hz), 4.98 (1H, d, J=10 Hz), 6.44 (1H, d, J=15 Hz), 6.63 (1H, br s), 7.22 (1H, d J=8 Hz), 7.35–7.48 (6H, m), 7.52 (1H, d, J=15 Hz), 7.70–7.77 (4H, m), 7.83 (1H, dd, J=8, 3 Hz), 8.05 (1H, br s), 8.22 (1H, d, J=8 Hz), 8.36 (1H, d, J=3 Hz).

(2) 3-[N-[(E)-3-(6-Acetamidopyridin-3-yl)acryloylglycyl]-N-methylamino]-1-hydroxymethyl-2,6-dichlorobenzene was obtained according to a similar manner to that of Preparation 18-(7).

mp: 207–209° C.

NMR (DMSO-d$_6$, δ): 2.10 (3H, s), 3.10 (3H, s), 3.47 (1H, dd, J=17, 4 Hz), 3.76 (1H, dd, J=17, 5 Hz), 4.74 (1H, d, J=5 Hz), 5.35 (1H, br s), 6.79 (1H, d, J=15 Hz), 7.37 (1H, d, J=15 Hz), 7.61 (1H, d, J=8 Hz), 7.65 (1H, d, J=8 Hz), 7.98 (1H, dd, J=8, 3 Hz), 8.11 (1H, d, J=8 Hz), 8.21 (1H, t, J=5 Hz), 8.47 (1H, s).

(3) 3-[N-[(E)-3-(6-Acetamidopyridin-3-yl)acryloylglycyl]-N-methylamino]-2,6-dichlorobenzyl bromide was obtained according to a similar manner to that of Preparation 18-(8).

mp: 222–223° C.

NMR (CDCl$_3$-CD$_3$OD, δ): 2.22 (3H, s), 3.27 (3H, s), 3.60 (1H, dd, J=17, 3 Hz), 3.94 (1H, dd, J=17, 3 Hz), 4.78 (2H, s), 6.49 (1H, d, J=15 Hz), 7.31 (1H, d, J=8 Hz), 7.49 (1H, d, J=8 Hz), 7.51 (1H, d, J=15 Hz), 7.88 (1H, dd, J=8, 3 Hz), 8.23 (1H, br d, J=8 Hz), 8.33 (1H, d, J=3 Hz).

Preparation 20

(1) To a solution of 4-hydroxybenzaldehyde (10 g) and potassium carbonate (17 g) in dimethylformamide (100 ml) was added ethyl bromoacetate (15 g) under ice-cooling, and the mixture was stirred for 2 hours at ambient temperature. Water was added thereto, and the mixture was extracted with ethyl acetate. The extract was washed with water and brine, dried over magnesium sulfate and concentrated. The residue was purified by flash chromatography (ethyl acetate:n-hexane, 1:4, V/V) to give 4-(ethoxycarbonylmethoxy) benzaldehyde (16 g).

mp: 39° C.

NMR (CDCl$_3$, δ): 1.32 (3H, t, J=7.5 Hz), 4.28 (2H, q, J=7.5 Hz), 4.71 (2H, s), 6.98 (2H, d, J=9 Hz), 7.83 (2H, d, J=9 Hz), 9.88 (1H, s).

(2) 4-(Ethoxycarbonylmethoxy)cinnamic acid was obtained according to a similar manner to that of Preparation 4.

mp: 154.2° C.

NMR (CDCl$_3$, δ): 1.30 (3H, t, J=7.5 Hz), 4.28 (2H, q, J=7.5 Hz), 4.66 (2H, s), 6.34 (1H, d, J=15 Hz), 6.91 (2H, d, J=9 Hz), 7.50 (2H, d, J=9 Hz), 7.73 (1H, d, J=15 Hz).

Preparation 21

4-Acetamidocinnamic acid (80 mg) was suspended in methanol (5 ml) and 10% palladium on carbon (15 mg) was added thereto. The mixture was stirred under hydrogen atmosphere at 25° C. for 3 hours. Catalyst was removed and the solution was concentrated to give 3-(4-acetamidophenyl) propionic acid (69 mg) as a solid.

mp: 127.1–137.8° C.

NMR (DMSO-d$_6$, δ): 2.00 (3H, s), 2.47 (2H, t, J=7.5 Hz), 2.74 (2H, t, J=7.5 Hz), 7.12 (2H, d, J=8 Hz), 7.45 (2H, d, J=8 Hz), 9.85 (1H, s).

Preparation 22

The following compounds were obtained according to a similar manner to that of Preparation 21.

(1) 3-[4-(Methylcarbamoyl)phenyl]propionic acid mp: 171.2° C.

NMR (DMSO-d$_6$, δ): 2.63 (2H, t, J=7.5 Hz), 2.76 (3H, d, J=5 Hz), 2.85 (2H, t, J=7.5 Hz), 7.30 (2H, d, J=8 Hz), 7.73 (2H, d, J=8 Hz), 8.35 (1H, q-like).

(2) 4-[2-(Methoxycarbonyl)ethyl]benzoic acid

NMR (DMSO-d$_6$, δ): 2.67 (2H, t, J=7.5 Hz) 2.93 (2H, t, J=7.5 Hz), 3.59 (3H, s), 7.35 (1H, d, J=8 Hz), 7.85 (1H, d, J=8 Hz).

(3) 3-[6-Acetamidopyridin-3-yl]propionic acid

NMR (DMSO-d$_6$, δ): 2.06 (3H, s), 2.49 (2H, t, J=7.5 Hz), 2.76 (2H, t, J=7.5 Hz), 7.63 (1H, dd, J=2, 8 Hz), 7.96 (1H, d, J=8 Hz), 8.15 (1H, d, J=8 Hz).

Preparation 23

(1) Methyl 3-[4-(2-pyridylmethylcarbamoyl)phenyl] propionate was obtained from 4-[2-(methoxycarbonyl) ethyl]benzoic acid and 2-pyridylmethylamine according to a similar manner to that of Example 7.

NMR (CDCl$_3$, δ): 2.65 (2H, t, J=7.5 Hz), 3.00 (2H, t, J=7.5 Hz), 3.67 (3H, s), 4.76 (2H, d, J=5 Hz), 7.22 (1H, dd, J=5, 8 Hz), 7.25–7.36 (3H, m), 7.55 (1H, brpeak) 7.68 (1H, td, J=8, 2 Hz), 7.80 (2H, d, J=8 Hz), 8.57 (1H, d, J=5 Hz).

(2) 3-[4-(2-Pyridylmethylcarbamoyl)phenyl]propionic acid was obtained according to a similar manner to that of Preparation 3.

mp: 83.8° C.

NMR (DMSO-d$_6$, δ): 2.57 (2H, t, J=7.5 Hz), 2.88 (2H, t, J=7.5 Hz), 4.56 (2H, d, J=5 Hz), 7.25 (1H, dd, J=5, 8 Hz), 7.28–7.37 (3H, m), 7.74 (1H, td, J=8, 2 Hz), 7.83 (2H, d, J=8 Hz), 8.50 (1H, d, J=5 Hz), 9.05 (1H, t, J=5 Hz).

Preparation 24

To a suspension of (E)-3-(6-acetylaminopyridin-3-yl)-acrylic acid (460 mg) in ethanol (5.4 ml) was added 1N sodium hydroxide (5.4 ml) at ambient temperature, and the mixture was stirred for 3 hours at 50° C. The reaction mixture was adjusted to pH 7, and the resulting precipitate was collected by filtration and dried to give (E)-(6-aminopyridin-3-yl)acrylic acid (295 mg).

mp: 243.6–246.4° C.

NMR (DMSO-d$_6$, δ): 6.21 (1H, d, J=15 Hz), 6.45 (1H, d, J=8 Hz), 6.52 (2H, s), 7.42 (1H, d, J=15 Hz), 7.75 (1H, d, J=8 Hz), 8.11 (1H, s).

Preparation 25

(1) To a suspension of 4-amino-N-methylbenzamide (500 mg) in tetrahydrofuran (5 ml) was added di-tert-butyl dicarbonate (799 mg) and the mixture was stirred for 18 hours at 50° C. The mixture was concentrated and the residue was dissolved in ethyl acetate. The solution was stirred under ice-cooling, and the resulting precipitates were collected by filtration to give N-(tert-butoxycarbonyl)-4-methylcarbamoylaniline (500 mg).

mp: 185.2° C.

NMR (CDCl$_3$, δ): 1.54 (9H, s), 3.00 (3H, d, J=6 Hz), 6.12 (1H, br s), 6.69 (1H, br s), 7.43 (2H, d, J=9 Hz), 7.70 (2H, d, J=9 Hz), (2) Sodium hydride (60% dispersion in mineral oil, 41.9 mg) was added to a solution of N-(tert-butoxycarbonyl)-4-methylcarbamoylaniline (250 mg) in dimethylformamide (2.5 ml) in ice water bath under nitrogen and stirred for 30 minutes under same condition. To the mixture was added tert-butylbromoacetate (234 mg) and stirred at ambient temperature for 20 hours. The reaction mixture was poured into water and extracted with chloroform. The organic layer was separated, washed with brine, dried over magnesium sulfate and evaporated in vacuo. The residue was recrystallized from ethyl acetate—n-hexane to give N-(tert-butoxycarbonyl)-N-(tert-butoxycarbonylmethyl)-4-methylcarbamoylaniline (280 mg).

mp: 163.7–165.9° C.

NMR (CDCl$_3$, δ): 1.46 (9H, s), 1.49 (9H, s), 3.00 (3H, d, J=5 Hz), 4.19 (2H, s), 6.11 (1H, br q, J=5 Hz), 7.33 (2H, br q, J=9 Hz), 7.71 (2H, d, J=9 Hz), (3) Trifluoroacetic acid (3.3 ml) was added to a solution of N-(tert-butoxycarbonyl)-N-(tert-butoxycarbonylmethyl)-4-methylcarbamoylaniline (250 mg) in ice water bath and stirred for 20 hours at ambient temperature. The solvent was evaporated under reduced pressure. The residue was pulverized with diethyl ether to give N-(4-methylcarbamoylphenyl) glycine (125 mg).

mp: 233.5° C.

NMR (DMSO-d$_6$, δ): 2.72 (3H, d, J=5 Hz), 3.85 (3H, s), 6.55 (2H, d, J=9 Hz), 7.60 (2H, d, J=9 Hz), 7.99 (1H, br q, J=5 Hz).

Preparation 26

To a mixture of naphthalene-2,6-dicarboxylic acid (5 g), methylamine hydrochloride (1.64 g) and 1-hydroxybenzotriazole (3.75 g) in dimethylformamide (50 ml) was added 1-ethyl-3-(3-dimethylaminopropyl) carbodiimide (3.79 g) under ice-cooling. The mixture was stirred for 1 hour at the same temperature and then at ambient temperature overnight. The mixture was diluted with water, and the precipitates were collected by filtration to give 6-(methylcarbamoyl)naphthalene-2-carboxylic acid (4.07 g).

mp: >275.7° C.

NMR (DMSO-d$_6$, δ); 2.82 (3H, d, J=5 Hz), 7.90–8.14 (3H, m), 8.20 (1H, d, J=7.5 Hz), 8.45 (1H, br d, J=7.5 Hz), 8.58–8.74 (2H, m).

Preparation 27

(1) To a mixture of 2,4-dichlorophenol (3.20 g) and imidazole (2.67 g) in dimethylformamide (30 ml) was added triisopropylsilyl chloride (3.97 g) in water bath under nitrogen atmosphere, and the mixture was stirred for 3 hours under the same condition. The mixture was poured into water and extracted with ethyl acetate. The organic layer was washed with water and brine, dried over magnesium sulfate and concentrated in vacuo. The residue was purified by silica gel column chromatography (n-hexane) to give 1,3-dichloro-4-triisopropylsilyloxybenzene (5.12 g).

NMR (CDCl$_3$, δ): 1.12 (18H, d, J=7.5 Hz), 1.23–1.39 (3H, m), 6.83 (1H, d, J=8 Hz), 7.06 (1H, d, J=8 Hz), 7.34 (1H, d, J=2 Hz).

(2) To a solution of 1,3-dichloro-4-triisopropylsilyloxybenzene (6.00 g) in tetrahydrofuran (50 ml) at −60° C. was added dropwise n-butyllithium, 1.6M solution of hexane (12.9 ml) over 30 minutes under nitrogen and the mixture was stirred for 1 hour at the same temperature. A solution of ethyl chloroformate in tetrahydrofuran (20 ml) was added dropwise to the mixture over 20 minutes at −60° C. The resulting mixture is stirred for 1 hour at −60° C., the cooling bath was removed, and temperature was allowed to rise to 20° C. A solution of ammonium chloride (2 g) in water (37 ml) was then added over 5 minutes followed by ethyl acetate (40 ml) and brine (40 ml). The organic layer was separated, washed with water and brine, dried over magnesium sulfate and evaporated in vacuo. The residue was chromatographed on silica gel eluting with a mixture of ethyl acetate and hexane (1:10 to 1:6) to give ethyl 2,6-dichloro-3-triisopropylsilyloxybenzoate (1.59 g) as an oil.

NMR (CDCl$_3$, δ): 1.12 (18H, d, J=7.5 Hz), 1.23–1.38 (3H, m), 1.41 (3H, t, J=7.5 Hz), 4.46 (2H, q, J=7.5 Hz), 6.85 (1H, d, J=8 Hz), 7.15 (1H, d, J=8 Hz).

(3) Ethyl 2,6-dichloro-3-hydroxybenzoate was obtained according to a similar manner to that of Preparation 18-(7).

NMR (CDCl$_3$, δ): 1.42 (3H, t, J=7.5 Hz), 4.45 (2H, q, J=7.5 Hz), 7.01 (1H, d, J=8 Hz), 7.23 (1H, d, J=8 Hz), (4) To a suspension of sodium hydride (60% in oil, 474 mg) in N,N-dimethylformamide (2 ml) was added a solution of ethyl 2,6-dichloro-3-hydroxybenzoate (2.42 g) in N,N-dimethylformamide (10 ml) under nitrogen at ambient temperature and the mixture was stirred for 1 hour at the same temperature. Chloromethyl methyl ether (1.15 ml) was added thereto and the mixture was stirred for 1 hour at the same temperature. The reaction mixture was poured into water and extracted with ethyl acetate. The organic layer was washed with water and brine, dried over magnesium sulfate and evaporated in vacuo. The residue was chromatographed on silica gel eluting with a mixture of ethyl acetate and hexane (1:8, V/V) to give ethyl 2,6-dichloro-3-(methoxymethoxy)benzoate (2.58 g) as an oil.

NMR (CDCl$_3$, δ): 1.42 (3H, t, J=7.5 Hz), 3.50 (3H, s), 4.46 (2H, q, J=7.5 Hz), 5.23 (2H, s), 7.16 (1H, d, J=8 Hz), 7.25 (1H, d, J=8 Hz).

(5) To a suspension of lithium aluminum hydride (347 mg) in tetrahydrofuran was dropwise added a solution of ethyl 2,6-dichloro-3-(methoxymethoxy)benzoate (2.55 g) in tetrahydrofuran at 0° C. under nitrogen atmosphere, and the mixture was stirred for 30 minutes at the same temperature and for 18 hour at ambient temperature. Water was dropwise added thereto at 0° C., and the mixture was extracted with ethyl acetate. The organic layer was washed with water and brine, dried over magnesium sulfate and evaporated in vacuo. The residue was purified by flash chromatography (n-hexane:ethyl acetate=6:1, V/V) to give 2,6-dichloro-3-(methoxymethoxy)benzyl alcohol.

NMR (CDCl$_3$, δ): 2.14 (1H, t, J=7.5 Hz), 3.51 ( 3H, s), 4.47 (2H, d, J=7.5 Hz), 5.23 (2H, s), 7.11 (1H, d, J=8 Hz), 7.26 (1H, d, J=8 Hz).

(6) To a solution of 2,6-dichloro-3-(methoxymethoxy) benzyl alcohol (1.1 g) and triethylamine (563 mg) in dichloromethane was added a solution of methanesulfonyl chloride (585 mg) in dichloromethane at <20° C. over 5 minutes under nitrogen atmosphere, and the mixture was stirred at the same temperature for 30 minutes and under ice-cooling for 30 minutes. The reaction mixture was washed with saturated sodium bicarbonate solution and brine, dried over magnesium sulfate and evaporated in vacuo to give 1,3-dichloro-2-methanesulfonyloxymethyl-4-(methoxymethoxy)benzene.

NMR (CDCl$_3$, δ): 3.10 (3H, s), 3.52 (3H, s), 5.25 (2H, s), 5.53 (2H, s), 7.23 (1H, d, J=8 Hz), 7.32 (1H, d, J=8 Hz).

Preparation 28

(1) To a suspension of (E)-3-(6-acetylaminopyridin-3-yl) acrylic acid (200 mg) in a mixture of dichloromethane (3 ml) and methanol (3 ml) was added a solution of 10% trimethylsilyldiazomethane (3 ml) at ambient temperature and the mixture was stirred for 3 hours. The reaction mixture was evaporated in vacuo, poured into water and extracted with dichloromethane. The organic layer was washed with water and brine, dried over magnesium sulfate and evaporated in vacuo. The residue was collected by vacuum filtration and washed with diisopropyl ether to give methyl (E)-3-(6-acetylaminopyridin-3-yl)acrylate (197 mg) as a powder.

mp: 171.5–200° C.

NMR (CDCl$_3$, δ): 2.22 (3H, s), 3.80 (3H, s), 6.41 (1H, d, J=16 Hz, 7.64 (1H, d, J=16 Hz), 7.89 (1H, dd, J=2, 8 Hz), 8.07 (1H, br s), 8.25 (1H, d, J=8 Hz), 8.38 (1H, d, J=2 Hz), (2) To a suspension of sodium hydride (60% in oil, 20.6 mg) in N,N-dimethylformamide (1 ml) was added dropwise a solution of methyl (E)-3-(6-acetylaminopyridin-3-yl) acrylate (180 mg) in N,N-dimethylformamide (2 ml) at 0° C. under nitrogen and the mixture was stirred for 1 hour. Methyl iodide (116 mg) was added to the mixture under the same condition and the mixture was stirred for 2 hours. The reaction mixture was poured into water and extracted with ethyl acetate. The organic layer was washed with water and brine, dried over magnesium sulfate and evaporated in vacuo. The residue was collected by vacuum filtration and washed with diisopropyl ether to give methyl (E)-3-[6-(N-methyl-N-acetylamino)pyridin-3-yl]acrylate (115 mg) as a powder.

mp: 94.3° C.

NMR (CDCl$_3$, δ): 2.20 (3H, s), 3.44 (3H, s), 3.82 (3H, s), 6.48 (1H, d, J=16 Hz), 7.48 (1H, br d, J=8 Hz), 7.67 (1H, d, J=16 Hz), 7.87 (1H, dd, J=2, 8 Hz), 8.56 (1H, d, J=2 Hz).

(3) To a solution of methyl (E)-3-[6-(N-methyl-N-acetylamino)pyridin-3-yl]acrylate (110 mg) in methanol (3 ml) was added 1N sodium hydroxide solution (1.1 ml) at ambient temperature and the mixture was stirred at 50° C. for 4 hours. The reaction mixture was evaporated in vacuo and was dissolved in water. The solution was adjusted to pH 6 with 1N hydrochloric acid, and the precipitate was cooled by vacuum filtration to give (E)-3-[6-(methylamino)pyridin-3-yl]acrylic acid (72 mg) as a powder.

mp: 227° C.

NMR (CDCl₃, δ): 2.80 (1H, d, J=5 Hz), 6.23 (1H, d, J=16 Hz), 6.47 (1H, d, J=8 Hz), 7.09 (1H, q, J=5 Hz), 7.45 (1H, d, J=16 Hz), 7.76 (1H, dd, J=2, 8 Hz), 8.20 (1H, d, J=2 Hz).

Preparation 29

(1) To a solution of 2-methylnicotinic acid (470 mg) in dichloromethane (6 ml) were dropwise added oxalyl chloride (522 mg) and dimethylformamide (1 drop) at 0° C. under nitrogen atmosphere, and the mixture was stirred for 1 hour at the same condition. The mixture was concentrated and the residue was pulverized with diethyl ether to give 2-methylnicotinoyl chloride hydrochloride (671 mg) as a solid.

NMR (CDCl₃, δ): 3.23 (3H, s), 7.96 (1H, dd, J=6, 8 Hz), 8.93 (1H, d, J=6 Hz), 9.08 (1H, d, J=8 Hz).

(2) To a mixture of 10% trimethylsilyldiazomethane in hexane (4.2 ml) and triethylamine (527 mg) in tetrahydrofuranacetonitrile chloride hydrochloride (500 mg) in an ice water bath. The mixture was stirred for 7 hours in an ice water bath and allowed to stand for 18 hours at 0° C., then evaporated in vacuo. Saturated aqueous sodium bicarbonate solution was added to the residue and the mixture was extracted with ethyl acetate. The organic layer was washed with water and brine, and dried over magnesium sulfate. Evaporation of the solvent gave crude 3-diazoacetyl-2-methylpyridine as an yellow oil.

Benzyl alcohol (2 ml) and 2,4,6-trimethylpyridine (2 ml) were added to the residue. The mixture was stirred at 180° C.–185° C. for 20 minutes. The reaction mixture was poured into water and extracted with ethyl acetate. The organic layer was washed with water and brine, and dried over magnesium sulfate. The solvent, 2,4,6-trimethylpyridine and excess benzyl alcohol were evaporated in vacuo to give crude benzyl 2-(2-methyl-3-pyridyl)acetate as an oil.

NMR (CDCl₃, δ): 2.50 (3H, s), 3.67 (2H, s), 5.14 (2H, s), 7.10 (1H, dd, J=8, 6 Hz), 7.23–7.40 (5H, m), 7.49 (1H, dd, J=8, 2 Hz), 8.49 (1H, dd, J=6, 2 Hz).

(3) The residue including benzyl 2-(2-methyl-3-pyridyl) acetate obtained in Preparation 29-(2) was dissolved in methanol (5 ml), and 10% palladium on carbon was added thereto. The mixture was stirred under hydrogen atmosphere for 3 hours. The reaction mixture was diluted with water and washed with ethyl acetate. The solvent was removed in vacuo to give 2-(2-methyl-3-pyridyl)acetic acid (90 mg).

NMR (DMSO-d₆, δ): 2.40 (3H, s), 3.62 (2H, s), 7.15 (1H, dd, J=6, 8 Hz), 7.55 (1H, d, J=8 Hz), 8.30 (1H, d, J=6 Hz),

Preparation 30

(1) 6-Methylnicotinoyl chloride hydrochloride was obtained by reacting 6-methyl nicotinic acid with oxalyl chloride according to a similar manner to that of Preparation 29-(1).

NMR (CDCl₃, δ): 3.13 (3H, s), 7.84 (1H, d, J=8 Hz), 8.82 (1H, dd, J=2, 8 Hz), 9.35 (1H, d, J=2 Hz).

(2) Benzyl 2-(6-methyl-3-pyridyl)acetate was obtained according to a similar manner to that of Preparation 29-(2).

NMR (CDCl₃, δ): 2.54 (3H, s), 3.63 (2H, s), 5.14 (2H, s), 7.12 (1H, d, J=8 Hz), 7.19–7.46 (5H, m), 7.53 (1H, dd, J=8, 2 Hz), 8.40 (1H, d, J=2 Hz).

(3) 2-(6-Methyl-3-pyridyl)acetic acid was obtained according to a similar manner to that of Preparation 29-(3).

NMR DMSO-d₆, δ): 2.43 (3H, s), 3.56 (2H, s), 7.20 (1H, d, J=8 Hz), 7.55 (1H, dd, J=2, 8 Hz), 8.30 (1H, d, J=2 Hz).

Preparation 31

(1) 2-(tert-Butoxycarbonylamino)benzothiazole was obtained by reacting 2-aminobenzothiazole with di-tert-butyl dicarbonate according to a similar manner to that of Preparation 25-(1).

NMR (CDCl₃, δ): 1.59 (9H, s), 7.22–7.30 (1H, m), 7.40 (1H, t, J=8 Hz), 7.79 (8H, d), 7.85 (8H,d).

(2) 2-(N-tert-Butoxycarbonyl-N-tert-butoxycarbonylmethylamino)benzothiazole was obtained according to a similar manner to that of Preparation 25-(2).

NMR (CDCl₃, δ): 1.46 (9H, s), 1.57 (9H, s), 4.86 (2H, s), 7.24 (1H, t, J=8 Hz), 8.38 (1H, t, J=8 Hz), 7.71–7.78 (2H, m).

(3) 2-(Carboxymethylamino benzothiazole was obtained according to a similar manner to that of Preparation 25-(3).

NMR DMSO-d₆, δ): 4.10 (2H, d, J=6 Hz), 7.04 (1H, t, J=8 Hz), 7.22 (1H, t, J=8 Hz), 7.40 (1H, d, J=8 Hz), 7.68 (1H, d, J=8 Hz), 8.32 (1H, t, J=6 Hz).

Preparation 32

(1) A mixture of p-toluidine (10 g) and diethyl 2-methyl-3-oxosuccinate (18.9 g) in dichloromethane (50 ml) was refluxed for 2 days. The reaction mixture was poured onto 0.5N hydrochloric acid (200 ml) and extracted with dichloromethane. The organic layer was washed with water, 0.5N sodium hydroxide solution and brine, dried over magnesium sulfate, and concentrated. The obtained residue was added to heated diphenyl (80 g) and the mixture was refluxed for 15 minutes. The reaction mixture was allowed to stand at ambient temperature, and the resulting precipitates were collected by filtration to give ethyl 1,4-dihydro-3,6-dimethyl-4-oxoquinoline-2-carboxylate (16.3 g).

mp: 190.1–192.7° C.

NMR (CDCl₃, δ): 1.47 (3H, t, J=7 Hz), 2.15 (3H, s), 2.47 (3H, s), 4.51 (2H, q, J=7 Hz), 7.30 (1H, d, J=8 Hz), 7.45 (1H, dd, J=2, 8 Hz), 8.13 (1H, s-like), 9.20 (1H, br s).

(2) To a mixture of ethyl 1,4-dihydro-3,6-dimethyl-4-oxoquinoline-2-carboxylate (4.0 g) and phosphoryl chloride (10 g) was added N,N-dimethylaniline (3.95 g) at ambient temperate and the mixture was stirred for 1 hour. The solvent was removed in vacuo, and the residue was poured into ice-water and extracted with ethyl acetate. The organic layer was washed with water, saturated sodium bicarbonate solution and brine, dried over magnesium sulfate and concentrated in vacuo. The residue was purified by flash chromatography (n-hexane-dichloromethane) to give ethyl 4-chloro-3,6-dimethylquinoline-2-carboxylate (3.17 g) as an oil.

NMR (CDCl₃, δ): 1.49 (3H, t, J=7 Hz), 2.61 (3H, s), 2.68 (3H, s), 4.55 (2H, q, J=7 Hz), 7.59 (1H, d, J=8 Hz), 8.00 (1H, s-like), 8.06 (1H, dd, J=2, 8 Hz).

(3) A mixture of ethyl 4-chloro-3,6-dimethylquinoline-2-carboxylate (3.0 g), triethylamine (2.4 ml) and 10% palladium on carbon (300 mg) in ethyl acetate (30 ml) was stirred for 4 hours at ambient temperature under hydrogen atmosphere. After filtration the filtrate was concentrated in vacuo and diluted with dichloromethane. The mixture was washed with saturated sodium bicarbonate solution and water, dried over magnesium sulfate and concentrated in vacuo. The residue was purified by flash chromatography (dichloromethane-ethyl acetate) to give ethyl 3,6-dimethylquinoline-2-carboxylate.

NMR (CDCl₃, δ): 1.47 (3H, t, J=7 Hz), 2.55 (3H, s), 2.66 (3H, s), 4.53 (2H, q, J=7 Hz), 7.49–7.55 (2H, m), 7.92 (1H, s), 8.06 (1H, d, J=8 Hz).

(4) To a solution of ethyl 3,6-dimethylquinoline-2-carboxylate (1.0 g) in tetrachloromethane (10 ml) were added N-bromosuccimide (815 mg) and 2,2'-azobis (2,4-dimethyl-4-methoxyvaleronitrile) at ambient temperature under nitrogen atmosphere, and the mixture was heated at 90° C. for 1 hour. The reaction mixture was poured into 5% sodium thiosulfate solution and extracted with dichloromethane. The organic layer was washed with water, dried over magnesium sulfate, and concentrated in vacuo. The residue was purified by flash chromatography (n-hexane—ethyl acetate) to give ethyl 6-bromomethyl-3-methylquinoline-2-carboxylate (802 mg) as a solid.

NMR (CDCl$_3$, δ): 1.49 (3H, t, J=7.5 Hz), 2.66 (3H, s), 4.54 (2H, q, J=7.5 Hz), 4.65 (3H, s), 7.71 (1H, d, J=8 Hz), 7.77 (1H, d, J=2 Hz), 8.00 (1H, s-like), 8.16 (1H, d, J=8 Hz).

(5) To a solution of ethyl 6-bromomethyl-3-methylquinoline- 2-carboxylate (700 mg) in dimethylformamide (7 ml) was added sodium acetate (373 mg) at ambient temperature, and the mixture was stirred for 24 hours at the same temperature. The reaction mixture was poured into water and extracted with ethyl acetate. The organic layer was washed with water, sodium bicarbonate solution and brine, dried over magnesium sulfate, and concentrated in vacuo. The residue was purified by preparative thin-layer chromatography (n-hexane:ethyl acetate=1:2, V/V) to give ethyl 6-acetoxymethyl-3-methylquinoline-2-carboxylate (452 mg) as an oil.

NMR (CDCl$_3$, δ): 1.48 (3H, t, J=7.5 Hz), 2.15 (3H, s), 2.67 (3H, s), 4.53 (2H, q, J=7.5 Hz), 5.29 (2H, s), 7.66 (1H, dd, J=2, 8 Hz), 7.75 (1H, s-like), 8.01 (1H, s-like), 8.18 (1H, d, J=8 Hz).

(6) A mixture of ethyl 6-acetoxymethyl-3-methylquinoline-2-carboxylate (420 mg) and potassium carbonate in methanol was stirred for 30 minutes under ice-cooling. After filtration the filtrate was concentrated and partitioned between ethyl acetate and water. The organic layer was washed with water, dried over magnesium sulfate and concentrated to give methyl 6-hydroxymethyl-3-methylquinoline-2-carboxylate (20 mg).

mp: 84.2° C.

NMR (CDCl$_3$, δ): 2.70 (3H, s), 4.05 (3H, s), 4.90 (2H, s), 7.68 (1H, dd, J=8 Hz), 7.76 (1H, s-like), 8.01 (1H, s-like), 8.17 (1H, d, J=8 Hz).

(7) To a mixture of methyl 6-hydroxymethyl-3-methylquinoline-2-carboxylate (193 mg), triethylamine (422 mg) dimethyl sulfoxide (2 ml) and dichloromethane (2 ml) was added portionwise sulfur trioxide pyridine complex (266 mg) in water bath and the mixture was stirred for 2 hours at the same temperature. The reaction mixture was poured into water and extracted with ethyl acetate. The organic layer was washed with water and brine, dried over magnesium sulfate and evaporated in vacuo. The residue was purified by preparative thin-layer chromatography (n-hexane:ethyl acetate=1:1, V/V) to give methyl 6-formyl-3-methylquinoline-2-carboxylate (149 mg).

mp: 117.8–120.7° C.

NMR (CDCl$_3$, δ): 2.71 (3H, s), 4.08 (3H, s), 8.15–8.28 (2H, m), 8.28–8.35 (2H, m), 10.20 (1H, s).

(8) To a mixture of water (0.8 ml) and tert-butyl alcohol (3 ml) were added methyl 6-formyl-3-methylquinoline-2-carboxylate (140 mg) , 2-methyl-2-butene (190 mg) and sodium dihydrogenphosphate (105 mg) in water bath. To the mixture was added dropwise sodium chloride (244 mg) and the mixture was stirred for 1 hour at the same temperature. The reaction mixture was cooled in an ice bath, adjusted to pH 4 with 1M hydrochloric acid and extracted with dichloromethane. The organic layer was dried over magnesium sulfate and evaporated in vacuo. The residue was purified by preparative thin-layer chromatography (dichloromethane:methanol=10:1, V/V) followed by crystallization from methanol-isopropyl ether to give 2-methoxycarbonyl-3-methylquinoline-6-carboxylic acid (121 mg) as crystals.

mp: 215° C.

NMR (CDCl$_3$, δ): 2.57 (3H, s), 3.96 (3H, s), 8.11 (1H, dd, J=2, 8 Hz), 8.21 (1H, dd, J=2, 8 Hz), 8.53 (1H, d, J=2 Hz), 8.62 (1H, d, J=2 Hz).

EXAMPLE 1

To a mixture of 8-[3-(n-glycyl-N-methylamino)2,6-dichlorobenzyloxy]-2-methylquinoline (1.65 g), (E)-3-(6-ethoxycarbonyl-3-pyridyl)acrylic acid (1.04 g) and dimethylformamide (25 ml) were added 1-ethyl-3-(3-dimethylaminopropyl)carbodiimide hydrochloride (939 mg) and 1-hydroxybenzotriazole (717 mg). After being stirred for 4 hours at ambient temperature, the mixture was poured into water and extracted with ethyl acetate. The organic layer was separated, washed with water, dried over magnesium sulfate and evaporated in vacuo. The residue was purified by silica gel column chromatography (dichloromethane—methanol) to give 8-[2,6-dichloro-3-[N-[(E)-3-(6-ethoxycarbonylpryidin-3-yl)acryloylglycyl]-N-methylamino]benzyloxy]-2-methylquinoline (2.07 g) as an amorphous powder.

NMR (CDCl$_3$, δ): 1.45 (3H, t, J=7.5 Hz), 2.72 (3H, s), 3.27 (3H, s), 3.70 (1H, dd, J=18, 4 Hz), 3.94 (1H, dd, J=18, 4 Hz), 4.49 (2H, q, J=7.5 Hz), 5.59–5.70 (2H, m) 6.66 (1H, d, J=16 Hz), 6.80 (1H, t-like), 7.22–7.35 (3H, m), 7.37–7.53 (3H, m), 7.60 (1H, d, J=16 Hz), 7.88–7.94 (1H, m), 8.02 (1H, d, J=8, Hz), 8.12 (1H, d, J=8 Hz), 8.81–8.86 (1H, m).

EXAMPLE 2

The following compounds were obtained according to a similar manner to that of Example 1.

(1) 8-[3-[N-[(E)-3-(6-Aminopyridin-3-yl)acryloylglycyl]-N-methylamino]-2,6-dichlorobenzyloxy]-2-methylquinoline NMR (CDCl$_3$, δ): 2.73 (3H, s) 3.27 (3H, s), 3.65 (3H, dd, J=17, 4 Hz), 3.94 (1H, dd, J=17, 5 Hz), 4.75 (2H, s), 5.64 (2H, s), 5.84 (1H, d, J=10 Hz) 6.30 (1H, d, J=15 Hz), 6.48 (1H, d, J=8.5 Hz), 6.62 (1H, br t, J=4 Hz), 7.23–7.35 (3H), 7.39–7.52 (4H) 7.60 (1H, dd, J=8.5, 1.5 Hz), 8.02 (1H, d, J=8.5 HZ), 8.16 (1H, d, J=1.5 HZ).

(2) 8-[2,6-Dichloro-3-[N-[4-(methoxycarbonyl)cinnamoylglycyl]-N-methylamino]benzyloxy]-2-methylquinoline NMR (CDCl$_3$, δ): 2.74 (3H, s), 3.27 (3H, s), 3.64 (1H, dd, J=18, 4 Hz), 3.87–4.00 (4H, m), 5.60–5.70 (2H, m), 6.57 (1H, d, J=16 Hz), 6.75 (1H, t-like), 7.24–7.63 (11H, m), 7.99–8.05 (1H, m).

(3) 8-[2,6-Dichloro-3-[N-[4-ethoxycarbonylmethoxy)cinnamoylglycyl]-N-methylamino]benzyloxy]-2-methylquinoline NMR (CDCl$_3$, δ): 1.31 (3H, t, J=7.5 Hz) 2.75 (3H, s), 3.26 (3H, s), 3.65 (1H, dd, J=18, 4 Hz), 3.95 (1H, dd, J=18, 5 Hz), 4.29 (2H, q, J=7.5 Hz), 4.64 (2H, s), 5.64 (1H, d, J=9 Hz), 5.67 (1H, d, J=9 Hz), 6.35 (1H, d, J=15 Hz), 6.57 (1H, br t, J=5 Hz), 6.85–6.93 (2H, m) 7.21–7.34 (3H, m), 7.37–7.58 (6H, m), 8.03 (1H, d, J=8 Hz).

(4) 8-[3-[N-[3-(4-Acetamidophenyl)propionylglycyl]-N-methylamino]-2,6-dichlorobenzyloxy]-2-methylquinoline NMR (CDCl₃, δ): 2.04 (3H, s), 2.51 (2H, t, J=7.5 Hz), 2.68 (3H, s), 2.88 (2H, t, J=7.5 Hz), 3.21 (3H, s), 3.44 (1H, dd, J=4, 18 Hz), 3.70 (1H, dd, J=5, 18 Hz), 5.59 (2H, s-like), 6.38 (1H, t-like), 7.06 (2H, d, J=8 Hz), 7.13 (1H, d, J=8 Hz), 7.21–7.34 (3H, m), 7.34–7.49 (4H, m), 8.04 (1H, d, J=8 Hz), 8.15 (1H, s).

its hydrochloride

NMR (DMSO-d₆, δ): 2.01 (3H, s), 2.39 (2H, t, J=7.5 Hz), 2.70 (2H, t, J=7.5 Hz), 2.90 (3H, s), 3.12 (3H, s), 3.41 (1H, dd, J=5, 18 Hz), 3.73 (1H, dd, J=5, 18 Hz), 5.60 (1H, d, J=10 Hz), 5.66 (1H, d, J=10 Hz), 7.08 (2H, d, J=8 Hz), 7.44 (2H, d, J=8 Hz), 7.76–7.99 (6H, m), 8.10 (1H, t, J=8 Hz), 8.98 (1H, brpeak).

(5) 8-[2,6-Dichloro-3-[N-methyl-N-[3-[4-(methylcarbamoyl)-phenyl]propionylglycyl]amino]benzyloxy]-2-methylquinoline NMR (CDCl₃, δ): 2.51 (2H, t, J=7.5 Hz), 2.71 (3H, s), 2.93–3.01 (5H, m), 3.23 (3H, s), 3.46 (1H, dd, J=4, 18 Hz), 3.78 (1H, dd, J=4, 18 Hz), 5.63 (2H, s), 6.17 (1H, q-like), 6.36 (1H, t-like), 7.20–7.33 (5H, m), 7.37–7.50 (3H, m), 7.66 (2H, d, J=8 Hz), 8.03 (1H, d, J=8 Hz), its hydrochloride NMR (DMSO-d₆, δ): 2.46 (2H, t, J=7.5 Hz), 2.76 (3H, d, J=5 Hz), 2.82 (3H, t, J=7.5 Hz), 2.90 (3H, s), 3.13 (3H, s), 3.43 (1H, dd, J=5, 16 Hz), 3.73 (1H, dd, J=5, 16 Hz), 5.60 (1H, d, J=10 Hz), 5.66 (1H, d, J=10 Hz), 7.26 (2H, d, J=8 Hz), 7.72 (2H, d, J=8 Hz), 7.77–8.01 (6H, m), 8.13 (1H, t-like), 8.38 (1H, q-like), 8.94–9.04 (1H, m).

(6) 8-[2,6-Dichloro-3-[N-methyl-N-[3-[4-(2-pyridylmethylcarbamoyl)phenyl]propionylglycyl]amino]-benzyloxy]-2-methylquinoline NMR (CDCl₃, δ): 2.54 (2H, t, J=7.5 Hz), 2.73 (3H, s), 3.00 (2H, t, J=7.5 Hz), 3.22 (3H, s), 3.47 (1H, dd, J=4, 17 Hz), 3.79 (1H, dd, J=5, 17 Hz), 4.75 (2H, d, J=6 Hz), 5.64 (2H, s), 6.38 (1H, t-like), 7.17–7.57 (11H, m), 7.68 (1H, td, J=8, 2 Hz), 7.79 (2H, d, J=8 Hz), 8.03 (1H, d, J=8 Hz), 8.56 (1H, d, J=5 Hz).

its dihydrochloride

NMR (DMSO-d₆, δ): 2.47 (2H, t, J=7.5 Hz), 2.83 (2H, t, J=7.5 Hz), 2.90 (3H, s), 3.13 (3H, s), 3.43 (1H, dd, J=4, 16 Hz), 3.73 (1H, dd, J=4, 16 Hz), 4.78 (2H, d, J=5 Hz), 5.60 (1H, d, J=10 Hz), 5.65 (1H, d, J=10 Hz), 7.32 (2H, d, J=8 Hz), 7.75–8.00 (10H, m), 8.15 (1H, t, J=5 Hz), 8.40 (1H, t, J=8 Hz), 8.78 (1H, d, J=5 Hz), 8.95 (1H, d-like), 9.40 (1H, t, J=5 Hz).

(7) 8-[2,6-Dichloro-3-[N-methyl-N-[N-[4-(methylcarbamoyl)-phenyl]glycylglycyl]amino]benzyloxy]-2-methylquinoline mp: 280.1° C.

NMR (DMSO-d₆, δ): 2.59 (3H, s), 2.74 (3H, d, J=5 Hz), 3.12 (3H, s), 3.40 (1H, dd, J=17, 4 Hz), 3.65 (1H, dd, J=17, 5 Hz), 3.71 (2H, d, J=6 Hz), 5.46 (1H, d, J=9 Hz), 5.52 (1H, d, J=9 Hz), 6.44–6.60 (3H, m), 7.32–7.69 (6H, m), 7.75 (2H, s), 7.94–8.10 (2H, m), 8.20 (1H, d, J=8 Hz).

its dihydrochloride

NMR (CDCl₃-OD, δ): 2.97 (3H, s), 3.04 (3H, s), 3.21 (3H, s), 3.80 (2H, s), 3.93 (1H, d, J=17 Hz), 4.00 (1H, d, J=17 Hz), 5.60 (1H, d, J=9 Hz), 5.65 (1H, d, J=9 Hz), 6.86–6.95 (2H, d, J=9 Hz), 7.45–7.68 (5H, m), 7.70–7.90 (3H, m), 8.80 (1H, d, J=8 Hz), (8) 8-[2,6-Dichloro-3-[N-methyl-N-[[6-(methylcarbamoyl)-naphthalene-2-carbonyl]glycyl]amino]benzyloxy]-2-methylquinoline NMR (CDCl₃, δ): 2.70 (3H, s), 3.04 (3H, d, J=4.5 Hz), 3.27 (3H, s), 3.75 (1H, dd, J=17, 4 Hz), 4.03 (1H, dd, J=17, 5 Hz), 5.64 (2H, s), 6.59 (1H, br q, J=4.5 Hz), 7.26–7.50 (6H, m), 7.36 (1H, br t, J=4.5 Hz), 7.84–7.95 (4H, m), 8.03 (1H, d, J=8 Hz), 8.31 (2H, br d, J=8 Hz).

(9) 8-[2,6-Dichloro-3-[N-[(2-methoxycarbonyl-3-methylquinoline-6-carbonyl)glycyl]-N-methylamino]benzyloxy]-2-methylquinoline NMR (CDCl₃, δ): 2.70 (3H, s), 2.75 (3H, s), 3.30 (3H, s), 3.79 (1H, dd, J=4, 18 Hz), 4.01–4.11 (5H, m), 5.67 (2H, s), 7.25–7.55 (7H, m), 8.00–8.15 (3H, m), 8.24 (1H, d, J=8 Hz), 8.29 (1H, d, J=2 Hz).

(10) 8-[2,6-Dichloro-3-[N-methyl-N-[4-(methylcarbamoyl)cinnamoylglycyl]amino]benzyloxy]-4-methoxy-2-methylquinoline NMR (CDCl₃, δ): 2.67 (3H, s), 3.00 (3H, d, J=5 Hz), 3.26 (3H, s), 3.15 (1H, dd, J=17, 4 Hz), 3.92 (1H, dd, J=17, 5 Hz), 4.02 (3H, s), 5.59 (1H, d, J=10 Hz), 5.63 (1H, d, J=10 Hz), 6.38 (1H, br d, J=5 Hz), 6.52 (1H, d, J=15 Hz), 6.65 (1H, s), 6.76 (1H, br s), 7.21–7.31 (2H, m), 7.38 (1H, t, J=8 Hz), 7.43–7.61 (4H, m), 7.75 (2H, d, J=8 Hz), 7.83 (1H, d, J=8 Hz).

its hydrochloride

NMR (CDCl₃-CD₃OD, δ): 2.99 (3H, s), 3.00 (3H, br s), 3.29 (3H, s), 3.89 (1H, d, J=17 Hz), 4.10 (1H, d, J=17 Hz), 4.36 (3H, s), 5.51 (1H, d, J=10 Hz), 5.68 (1H, d, J=10 Hz), 6.63 (1H, d, J=15 Hz), 7.35–7.43 (2H, m), 7.48–7.59 (6H, m), 7.70–7.81 (4H, m), 7.95 (1H, d, J=8 Hz).

(11) 8-[3-[N-[(E)-3-(6-Acetylaminopyridin-3-yl)acryloylglycyl]-N-methylamino]2,6-dichlorobenzyloxy]-4-methoxy-2-methylquinoline NMR (CDCl₃, δ): 2.21 (3H, s), 2.69 (3H, s), 3.27 (3H, s), 3.67 (1H, dd, J=17, 4 Hz), 3.94 (1H, dd, J=17, 5 Hz), 4.01 (3H, s), 5.59 (1H, d, J=10 Hz), 5.64 (1H, d, J=10 Hz), 6.48 (1H, d, J=15 Hz), 6.65 (1H, s), 6.74 (1H, br t, J=5 Hz), 7.23 (1H, d, J=8 Hz), 7.30 (1H, d, J=8 Hz), 7.38 (1H, d, J=15 Hz), 7.81 (1H, br d, J=8 Hz), 7.51 (1H, d, J=15 Hz), 7.81 (1H, br d, J=8 Hz), 8.11 (1H, br s), 8.19 (1H, br d, J=8 Hz), 8.32 (1H, br s).

its dihydrochloride

NMR (CDCl₃-CD₃OD, δ): 2.42 (3H, s), 3.04 (3H, s), 3.28 (3H, s), 3.90 (1H, d, J=17 Hz), 4.26 (1H, d, J=17 Hz), 4.38 (3H, s), 5.48 (1H, d, J=10 Hz), 5.68 (1H, d, J=10 Hz), 6.92 (1H, d, J=15 Hz), 7.34–7.41 (2H, m), 7.51–7.59 (2H, m), 7.62 (1H, d, J=8 Hz), 7.74 (1H, t, J=8 Hz), 7.96 (1H, d, J=8 Hz), 8.09 (1H, d, J=8 Hz), 8.52 (1H, br d, J=8 Hz), 8.87 (1H, br s).

(12) 8-[2,6-Dichloro-3-[N-methyl-N-[(E)-3-[6-(methylamino)pyridin-3-yl]acryloylglycyl]amino]-benzyloxy]-2-methylquinoline NMR (CDCl₃, δ): 2.73 (3H, s), 2.96 (3H, d, J=5 Hz), 3.27 (3H, s), 3.63 (1H, dd, J=4, 17 Hz), 3.94 (1H, dd, J=4, 17 Hz), 4.83 (1H, q-like), 5.59–5.70 (2H, m), 6.27 (1H, d, J=16 Hz), 6.38 (1H, d, J=8 Hz), 6.53 (1H, t-like), 7.23–7.34 (3H, m), 7.36–7.51 (4H, m), 7.60 (1H, dd, J=8 Hz), 8.01 (1H, d, J=8 Hz), 8.20 (1H, d, J=2 Hz).

(13) 8-[3-[N-[3-(6-Acetamidopyridin-3-yl)propionylglycyl]-N-methylamino]-2,6-dichlorobenzyloxy]-2-methylquinoline NMR (CDCl₃, δ): 2.20 (3H, s), 2.46 (2H, t, J=7.5 Hz), 2.73 (3H, s), 2.88 (2H, t, J=7.5 Hz), 3.23 (3H, s), 3.50 (1H, dd, J=4, 17 Hz), 3.84 (1H, dd, J=5, 17 Hz), 5.56–5.69 (2H, m), 6.96 (1H, t-like), 7.16–7.33 (3H, m), 7.33–7.56 (4H, m), 7.96–8.05 (2H, m), 8.11 (1H, d, J=8 Hz), 8.69 (1H, s).

(14) 8-[3-[N-[2-(2-Benzothiazolylamino)acetylglycyl]-N-methylamino]-2,6-dichlorobenzyloxy]-2-methylquinoline NMR (CDCl$_3$δ): 2.64 (3H, s), 3.21 (3H, s), 3.91 (2H, t, J=5 Hz), 4.10 (1H, d, J=16 Hz), 4.20 (1H, d J=16 Hz), 5.58 (2H, s), 6.85–7.35 (7H, m), 7.40–7.61 (5H, m), 8.05 (1H, d, J=8 Hz).

EXAMPLE 3

To a solution of 8-[2,6-dichloro-3-[N-[(E)-3-(6-ethoxycarbonylpyridin-3-yl)acryloylglycyl]-N-methylamino]benzyloxy]-2-methylquinoline (2.07 g) in ethanol (20 ml) was added 1N sodium hydroxide solution (3.75 ml) at ambient temperature. The mixture was stirred for 3 hours at 60° C. The reaction mixture was adjusted to pH 4 with 1N hydrochloric acid and concentrated. The residue was purified by flash chromatography (dichloromethane—methanol) to give 8-[3-[N-[(E)-3-(6-carboxypyridin-3-yl)acryloylglycyl]-N-methylamino]-2,6-dichlorobenzyloxy]-2-methylquinoline (1.71 g) as an amorphous powder.

NMR (DMSO-d$_6$, δ): 2.58 (3H, s), 3.13 (3H, s), 3.50 (1H, dd, J=4, 16 Hz), 3.80 (1H, dd, J=4, 16 Hz), 5.46 (1H, d, J=10 Hz), 5.53 (1H, d, J=10 Hz), 6.95 (1H, d, J=16 Hz), 7.30–7.57 (5H, m), 7.78 (2H, s-like), 8.02 (1H, d, J=8 Hz), 8.10 (1H, d, J=7.5 Hz), 8.20 (1H, d, J=8 Hz), 8.45 (1H, t-like), 8.85 (1H, s-like).

EXAMPLE 4

8-[3-[N-(4-Carboxycinnamoylglycyl)-N-methylamino]-2,6-dichlorobenzyloxy]-2-methylquinoline was obtained according to a similar manner to that of Example 3.

mp: 237.8–240.9° C.

NMR (DMSO-d$_6$, δ): 2.61 (3H, s), 3.15 (3H, s), 3.51 (1H, dd, J=4, 18 Hz), 3.81 (1H, dd, J=4, 18 Hz), 5.48 (1H, d, J=10 Hz), 5.54 (1H, d, J=10 Hz), 6.90 (1H, d, J=16 Hz), 7.32–7.60 (5H, m), 7.64–7.75 (2H, m), 7.75–7.85 (2H, m), 7.96 (2H, d, J=8 Hz), 8.21 (1H, d, J=8 Hz), 8.35–8.44 (1H, m).

EXAMPLE 5

To a mixture of 8-[3-[N-[(E)-3-(6-aminopyridin-3-yl)acryloylglycyl]-N-methylamino]-2,6-dichlorobenzyloxy]-2-methylquinoline (90.0 mg), 2-pyrazinecarboxylic acid (24.3 mg) and dimethylformamide (0.9 ml) were added 1-ethyl-3-(3-dimethylaminopropyl)carbodiimide hydrochloride (43.9 mg) and 1-hydroxybenzotriazole (35.4 mg). After being stirred for 37 hours at ambient temperature, the mixture was poured into saturated sodium bicarbonate solution and extracted with chloroform. The organic layer was separated, washed with water, dried over magnesium sulfate and evaporated in vacuo. The residue was purified by preparative thin-layer chromatography (chloroform—methanol) to give 8-[2,6-dichloro-3-[N-methyl-N-[(E)-3-[6-(2-pyrazinecarboxamido)-pyridin-3-yl]acryloylglycyl]amino]benzyloxy]-2-methylquinoline (43.7 mg) as a solid.

mp: 220–231° C.

NMR (CDCl$_3$, δ): 2.72 (3H, s), 3.28 (3H, s), 3.69 (3H, dd, J=16.5, 4.5 Hz), 3.96 (1H, dd, J=16.5, 4.5 Hz), 5.64 (2H, s), 6.52 (1H, d, J=16.0 Hz), 6.73 (1H, br t, J=4.5 Hz), 7.22–7.51 (7H, m), 7.56 (1H, d, J=16.0 Hz), 7.92 (1H, dd, J=8.5, 1.0 Hz), 8.03 (1H, d, J=8.5 Hz), 8.42 (1H, d, J=8.5 Hz), 8.47 (1H, d, J=1.0 Hz), 8.62 (1H, d, J=1.0 Hz), 8.83 (1H, d, J=1.0 Hz), 9.51 (1H, s).

its trihydrochloride mp: 190–193° C.

NMR (DMSO-d$_6$, δ): 2.92 (3H, s), 3.17 (3H, s), 3.60 (1H, dd, J=16.5, 4.5 Hz), 3.91 (1H, dd, J=16.5, 4.5 Hz), 5.62 (1H, d, J=11.0 Hz), 5.68 (1H, d, J=11.0 Hz), 6.88 (1H, d, J=16.0 Hz), 7.43 (1H, d, J=16.0 Hz), 7.80–8.00 (5H, m), 8.14 (1H, dd, J=8.5, 1.0 Hz), 8.31 (1H, d, J=8.5 Hz), 8.37 (1H, t, J=4.5 Hz), 8.61 (1H, d, J=1.0 Hz), 8.86 (1H, m), 8.95–9.03 (2H, m), 9.35 (1H, s).

EXAMPLE 6

The following compounds were obtained according to a similar manner to that or Example 5.

(1) 8-[2,6-Dichloro-3-[N-methyl-N-[(E)-3-[6-(6-methylpyridine-3-carboxamido)pyridin-3-yl]-acryloylglycyl]amino]benzyloxy]-2-methylquinoline mp: 167–177° C.

NMR (CDCl$_3$, δ): 2.65 (3H, s), 2.73 (3H, s), 3.27 (3H, s), 3.67 (1H, dd, J=16.5, 4.5 Hz), 3.96 (1H, dd, J=16.5, 4.5 Hz), 5.62 (1H, d, J=11.0 Hz), 5.69 (1H, d, J=11.0 Hz), 6.51 (1H, d, J=16.0 Hz), 6.72 (1H, br t, J=4.5 Hz), 7.23–7.33 (4H, m), 7.38–7.46 (2H, m), 7.49 (1H, d, J=8.5 Hz), 7.55 (1H, d, J=16.0 Hz), 7.90 (1H, dd, J=8.5, 1.0 Hz), 8.03 (1H, d, J=8.5 Hz), 8.13 (1H, dd, J=8.5, 1.0 Hz), 8.38 (1H, d, J=8.5 Hz), 8.40 (1H, d, J=1.0 Hz), 8.71 (1H, s), 9.04 (1H, d, J=1.0 Hz), its trihydrochloride mp: 198–213° C.

NMR (DMSO-d$_6$, δ): 2.72 (3H, s), 2.93 (3H, s), 3.17 (3H, s), 3.62 (1H, dd, J=16.5, 4.5 Hz), 3.91 (1H, dd, J=16.5, 4.5 Hz), 5.66 (2H, s), 6.88 (1H, d, J=16.0 Hz), 7.44 (1H, d, J=16.0 Hz), 7.75–8.01 (8H, m), 8.08–8.18 (1H, m), 8.26 (1H, d, J=8.5 Hz), 8.32–8.42 (1H, m), 8.59–8.70 (2H, m), 8.93–9.07 (1H, m), 9.20 (1H, s).

(2) 8-[2,6-Dichloro-3-[N-methyl-N-[(E)-3-[6-(2-methylthiopyridine-3-carboxamido)pyridin-3-yl]-acryloylglycyl]amino]benzyloxy]-2-methylquinoline NMR (CDCl$_3$, δ): 2.61 (3H, s), 2.73 (3H, s), 3.26 (3H, s), 3.68 (1H, dd, J=5, 18 Hz), 3.95 (1H, dd, J=5, 18 Hz), 5.65 (2H, s-like), 6.51 (1H, d, J=16 Hz), 6.79 (1H, t-like), 7.13 (1H, dd, J=6, 8 Hz), 7.24–7.35 (3H, m), 7.35–7.61 (4H, m), 7.90 (1H, dd, J=2, 8 Hz), 7.95 (1H, dd, J=2, 8 Hz), 8.03 (1H, d, J=8 Hz), 8.35–8.45 (2H, m), 8.58 (1H, dd, J=2, 6 Hz), 8.89 (1H, s).

its trihydrochloride

NMR (DMSO-d$_6$, δ): 2.49 (3H, s), 2.91 (3H, s), 3.16 (3H, s), 3.60 (1H, d, J=18 Hz), 5.57–5.71 (2H, m), 6.86 (1H, d, J=16 Hz), 7.75–8.03 (7H, m), 8.03–8.15 (1H, m), 8.22 (1H, d, J=8 Hz), 8.29–8.40 (1H, m), 8.51–8.65 (2H, m), 8.98 (1H, brpeak).

(3) 8-[2,6-Dichloro-3-[N-methyl-N-[(E)-3-[6-[(2-pyridyl)acetamido]pyridin-3-yl]acryloylglycyl]amino]-benzyloxy]-2-methylquinoline NMR (CDCl$_3$δ): 2.74 (3H, s), 3.26 (3H, s), 3.65 (1H, dd, J=4, 18 Hz), 3.86–4.00 (3H, m), 5.68–5.70 (2H, m), 6.44 (1H, m, J=16 Hz), 6.64 (1H, t-like), 7.20–7.35 (6H, m), 7.35–7.55 (4H, m), 7.70 (1H, td, J=8, 2 Hz), 7.80 (1H, dd, J=2 Hz), 8.03 (1H, d, J=8 Hz), 8.21 (1H, d, J=8 Hz), 8.39 (1H, d, J=2 Hz), 8.70 (1H, d, J=6 Hz), its trihydrochloride NMR (CDCl$_3$δ): 2.86 (3H, s), 3.14 (3H, s), 3.57 (1H, dd, J=4, 16 Hz), 3.87 (1H, dd, J=4, 16 Hz), 4.32 (2H, s), 5.55–5.66 (2H, m), 6.81 (1H, d, J=16 Hz), 7.38 (1H, d, J=16 Hz), 7.71–7.95 (10H, m), 7.95–8.10 (1H, m), 8.31 (1H, t, J=6 Hz), 8.40 (1H, t, J=8 Hz), 8.53 (1H, d, J=2 Hz), 8.83 (1H, d, J=6 Hz), 8.90 (1H, brpeak), (4) 8-[2,6-Dichloro-3-[N-methyl-N-[(E)-3-[6-[(3-pyridyl)acetamido]pyridin-3-yl]acryloylglycyl]amino]-benzyloxy]-2-methylquinoline NMR (CDCl₃, δ): 2.73 (3H, s), 3.27 (3H, s), 3.66 (1H, dd, J=4, 18 Hz), 3.75 (2H, s), 3.94 (1H, dd, J=4, 18 Hz), 5.59–5.70 (2H, m), 6.46 (1H, d, J=16 Hz), 6.67 (1H, t-like), 7.20–7.36 (4H, m), 7.36–7.55 (4H, m), 7.70 (1H, d, J=8 Hz), 7.83 (1H, dd, J=2, 8 Hz), 7.97–8.06 (2H, m), 8.19 (1H, d, J=8 Hz), 8.33 (1H, d, J=2 Hz), 8.54–8.62 (2H, m).

its trihydrochloride

NMR (DMSO-d₆, δ): 2.88 (3H, s), 3.15 (3H, s), 3.57 (1H, dd, J=4, 16 Hz), 3.89 (1H, dd, J=4, 16 Hz), 4.09 (2H, s) 5.57–5.70 (2H, m), 6.81 (1H, d, J=16 Hz), 7.38 (1H, d, J=16 Hz), 7.75–7.95 (8H, m), 7.95–8.10 (2H, m), 8.30 (1H, t, J=6 Hz), 8.49 (1H, d, J=8 Hz), 8.53 (1H, d, J=2 Hz), 8.83 (1H, d, J=6 Hz), 8.88 (1H, s-like), 8.93 (1H, brpeak).

(5) 8-[2,6-dichloro-3-[N-methyl-N-[(E)-3-[6-(2-pyridinecarboxamido)pyridin-3-yl]acryloylglycyl]amino]-benzyloxy]-2-methylquinoline NMR (CDCl₃, δ): 2.75 (3H, s), 3.27 (3H, s), 3.68 (1H, dd, J=5, 18 Hz), 3.95 (1H, dd, J=5, 18 Hz), 5.60–5.70 (2H, m), 6.51 (1H, d, J=16 Hz), 7.23–7.30 (3H, m), 7.33 (1H, d, J=8 Hz), 7.38–7.61 (5H, m), 7.87–7.96 (2H, m), 8.03 (1H, d, J=8 Hz), 8.30 (1H, d, J=8 Hz), 8.41–8.49 (2H, m), 8.65 (1H, d, J=5 Hz).

its trihydrochloride

NMR (DMSO-d₆, δ): 2.93 (3H, s), 3.15 (3H, s), 3.60 (1H, dd, J=5, 16 Hz), 3.92 (1H, dd, J=5, 16 Hz), 5.63 (1H, d, J=10 Hz) 5.70 (1H, d, J=10 Hz), 6.86 (1H, d, J=16 Hz), 7.43 (1H, d, J=16 Hz), 7.70–8.03 (8H, m), 8.09–8.19 (2H, m), 8.24 (1H, d, J=8 Hz), 8.30–8.40 (2H, m), 8.58 (1H, d, J=2 Hz), 8.78 (1H, d, J=5 Hz), 9.03 (1H, br d, J=8 Hz).

(6) 8-[2,6-Dichloro-3-[N-methyl-N-[(E)-3-[6-(3-pyridinecarboxamido)pyridin-3-yl]acryloylglycyl]-amino]benzyloxy]-2-methylquinoline NMR (CDCl₃, δ): 2.71 (3H, s), 3.26 (3H, s), 3.68 (1H, dd, J=4, 18 Hz), 3.93 (1H, dd, J=4, 18 Hz), 5.56–5.70 (2H, m), 6.52 (1H, d, J=16 Hz), 6.72 (1H, t-like), 7.21–7.56 (10H, m), 7.89 (1H, dd, J=2, 8 Hz), 8.00–8.10 (2H, m), 8.41 (1H, d, J=2 Hz), 8.71 (1H, d, J=6 Hz), 8.92 (1H, d, J=2 Hz).

its trihydrochloride

NMR (CDCl₃, δ): 2.92 (3H, s), 3.15 (3H, s), 5.59–5.72 (2H, m), 6.86 (1H, d, J=16 Hz), 7.43 (1H, d, J=16 Hz), 7.60–8.01 (6H, m), 8.10 (1H, dd, J=2, 8 Hz), 8.25 (1H, d, J=8 Hz), 8.31–8.49 (2H, m), 8.53–8.65 (2H, m), 8.88 (1H, d, J=6 Hz), 8.95–9.04 (1H, m), 9.13 (1H, s-like), 9.23 (1H, s-like).

(7) 8-[2,6-Dichloro-3-[N-[(E)-3-[6-(2-methoxypyridine-3-carboxamido)pyridin-3-yl]acryloylglycyl]-N-methylamino]benzyloxy]-2-methylquinoline NMR (CDCl₃, δ): 2.71 (3H, s), 3.26 (3H, s), 3.67 (1H, dd, J=4, 16 Hz), 3.94 (1H, dd, J=4, 16 Hz), 4.23 (3H, s), 5.57–5.70 (2H, m), 6.50 (1H, d, J=16 Hz), 6.74 (1H, t-like), 7.12 (1H, dd, J=8, 6 Hz), 7.20–7.35 (4H, m), 7.35–7.50 (3H, m), 7.55 (1H, d, J=16 Hz), 7.87 (1H, dd, J=2, 8 Hz), 8.03 (1H, d, J=8 Hz), 8.35 (1H, dd, J=6, 2 Hz), 8.38–8.48 (2H, m), 8.57 (1H, dd, J=8, 2 Hz).

its trihydrochloride

NMR (DMSO-d₆, δ): 2.95 (3H, s), 3.16 (3H, s), 3.60 (1H, dd, J=4, 16 Hz), 5.55–5.72 (2H, m), 6.60 (1H, t, J=8 Hz), 6.85 (1H, d, J=16 Hz), 7.40 (1H, d, J=16 Hz), 7.65–8.01 (8H, m), 8.01–8.12 (1H, m), 8.20–8.41 (12H, m), 8.43–8.60 (2H, m), 8.99 (1H, brpeak).

(8) 8-[2,6-Dichloro-3-[N-methyl-N-[(E)-3-[6-(2-methylpyridine-3-carboxamido)pyridin-3-yl]acryloylglycyl]amino]benzyloxy]-2-methylquinoline NMR (CDCl₃, δ): 2.71 (1H, s), 2.76 (3H, s), 3.25 (3H, s), 3.69 (1H, dd, J=4, 18 Hz), 3.95 (1H, dd, J=5, 18 Hz), 5.63 (3H, s), 6.48 (1H, d, J=16 Hz), 6.87 (1H, t-like), 7.18–7.37 (4H, m), 7.37–7.57 (4H, m), 7.85 (1H, dd, J=2, 8 Hz), 7.89 (1H, dd, J=2, 8 Hz), 8.04 (1H, d, J=8 Hz), 8.20 (1H, d, J=2 Hz), 8.37 (1H, d, J=8 Hz), 8.63 (1H, d, J=6 Hz), 8.93 (1H, s).

(9) 8-[2,6-Dichloro-3-[N-methyl-N-[(E)-3-[6-[2-(6-methyl-3-pyridyl)acetamido]pyridin-3-yl]acryloylglycyl]amino]-benzyloxy]-2-methylquinoline NMR (CDCl₃, δ): 2.57 (3H, s), 2.73 (3H, s), 3.26 (3H, s), 3.66 (1H, dd, J=4, 18 Hz), 3.72 (2H, s), 3.94 (1H, dd, J=4, 18 Hz), 5.58–5.70 (2H, m), 6.46 (1H, d, J=16 Hz), 6.68 (1H, t-like), 7.18 (1H, d, J=8 Hz), 7.23–7.62 (8H, m), 7.81 (1H, dd, J=2, 8 Hz), 7.98–8.05 (2H, m), 8.19 (1H, d, J=8 Hz), 8.32 (1H, d, J=2 Hz), 8.45 (1H, d, J=2 Hz).

its trihydrochloride

NMR (DMSO-d₆, δ): 2.74 (3H, s), 2.89 (3H, s), 3.14 (3H, s), 3.57 (1H, dd, J=4, 16 Hz), 3.88 (1H, dd, J=4, 16 Hz), 4.04 (2H, s), 5.56–5.70 (2H, m), 6.81 (1H, d, J=16 Hz), 7.40 (1H, d, J=16 Hz), 7.78–8.13 (10H, m), 8.32 (1H, t-like), 8.42 (1H, d, J=2, 8 Hz), 8.53 (1H, d, J=2 Hz), 8.75 (1H, d, J=2 Hz), 8.94 (1H, brpeak).

(10) 8-[2,6-Dichloro-3-[N-methyl-N-[(E)-3-[6-[2-(2-methyl-3-pyridyl)acetamido]pyridin-3-yl]acryloylglycyl]amino]-benzyloxy]-2-methylquinoline NMR (CDCl₃, δ): 2.58 (3H, s), 2.73 (3H, s), 3.26 (3H, s), 3.65 (1H, dd, J=4, 18 Hz), 3.77 (2H, s), 3.93 (1H, dd, J=5, 18 Hz), 5.60–5.70 (2H, m), 6.47 (1H, d, J=16 Hz), 6.68 (1H, t-like), 7.18 (1H, dd, J=6, 8 Hz), 7.22–7.35 (3H, m), 7.35–7.59 (5H, m), 7.80–7.90 (2H, m), 8.02 (1H, d, J=8 Hz), 8.21 (1H, d, J=8 Hz), 8.32 (1H, d, J=2 Hz) 8.50 (1H, d, J=6 Hz).

its trihydrochloride

NMR (DMSO-d₆, δ): 2.74 (3H, s), 2.90 (3H, s), 3.15 (3H, s), 3.56 (1H, dd, J=5, 16 Hz), 4.11 (2H, s), 5.56–5.69 (2H, m), 6.31 (1H, d, J=16 Hz), 7.38 (1H, d, J=16 Hz), 7.76–8.10 (10H, m), 8.31 (1H, t-like), 8.47 (1H, d, J=8 Hz), 8.53 (1H, d, J=2 Hz), 8.71 (1H, dd, J=2, 6 Hz), 8.95 (1H, br s).

EXAMPLE 7

To a mixture of 8-[3-[N-[(E)-3-(6-carboxypyridin-3-yl)-acryloylglycyl]-N-methylamino]-2,6-dichlorobenzyloxy]-2-methylquinoline (100 mg), 2-aminopyrazine (19.7 mg) and N,N-dimethylformamide (2 ml) were added 1-ethyl-3-(3-dimethylaminopropyl) carbodiimide hydrochloride (43 mg) and 1-hydroxybenzotriazole (35 mg), and the mixture was stirred for 36 hours at ambient temperature. The mixture was poured into water and extracted with ethyl acetate. The organic layer was washed with water, saturated sodium bicarbonate solution and brine, dried over magnesium sulfate, and concentrated in vacuo. The residue was purified by preparative thin-layer chromatography (methylene chloride—methanol) to give 8-[2,6-dichloro-3-[N-methyl-N-[(E)-3-[6-(2-pyrazinylcarbamoyl)-pyridin-3-yl]acryloylglycyl]amino]benzyloxy]-2-methylquinoline (21 mg) as an amorphous powder.

NMR (CDCl₃, δ): 2.71 (3H, s), 3.30 (3H, s), 3.76 (1H, d, J=16 Hz), 4.02 (1H, d, J=16 Hz), 5.64 (2H, s), 6.71 (1H, d, J=16 Hz), 7.22–7.43 (3H, m), 7.43–7.58 (3H, m), 7.64 (1H, d, J=16 Hz), 7.99 (1H, dd, J=2, 8 Hz), 8.09 (1H, d, J=8 Hz), 8.23 (1H, d, J=8 Hz), 8.33–8.47 (2H, m), 8.71 (1H, s-like), 9.25 (1H, s).

its trihydrochloride

NMR (DMSO-d$_6$, δ): 2.85 (3H, s), 3.15 (3H, s), 3.91 (1H, dd, J=5, 18 Hz), 5.55–5.69 (2H, m), 7.08 (1H, d, J=16 Hz), 7.55 (1H, d, J=16 Hz), 7.68–7.93 (8H, m), 8.21–8.33 (2H, m), 8.41–8.53 (2H, m), 8.85 (1H, brpeak), 8.94 (1H, s-like), 9.49 (1H, s-like).

EXAMPLE 8

The following compounds were obtained according to a similar manner to that of Example 7.

(1) 8-[2,6-Dichloro-3-[N-methyl-N-[(E)-3-[6-(2-thiazolycarbomyl)pyridin-3-yl]acryloylglycyl]amino]-benzyloxy]-2-methylquinoline mp: 144–155° C.

NMR (CDCl$_3$, δ): 2.73 (3H, s), 3.30 (3H, s), 3.72 (1H, dd, J=16.5, 4.5 Hz), 3.97 (1H, dd, J=16.5, 4.5 Hz), 5.67 (2H, s), 6.70 (1H, d, J=16.0 Hz), 6.83 (1H, br t, J=4.5 Hz), 7.08 (1H, d, J=3.0 Hz), 7.23–7.37 (4H, m), 7.39–7.57 (4H, m), 7.63 (1H, d, J=16.0 Hz), 7.96–8.09 (2H, m), 8.27 (1H, d, J=8.5 Hz), 8.73 (1H, s).

its trihydrochloride mp: 161–165° C.

NMR (DMSO-d$_6$, δ): 2.93 (3H, s), 3.16 (3H, s), 3.61 (1H, dd, J=16.5, 4.5 Hz), 3.91 (1H, dd, J=16.5, 4.5 Hz), 5.62 (1H, d, J=11.0 Hz), 5.68 (1H, d, J=11.0 Hz), 7.10 (1H, d, J=16.0 Hz), 7.73 (1H, d, J=2.5 Hz), 7.54 (1H, d, J=16.0 Hz), 7.59 (1H, d, J=2.5 Hz), 7.80–7.99 (5H, m), 8.21 (1H, d, J=7.5 Hz), 8.27 (1H, dd, J=7.5, 1.0 Hz), 8.49 (1H, t, J=4.5 Hz), 8.91–9.03 (2H, m).

(2) 8-[2,6-Dichloro-3-[N-[(E)-3-[6-(1-isoquinolylcarbamoyl)-pyridin-3-yl]acryloylglycyl]-N-methylamino]benzyloxy]-2-methylquinoline mp: 127–135° C.

NMR (CDCl$_3$, δ): 2.72 (3H, s), 3.28 (3H, 3.72 (1H, dd, J=16.5, 4.5 Hz), 3.98 (1H, dd, J=16.5, 4.5 Hz), 5.64 (2H, s), 6.70 (1H, d, J=16.0 Hz), 6.87 (1H, br t, J=4.5 Hz), 7.23–7.47 (6H, m), 7.51 (1H, d, J=8.5 Hz), 7.57 (1H, d, J=5.5 Hz), 7.60–7.70 (2H, m), 7.73 (1H, t, J=7.5 Hz), 7.86 (1H, d, J=7.5 Hz), 8.00 (1H, dd, J=7.5, 1.0 Hz), 8.03 (1H, d, J=8.5 Hz), 8.13 (1H, d, J=7.5 Hz), 8.32 (1H, d, J=7.5 Hz), 8.43 (1H, d, J=5.5 Hz), 8.76 (1H, s).

its trihydrochloride mp: 143–145° C.

NMR (DMSO-d$_6$, δ): 2.93 (3H, s), 3.17 (3H, s), 3.63 (1H, dd, J=16.5, 4.5 Hz), 3.94 (1H, dd, J=16.5, 4.5 Hz), 5.63 (1H, d, J=11.0 Hz), 5.70 (1H, d, J=11.0 Hz), 7.13 (1H, d, J=16.0 Hz), 7.61 (1H, d, J=16.0 Hz), 7.78–8.02 (9H, m), 8.13 (1H, d, J=8.5 Hz), 8.25–8.37 (3H, m), 8.41 (1H, d, J=7.0 Hz), 8.53 (1H, t, J=4.5 Hz), 8.93–9.07 (2H, m).

(3) 8-[2,6-Dichloro-3-[N-methyl-N-[4-[(1-oxo-3-pyridyl-methyl)carbamoyl]cinnamoylglycyl]amino]benzyloxy]-2-methylquinoline mp: 142–163° C.

NMR (CDCl$_3$, δ): 2.70 (3H, s), 3.25 (3H, s), 3.63 (1H, dd, J=16.5, 4.5 Hz), 3.97 (1H, dd, J=16.5, 4.5 Hz), 4.51–4.62 (2H, m), 5.64 (2H, s), 6.56 (1H, d, J=16.0 Hz), 7.03 (1H, br t, J=4.5 Hz), 7.13–7.37 (6H, m), 7.40–7.51 (5H, m), 7.56 (1H, d, J=16.0 Hz), 7.77–7.90 (3H, m), 7.99–8.07 (2H, m), 8.11 (1H, s).

(4) 8-[2,6-Dichloro-3-[N-[(E)-3-[6-(6-methoxypyridin-3-ylcarbamoyl)pyridin-3-yl]acryloylglycyl]-N-methylamino]benzyloxy]-2-methylquinoline mp: 168–183° C.

NMR (CDCl$_3$, δ): 2.73 (3H, s), 3.27 (3H, 3.70 (1H, dd, J=16.5, 4.5 Hz), 3.96 (1H, s), 3.98 (1H, dd, J=16.5, 4.5 Hz), 5.66 (2H, s), 6.68 (1H, d, J=16.0 Hz), 6.78–6.83 (2H, m), 7.24–7.37 (3H, m), 7.39–7.48 (2H, m), 7.51 (1H, d, J=8.5 Hz), 7.64 (1H, d, J=16.0 Hz), 7.97–8.07 (2H, m), 8.18 (1H, dd, J=8.5, 1.0 Hz), 8.26 (1H, d, J=8.5 Hz), 8.44 (1H, d, J=1.0 Hz), 8.69 (1H, s), 9.82 (1H, s).

(5) 8-[2,6-Dichloro-3-[N-methyl-N-[(E)-3-[6-(4-methyloxazol-2-ylcarbamoyl)pyridin-3-yl]acryloylglycyl]amino]-benzyloxy]-2-methylquinoline mp: 128–139° C.

NMR (CDCl$_3$, δ): 2.19 (3H, s), 2.72 (3H, s), 3.28 (3H, s), 3.73 (1H, dd, J=16.5, 5.5 Hz), 3.97 (1H, dd, J=16.5, 5.5 Hz), 5.64 (2H, s), 6.69 (1H, d, J=15.0 Hz), 6.88 (1H, br t, J=5.5 Hz), 7.21–7.35 (5H, m), 7.40–7.53 (3H, m), 7.61 (1H, d, J=15.0 Hz), 7.98 (1H, dd, J=8.5, 1.0 Hz), 8.03 (1H, d, J=8.0 Hz), 8.25 (1H, d, J=8.5 Hz), 8.68 (1H, d, J=1.0 Hz).

(6) 8-[2,6-Dichloro-3-[N-methyl-N-[(E)-3-[6-(2-methyl-2h-pyrazol-3-ylcarbamoyl)pyridin-3-yl]acryloylglycyl]-amino]benzyloxy]-2-methylquinoline NMR (CDCl$_3$, δ): 2.74 (3H, s), 3.27 (3H, s), 3.70 (1H, dd, J=4, 18 Hz), 3.85 (3H, s), 3.95 (1H, dd, J=4, 18 Hz), 5.60–5.70 (2H, m), 6.65 (1H, d, J=16 Hz), 6.75 (1H, t-like), 6.83 (1h, d, J=2 Hz), 7.20–7.36 (5H, m), 7.36–7.54 (3H, m), 7.62 (1H, d, J=16 Hz), 7.97 (1H, dd, J=2, 8 Hz), 8.03 (1H, d, J=8 Hz), 8.24 (1H, d, J=8 Hz), 8.68 (1H, d, J=2 Hz).

its trihydrochloride

NMR (DMSO-d$_6$, δ): 2.92 (3H, s), 3.15 (3H, s), 3.80 (3H, s), 3.91 (1H, dd, J=5, 16 Hz), 5.61 (1H, d, J=10 Hz), 5.68 (1H, d, J=10 Hz), 6.61 (1H, d, J=2 Hz), 7.06 (1H, d, J=16 Hz), 7.54 (1H, d, J=16 Hz), 7.59–7.76 (2H, m), 7.76–8.01 (6H, m), 8.15 (1H d, J=8 Hz), 8.24 (1H, dd, J=8, 2 Hz), 8.45 (1H, t-like), 8.88 (1H, d, J=2 Hz), 8.99 (1H, brpeak).

EXAMPLE 9

To a solution of 3-[N-[4-(methylcarbamoyl)-cinnamoylglycyl]-N-methylamino]-2,6-dichlorobenzyl bromide (60 mg) and 4-ethoxy-8-hydroxy-2-methylquinoline (24.9 mg) in dimethylformamide (0.6 ml) was added potassium carbonate (48.5 mg), and the mixture was stirred for 5 hours at ambient temperature. Water was added thereto, and the mixture was extracted with dichloromethane. The extract was washed with water, dried over magnesium sulfate and concentrated. The residue was purified by preparative thin-layer chromatography (dichloromethane:methanol=15:1, V/V) to give 8-[2,6-dichloro-3-[N-methyl-N-[4-(methylcarbamoyl)cinnamoylglycyl]-amino]benzyloxy]-4-ethoxy-2-methylquinoline (67 mg) as an amorphous powder.

NMR (CDCl$_3$, δ): 1.56 (3H, t, J=7.5 Hz), 2.66 (3H, s), 3.00 (3H, d, J=5 Hz), 3.26 (3H, s), 3.65 (1H, dd, J=17, 4 Hz), 3.93 (1H, dd, J=17, 5 Hz), 4.22 (2H, q, J=7.5 Hz), 5.59 (1H, d, J=10 Hz), 5.64 (1H, d, J=10 Hz), 6.31 (1H, br d, J=5 Hz), 6.52 (1H, d, J=15 Hz), 6.61 (1H, s), 6.73 (1H, br s), 7.21–7.31 (2H, m), 7.37 (1H, t, J=8 Hz), 7.43–7.61 (4H, m), 7.74 (2H, d, J=8 Hz), 7.87 (1H, d, J=8 Hz).

its hydrochloride

NMR (CDCl$_3$, δ): 1.68 (3H, br t, J=7.5 Hz), 2.98 (3H, s), 3.00 (3H, s), 3.29 (3H, s), 3.88 (1H, d, J=17Hz), 4.10 (1H, d, J=17Hz), 4.60 (2H, q, J=7.5Hz), 5.52 (1H, d, J=10Hz), 5.69 (1H, d, J=10Hz), 6.63 (1H, d, J=15Hz), 7.29–7.32 (1H, overlapped with H$_2$O), 7.41 (1H, d, J=15Hz), 7.50–7.60 (5H, m), 7.72 (1H, d, J=8Hz), 7.79 (2H, d, J=8Hz), 7.98 (1H, d, J=8Hz).

EXAMPLE 10

The following compounds were obtained according to a similar manner to that of Example 9.

(1) 8-[2,6-Dichloro-3-[N-methyl-N-[4-(methylcarbamoyl)-cinnamoylglycyl]amino]benzyloxy]-4-isopropoxy-2-methylquinoline NMR (CDCl$_3$, δ) : 1.48 (6H, d, J=7Hz), 2.64 (3H, s), 3.00 (3H, d, J=5Hz), 3.25 (3H, s), 3.66 (1H, dd, J=17, 4Hz), 3.93 (1H, dd, J=17, 5Hz), 4.75–4.85 (1H, m), 5.59 (1H, d, J=10Hz), 5.62 (1H, d, J=10Hz), 6.32 (1H, br d, J=5Hz), 6.52 (1H, d, J=15Hz), 6.61 (1H, s), 6.75 (1H, br, s), 7.20–7.38 (3H, m), 7.42–7.60 (4H, m), 7.74 (2H, d, J=8Hz), 7.83 (1H, d, J=8Hz).

its hydrochloride

NMR (CDCl$_3$-CD$_3$OD, δ) : 1.60 (6H, br d, J=7Hz), 2.98 (3H, s), 2.99 (3H, s), 3.28 (3H, s), 3.88 (1H, d, J=17Hz), 4.15 (1H, d, J=17Hz), 5.15–5.26 (1H, m), 5.50 (1H, d, J=10Hz), 5.67 (1H, d, J=10Hz), 6.64 (1H, d, J=15Hz), 7.25 (1H, br s), 7.39 (1H, d, J=15Hz), 7.49–7.61 (5H, m), 7.71 (1H, t, J=8Hz), 7.79 (2H, br d, J=8Hz), 7.95 (1H, d, J=8Hz).

(2) 8-[2,6-Dichloro-3-[N-methyl-N-[4-(methylcarbamoyl)-cinnamoylglycyl]amino]benzyloxy]-4-(2-methoxyethoxy)-2-methylquinoline NMR (CDCl$_3$, δ) : 2.66 (3H, s), 3.00 (3H, d, J=5Hz), 3.24 (3H, s), 3.50 (3H, s), 3.63 (1H, dd, J=17, 4Hz), 3.87–3.98 (3H, m), 4.29–4.33 (2H, m), 5.61 (2H, br s), 6.31 (1H, br d, J=5Hz), 6.52 (1H, d, J=15Hz), 6.63 (1H, s), 6.73 (1H, br s), 7.21–7.61 (7H, m), 7.74 (2H, d, J=8Hz), 7.98 (1H, d, J=8Hz).

its hydrochloride

NMR (CDCl$_3$-CD$_3$OD, δ) : 2.99 (3H, s), 3.00 (3H, s), 3.28 (3H, s), 3.49 (3H, s), 3.78 (1H, br d, J=17Hz), 3.92–4.00 (2H, m), 4.13 (1H, br d, J=17Hz), 4.68–4.75 (2H, m), 5.52 (1H, d, J=10Hz), 5.67 (1H, d, J=10Hz), 6.65 (1H, d, J=15Hz), 7.32–7.60 (7H, m), 7.69–7.82 (3H, m), 8.00 (1H, d, J=8Hz).

(3) 8-[2,6-Dichloro-3-[N-methyl-N-[4-(methylcarbamoyl)-cinnamoylglycyl]amino]benzyloxy]-4-(2-dimethylaminoethoxy)-2-methylquinoline NMR (CDCl$_3$, δ) : 2.41 (6H, s), 2.66 (3H, s), 2.91 (2H, t, J=6Hz), 3.00 (3H, d, J=5Hz), 3.25 (3H, s), 3.64 (1H, dd, J=17, 4Hz) 3.92 (1H, dd, J=17, 5Hz), 4.29 (2H, t, J=6Hz), 5.59 (1H, d, J=10Hz), 5.64 (1H, d, J=10Hz), 6.29 (1H, br d, J=5Hz), 6.52 (1H, d, J=15Hz), 6.63 (1H, s), 6.73 (1H, br t, J=5Hz), 7.21–7.29 (3H, m), 7.33–7.60 (4H, m), 7.74 (2H, d, J=8Hz), 7.83 (1H, d, J=8Hz).

its dihydrochloride

NMR (CDCl$_3$-CD$_3$OD, δ) : 2.87–3.00 (8H, m), 3.06 (6H, br s), 3.29 (3H, s), 3.79–3.99 (4H, m), 5.02–5.14 (2H, m), 5.49 (1H, d, J=10Hz), 5.69 (1H, d, J=10Hz), 6.59 (1H, d, J=15Hz), 7.38–7.61 (7H, m), 7.71–7.82 (3H, m), 8.42 (1H, d, J=8Hz).

(4) 4-Cyclopentyloxy-8-[2,6-dichloro-3-[N-methyl-N-[4-(methylcarbamoyl)-cinnamoylglycyl]amino]benzyloxy]-2-methylquinoline NMR (CDCl$_3$, δ) : 1.62–2.06 (8H, m), 2.64 (3H, s), 3.00 (4Hz), 3.92 (1H, dd, J=17, 5Hz), 4.94–5.00 (1H, m), 5.59 (1H, d, J=10Hz), 5.62 (1H, d, J=10Hz), 6.36 (1H, br d, J=5Hz), 6.52 (1H, d, J=15Hz), 6.61 (1H, s), 6.76 (1H, br s), 7.20–7.38 (3H, m), 7.42–7.60 (4H, m), 7.73 (2H, br d, J=8Hz), 7.80 (1H, d, J=8Hz).

its hydrochloride

NMR (CDCl$_3$-CD$_3$OD, δ) : 1.76–2.26 (8H, m), 2.99 (6H, s), 3.28 (3H, s), 3.88 (1H, d, J=17Hz), 4.20 (1H, d, J=17Hz), 5.30–5.38 (1H, m), 5.51 (1H, d, J=10Hz), 5.63 (1H, d, J=10Hz), 6.67 (1H, d, J=15Hz), 7.15 (1H, br s), 7.37 (1H, d, J=15Hz), 7.45–7.60 (5H, m), 7.67–7.79 (3H, m), 7.89 (1H, d, J=8Hz).

(5) 8-[2,6-Dichloro-3-[N-methyl-N-[4-(methylcarbamoyl)-cinnamoylglycyl]amino]benzyloxy]-4-dimethylamino-2-methylquinoline NMR (CDCl$_3$, δ) : 2.66 (3H, br s), 3.00 (3H, d, J=5Hz), 3.09 (6H, br s), 3.25 (3H, s), 3.72 (1H, br dd, J=17, 4Hz), 3.99 (1H, br dd, J=17, 5Hz), 5.09 (2H, s), 6.48 (1H, br s), 6.57 (1H, br d, J=15Hz), 6.67 (1H, s), 7.20–7.56 (8H, m), 7.68–7.74 (3H, m).

its dihydrochloride

NMR (CDCl$_3$-CD$_3$OD, δ) : 2.71 (3H, s), 2.99 (3H, s), 3.28 (3H, s), 3.50 (6H, s), 3.87 (1H, d, J=17Hz), 4.19 (1H, d, J=17Hz), 5.47 (1H, d, J=10Hz), 5.62 (1H, d, J=10Hz), 6.63 (1H, d, J=15Hz), 6.72 (1H, br s), 7.33 (1H, d, J=15Hz), 7.41–7.61 (6H, m), 7.77–7.82 (3H, m).

(6) 8-[2,6-Dichloro-3-[N-methyl-N-[4-(methylcarbamoyl)-cinnamoylglycyl]amino]benzyloxy]-4-ethoxycarbonylmethylamino-2-methylquinoline NMR (CDCl$_3$-CD$_3$OD, δ) : 1.32 (3H, t, J=7.5Hz), 2.54 (3H, s), 2.98 (3H, s), 3.25 (3H, s), 3.73 (1H, d, J=17Hz), 3.97 (1H, d, J=17Hz), 4.15 (2H, br s), 4.30 (2H, q, J=7.5Hz), 5.50 (1H, d, J=10Hz), 5.56 (1H, d, J=10Hz), 6.21 (1H, s), 6.52 (1H, d, J=15Hz), 7.26 (1H, br d, J=7.5Hz), 7.36–7.52 (6H, m), 7.62–7.78 (3H, m).

its dihydrochloride

NMR (CDCl$_3$-CD$_3$OD, δ) : 1.30 (3H, t, J=7.5Hz), 2.66 (3H, s), 2.99 (3H, s), 3.29 (3H, s), 3.91 (2H, br s), 4.25 (2H, q, J=7.5Hz), 4.41 (2H, br s), 5.46 (1H, d, J=10Hz), 5.62 (1Hz, d, J=10Hz), 6.24 (1H, s), 6.58 (1H, d, J=15Hz), 7.38 (1H, d, J=15Hz), 7.42–7.48 (3H, m), 7.50 (1H, d, J=7.5Hz), 7.58 (1H, d, J=7.5Hz), 7.66 (1H, t, J=7.5Hz), 7.78 (2H, d, J=7.5Hz), 8.35 (1H, br d, J=7.5 Hz).

(7) 4-Allylamino-8-[2,6-dichloro-3-[N-methyl-N-[4-(methylcarbamoyl)-cinnamoylglycyl]amino]benzyloxy]-2-methylquinoline NMR (CDCl$_3$-CD$_3$OD, δ) : 2.54 (3H, s), 2.98 (3H, s), 3.25 (3H, s), 3.79 (1H, d, J=17Hz), 3.94 (1H, d, J=17Hz), 4.08 (2H, br d, J=6Hz), 5.20–5.33 (2H, m), 5.48 (1H, d, J=10Hz), 5.57 (1H, d, J=10Hz), 5.88–6.02 (1H, m), 6.29 (1H, s), 6.56 (1H, d, J=15Hz), 7.29 (1H, d, J=8Hz), 7.39–7.54 (6H, m), 7.69 (2H, d, J=8Hz), 7.88 (1H, br d, J=8Hz).

its dihydrochloride

NMR (CDCl$_3$-CD$_3$OD, δ) : 2.61 (3H, s), 2.99 (3H, s), 3.28 (3H, s), 3.91 (2H, br s), 4.22 (2H, br d, J=6Hz), 5.20–5.31 (2H, m), 5.44 (1H, d, J=10Hz), 5.61 (1H, d, J=10Hz), 5.83–5.98 (1H, m), 6.29 (1H, s), 6.58 (1H, d, J=15Hz), 7.32–7.47 (4H, m), 7.50 (1H, d, J=8Hz), 7.66 (1H, d, J=8Hz), 7.63 (1H, t, J=8Hz), 7.78 (2H, d, J=8Hz), 8.42 (1H, br d, J=8Hz).

(8) 8-[2,6-Dichloro-3-[N-methyl-N-[4-(methylcarbamoyl)-cinnamoylglycyl]amino]benzyloxy]-4-(2-dimethylaminoethylamino)-2-methylquinoline NMR (CDCl$_3$, δ) : 2.31 (6H, s), 2.57 (3H, s), 2.69 (2H, br t, J=6Hz), 2.99 (3H, d, J=5Hz), 3.21–3.33 (5H , m), 3.69 (1H, br dd, J=17, 4Hz), 3.93 (1H, br dd, J=17, 5Hz), 5.57 (1H, d, J=10Hz), 5.61 (1H, d, J=10Hz), 5.79 (1H, br s), 6.31 (1H, s), 6.45 (1H, br s), 6.53 (1H, d, J=15Hz), 6.88 (1H, br s), 7.19 (1H, br d, J=8Hz), 7.25–7.37 (2H, m), 7.40–7.60 (5H, m), 7.73 (2H, br d, J=8Hz).

its trihydrochloride

NMR (CDCl$_3$-CD$_3$OD, δ) : 2.75 (3H, br s), 2.99 (9H, br s), 3.18–3.27 (3H, overlapped with H$_2$O), 3.57–3.68 (2H, m), 3.81 (1H, d, J=17Hz), 3.95 (1H, d, J=17Hz), 4.10–4.20 (2H, m), 5.46 (1H, d, J=10Hz), 5.67 (1H, d, J=10Hz), 6.59 (1H, d, J=15Hz), 7.40–7.70 (8H, m), 7.80 (2H, d, J=8Hz), 8.33 (1H, br d, J=8Hz).

(9) 8-[2,6-Dichloro-3-[N-methyl-N-[4-(methylcarbamoyl)-cinnamoylglycyl]amino]benzyloxy]-4-(2-methyloxyethylamino)-2-methylquinoline NMR (CDCl$_3$-CD$_3$OD, δ) : 2.53 (3H, s), 2.98 (3H, s), 3.26 (3H, s), 3.41 (3H, s), 3.55 (2H, br t, J=6Hz), 3.70–3.80 (3H, m), 3.97 (1H, br d, J=17Hz), 5.49 (1H, d, J=10Hz), 5.56 (1H, d, J=10Hz), 6.39 (1H, s), 6.54 (1H, d, J=15Hz), 7.22 (1H, br d, J=7.5Hz), 7.38–7.53 (6H, m), 7.64–7.71 (3H, m).
its dihydrochloride
NMR (CDCl$_3$-CD$_3$OD, δ) : 2.63 (3H, s), 2.99 (3H, s), 3.29 (3H, s), 3.38 (3H, s), 3.78 (4H, s), 3.92 (2H, br s), 5.45 (1H, d, J=10Hz), 5.61 (1H, d, J=10Hz), 6.53–6.63 (2H, m), 7.36–7.68 (7H, m), 7.79 (2H, br d, J=7.5Hz), 8.31 (1H, d, J=7.5Hz).

(10) 4-[Bis(2-methoxyethyl)amino]-8-[2,6-dichloro-3-[N-methyl-N-[4-(methylcarbamoyl)-cinnamoylglycyl]amino]benzyloxy]-2-methylquinoline NMR (CDCl$_3$, δ) : 2.68 (3H, br s), 3.00 (3H, d, J=5Hz), 3.25 (3H, s), 3.30 (6H, s), 3.50–3.74 (9H, m), 3.98 (1H, br dd, J=17, 5Hz), 5.60 (2H, s), 6.36 (1H, br s), 6.57 (1H, d, J=15Hz), 6.88 (1H, s), 7.21 (1H, br d, J=8Hz), 7.30–7.60 (6H, m), 7.73 (2H, br d, J=8Hz), 7.79 (1H, d, J=8Hz).
its dihydrochloride
NMR (CDCl$_3$-CD$_3$OD, δ) : 2.71 (3H, s), 2.99 (3H, s), 3.28 (3H, s), 3.38 (6H, s), 3.24–3.71 (4H, m), 3.88 (1H, d, J=17Hz), 4.00–4.08 (4H, m), 4.19 (1H, d, J=17Hz), 5.47 (1H, d, J=10Hz), 5.64 (1H, d, J=17Hz), 6.65 (1H, d, J=15Hz), 6.97 (1H, br s), 7.38 (1H, d, J=15Hz), 7.44 (1H, d, J=8Hz), 7.49–7.61 (5H, m), 7.81 (2H, d, J=8Hz), 7.94 (1H, d, J=8Hz).

(11) 8-[2,6-Dichloro-3-[N-methyl-N-[4-(methylcarbamoyl)-cinnamoylglycyl]amino]benzyloxy]-2-methyl-4-(piperidino)quinoline NMR (CDCl$_3$, δ) : 1.64–1.90 (6H, m), 2.63 (3H, s), 2.99 (3H, d, J=5Hz), 3.10–3.28 (7H, m), 3.70 (1H, br d, J=17Hz), 3.96 (1H, br d, J=17Hz), 5.58 (1H, d, J=10Hz), 5.62 (1H, d, J=10Hz), 6.36 (1H, br d, J=5Hz), 6.55 (1H, d, J=15Hz), 6.72 (1H, s), 7.20 (1H, d, J=8Hz), 7.28–7.59 (7H, m), 7.64 (1H, d, J=8Hz), 7.73 (2H, br d, J=8Hz),
its dihydrochloride
NMR (CDCl$_3$-CD$_3$OD, δ) : 1.81–1.96 (6H, m), 2.78 (3H, br s), 2.99 (3H, s), 3.27 (3H, s), 3.69–3.79 (4H, m), 3.87 (1H, br d, J=17Hz), 4.28 (1H, br d, J=17Hz), 5.48 (1H, br d, J=10Hz), 5.61 (1H, br d, J=10Hz), 6.68 (1H, br d, J=15Hz), 6.85 (1H, br s), 7.32 (1H, br d, J=15Hz), 7.39–7.62 (7H, m), 7.78 (2H, br d, J=8Hz).

(12) 8-[2,6-Dichloro-3-[N-methyl-N-[4-(methylcarbamoyl)-cinnamoylglycyl]amino]benzyloxy]-2-methyl-4-(morpholino)quinoline NMR (CDCl$_3$, δ) : 2.67 (3H, br s), 3.00 (3H, d, J=5Hz), 3.15–3.28 (7H, m), 3.68 (1H, br dd, J=17, 4Hz), 3.88–4.02 (5H, m), 5.62 (2H, br s), 6.37 (1H, br s), 6.53 (1H, br d, J=15Hz), 6.72–6.80 (2H, m), 7.20–7.70 (8H, m), 7.75 (2H, br d, J=8Hz).
its dihydrochloride
NMR (CDCl$_3$-CD3OD, δ) : 2.80–2.90 (3H, overlapped with H$_2$O), 2.98 (3H, s), 3.28 (3H, s), 3.74–3.82 (4H, m), 3.88 (1H, d, J=17Hz), 3.97–4.03 (4H, m), 4.12 (1H, d, J=17Hz), 5.49 (1H, d, J=10Hz), 5.65 (1H, d, J=10Hz), 6.65 (1H, d, J=15Hz), 7.07 (1H, br s), 7.38 (1H, d, J=15Hz), 7.46–7.69 (7H, m), 7.79 (2H, br d, J=8Hz).

EXAMPLE 11

(1) 8-[3-Glycylamino-2,6-dichlorobenzyloxy]-2-methylquinoline was obtained from 8-[2,6-dichloro-3-(phthalimidoacetylamino)benzyloxy]-2-methylquinoline according to a similar manner to that of Preparation 11.

NMR (CDCl$_3$, δ) : 2.73 (3H, s), 3.52 (2H, s), 5.62 (2H, s), 7.20–7.45 (5H, m), 8.01 (1H, d, J=8.5Hz), 8.51 (1H, d, J=8.5Hz).

(2) 8-[3-[(E)-3-(6-Acetamidopyridin-3-yl)acryloylglycylamino]-2,6-dichlorobenzyloxy]2-methylquinoline was obtained according to a similar manner to that of Example 1.
mp: 272–282° C.
NMR (DMSO-d$_6$, δ) : 2.11 (3H, s), 2.60 (3H, s), 4.14 (2H, d, J=5.5Hz), 5.47 (2H, s), 6.76 (1H, d, J=16Hz), 7.34–7.57 (5H, m), 7.60 (1H, d, J=9Hz), 7.92 (1H, d, J=9.0Hz), 8.00 (1H, d, J=9.0Hz), 8.11 (1H, d, J=9.0Hz), 8.20 (1H, d, J=9.0Hz), 8.45–8.60 (2H, m), 9.80 (1H, s), 10.67 (1H, s).

EXAMPLE 12

(1) 8-[2,6-Dichloro-3-(N-ethyl-N-phthalimidoacetylamino)benzyloxy]-2-methylquinoline was obtained by reacting 8-[2,6-dichloro-3-(phthalimidoacetylamino)benzyloxy]-2-methylquinoline with ethyl iodide according to a similar manner to that of Preparation 10.

NMR (CDCl$_3$, δ) : 1.23 (3H, t, J=6Hz), 2.73 (3H, s), 3.39 (1.2H, q, J=6Hz), 3.95–4.10 (2.8Hz), 5.70 (1H, d, J=12Hz), 5.75 (1H, d, J=12Hz), 7.24–7.47 (5H), 7.53 (1H, d, J=8Hz), 7.70–7.76 (2H), 7.83–7.89 (2H), 8.02 (1H, d, J=8Hz).

(2) 8-[2,6-Dichloro-3-(N-ethyl-N-glycylamino)benzyloxy]-2-methylquinoline was obtained according to a similar manner to that of Preparation 11.

NMR (CDCl$_3$, δ) : 1.13 (1.5H, t, J=6Hz), 1.14 (1.5H, t, J=6Hz), 2.74 (3H, s), 2.94 (1H, d, J=18Hz), 3.04 (1H, d, J=18Hz), 3.33 (1H, q, J=6Hz), 4.10 (1H, q, J=6Hz), 5.67 (2H, s), 7.16–7.48 (6H), 8.02 (1H, d, J=8Hz).

(3) 8-[3-[N-[(E)-3-(6-Acetamidopyridin-3-yl)acryloylglycyl]N-ethylamino]-2,6-dichlorobenzyloxy]-2-methylquinoline was obtained according to a similar manner to that of Example 1.

NMR (CDCl$_3$, δ) : 1.18 (3H, t, J=6Hz), 2.23 (3H, s), 2.74 (3H, s), 3.38 (1H, q, J=6Hz), 3.64 (1H, dd, J=18, 4Hz), 3.92 (1H, dd, J=18, 4Hz), 4.15 (1H, q, J=6Hz), 5.67 (2H, s), 6.47 (1H, d, J=15Hz), 6.71 (1H, t, J=4Hz), 7.23–7.56 (7H), 7.83 (1H, dd, J=8, 2Hz), 8.02 (1H, d, J=8Hz), 8.10 (1H, s), 8.20 (1H, d, J=8Hz), 8.35 (1H, d, J=2Hz),
its dihydrochloride
NMR (CDCl$_3$-CD$_3$OD, δ) : 1.20 (3H, t, J=6Hz), 2.42 (3H, s), 3.12 (3H, s), 3.67 (1H, q, J=6Hz), 3.86 (1H, d, J=18Hz), 3.96 (1H, q, J=6Hz), 4.23 (1H, d, J=18Hz), 5.56 (1H, d, J=10Hz), 5.76 (1H, d, J=10Hz), 6.86 (1H, d, J=15Hz), 7.42 (1H, d, J=15Hz), 7.56–7.70 (3H), 7.80–8.02 (4Hz), 8.53 (1H, d, J=8Hz), 8.81 (1H, s), 8.90 (1H, d, J=8Hz).

(4) 8-[2,6-Dichloro-3-[N-ethyl-N-[4-(methylcarbamoyl)cinnamoylglycyl]amino]benzyloxy]-2-methylquinoline was obtained according to a similar manner to that of Example 1.

NMR (CDCl$_3$, δ) : 1.17 (3H, t, J=6Hz), 2.72 (3H, s), 3.02 (3H, d, J=4Hz), 3.37 ( 1H, q, J=6Hz), 3.64 (1H, dd, J=18, 4Hz), 3.90 (1H, dd, J=18, 4Hz), 4.15 (1H, q, J=6Hz), 5.67 (2H, s), 6.25 (1H, q, J=4Hz), 6.52 (1H, d, J=15Hz), 6.71 (1H, t, J=4Hz), 7.23–7.62 (9H), 7.75 (2H, d, J=8Hz), 8.03 (1H, d, J=8Hz).
its hydrochloride
NMR (CDCl$_3$-CD$_3$OD, δ) : 1.21 (3H, t, J=6H), 2.99 (3H), s), 3.11 (3H, s), 3.60 (1H, q, J=6Hz), 3.85–4.07 (3H), 5.60 (1H, d, J=12Hz), 5.75 ( 1H, d, J=12Hz), 6.64 (1H, d, J=15Hz), 7.44 (1H, d, J=15Hz), 7.50–7.98 (10H), 8.94 (1H, d, J=8Hz).

EXAMPLE 13

To a solution of 8-[3-(N-glycyl-N-methylamino)-2,6-dichlorobenzyloxy]-2-methylquinoline (404 mg) and triethylamine (120 mg) in dichloromethane (8 ml) was added bromoacetyl bromide (220 mg) at 5° C. After stirring for 30 minutes at the same temperature, the mixture was washed with water and saturated sodium bicarbonate solution, dried over magnesium sulfate, and concentrated. The residue was purified by flash chromatography (dichloromethane - methanol) to give 8-[3-[N-(bromoacetylglycol)-N-methylamino]-2,6-dichlorobenzyloxy]-2-methylquinoline (327 mg) as an amorphous powder.

NMR (CDCl$_3$, δ) : 2.77 (3H, s), 3.27 (3H, s), 3.55 (1H, dd, J=14, 4Hz), 3.83 (1H, dd, J=14, 4Hz), 3.89 (2H, s), 5.68 (2H, s), 7.23–7.47 (5H, m), 7.50 (1H, d, J=7.5Hz), 8.06 (1H, d, J=7.5Hz).

EXAMPLE 14

A mixture of 8-[3-[N-(bromoacetylglycyl)-N-methylamino]-2,6-dichlorobenzyloxy]-2-methylquinoline (200 mg) and tri-n-butylphosphine (140 µl) in tetrahydrofuran (4 ml) was stirred for 2 hours at ambient temperature. The mixture was concentrated, and the residue was purified by flash chromatography (dichloromethane - methanol) to give 8-[3-[N-[2-(tri-n-butylphosphonio)acetylglycyl]-N-methylamino]-2,6-dichlorobenzyloxy]-2-methylquinoline bromide (128 mg) as an amorphous powder.

NMR (DMSO-d$_6$, δ) : 0.91 (9H, t, J=7.5Hz), 1.31–1.56 (12H, m), 2.20–2.31 (6H, m), 2.61 (3H, s), 3.15 (3H, s), 3.43–3.58 (3H, m), 3.72 (1H, dd, J=15, 4Hz), 5.52 (2H, s), 7.37–7.57 (4H, m), 7.78 (2H, s), 8.22 (1H, d, J=7.5Hz), 8.74 (1H, t, J=4Hz).

EXAMPLE 15

A mixture of 8-[3-[N-(bromoacetylglycyl)-N-methylamino]-2,6-dichlorobenzyloxy]-2-methylquinoline (80 mg) 5-amino-1,3,4-thiadiazole-2-thiol (24 mg), potassium carbonate (42 mg) in dimethylformamide (2 ml) was stirred for 30 minutes at ambient temperature. To the mixture was added water, and the mixture was extracted with ethyl acetate twice. Combined organic layers were washed with water three times, dried over magnesium sulfate and concentrated. The residue was pulverized from diethyl ether to give 8-[3-[N-(5-amino-1,3,4-thiadiazol-2-ylthio)acetylglycol]-N-methylamino]-2,6-dichlorobenzyloxy]-2-methylquinoline (25 mg) as a solid.

mp: >120° C.

NMR (DMSO-d$_6$, δ) : 2.61 (3H, s), 3.14 (3H, s), 3.38 (1H, dd, J=18, 4Hz), 3.68 (1H, dd, J=18, 4Hz), 3.75 (2H, s), 5.47 (1H, d, J=9Hz), 5.55 (1H, d, J=9Hz), 7.30 (2H, s), 7.37–7.57 (4H, m), 7.77 (2H, s), 8.22 (1H, d, J=7.5Hz), 8.40 (1H, t, J=4.5Hz).

EXAMPLE 16

The following compounds were obtained according to a similar manner to that of Example 15.

(1) 8-[3-[N-[2-(2-Benzoxaxolylthio)acetylglycyl]-N-methylamino]-2,6-dichlorobenzyloxy]-2-methylquinoline NMR (DMSO-d$_6$, δ) : 2.59 (3H, s), 3.15 (3H, s), 3.43 (1H, dd, J=15, 4Hz), 3.71 (1H, dd, J=15, 4Hz), 4.20 (2H, s), 5.46 (1H, d, J=12Hz), 5.55 (1H, d, J=12Hz), 7.30–7.66 (8H, m), 7.77 (2H, s), 8.20 (1H, d, J=7.5Hz), 8.58 (1H, t, J=4Hz).

(2) 8-[3-[N-[2-Benzimidazolylthio)acetylglycyl]-N-methylamino]2,6-dichlorobenzyloxy]-2-methylquinoline mp: >120° C.

NMR (DMSO-d$_6$, δ) : 2.61 (3H, s), 3.13 (3H, s), 3.42 (1H, dd, J=15, 4Hz), 3.70 (1H, dd, J=15, 4Hz), 4.07 (2H, s), 5.46 (1H, d, J=15Hz), 5.53 (1H, d, J=15Hz), 7.09–7.16 (3H, m), 7.33–7.55 (5H, m), 7.75 (2H, s), 8.19 (1H, d, J=7.5Hz), 8.58 (1H, t, J=4Hz).

(3) 8-[3-[N-[2-(2-Benzothiadiazolyltio)acetylglycyl]-N-methylamino]-2,6-dichlorobenzyloxy]-2-methylquinoline mp: 174–175° C.

NMR (DMSO-d$_6$, δ) : 2.60 (3H, s), 3.15 (3H, s), 3.45 (1H, dd, J=14, 4Hz), 3.72 (1H, dd, J=14, 4Hz), 4.22 (2H, s), 5.47 (1H, d, J=14Hz), 5.54 (1H, d, J=14Hz),7.33–7.56 (6H, m), 7.76 (2H, s), 7.86 (1H, d, J=7.5Hz), 8.02 (1H, d, J=7.5Hz), 8.21 (1H, d, J=7.5Hz), 8.57 (1H, t, J=5Hz).

(4) 8-[2,6-Dichloro-3-[N-[2-(6-ethoxybenzothiazol-2-ylthio)-acetylglycyl]-N-methylamino]benzyloxy]-2-methylquinoline NMR (DMSO-d$_6$, δ) : 1.36 (3H, t, J=7.5Hz), 2.59 (3H, s), 3.14 (3H, s), (3.44 (1H, dd, J=15, 4Hz), 3.71 (1H, dd, J=15, 4Hz), 4.06 (2H, q, J=7.5Hz), 4.15 (2H, s), 5.46 (1H, d, J=15Hz), 5.53 (1H, d, J=15Hz), 7.05 (1H, dd, J=7.5, 2Hz), 7.34–7.70 (6H, m), 7.73 (2H, s), 8.21 (1H, d, J=7.5Hz), 8.54 (1H, t, J=4Hz).

(5) 8-[3-[N-[2-(4-Aminophenylthio)acetylglycyl]-N-methylamino]-2,6-dichlorobenzyloxy]-2-methylquinoline NMR (CDCl$_3$, δ) : 2.75 (3H, s) 3.26 (3H, s), 3.47 (2H, s), 3.51 (1H, dd, J=14, 4Hz), 3.80 (1H, dd, J=14, 4Hz), 5.62 (2H, s), 6.60 (2H, d, J=7.5Hz), 7.22–7.32 (5H, m), 7.39–7.49 (3H, m), 7.62 (1H, t, J=4Hz), 8.02 (1H, d, J=7.5Hz).

EXAMPLE 17

A mixture of 8-[3-[N-[2-(4-aminophenylthio)-acetylglycyl]-N-methylamino]-2,6-dichlorobenzyloxy]-2-methylquinoline (56 mg) triethylamine (15 mg), and acetic anhydride (15 mg) in dichloromethane (2 ml) was stirred for 4 hours at ambient temperature. The resulting precipitates were collected by filtration to give 8-[3-[N-[2-(4-acetamidophenylthio)acetylglycyl]-N-methylamino)-2,6-dichlorobenzyloxy]-2-methylquinoline (30 mg) as a colorless crystal.

mp: 179–180° C.

NMR (DMSO-d$_6$, δ) : 2.04 (3H, s), 2.62 (3H, s), 3.16 (3H, s), 3.35 (1H, m), 3.66 (2H, s), 3.69 (1H, m), 5.49 (1H, d, J=14Hz), 5.57 (1H, d, J=14Hz), 7.28–7.59 (7H, m), 7.78 (2H, s), 8.20–8.35 (2H, m).

EXAMPLE 18

To a suspension of 8-[3-(N-glycyl-N-methylamino)-2,6-dichlorobenzyloxy]-2-methylquinoline (100 mg) in tetrahydrofuran were added triethylamine (18.8 mg) and 4-methoxycarbonylphenyl chloroformate (39.8 mg) at 0° C. under nitrogen atmosphere, and the mixture was stirred for 1 hour at the same temperature. The solvent was removed, and ethyl acetate and water were added to the residue. The organic layer was dried over magnesium sulfate and concentrated. The residue was purified by preparative thin-layer chromatography (ethyl acetate:n-hexane=2:1, V/V) to give 8-[2,6-dichloro-3-[N-[(4-methoxycarbonylphenoxycarbonyl)glycyl]-N-methylamino]benzyloxy]-2-methylquinoline (30 mg) as an amorphous powder.

NMR (CDCl$_3$, δ) : 2.74 (3H, s), 3.26 (3H, s), 3.54 (1H, dd, J=4, 16Hz), 3.81 (1H, dd, J=4, 16Hz), 3.89 (3H, s), 5.65 (2H, s), 5.95 (1H, t-like) 7.19 (2H, d, J=8Hz), 7.22–7.35 (2H, m), 7.35–7.52 (4H, m), 7.97–8.08 (3H, m).

EXAMPLE 19

To a solution of 8-[3-(N-glycyl-N-methylamino)-2,6-dichlorobenzyloxy]-2-methylquinoline (80 mg) and triethylamine (40 mg) in dimethylformamide was added phenyl 2-benzothiazolylcarbamate (56.2 mg) under nitrogen atmosphere, and the mixture was stirred for 2 hours at 80° C. The reaction mixture was poured into water and extracted with ethyl acetate. The organic layer was washed with water and brine, dried over magnesium sulfate and evaporated in vacuo to give 8-[3-[N-[N'-(2-benzothiazolyl)ureidoacetyl]-N-methylamino]-2,6-dichlorobenzyloxy]-2-methylquinoline (85 mg) as a powder.

NMR (DMSO-$d_6$, δ) : 2.61 (3H, s), 3.17 (3H, s), 3.51 (1H, dd, J=4, 16Hz), 3.77 (1H, dd, J=4, 16Hz), 5.48 (1H, d, J=10Hz), 5.56 (1H, d, J=10Hz), 7.10 (1H, t-like), 7.21 (1H, t, J=8Hz), 7.31–7.66 (7H, m), 7.80 (2H, s-like), 7.88 (1H, d, J=8Hz), 8.21 (1H, d, J=8Hz).

EXAMPLE 20

To a solution of methyl 2-aminoisonicotinate (500 mg) and triethylamine (549.6 μl) in dichloromethane (5 ml) was added phenyl chloroformate (433 μl) at 0° C., under nitrogen atmosphere. After stirring for 2.5 hours at 0° C., the reaction mixture was concentrated. The residue was dissolved in dimethylformamide (13 ml), and 8-[3-(N-glycyl-N-methylamino)-2,6-dichlorobenzyloxy]-2-methylquinoline (1.33 g), and triethylamine (917 μl) were added thereto at ambient temperature under nitrogen atmosphere. The mixture was stirred for 91 hours, and chloroform was added thereto. The organic solution was washed with water, saturated sodium bicarbonate solution and brine and dried over magnesium sulfate. The solvent was removed, and the residue was crystallized from ethyl acetate to give 8-[2,6-dichloro-3-[N-[N'-(4-methoxycarbonylpyridin-2-yl)ureidoacetyl]-N-methylamino]benzyloxy]-2-methylquinoline (916 mg).

mp: 217–220° C.

NMR (DMSO-$d_6$, δ) : 2.61 (3H, s), 3.16 (3H, s), 3.53 (1H, dd, J=16.5, 5.5Hz), 3.77 (1H, dd, J=16.5, 5.5Hz), 3.87 (3H, s), 5.48 (1H, d, J=10.0Hz), 5.55 (1H, d, J=10.0Hz), 7.33–7.58 (4H, m), 7.47 (1H, t, J=8.5Hz), 7.78 (1H, d, J=8.5Hz), 7.80 (1H, d, J=8.5Hz), 7.99 (1H, s), 8.11 (1H, m), 8.21 (1H, d, J=8.5Hz), 8.37 (1H, d, J=6.0Hz), 9.69 (1H, s).

its dihydrochloride mp: 168–173° C.

NMR (DMSO-$d_6$, δ) : 2.11 (3H, s), 2.92 (3H, s), 3.12 (3H, s), 3.66 (1H, dd, J=16.5, 4.5Hz), 3.86 (1H, dd, J=16.5, 4.5Hz), 5.57 (1H, d, J=11.5Hz), 5.61 (1H, d, J=11.5Hz), 6.88 (1H, d, J=8.5Hz), 7.46 (1H, d, J=8.5Hz), 7.66 (1H, t, J=8.5Hz), 7.73 (1H, d, J=8.5Hz), 7.77 (1H, d, J=8.5Hz), 7.83–8.00 (4H, m), 8.57 (1H, br s), 9.01 (1H, br d, J=8.5Hz), 9.48 (1H, br s).

EXAMPLE 21

[3-[N-[N'-Acetamidopyridin-2-yl)ureidoacetyl]-N-methylamino]-2,6-dichlorobenzyloxy]-2 -methylquino line was obtained according to a similar manner to that of Example 20.

mp: 129–134° C.

NMR (CDCl$_3$, δ) : 2.16 (3H, s), 2.71 (3H, s), 3.23 (3H, s), 3.72 (1H, dd, J=16.5, 4.5Hz), 3.93 (1H, dd, J=16.5, 4.5Hz), 5.56 (1H, d, J=10.0Hz), 5.61 (1H, d, J=10.0Hz), 6.40 (1H, d, J=8.5Hz), 7.22–7.34 (5H, m), 7.40–7.52 (3H, m), 7.70 (1H, d, J=8.5Hz), 7.90 (1H, br s), 8.03 (1H, d, J=8.5Hz), 8.90 (1H, s).

EXAMPLE 22

(1) To a stirred solution of N,N'-carbonyldiimidazole (7.14 g) in 1,4-dioxane (250 ml) was added 3-ethoxycarbonylaniline (7.28 g) at 0° C. and the solution was stirred at ambient temperature for 15 hours and then at 40° C. for 5 hours. To the mixture was added 8-[2,6-dichloro-3-(N-glycyl-N-methylamino)benzyloxy]-2-methylquinoline (14.84 g) at ambient temperature and the resulting mixture was heated at 100° C. for 4 hours. After cooling, the mixture was concentrated in vacuo and the residue was purified by flash chromatography (methanol-chloroform) to afford N,N'-bis[[N-[2,4-dichloro-3-(2-methylquinolin-8-yloxymethyl)phenyl]-N-methylamino]-carbonylmethyl]urea (17.63 g).

NMR (CDCl$_3$, δ) : 2.71 (3H x 2, s), 3.19 (3H x 2, s), 3.44 (1H x 2, dd, J=15, 4Hz), 3.72 (1H x 2, dd, J=15, 5Hz), 5.45–5.78 (6H, m), 7.13–7.60 (12H, m), 8.00 (1H x 2, d, J=9Hz).

(2) A mixture of N,N'-bis[[N-2,4-dichloro-3-(2-methylquinolin-8-yloxymethyl)phenol]-N-methylamino]-carbonylmethyl]urea 16 g), 1N sodium hydroxide solution (40 ml) in dioxane (200 ml) was stirred for 4 hours at 80° C. The solvent was removed in vacuo, and water was added to the residue. The resulting precipitates were collected by filtration and washed with water to give 8-[2,6-dichloro-3-methylaminobenzyloxy]-2-methylquinoline (7.20 g) as a solid.

NMR (CDCl$_3$, δ) : 2.73 (3H, s), 2.90 (3H, d, J=6Hz), 4.50 (1H, q-like), 5.60 (2H, s), 6.61 (1H, d, J=8Hz), 7.20–7.32 (3H, m), 7.33–7.43 (12H, m), 8.00 (1H, d, J=8Hz).

(3) 8-[2,6-Dichloro-3-(N-methyl-N-phenoxycarbonylamino)benzyloxy]-2-methylquinoline was obtained by reacting 8-[2,6-dichloro-3-methylaminobenzyloxy]-2-methylquinoline with phenyl chloroformate according to a similar manner to that of Example 18.

NMR (CDCl$_3$, δ) : 2.71 (3H, s), 3.30 (3H, s), 5.64 (1H, d, J=10Hz), 5.70 (1H, d, J=10Hz), 7.00–7.06 (2H, m), 7.03–7.50 (9H, m), 8.00 (1H, d, J=8Hz).

(4) To a solution of bis(trichloromethyl)carbonate (232 mg), pyridine (273 mg) in dichloromethane was added 8-(2,6-dichloro-3-methylaminobenzyloxy)-2-methylquinoline (800 mg) at 0° C. under nitrogen atmosphere, and the mixture was stirred for 1 hour at ambient temperature. To the mixture were added glycine ethyl ester hydrochloride (289 mg) and triethylamine (582 mg), and the mixture was stirred for 3 hours at ambient temperature. The mixture was poured into water and extracted with dichloromethane. The organic layer was washed with water and brine, dried over magnesium sulfate and concentrated. The residue was purified by flash chromatography (chloroform) to give 8-[2,6-dichloro-3-(N'-ethoxycarbonylmethyl-N-methylureido)benzyloxy]-2-methylquinoline (512 mg) as a powder.

NMR (CDCl$_3$, δ) : 1.24 (3H, t, J=7.5Hz), 2.73 (3H, s), 3.22 (3H, s), 3.85 (1H, brpeak), 4.04 (1H, brpeak), 4.16 (2H, q, J=7.5Hz), 4.80 (1H, t-like), 5.61 (2H, s), 7.21–7.35 (2H, m), 7.35–7.51 (4H, m), 8.03 (1H, d, J=8Hz).

EXAMPLE 23

8-[2,6-Dichloro-3-[N'-(ethoxycarbonylmethyl)ureido]-benzyloxy]-2-methylquinoline was obtained from 8-(2,6-dichloro-3-aminobenzyloxy)-2-methylquinoline and glycine ethyl ester hydrochloride according to a similar manner to that of Example 22-(4).

NMR (CDCl$_3$, δ) : 1.06 (3H, t, J=7.5Hz), 2.21 (3H, s), 3.89–4.06 (4H, m), 5.36 (2H, s), 7.13 (1H, dd, J=8, 2Hz), 7.24–7.42 (3H, m), 7.56 (1, t-like), 8.01 (1H, d, J=8Hz), 8.39 (1H, d, J=8Hz), 8.50 (1H, s).

EXAMPLE 24

The following compounds were obtained according to a similar manner to that of Example 3.

(1) 8-[3-[N-[4-Carboxymethoxy)cinnamoylglycyl]-N-methylamino]-2,6-dichlorobenzyloxy]-2-methylquinoline mp: 286.6–290.6° C.

NMR (DMSO-$d_6$, δ) : 2.60 (3H, s), 3.14 (3H, s), 3.49 (1H, dd, J=17, 4Hz), 3.79 (1H, dd, J=17, 5Hz), 4.44 (2H, s), 5.47 (1H, d, J=9Hz), 5.54 (1H, d, J=9Hz), 6.62 (1H, d, J=15Hz), 6.87 (2H, d, J=9Hz), 7.27–7.58 (7H, m), 7.75 (1H, d, J=9Hz), 7.79 (1H, d, J=9Hz), 8.16 (1H, m), 8.20 (1H, d, J=9Hz).

(2) 8-[3-[N-[(2-Carboxy-3-methylquinoline-6-carbonylglycyl]-N-methylamino]-2,6-dichlorobenzyloxy]-2-methylquinoline NMR (DMSO-$d_6$, δ) : 2.57 (3H, s), 2.61 (3H, s), 3.17 (3H, s), 3.63 (1H, dd, J=16, 5Hz), 3.92 (1H, dd, J=16, 5Hz), 5.50 (2H, s), 7.33–7.66 (4H, m), 7.75–7.88 (2H, m), 8.06–8.36 (3H, m), 8.36–8.55 (2H, m), 8.96 (1H, t-like0.

(3) 8-[3-[N-[N'-(4-Carboxypyridin-2-yl)ureidoacetyl]-N-methylamino]-2,6-dichlorobenzyloxy]-2-methylquinoline mp: 201–207° C.

NMR (DMSO-$d_6$, δ) : 2.61 (3H, s), 3.16 (3H, s), 3.54 (1H, dd, J=16.5, 5Hz), 3.78 (1H, dd, J=16.5, 5.5Hz), 5.47 (1H, d, J=10.0Hz), 5.53 (1H, d, J=10.Hz), 7.30–7.58 (4H, m), 7.47 (1H, t, J=8.5Hz), 7.77 (1H, d, J=8.5Hz), 7.80 (1H, d, J=8.5Hz), 7.90 (1H, s), 8.21 (1H, d, J=8.5Hz), 8.30 (1H, m), 8.34 (1H, d, J=6.0Hz), 9.66 (1H, s).

(4) 8-[3-(N'-Carboxymethylureido)-2,6-dichlorobenzyloxy]-2-methylquinoline

NMR (DMSO-$d_6$, δ) : 2.60 (3H, s), 3.86 (1H, d, J=6Hz), 5.42 (2H, s), 7.35–7.55 (6H, m), 8.20 (1H, d, J=8Hz), 8.26 (1H, d, J=8Hz), 8.50 (1H, s).

(5) 8-[3-(N'-Carboxymethyl-N-methylureido)-2,6-dichlorobenzyloxy]-2-methylquinoline NMR (DMSO-$d_6$, δ) : 2.61 (3H, s), 3.10 (3H, s), 3.61 (2H, d, J=6Hz), 5.46 (2H, s), 6.46 (1H, brpeak, 7.38–7.58 (5H, m), 7.67 (1H, d, J=8Hz), 8.21 (1H, d, J=8Hz).

EXAMPLE 25

The following compounds were obtained according to a similar manner to that of Example 7.

(1) 8-[2,6-Dichloro-[3-[N-methyl-N-[4-(methylcarbamoyl)-cinnamoylglycyl]amino]benzyloxy]-2-methylquinoline (from 8-[3-[N-[4-(carboxymethoxy)-cinnamoylglycyl]-N-methylamino]-2,6-dichlorobenzyloxy]-2-methylquinoline and methylamine hydrochloride)

NMR (CDCl$_3$, δ) : 2.74 (3H, s), 2.90 (3H, d, J=5Hz), 3.27 (3H, s), 3.65 (1H, dd, J=17, 4Hz), 3.94 (1H, dd, J=17, 5Hz), 4.50 (2H, s), 5.63 (1H, d, J=9Hz), 5.66 (1H, d, J=9Hz), 6.36 (1H, d, J=15Hz), 6.55 (1H, br s), 6.61 (1H, br t, J=5Hz), 6.88 (2H, d, J=9Hz), 7.22–7.34 (3H, m), 7.37–7.58 (6H, m), 8.02 (1H, d, J=9Hz).

its hydrochloride

NMR (DMSO-$d_6$, δ) : 2.90 (3H, s), 3.16 (3H, s), 3.29 (3H, s), 3.87 (1H, d, J=17Hz), 4.02 (1H, d, J=17Hz), 4.50 (2H, s), 5.60 (1H, d, J=9Hz), 5.70 (1H, d, J=9Hz), 6.46 (1H, d, J=15Hz), 6.84–6.97 (2H, m), 7.36–7.67 (7H, m), 7.75–7.95 (4H, m), 8.88 (1H, br d, J=7.5Hz).

(2) 8-[2,6-Dichloro-3-[N-methyl-N-[2-(methylcarbamoyl)-3-methylquinoline-6-carbonyl]glycyl] amino]benzyloxy]-2-methylquinoline (from 8-[3-[N-[(2-carboxy-3-methylquinoline-6-carbonyl)glycyl]-N-methylamino]-2,6-dichlorobenzyloxy]-2-methylquinoline and methylamine hydrochloride)

NMR (CDCl$_3$, δ) : 2.74 (3H, s), 2.88 (3H, s), 3.07 (3H, d, J=5Hz), 3.31 (3H, s), 3.79 (1H, dd, J=4, 17Hz), 4.08 (1H, dd, J=5, 17Hz), 5.66 (2H, s), 7.23–7.48 (6H, m), 7.51 (1H, d, J=8Hz), 8.03 (1H, d, J=8Hz), 8.05–8.11 (2H, m), 8.19 (1H, q-like), 8.28 (1H, s-like).

its dihydrochloride

NMR (DMSO-$d_6$, δ) : 2.61 (3H, s), 2.85 (3H, d, J=5Hz), 2.90 (3H, s), 3.17 (3H, s), 3.70 (1H, d, J=5, 16Hz), 2.98 (1H, dd, J=5, 16Hz), 5.60 (1H, d, J=10Hz), 5.66 (1H, d, J=10Hz), 7.78–7.98 (2H, m), 8.05–8.18 (2H, m), 8.33 (1H, s-like), 8.45 (1H, s-like), 8.70 (1H, q-like), 8.92–9.07 (2H, m).

(3) 8-[2,6-Dichloro-3-[N-[N'-[4-dimethylcarbamoyl)pyridin-2-yl]ureidoacetyl]-N-methylamino]benzyloxy]-2-methylquinoline (from 8-[3-[N-[N'-(4-carboxypyridin-2-yl-ureidoacetyl]-M-nethylamino]2,6-dichlorobenzyloxy]-2-methylquinoline and dimethylamine hydrochloride)

mp: 118–123° C.

NMR (DMSO-$d_6$, δ) : 2.60 (3H, s), 2.83 (3H, s), 2.97 (3H, s), 3.16 (3H, s), 3.53 (1H, dd, J=16.5, 5.5Hz), 3.78 (1H, dd, J=16.5, 5.5Hz), 5.47 (1H, d, J=10.0Hz), 5.53 (1H, d, J=10.0Hz), 6.91 (1H, d, J=5.5Hz), 7.30–7.58 (4H, m), 7.47 (1H, t, J=8.5Hz), 7.76 (1H, d, J=8.5Hz), 7.80 (1H, d, J=8.5Hz), 8.21 (1H, d, J=8.5Hz), 8.26 (1H, d, J=5.5Hz), 8.32 (1H, m), 9.59 (1H, s).

its dihydrochloride mp: 166–173° C.

NMR (DMSO-$d_6$, δ) : 2.85 (3H, s), 2.93 (3H, s), 2.97 (3H, s), 3.13 (3H, s), 3.60 (1H, dd, J=16.5, 5.5Hz), 3.82 (1H, dd, J=16.5, 5.5Hz), 5.61 (2H, s), 6.96 (1H, d, J=6.0Hz), 7.33 (1H, s), 7.78–7.99 (6H, m), 8.23 (1H, d, J=6.0Hz), 8.29 (1H, m), 9.00 (1H, br d, J=8.5Hz), 9.87 (1H, s).

(4) 8-[2,6-Dichloro-3-[N'-(phenylcarbamoylmethyl)-ureido]benzyloxy]-2-methylquinoline (from 8-[3-N'-carboxymethylureido)-2,6-dichlorobenzyloxy]-2-methylquinoline and aniline)

NMR (DMSO-$d_6$, δ) : 2.60 (3H, s), 4.01 (1H, d, J=6Hz), 5.44 (2H, s), 7.05 (1H, t, J=8Hz), 7.27–7.55 (9H, m), 7.61 (2H, d, J=8Hz), 8.21 (1H, d, J=8Hz), 8.28 (1H, d, J=8Hz), 8.58 (1H, s).

(5) 8-[2,6-Dichloro-3-[N'-(phenylcarbamoylmethyl)-N-methylureido]benzyloxy]-2-methylquinoline (from 8-[3-N'-carboxymethyl-N-methylureido)-2,6-dichlorobenzyloxy]-2-methylquinoline and aniline)

NMR (CDCl$_3$, δ) : 2.50 (3H, s), 3.27 (3H, s), 5.59 (2H), s), 6.08 (1H, t-like), 6.83–6.98 (3H, m), 7.10 (1H, d, J=8Hz), 7.20–7.30 (3H, m), 7.38–7.55 (4H, m), 7.91 (1H, d, J=8Hz), 8.46 (1H, s).

(6) 8-[3-[N'-(Benzylcarbamoylmethyl)-N-methylureido]-2,6-dichlorobenzyloxy]-2-methylquinoline (from 8-[3-N'-carboxymethyl-N-methylureido)-2,6-dichlorobenzyloxy]-2-methylquinoline and benzylamine)

NMR (CDCl$_3$, δ) : 2.65 (3H, s), 3.20 (3H, s), 3.70–4.48 (4H, brpeak), 5.41–5.60 (2H, brpeak), 5.65 (1H, t-like), 7.35 (4H, m), 7.42–7.50 (3H, m), 8.05 (1H, d, J=8Hz).

EXAMPLE 26

To a mixture of 8-[2,6-dichloro-3-[N-methyl-N-[(E)-3-(6-methylaminopyridin-3-yl)acryloylglycyl]amino] benzyloxy]-2-methylquinoline (100 mg) and triethylamine (23.3 mg) in dichloromethane was added acetyl chloride (15.3 mg) under nitrogen in ice water bath, and the mixture was stirred for 3 hours at room temperature. The reaction mixture was poured into water and extracted with ethyl acetate. The organic layer was washed with water, saturated sodium bicarbonate solution and brine, dried over magnesium sulfate and evaporated in vacuo. The residue was purified by preparative thin-layer chromatography (dichloromethane:methanol=20:1, V/V) to give 8-[2,6-dichloro-3-[N-methyl-N[(E)-3-[6-(N-methylacetamido)pyridin-3-yl]acryloylglycyl]amino]-benzyloxy]-2-methylquinoline (50 mg) as an amorphous powder.

NMR (CDCl$_3$, δ) : 2.17 (3H, s), 2.71 (3H, s), 3.29 (3H, s), 3.41 (3H, s), 3.70 (1H, dd, J=4, 16Hz), 3.95 (1H, dd, J=4, 16Hz), 5.60–5.69 (2H, m), 6.52 (1H, d, J=16Hz), 6.72 (1H, t-like), 7.22–7.52 (7H, m), 7.56 (1H, d, J=16Hz), 7.83 (1H, dd, J=2, 8Hz), 8.03 (1H, d, J=8Hz), 8.54 (1H, d, J=2Hz).
its dihydrochloride NMR (DMSO-d$_6$, δ) : 2.10 (3H, s), 2.88 (3H, s), 3.13 (3H, s), 3.31 (3H, s), 3.89 (1H, dd, J=4, 16Hz), 5.56–5.70 (2H, m), 6.87 (1H, d, J=16Hz), 7.42 (1H, d, J=16Hz), 7.61 (1H, d, J=8Hz), 7.66–7.97 (6H, m), 8.03 (1H, d, J=8Hz), 8.35 (1H, t-like), 8.61 (1H, d, J=2Hz), 8.91 (1H, brpeak).

EXAMPLE 27

(1) A solution of 8-hydroxy-2-methylquinoline (737 mg) in dimethylformamide was dropwise added to a solution of sodium hydride (60% in oil, 185 mg) in dimethylformamide under ice-bath cooling, and the mixture was stirred for 1 hour at the same temperature. To the mixture was added 2,6-dichloro-1-methylsulfonyloxymethyl-3-(methoxymethoxy)benzene (1.46 g) under ice-bath cooling, and the mixture was stirred for 1 hour at the same temperature. The reaction mixture was poured into water and extracted with ethyl acetate. The organic layer was washed with water and brine, dried over magnesium sulfate and evaporated in vacuo. The residue was purified by silica gel column chromatography (ethyl acetate-n-hexane) to give 8-[2,6-dichloro-3-(methoxymethoxy)-benzyloxy]-2-methylquinoline as an oil.

NMR (CDCl$_3$, δ) : 2.75 (3H, s), 3.53 (3H, s), 5.26 (2 H, s), 5.63 (2H, s), 7.15 (1H, d, J=8Hz), 7.23–7.45 (5H, m), 8.00 (1H, d, J=8Hz).

(2) To a solution of 8-[2,6-dichloro-3-(methoxymethoxy)benzyloxy]-2-methylquinoline (1.57 g) in methanol was dropwise added conc. hydrochloric acid (2.7 ml) at 0° C., and the mixture was stirred for 5 minutes. The solvent was removed, and water was added thereto. The mixture was neutralized with saturated sodium bicarbonate solution, and the resulting participates were collected by filtration to give 8-(2,6-dichloro-3-hydroxybenzyloxy)-2-methylquinoline (734 mg) as a solid.

NMR (DMSO-d$_6$, δ) : 2.73 (3H, s), 5.44 (2H, s), 7.10 (1H, d, J=8Hz), 7.34 (1H, d, J=8Hz), 7.53–7.76 (4H, m), 8.48–8.64 (1H, brpeak).

(3) 8-[2,6-Dichloro-3-(2-phthalimidoethoxy)benzyloxy]-2-methylquinoline was obtained by reacting 8-[2,6-dichloro-3-hydroxybenzyloxy]-2-methylquinoline with 2-phthalimodoethyl bromide according to a similar manner to that of Preparation 27-(4).

NMR (CDCl$_3$, δ) : 2.70 (3H, s), 4.16 (2H, t, J=5Hz), 4.28 (2H, t, J=5Hz), 5.55 (2H, s), 6.95 (1H, d, J=8Hz), 7.20 (1H, dd, J=2, 8Hz), 7.23–7.31 (2H, m), 7.31–7.43 (2H, m), 7.67–7.76 (2H, m), 7.79–7.91 (2H, m), 7.99 (1H, d, J=8Hz).

(4) 8-[3-(2-Aminoethoxy)-2,6-dichlorobenzyloxy]-2-methylquinoline was obtained according to a similar manner to that of Preparation 11.

NMR (CDCl$_3$, δ) : 2.72 (3H, s), 3.17 (2H, t, J=5Hz), 4.08 (2H, t, J=5Hz), 5.60 (2H, s), 5.90 (1H, d, J=8Hz), 7.20–7.30 (3H, m), 7.30–7.46 (2H, m), 8.03 (1H, d, J=8Hz).

(5) To a solution of 8-[3-(2-aminoethoxy)-2,6-dichlorobenzyloxy]-2-methylquinoline (11 mg) in dichloromethane were added pyridine (3.46 g) and acetic anhydride (4.47 mg), and the mixture was stirred for 30 minutes. The reaction mixture concentrated, and the reside was purified by preparative thin-layer chromatography (dichloromethane:methanol=10:1, V/V) to give 8-[3-(2-acetamidoethoxy)-2,6-dichlorobenzyloxy]-2-methylquinoline (6 mg) as an amorphous powder.

NMR (CDCl$_3$, δ) : 1.97 (3H, s), 2.71 (3H, s), 3.61 (2H, q, J=5Hz), 4.10 (2H, t, J=5Hz), 5.56 (2H, s), 6.83 (1H, d, J=8Hz), 6.99 (1H, t-like), 7.20–7.28 (2H, m), 7.31 (1H, d, J=8Hz), 7.41 (2.2H, d-like), 8.04 (1H, d, J=8Hz).

(6) 8-[2,6-Dichloro-3-[2-[4-methylcarbamoyl)cinnamimido]-ethoxy]benzyloxy]-2-methylquinoline was obtained from 8-[2-aminoethoxy)-2,6-dichlorobenzyloxy]-2-methylquinoline and 4-(methylcarbamoyl)cinnamic acid according to a similar manner to that of Example 1.

NMR (CDCl$_3$, δ) : 2.42 (3H, s), 2.78 (3H, d, J=5Hz), 3.75 (2H, q, J=5Hz), 4.14 (2H, t, J=5Hz), 5.49 (2H, s), 6.66 (1H, d, J=8Hz), 6.72 (1H, d, J=16Hz), 6.99 (1H, d, J=8Hz), 7.21–7.29 (1H, m), 7.35–7.51 (4Hz, m), 7.55 (1H, d, J=16Hz), 7.77 (2H, d, J=8Hz), 7.97 (1H, q-like), 8.00–8.07 (2H, m).

EXAMPLE 28

(1) 8-[2,6-Dichloro-3-[N-ethoxycarbonylmethyl-N-phthalimidoacetyl)amino]benzyloxy]-2-methylquinoline was obtained by reacting 8-[2,6-dichloro-3-(phthalimodoacetylamino)benzyloxy]-2-methylquinoline with ethyl bromoacetate according to a similar manner to that of Preparation 10.

mp: 211–213° C.

NMR (CDCl$_3$, δ) : 1.28 (3H, t, J=7.5Hz), 2.73 (3H, s), 3.68 (1H, d, J=17Hz), 4.03 (1H, d, J=17Hz), 4.13–4.30 (3H), 5.00 (1H, d, J=17Hz), 5.65 (1H, d, J=10Hz), 5.70 (1H, d, J=10Hz), 7.23–7.31 (2H), 7.36–7.49 (3H), 7.69–7.75 (2H), 7.81–7.91 (3H), 8.01 (1H, d, J=8Hz).

(2) To the solution of 8-[2,6-dichloro-3-[N-ethoxycarbonylmethyl-N-(phthalimodoacetyl)amino]benzyloxy]-2-methylquinoline (572 mg) in dichloromethane (5.3 ml) was added 30% solution of methylamine in methanol (2 ml) at ambient temperature. After stirring for 24 hours, the reaction mixture was evaporated in vacuo. The residue was purified by flash column chromatography (silica gel 50 ml) eluting with dichloromethane:methanol (20:1, V/V) and by crystallizing from isopropyl ether to give 8-[2,6-dichloro-3-2,5-dioxopiperazin-1-yl)benzyloxy]-2-methylquinoline (187 mg) as colorless crystals.

mp: 211–213° C.

NMR (CDCl$_3$, δ) : 2.74 (3H, s), 4.09–4.21 (3H), 4.40 (1H, d, J=17Hz), 5.62 (2H, s), 6.38 (1H, br s), 7.21–7.51 (6H), 8.01 (1H, d, J=8Hz).

(3) 8-[2,6-Dichloro-3-(4-ethoxycarbonylmethyl-2,5-dioxopiperazin-1-yl)benzyloxy]-2-methylquinoline was obtained by reacting 8-[2,6-dichloro-3- 2,5-dioxopiperazin-1-yl)benzyloxy]-1-methylquinoline with ethyl bromoacetate according to a similar manner to that of Preparation 10.

NMR (CDCl$_3$, δ) : 1.31 (3H, t, J=7.5Hz), 2.74 (3H, s), 4.11–4.36 (7H), 4.48 (1H, d, J=17Hz), 5.61 (2H, s), 7.21–7.32 (3H), 7.36–7.51 (3H), 8.02 (1H, d, J=8Hz).

(4) 8-[2,6-Dichloro-3-(4-carboxymethyl-2,5-dioxopiperazin-1-yl)benzyloxy]-2-methylquinoline was obtained according to a similar manner to that of Example 3.

NMR (DMSO-d$_6$, δ) : 2.61 (3H, s), 4.00–4.37 (5H, m), 4.50 (1H, d, J=16Hz), 5.46 (2H, s), 7.37–7.56 (4H, m), 7.69 (1H, d, J=8Hz), 7.74 (1H, d, J=8Hz), 8.21 (1H, d, J=8Hz).

(5) 8-[2,6-Dichloro-3-[4-[4-(methylcarbamoyl) phenylcarbamoylmethyl]-2,5-dioxopiperazin-1-yl]benzyloxy]-2-methylquinoline was obtained from 8-[2,6-dichloro-3-(4-carboxymethyl-2,5-dioxopiperazin-1-yl)benzyloxy]-2-methylquinoline and 4-amino-N-methylbenzamide according to a similar manner to that of Example 7.

NMR (CDCl$_3$-CD$_3$OD, δ) : 2.62 (3H, s), 3.89 (3H, s), 4.07 (1H, d, J=16Hz), 4.18 (1H, d, J=16Hz), 4.27–4.41 (4H, m), 5.50 (2H, s), 7.19–7.30 (4H, m), 7.37–7.44 (3H, m), 7.56 (2H, d, J=8Hz), 7.70 (2H, d, J=8Hz), 8.02 (1H, d, J=8Hz).

PREPARATION 33

The following compounds were obtained according to a similar manner to that of Preparation 12.

(1) 8-Hydroxy-2-methyl-4-(2,2,2-trifluoroethoxy)quinoline mp: 117–119° C.

NMR (CDCl$_3$, δ) : 2.69 (3H, s), 4.56 (2H, q, J=7.5Hz), 6.60 (1H, s), 7.17 (1H, d, J=8Hz), 7.38 (1H, t, J=8Hz), 7.60 (1H, d, J=8Hz).

(2) 8-Hydroxy-4-propoxy-2-methylquinoline mp:60–62° C.

NMR (CDCl$_3$, δ) : 1.13 (3H, t, J=7.5Hz), 1.89–2.03 (2H, m), 2.65 (3H, s), 4.12 (2H, t, J=8Hz), 6.61 (1H, s), 7.11 (1H, d, J=8Hz), 7.30 (1H, t, J=8Hz), 7.60 (1H, d, J=8Hz).

EXAMPLE 29

The following compounds were obtained according to a similar manner to that of Example 9.

(1) 8-[3-[N-[(E)-3-(6-Acetylaminopyridin-3-yl)acryloylglycy]-N-methylamino]-2,6-dichlorobenzyloxy]-4-dimethylamino-2-methylquinoline (NMR (CDCl$_3$, δ) : 2.21 (3H,s), 2.72 (3H, br s), 3.11 (6H, br s), 3.26 (3H, s), 3.76 (1H, br d, J=17Hz), 4.00 (1H, dd, J=17.5Hz), 5.59 (2H, s), 6.53 (1H, br d, J=15Hz), 6.67 (1H, s), 7.21–7.52 (5H, m), 7.70 (1H, d, J=8Hz), 7.78 (1H, br d, J=8Hz), 8.10 (1H, br d, J=8Hz), 8.20 (1H, s), 8.31 (1H, s).
its trihydrochloride (NMR (CDCl$_3$-CD$_3$OD, δ) : 2.44 (3H, s), 2.77 (3H, br s), 3.27 (3H, s), 3.51 (6H, s), 3.85 (1H, d, J=17Hz), 4.42 (1H, d, J=17Hz), 5.42 (1H, d, J=10Hz), 5.62 (1H, d, J=10Hz), 6.75 (1H, br s), 6.94 (1H, br d, J=15Hz), 7.27 (1H, br d, J=15Hz), 7.43 (1H, d, J=8Hz), 7.50–7.68 (3H, m), 7.82 (1H, d, J=8Hz), 8.14 (1H, br d, J=8Hz), 8.35 (1H, br d, J=8Hz), 8.90 (1H, br s).

(2) 8-[3-[N-[(E)-3-(6-Acetylaminopyridin-3-yl)acryloylglycy]-N-methylamino]-2,6-dichlorobenzyloxy]-4-ethoxy-2-methylquinoline NMR (CDCl$_3$, δ) : 1.55 (3H, br t, J=7.5Hz), 2.20 (3H, s), 2.66 (3H, s), 3.25 (3H, s), 3.66 (1H, dd, J=17, 4Hz), 3.93 (1H, dd, J=17, 5Hz), 4.16–4.29 (2H, m), 5.59 (2H, br s) 6.47 (1H, d, J=15Hz), 6.61 (1H, s), 6.73 (1H, br s), 7.19–7.55 (5H, m), 7.76–7.89 (2H, m), 8.08–8.21 (2H, m), 8.32 (1H, br s).
its dihydrochloride NMR (CDCl$_3$-CD$_3$OD, δ) : 1.63–1.72 (3H, m), 2.42 (3H, s), 3.02 (3H, br s), 3.28 (3H, s), 3.85 (1H, d, J=17Hz), 4.29 (1H, d, J=17Hz), 4.56–4.66 (2H, m), 5.48 (1H, d, J=10Hz), 5.67 (1H, d, J=10Hz), 6.92 (1H, br d, J=15Hz), 7.16–7.63 (5H, m), 7.72 (1H, t, J=8Hz), 7.98 (1H, d, J=8Hz), 8.10–8.16 (1H, m), 8.44–8.51 (1H, m), 8.84–8.92 (1H, m).

(3) 8-[2,6-Dichloro-3-[N-methyl-N-[4-methylcarbamoyl)cinnamoylglycyl]amino]benzyloxy]-2-methyl-4-(2,2,2-trifluoroethoxy)quinoline NMR (CDCl$_3$, δ) : 2.69 (3H, s), 3.01 (3H, d, J=5Hz), 3.25 (3H, s), 3.63 (1H, dd, J=4, 18Hz), 3.92 (1H, dd, J=4, 18Hz), 4.55 (2H, q, J=8Hz), 5.60 (1H, d, J=10Hz), 5.65 (1H, d, J=10Hz), 6.23 (1H, q-like), 6.53 (1H, d, J=16Hz), 6.62 (1H, s-like), 6.70 (1H, t-like), 7.27–7.35 (2H, m), 7.39–7.63 (5H, m), 7.75 (2H, d, J=8Hz), 7.85 (1H, d, J=8Hz).
its hydrochloride NMR (DMSO-d$_6$, δ) : 2.79 (3H, d, J=3Hz), 2.88 (3H, s), 3.13 (3H, s), 3.60 (1H, dd, J=5, 16Hz), 5.36 (2H, q, J=8Hz), 5.60 (1H, d, J=10Hz), 5.66 (1H, d, J=10Hz), 6.88 (1H, d, J=16Hz), 7.41 (1H, d, J=16Hz), 7.55–7.67 (2H, m), 7.73 (1H, s-like), 7.80–8.01 (7H, m), 8.38 (1H, t-like), 8.51 (1H, q-like).

(4) 8-[3-[N-[(E)-3-(6-Acetylaminopyridin-3-yl)acryloylglycy]-N-methylamino]-2,6-dichlorobenzyloxy]-2-methyl-4-(2,2,2-trifluoroethoxy)quinoline NMR (CDCl$_3$, δ) : 2.21 (3H, s), 2.70 (3H, s), 3.26 (3H, s), 3.65 (1H, dd, J=17 and 4Hz), 3.94 (1H, dd, J=17 and 5Hz), 4.55 (1H, q, J=7.5Hz), 5.59 (1H, d, J=9Hz), 5.64 (1H, d, J=9Hz), 6.45 (1H, d, J=15Hz), 6.61 (1H, s), 6.71 (1H, br t, J=4Hz), 7.29 (1H, d, J=9Hz), 7.30 (1H, d J=8Hz), 7.42 (1H, d, J=9Hz), 7.48 (1H, t, J=8Hz), 7.52 (1H, d, J=15Hz), 7.81 (1H, dd, J=9 and 1Hz), 7.85 (1H, d, J=9Hz), 8.14 (1H, br s), 8.20 (1H, d, J=9Hz), 8.35 (1H, d, J=1Hz).
its dihydrochloride NMR (CDCl$_3$-CD$_3$OD, δ) : 2.41 (3H, s), 3.09 (3H, br s), 3.28 (3H, s), 3.92 (1H, d, J=17Hz), 4.15 (1H, d, J=17Hz), 5.10 (2H, br q, J=9Hz), 5.49 (1H, d, J=9Hz), 5.68 (1H, d, J=9Hz), 6.89 (1H, br d, J=15Hz), 7.41 (1H, d, J=15Hz), 7.53–7.64 (3H, m), 7.70–7.84 (2H, m), 7.99 (1H, d, J=9Hz), 8.04 (1H, d, J=8Hz), 8.59 (1H, br d, J=8Hz), 8.88 (1H, br s).

(5) 8-[2,6-Dichloro-3-[N-methyl-N-[4-methylcarbamoyl)cinnamoylglycyl]amino]benzyloxy]-4-propoxy-2-methylquinoline NMR (CDCl$_3$, δ) : 1.13 (3H, t, J=7.5Hz), 1.91–2.02 (2H, m), 2.66 (3H, br s), 3.00 (3H, d, J=5Hz), 3.25 (3H, s), 3.64 (1H, dd, J=17, 4Hz), 3.93 (1H, dd, J=17, 5Hz), 4.13 (2H, br t, J=7.5Hz), 5.60 (1H, d, J=10Hz), 5.65 (1H, d, J=10Hz), 6.33 (1H, br d, J=5Hz), 6.53 (1H, d, J=15Hz), 6.63 (1H, s), 6.72 (1H, br s), 7.22–7.32 (2H, m), 7.37 (1H, br t, J=8Hz), 7.47 (1H, d, J=8Hz), 7.51 (2H, d, J=8Hz), 7.58 (1H, d, J=15Hz), 7.75 (2H, d, J=8Hz), 7.88 (1H, d, J=8Hz).
its hydrochloride NMR (CDCl$_3$-CD$_3$OD, δ) : 1.18 (3H, t, J=7.5Hz), 2.00–2.13 (2H, m), 2.98 (3H, s), 3.00 (3H, s), 3.29 (3H, s), 3.88 (1H, d, J=17Hz), 4.15 (1H, d, J=17Hz), 4.49 (2H, br t, J=7.5Hz), 5.51 (1H, d, J=10Hz), 5.68 (1H, d, J=10Hz), 6.65 (1H, d, J=15Hz), 7.26 (1H, br s), 7.39 (1H, d, J=15Hz), 7.48–7.60 (5H, m), 7.69–7.81 (3H, m), 7.97 (1H, br d, J=8Hz).

(6) 8-[3-[N-[(E)-3-(6-Acetylaminopyridin-3-yl)acryloylglycyl]-N-methylamino]-2,6-dichlorobenzyloxy]-4-propoxy-2-methylquinoline NMR (CDCl$_3$, δ) : 1.15 (3H, t, J=5Hz), 1.91–2.02 (2H, m), 2.21 (3H, s), 2.68 (3H, s), 3.28 (3H, s), 3.67 (1H, dd, J=17, 4Hz), 3.96 (1H, dd, J=17, 5Hz), 4.13 (2H, br t, J=7.5Hz), 5.61 (1H, d, J=10Hz), 5.68 (1H, d, J=10Hz), 6.48 (1H, d, J=15Hz), 6.63 (1H, s), 6.73 (1H, br s), 7.21–7.40 (3H, m), 7.45–7.58 (2H, m), 7.79–7.90 (2H, m ), 8.12–8.23 (2H, m), 8.34 (1H, br s).
its dihydrochloride NMR (CDCl$_3$-CD$_3$OD, δ) : 1.18 (3H, t, J=7.5Hz), 2.00–2.13 (2H, m), 2.42 (3H, s), 3.00 (3H, br s), 3.28 (3H, s), 3.88 (1H, d, J=17Hz), 4.29 (1H, d, J=17Hz), 4.49 (2H, br t, J=7.5Hz), 5.47 (1H, d, J=10Hz), 5.66 (1H, d, J=10Hz), 6.90 (1H, br d, J=15Hz), 7.25 (1H, br s), 7.36 (1H, br d, J=15Hz), 7.50–7.64 (3H, m), 7.73 (1H, t, J=8Hz), 7.97 (1H, d, J=8Hz), 8.13 (1H, br d, J=8Hz), 8.48 (1H, br d, J=8Hz), 8.90 (1H, br s).

(7) 8-[3-[N-[(E)-3-(6-Acetylaminopyridin-3-yl)acryloylglycyl]-N-methylamino]-2,6-dichlorobenzyloxy]-4-isopropoxy-2-methylquinoline NMR (DMSO-$d_6$, δ) : 2.19 (3H, s), 2.66 (3H, s), 3.26 (3H, s), 3.69 (1H, dd, J=4, 18Hz), 3.95 (1H, dd, J=4,18Hz), 4.80 (1H, m), 5.50–5.65 (2H, m), 6.46 (1H, d, J=16Hz), 6.61 (1H, s-like), 6.96 (1H, brpeak), 7.17–7.58 (5H, m), 7.72–7.90 (2H, m), 8.16 (1H, d, J=8Hz), 8.30 (1H, s-like), 8.60 (1H, brpeak).

its dihydrochloride

NMR (DMSO-$d_6$, δ) : 1.49 (6H, d, J=7Hz), 2.11 (3H, s), 2.85 (3H, s), 3.14 (3H, s), 3.59 (1H, dd, J=4, 16Hz), 3.90 (1H, dd, J=4, 16Hz), 5.24 (1H, m), 5.60 (1H, d, J=10Hz), 5.66 (1H, d, J=10Hz), 6.79 (1H, d, J=16Hz), 7.37 (1H, d, J=16Hz), 7.60 (1H, s-like), 7.75–8.05 (7H, m), 8.11 (1H, d, J=8Hz), 8.31 (1H, t-like), 8.48 (1H, d-like).

(8) 8-[3-[N-[(E)-3-(6-Acetylaminopyridin-3-yl)acryloylglycyl]-N-methylamino]-2,6-dichlorobenzyloxy]-4-(2-methoxyethoxy)-2-methylquinoline NMR (CDCl$_3$, δ) : 2.21 (3H, s), 2.67 (3H, s), 3.25 (3H, s), 3.50 (3H, s), 3.65 (1H, dd, J=4, 18Hz), 3.85–4.02 (3H, m), 4.32 (2H, t, J=5Hz), 5.62 (2H, s-like), 6.47 (1H, d, J=16Hz), 6.65 (1H, s-like), 6.71 (1H, brpeak), 7.19–7.41 (3H, m), 7.41–7.57 (2H, m), 7.78–7.92 (2H, m), 8.07 (1H, s-like), 8.19 (1H, d, J=8Hz), 8.34 (1H, d, J=2Hz).

its dihydrochloride

NMR (DMSO-$d_6$, δ) : 2.10 (3H, s), 2.85 (3H, s), 3.14 (3H, s), 3.37 (3H, s), 3.59 (1H, dd, J=4, 16Hz), 3.84–3.96 (3H, m), 4.61–4.68 (2H, m), 5.60 (1H, d, J=10Hz), 5.66 (1H, d, J=10Hz), 6.79 (1H, d, J=16Hz), 7.37 (1H, d, J=16Hz), 7.60 (1H, s-like), 7.78–8.03 (7H, m), 8.11 (1H, d, J=8Hz), 8.31 (1H, t-like), 8.47 (1H, d, J=2Hz).

EXAMPLE 30

(1) Methyl (E)-3-(indol-5-yl)acrylate was obtained by reacting indole-5-carbaldehyde with methyl (triphenylphosphoranilidene)acetate according to a similar manner to that of Preparation 1.

mp: 139.6–142.2° C.

NMR (CDCl$_3$, δ) : 3.80 (3H, s), 6.44 (1H, d, J=15Hz), 6.59 (1H, d-like), 7.20–7.27 (2H, m), 7.33–7.46 (2H, m), 7.75–7.88 (2H, m), 8.27 ( 1H, brpeak)

(2) (E)-3-(Indol-5-yl)acrylic was obtained according to a similar manner to that of Preparation 3.

mp: >185° C. (dec.)

NMR (DMSO-$d_6$, δ) : 6.39 (1H, d, J=16Hz), 6.49 (1H, t-like), 7.36–7.50 (3H, m), 7.69 (1H, d, J=16Hz), 7.83 (1H, s-like).

(3) 8-[2,6-Dichloro-3-[N-methyl-N-[(E)-3-(indol-5-yl)acrylglycyl]amino]benzyloxy]-2-methylquinoline was obtained according to a similar manner to that of Example 1.

NMR (CDCl$_3$, δ) : 2.71 (3H, s), 3.22 (3H, s), 3.62 (1H, dd, J=4, 18Hz), 3.93 (1H, dd, J=4, 18Hz), 5.63 (2H, s-like), 6.43 (1H, d, J=16Hz), 6.50–6.59 (2H, m), 7.17–7.22 (1H, m), 7.22–7.50 (8H, m), 7.70 (1H, d, J=16Hz), 7.76 (1H, s-like), 8.03 (1H, d, J=8Hz), 8.55 (1H, br s).

its dihydrochloride

NMR (DMSO-$d_6$, δ) : 2.90 (3H, s), 3.15 (3H, s), 3.59 (1H, dd, J=4, 16Hz), 3.88 (1H, dd, J=4, 16Hz) 5.54–5.69 (2H, m), 6.47 (1H, s-like), 6.66 (1H, d, J=16Hz), 7.29–7.52 (4H, m), 7.71 (1H, s-like), 7.76–8.02 (6H, m), 8.19 (1H, t-like), 8.95 (1H, brpeak).

EXAMPLE 31

(1) 4-Acetamido-3-methylcinnamic acid was obtained by reacting 4-acetamido-3-methylbenzaldehyde with malonic acid according to a similar manner to that of Preparation 4.

mp: 262–263° C. (dec.)

NMR (DMSO-$d_6$, δ) : 2.09 (3H, s), 2.23 (3H, s), 6.43 (1H, d, J=16Hz), 7.43–7.61 (4H), 9.33 (1H, s).

(2) 8-[3-[N-(4-Acetamido-3-methylcinnamoylglycyl)-N-methylamino]2,6-dichlorobenzyloxy]-2-methylquinoline was obtained according to a similar manner to that of Example 1.

NMR (CDCl$_3$, δ) : 2.22 (3H, s), 2.27 (3H, s), 2.73 (3H, s), 3.25 (3H, s), 3.63 (1H, dd, J=18, 4Hz), 3.94 (1H, dd, J=18, 4Hz), 5.64 (2H, s), 6.41 (1H, d, J=16Hz), 6.62 (1H, br s), 7.05 (1H, br s), 7.22–7.55 (9H), 7.89–8.06 (2H).

its hydrochloride

NMR (DMSO-$d_6$, δ) : 2.09 (3H, s), 2.22 (3H, s), 2.91 (3H, s), 3.15 ( 3H, s), 3.59 (1H, dd, J=18, 4Hz), 3.89 (1H, dd, J=18, 4Hz), 5.64 (2H, s), 6.72 (1H, d, J=16Hz), 7.26–8.00 (10H), 8.28 (1H, t, J=4Hz), 8.97 (1H, br s), 9.38 (1H, s).

EXAMPLE 32

(1) (E)-3-(6-Ethoxypryirin-3-yl)acrylic acid was obtained by reacting -6-etopyridine-3-carbaldehyde with malonic acid according to a similar manner to that of Preparation 4.

mp: 171–172° C.

NMR (CDCl$_3$-CD$_3$OD, δ) : 1.40 (3H, t, J=6Hz), 4.37 (2H, q, J=6Hz), 6.36 (1H, d, J=16Hz), 6.80 (1H, d, J=8Hz), 7.63 (1H, d, J=16Hz), 7.89 (1H, dd, J=8, 1Hz), 8.23 (1H, d, J=1Hz)

(2) 8-[2,6-Dichloro-3-[N-[(E)-3-yl)acrylglycyl]-N-methylamino]benzyloxy]-2-methylquinoline was obtained according to a similar manner to that of Example 1.

NMR (CDCl$_3$, δ) : 1.40 (3H, t, J=6Hz), 2.73 (3H, s), 3.27 (3H, s), 3.65 (1H, dd, J=16, 4Hz), 5.66 (3.94 (1H, dd, J=16, 4Hz), 4.38 (2H, q, J=6Hz), 5.66 (2H, s), 6.38 (1H, d, J=16Hz), 6.62 (1H, t, J=4Hz), 6.72 (1H, d, J=8Hz), 7.23–7.56 (7H), 7.73 (1H, dd, J=8, 2Hz), 8.03 (1H, d, J=8Hz), 8.23 (1H, s).

its dihydrochloride

NMR (DMSO-$d_6$, δ) : 1.33 (3H, t, J=6Hz), 2.92 (3H, s), 3.16 (3H, s), 3.58 (1H, dd, J=16, 4Hz), 3.69 (1H, dd, J=16, 4Hz), 4.33 (2H, q, J=6Hz), 5.65 (2H, s), 6.73 (1H, d, J=16Hz), 6.87 (1H, d, J=8Hz), 7.32–7.99 (8H), 8.23–8.36 (2H), 8.98 (1H, br s).

EXAMPLE 33

(1) To the solution of 2,6-dimethylbenzoic acid (20 g) in conc. sulfuric acid (100 ml) was dropwise added under ice-cooling a mixture of 70% nitric acid and conc. sulfuric acid (21.6 ml), which was prepared by dropwise adding conc. sulfuric acid (10.8 ml) to 70% nitric acid (15.1 ml) under ice-cooling, and the mixture was stirred for 1 hour at the same temperature. Ice-water was added to the reaction mixture, and the resulting precipitates were filtered off. The filtrate was concentrated, and the residue was purified by flash chromatography (dichloromethane:methanol=20:1 including 1% acetic acid) to give 2,6-dimethyl-3-nitrobenzoic acid (7.0 g) as a colorless crystal.

mp: 109–112° C.

NMR (CDCl$_3$, δ) : 2.48 (3H, s), 2.57 (2H, s), 7.22 (1H, d, J=8Hz), 7.87 (1H, d, J=8Hz).

(2) To a solution of 2,6-dimethyl-3-nitrobenzoic acid (3.09 g) in tetrahydrofuran (5 ml) was added borane-methyl sulfide complex (2.41 g) under ice-cooling, and the mixture was stirred for 30 minutes at the same temperature, for 1 hour at ambient temperature, and then for 4 hours under heating. To the mixture was added 1N hydrochloric acid under ice-cooling, and the mixture was allowed to stand overnight. The mixture was extracted with ethyl acetate twice, and the combined organic layer was washed with saturated sodium bicarbonate solution, water and brine, dried over magnesium sulfate and concentrated. The residue was recrystallized with diisopropyl ether to give 2,6-dimethyl-3-nitrobenzyl alcohol (2.296 g) as a pale yellow crystal.

mp: 99–101° C.

NMR (CDCl$_3$, δ) : 1.45 (1H, t, J=5Hz), 2.50 (3H, s), 2.56 (3H, s), 4.80 (2H, d, J=5Hz), 7.15 (1H, d, J=8Hz), 7.64 (1 H, d, J=8Hz).

(3) To a solution of 2,6-dimethyl-3-nitrobenzyl alcohol (1.5 g) in triethylamine (1.01 g) in dichloromethane (15 ml) was dropwise added methanesulfonyl chloride (1.04 g) under ice-cooling, and the mixture was stirred for 30 minutes at the same temperature. The reaction mixture was washed with saturated sodium bicarbonate solution and water, dried over magnesium sulfate and concentrated in vacuo to give a mixture of 2,6-dimethyl-3-nitrobenzyl methansulfonate and 2,6-dimethyl-3-nitrobenzyl chloride, which was used as a starting compound at the following example without further purification.

(4) 8-(2,6-Dimethyl-3-nitrobenzyloxy)-2-methylquinoline was obtained by reaction 8-hydroxy-2-methylquinoline with a mixture of 2,6-dimethyl-3-nitrobenzyl methansulfonate and 2,6-dimethyl-3-nitrobenzyl chloride obtained above according to a similar manner to that of Preparation 6.

mp: 150–152° C.

NMR (CDCl$_3$, δ) : 2.58 (3H, s), 2.65 (3H, s), 2.73 (3H, s), 5.39 (2H, s), 7.18–7.33 (3H, m), 7.38–7.50 (2H, m), 6.60 (1H, s), 7.72 (1H, d, J=8Hz), 8.04 (1H, d, J=8Hz).

(5) To a suspension of 8-(2,6-dimethyl-3-nitrobenzyloxy)-2-methylquinoline (2.34 g), ferric chloride (70.6 mg) and carbon (70.6 mg) in methanol (35 ml) was added hydrazine monohydrate (1.09 g) at 65° C., and the mixture was refluxed for 2 hours. Methanol (20 ml) was added thereto, and the mixture was refluxed for 1 hour. After cooling chloroform was added thereto, and the resulting precipitates were filtered off. The filtrate was concentrated and the residue was dissolved in chloroform. The solution was washed with saturated sodium bicarbonate solution, water and brine, dried over magnesium sulfate and concentrated. The residue was crystallized with ethyl acetate to give 8-(3-Amino-2,6-dimethylbenzyloxy)-2-methylquinoline (1.67 g) as a pale crystal.

mp: 204–205° C.

NMR (CDCl$_3$, δ) : 2.27 (3H, s), 2.37 (3H, s), 2.72 (3H, s) 3.57 (2H, br s), 5.32 (2H, s), 6.67 (1H, d, J=8Hz), 6.91 (1H, d, J=8Hz), 7.18–7.31 (2H, m), 7.36–7.42 (2H, m), 8.00 (1H, d, J=8Hz).

(6) 8-[2,6-Dimethyl-3-(phthalimidoacetylamino) benzyloxy]-2-methylquinoline was obtained according to a similar manner to that of Preparation 9.

mp: 266–268° C.

NMR (CDCl$_3$-CD$_3$OD, δ) : 2.22 (3H, s), 2.42 (3H, s), 2.68 (3H, s), 4.58 (2H, s), 5.28 (2H, s), 7.08 (1H, d, J=8Hz), 7.23–7.51 (5H, m), 7.73–7.80 (2H, m), 7.87–7.95 (2H, m), 8.08 (1H, d, J=8Hz).

(7) 8-[2,6-Dimethyl-3-[N-(phthalimidoacetyl)-N-methylamino]benzyloxy]-2-methylquinoline was obtained according to a similar manner to that of Preparation 10.

mp: 102–110° C.

NMR (CDCl$_3$, δ) : 2.51 (3H, s), 2.57 (3H, s), 2.73 (3H, s), 3.22 (3H, s), 3.96 (1H, d, J=17Hz), 4.19 (1H, d, J=17Hz), 5.38 (1H, d, J=10Hz), 5.43 (1H, d, J=10Hz), 7.17–7.32 (4H, m), 7.37–7.48 (2H, m), 7.67–7.74 (2H, m), 7.80–7.89 (2H, m), 8.02 (1H, d, J=8Hz).

(8) 8-[3-(N-Glycyl-N-methylamino)-2,6-dimethylbenzyloxy]-2-methylquinoline was obtained according to a similar manner to that of Preparation 11.

NMR (CDCl$_3$, δ) : 2.32 (3H, s), 2.53 (3H, s), 2.72 (3H, s), 2.93 (1H, d, J=17Hz), 3.93 (1H, d, J=17Hz), 3.22 (3H, s), 5.36 (2H, s), 7.03 (1H, d, J=8Hz), 7.14 (1H, d, J=8Hz), 7.20–7.32 (2H, m), 7.37–7.48 (2H, m), 8.03 (1H, d, J=8Hz).

(9) 8-[2,6-Dimethyl-3-[N-methyl-N-[4-(methylcarbamoyl)cinnamoylglycyl]amino]benzyloxy]-2-methylquinoline was obtained according to a similar manner to that of Example 1.

NMR (CDCl$_3$, δ): 2.37 (3H, s), 2.52 (3H, s), 2.72 (3H, s), 3.00 (3H, d, J=5 Hz), 3.26 (3H, s), 3.63 (1H, dd, J=17, 4 Hz), 3.88 (1H, dd, J=17, 5 Hz), 5.35 (2H, s), 6.22 (1H, br, d, J=5 Hz), 6.52 (1H, d, J=15 Hz), 6.75 (1H, br s), 7.08 (1H, d, J=8 Hz), 7.18 (1H, d, J=8 Hz), 7.22–7.32 (2H, m), 7.41–7.61 (5H, m), 7.73 (2H, d, J=8 Hz), 8.04 (1H, d, J=8 Hz).

its hydrochloride

NMR (CDCl$_3$—CD$_3$OD, δ): 2.30 (3H, s), 2.48 (3H, s), 2.99 (3H, s), 3.12 (3H, br s), 3.28 (3H, s), 3.80 (1H, d, J=17 Hz), 3.88 (1H, d, J=17 Hz), 5.29 (1H, d, J=10 Hz), 5.49 (1H, d, J=10 Hz), 6.61 (1H, d, J=15 Hz), 7.19–7.28 (2H, m), 7.40–7.53 (3H, m), 7.66 (1H, d, J=8 Hz), 7.75–7.97 (5H, m), 8.90 (1H, d, J=8 Hz).

(10) 8-[3-[N-[(E)-3-(6-Acetylaminopyridin-3-yl)-acryloylglycyl]-N-methylamino]-2,6-dimethylbenzyloxy]-2-methylquinoline was obtained according to a similar manner to that of Example 1.

NMR (CDCl$_3$, δ): 2.21 (3H, s), 2.36 (3H, s), 2.52 (3H, s), 2.72 (3H, s), 3.26 (3H, s), 3.63 (1H, dd, J=17, 4 Hz), 3.89 (1H, dd, J=17, 5 Hz), 5.36 (2H, s), 6.45 (1H, d, J=8 Hz), 6.72 (1H, br t, J=5 Hz), 7.08 (1H, d, J=8 Hz), 7.17 (1H, d, J=8 Hz), 7.22–7.32 (2H, m), 7.39–7.47 (2H, m), 7.50 (1H, d, J=15 Hz), 7.83 (1H, dd, J=8, 3 Hz), 8.00–8.08 (2H, m), 8.20 (1H, br d, J=8 Hz), 8.34 (1H, br s)

its dihydrochloride

NMR (CDCl$_3$—CD$_3$OD, δ): 2.30 (3H, s), 2.44 (3H, s), 2.46 (3H, s), 3.20 (3H, s), 3.27 (3H, s), 3.88 (1H, d, J=17 Hz), 3.96 (1H, d, J=17 Hz), 5.36 (1H, d, J=10 Hz), 5.48 (1H, d, J=10 Hz), 6.88 1H, d, J=15 Hz), 7.21–7.31 (2H, m), 7.48 (1H, d, J=15 Hz), 7.65 (1H, d, J=8 Hz), 7.78 (1H, d, J=8 Hz), 7.87 (1H, t, J=8 Hz), 7.99 (1H, d, J=8 Hz), 8.15 (1H, d, J=8 Hz), 8.44 (1H, d, J=8 Hz), 8.80–8.90 (2H, m).

EXAMPLE 34

The following compounds were obtained according to a similar manner to that of Example 20.

(1) 8-[3-[N-[N'-(6-Methoxycarbonylpyridin-2-yl)-ureidoacetyl]-N-methylamino]-2,6-dichlorobenzyloxy]-2-methylquinoline NMR (DMSO-d$_6$, δ): 2.60 (3H, s), 3.13 (3H, s), 3.53 (1H, dd, J=16.5, 5.5 Hz), 3.77 (1H, dd, J=16.5, 5.5 Hz), 3.88 (3H, s), 5.46 (1H, d, J=10.5 Hz), 5.52 (1H, d, J=10.5 Hz), 7.33–7.59 (4H, m), 7.62 (1H, d, J=8.5 Hz), 7.67–7.76 (1H, m), 7.77 (1H, d, J=8.5 Hz), 7.80 (1H, d, J=8.5 Hz), 7.80–7.91 (1H, m), 7.97 (1H, m), 8.20 (1H, d, J=8.5 Hz), 9.87 (1H, s).

(2) 8-[3-[N-[N'-(2-Acetamidopyridin-4-yl)ureidoacetyl]-N-methylamino]2,6-dichlorobenzyloxy]-2-methylquinoline (3) 8-[2,6-Dichloro-3-[N-[N'-(5-methoxycarbonylpyridin-3-yl)ureidoacetyl]-N-methylamino]benzyloxy]-2-methylquinoline mp: 177–187° C. NMR (DMSO-$d_6$, δ): 2.63 (3H, s), 3.17 (3H, s), 3.47 (1H, dd, J=16.5, 4.5 Hz), 3.69 (1H, dd, J=16.5, 4.5 Hz), 3.87 (3H, s), 5.50 (1H, d, J=10.0 Hz), 5.57 (1H, d, J=10.0 Hz), 6.62 (1H, t, J=4.5 Hz), 7.38–7.79 (6H, m), 8.27 (1H, m), 8.49 (1H, d, J=3.0 Hz), 8.63 (2H, t, J=3.0 Hz), 9.37 (1H, s).

EXAMPLE 35

The following compounds were obtained according to a similar manner to that of Example 3.

(1) 8-[3-[N-[N'-(6-Carboxypyridin-2-yl)ureidoacetyl]-N-methylamino]-2,6-dichlorobenzyloxy]-2-methylquinoline mp: 233–236° C. NMR (DMSO-$d_6$, δ): 2.60 (3H, s), 3.11 (3H, s), 3.54 (1H, dd, J=16.5, 5.5 Hz), 3.76 (1H, dd, J=16.5, 5.5 Hz), 5.46 (1H, d, J=10.0 Hz), 5.51 (1H, d, J=10.0 Hz), 7.36–7.63 (6H, m), 7.66–7.86 (3H, m), 8.20 (1H, m), 8.22 (1H, d, J=8.5 Hz), 9.77 (1H, m).

(2) 8-[3-[N-[N'-(5-Carboxypyridin-3-yl)ureidoacetyl]-N-methylamino]-2,6-dichlorobenzyloxy]-2-methylquinoline

EXAMPLE 36

The following compounds were obtained according to a similar manner to that of Example 7.

(1) 8-[2,6-Dichloro-3-[N-[N'-[6-(dimethylcarbamoyl)pyridin-2-yl]ureidoacetyl]-N-methylamino]benzyloxy]-2-methylquinoline (from 8-[3-[N-[N'-(6-carboxypyridin-2-yl)ureidoacetyl]-N-methylamino]2,6-dichlorobenzyloxy]-2-methylquinoline and dimethylamine hydrochloride)

mp: 110–130° C. NMR (CDCl₃, δ): 2.71 (3H, s), 3.03 (3H, s), 3.16 (3H, s), 3.23 (3H, s), 3.84 (1H, dd, J=16.5, 5.5 Hz), 4.11 (1H, dd, J=16.5, 5.5 Hz), 5.56 (1H, d, J=10.0 Hz), 5.62 (1H, d, J=10.0 Hz), 6.83 (1H, d, J=8.5 Hz), 7.13 (1H, d, J=7.5 Hz), 7.21–7.35 (3H, m), 7.38–7.49 (3H, m), 7.59 (1H, t, J=8.5 Hz), 8.05 (1H, d, J=8.5 Hz), 8.72 (1H, s), 9.16 (1H, m).

its dihydrochloride mp: 169–174° C. NMR (DMSO-$d_6$, δ): 2.93 (6H, s), 3.00 (3H, s), 3.15 (3H, s), 3.58 (1H, dd, J=16.5, 5.5 Hz), 3.82 (1H, dd, J=16.5, 5.5 Hz), 5.63 (2H, s), 7.06 (1H, d, J=7.5 Hz), 7.46 (1H, d, J=8.5 Hz), 7.77 (1H, t, J=7.5 Hz), 7.81–7.99 (6H, m), 8.13 (1H, m), 8.98 (1H, m), 9.62 (1H, s)

(2) 8-[2,6-Dichloro-3-[N-[N'-[5-(dimethylcarbamoyl)pyridin-3-yl]ureidoacetyl]-N-methylamino]benzyloxy]-2-methylquinoline (from 8-[3-[N-[N'-(5-carboxypyridin-3-yl)ureidoacetyl]-N-methylamino]-2,6-dichlorobenzyloxy]-2-methylquinoline and dimethylamine hydrochloride).

EXAMPLE 37

(1) 8-(2-Chloro-5-nitrobenzyloxy)-2-methylquinoline was obtained according to a similar manner to that of Preparation 6.

NMR (DMSO-$d_6$, δ): 2.69 (3H,s), 5.48 (2H, s), 7.32 (1H, d, J=7.5 Hz), 7.43 (1H, d, J=7.5 Hz), 7.46 (1H, d, J=7.5 Hz), 7.53 (1H, d, J=7.5 Hz), 7.83 (1H, d, J=7.5 Hz), 8.22 (2H, dd, J=7.5, 2.0 Hz), 8.77 (1H, d, J=2.0 Hz).

(2) 8-(5-Amino-2-chlorobenzyloxy)-2-methylquinoline was obtained according to a similar manner to that of Preparation 8.

mp: 176–178° C. NMR (DMSO-$d_6$, δ): 2.67 (3H, s), 5.22 (2H, s), 5.31 (2H, s), 6.55 (1H, dd, J=7.5, 2.0 Hz), 6.80 (1H, d, J=2.0 Hz), 7.10–7.16 (2H, m), 7.37–7.48 (3H, m), 8.19 (1H, d, J=7.5 Hz).

(3) 8-[2-Chloro-5-[N-methyl-N-(phthalimidoacetyl)amino]-benzyloxy]-2-methylquinoline was obtained according to a similar manners to those of Preparations 9 and 10.

mp: 120–124° C. NMR (DMSO-$d_6$, δ): 2.67 (3H, s), 3.18 (3H, bs), 4.06 (2H, bs), 5.42 (2H, bs), 7.29 (1H, d, J=7.5 Hz), 7.41–7.96 (10H, m), 8.19 (1H, d, J=7.5 Hz).

(4) 8-[5-(N-Glycyl-N-methylamino)-2-chlorobenzyloxy]-2-methylquinoline was obtained according to a similar manner to that of Preparation 11.

mp: 82–87° C. NMR (CDCl₃, δ): 2.83 (3H, s), 2.94 (2H, s), 3.19 (3H, s), 5.53 (2H, s), 6.95 (1H, d, J=7.5 Hz), 7.07 (1H, bd, J=7.5 Hz), 7.30–7.44 (3H, m), 7.46 (1H, d, J=8.5 Hz), 7.67 (1H, d, J=1.5 Hz), 8.05 (1H, d, J=8,5 Hz).

(5) 8-[2-Chloro-5-[N-methyl-N-[4-(methylcarbamoyl)-cinnamoylglycyl]amino]benzyloxy]-2-methylquinoline was obtained according to a similar manner to that of Example 1.

mp: 221–228° C. NMR (CDCl₃–CD₃OD, δ): 2.79 (3H, s), 3.00 (3H, s), 3.24 (3H, s), 3.76 (2H, s), 5.52 (2H, s), 6.52 (1H, d, J=15.0 Hz), 7.03 (1H, dd, J=7,5, 1.5 Hz), 7.19 (1H, dd, J=7.5, 1.5 Hz), 7.33–7.44 (3H, m), 7.49–7.60 (4H, m), 7.68 (1H, d, J=1.5 Hz), 7.76 (2H, d, J=7.5 Hz), 8.07 (1H, d, J=7.5 Hz).

its hydrochloride mp: 161–171° C. NMR (DMSO-$d_6$, δ): 2.79 (3H, d, J=4.5 Hz), 2.96 (3H, s), 3.20 (3H, bs), 3.42–4.00 (2H, m), 5.58 (2H, s), 6.85 (1H, d, J=15.0 Hz), 7.35 (1H, d, J=15.0 Hz), 7.51 (1H, dd, J=7.5, 1.5 Hz), 7.61–7.85 (5H, m), 7.63 (2H, d, J=8.5 Hz), 7.87 (2H, d, J=8.5 Hz), 7.91 (1H, d, J=7.5 Hz), 8.29 (1H, t, J=5.5 Hz), 8.53 (1H, q, J=4.5 Hz), 8.91 (1H, d, J=7.5 Hz).

(6) 8-[5-[N-[(E)-3-(6-Acetamidopyridin-3-yl)acryloylglycly]-N-methylamino]-2-chlorobenzyloxy]-2-methylquinoline was obtained according to a similar manner to that of Example 1.

mp: 204–205° C. NMR (CDCl₃—CD₃OD, δ): 2.22 (3H, s), 2.81 (3H, s), 3.24 (3H, s), 3.76 (2H, d, J=4.0 Hz), 5.52 (2H, s), 6.45 (1H, d, J=16.0 Hz), 6.82 (1H, bt, J=4.0 Hz), 7.03 (1H, dd, J=7.0, 1.5 Hz), 7.17 (1H, dd, J=8.5, 1.5 Hz), 7.33–7.41 (2H, m), 7.45–7.53 (2H, m), 7.66 (1H, d, J=1.5 Hz), 7.85 (1H, dd, J=8.5, 1.5 Hz), 8.06 (1H, d, J=8.5 Hz), 8.21 (1H, d, J=8.5 Hz), 8.33 (1H, d, J=1.5 Hz).

its dihydrochloride mp: 151–160° C. NMR (DMSO-$d_6$, δ): 2.11 (3H, s), 2.99 (3H, s), 3.20 (3H, bs), 3.62–3.82 (2H, m), 5.60 (2H, s), 6.77 (1H, d, J=16.0 Hz), 7.31 (1H, d, J=16.0 Hz), 7.52 (1H, dd, J=8.5, 1.5 Hz), 7.64–7.73 (2H, m), 7.77–7.89 (3H, m), 7.95–8.03 (2H, m), 8.10 (1H, d, J=8.5 Hz), 8.24 (1H, t, J=5.5 Hz), 8.47 (1H, d, J=1.5 Hz), 9.01 (1H, d, J=8.5 Hz).

EXAMPLE 38

(1) (E)-3-(2-Acetamidopyridin-4-yl)acrylic acid was obtained by reacting 2-acetamidopyridine-4-carbaldehyde with malonic acid according to a similar manner to that of Preparation 4.

mp: 281–282° C. NMR (DMSO-$d_6$, δ): 2.10 (3H, s), 6.63 (1H, d, J=16.0 Hz), 8.39 (1H, d, J=5.5 Hz), 7.51 (1H, d, J=16.0 Hz), 8.20 (1H, s), 8.34 (1H, d, J=5.5 Hz).

(2) 8-[3-[N-[(E)-3-(2-Acetamidopyridin-4-yl)acryloylglycyl]-N-methylamino]-2,6-dichlorobenzyloxy]-2-methylquinoline was obtained according to a similar manner to that of Example 1.

mp: 115–131° C. NMR (DMSO-d$_6$, δ): 2.11 (3H, s), 2.60 (3H, s), 3.13 (3H, s), 3.52 (1H, dd, J=16.5, 6.0 Hz), 3.82 (1H, dd, J=16.5, 6.0 Hz), 5.49 (1H, d, J=10.5 Hz), 5.54 (1H, d, J=10.5 Hz), 6.98 (1H, d, J=16.0 Hz), 7.23 (1H, d, J=5.5 Hz), 7.34 (1H, d, J=16.0 Hz), 7.35–7.50 (3H, m), 7.54 (1H, d, J=7.5 Hz), 7.78 (1H, d, J=8.5 Hz), 7.81 (1H, d, J=8.5 Hz), 8.21 (1H, d, J=7.5 Hz), 8.26 (1H, s), 8.32 (1H, d, J=5.5 Hz), 8.57 (1H, t, J=6.0 Hz).

its dihydrochloride mp: 166–171° C. NMR (DMSO-d$_6$, δ): 2.12 (3H, s), 2.91 (3H, s), 3.16 (3H, s), 3.61 (1H, dd, J=16.5, 6.0 Hz), 3.90 (1H, dd, J=16.5, 6.0 Hz), 5.62 (1H, d, J=11.5 Hz), 5.68 (1H, d, J=11.5 Hz), 7.02 (1H, d, J=16.0 Hz), 7.28 (1H, d, J=5.5 Hz), 7.34 (1H, d, J=16.0 Hz), 7.81 (1H, d, J=8.5 Hz), 7.85 (1H, d, J=8.5 Hz), 7.86–7.93 (3H, m), 7.97 (1H, d, J=8.5 Hz), 8.18 (1H, s), 8.33 (1H, d, J=5.5 Hz), 8.64 (1H, t, J=6.0 Hz), 9.02 (1H, d, J=8.5 Hz).

EXAMPLE 39

A mixture of 8-[3-[N-(bromoacetylglycyl)-N-methylamino]-2,6-dichlorobenzyloxy]-2-methylquinoline (90 mg), 4-nitro-1-(1-piperazinyl)benzene (48 mg) and potassium carbonate (94 mg) in dimethylformamide (2 ml) was stirred at ambient temperature for 1 hour and water added thereto. The mixture was extracted with ethyl acetate twice, and the combined organic layer was washed with water, dried and concentrated. The residue was purified by preparative thin-layer chromatography (10% methanol in dichloromethane) to give 8-[2,6-dichloro-3-[N-methyl-N-[2-[4-(4-nitrophenyl)piperazin-1-yl]acetylglycyl]amino]benzyloxy]-2-methylquinoline (44 mg).

mp: 178–181° C. NMR (CLCl$_3$, δ): 2.66–2.78 (4H, m), 2.75 (3H, s), 3.06 (1H, d, J=15 Hz), 3.12 (1H, d, J=15 Hz), 3.26 (2H, s), 3.43–3.54 (4H, s), 3.55 (1H, dd, J=18 and 4 Hz), 3.91 (1H, dd, J=18 and 4 Hz), 5.66 (2H, s), 6.84 (2H, d, J=7.5 Hz), 7.25–7.34 (4H, m), 7.38–7.53 (3H, m), 7.88 (1H, t, J=4 Hz), 8.03 (1H, d, J=7.5 Hz), 8.13 (2H, d, J=7.5 Hz).

EXAMPLE 40

(1) To methanol (5 ml) in dry ice-acetone bath was added thionyl chloride (0.41 ml) dropwise over 5 minutes. After (E)-3-(6-Aminopyridin-3-yl)acrylic acid (700 mg) was added to the mixture, the reaction mixture was heated at reflux for 1 hour, and the solvent was removed under reduced pressure. The reaction mixture was adjusted to pH 8 with saturated sodium bicarbonate aqueous solution and extracted with dichloromethane. The organic layer was washed with water and brine, dried over magnesium sulfate and evaporated in vacuo. The precipitate was collected by vacuum filtration and washed with isopropyl ether to give methyl (E)-3-(6-aminopyridin-3-yl)acrylate (725 mg) as a solid.

mp: 173–175° C. NMR (DMSO-d$_6$, δ): 3.67 (3H, s), 6.32 (1H, d, J=16 Hz), 6.45 (1H, d, J=8 Hz), 6.57 (2H, s), 7.51 (1H, d, J=16 Hz), 7.79 (1H, dd, J=2, 8 Hz), 8.15 (1H, d, J=2 Hz).

(2) To a mixture of methyl (E)-3-(6-aminopyridin-3-yl)acrylate (700 mg) and triethylamine (477 mg) in dichloromethane (6 ml) was added dropwise 4-bromobutyryl chloride (801 mg) under nitrogen in ice water bath and the mixture was stirred for 3 hours at the same temperature. The reaction mixture was poured into water and extracted with dichloromethane. The organic layer was washed with water, saturated sodium bicarbonate aqueous solution and brine, dried over magnesium sulfate and evaporated in vacuo. the residue was chromatographed on silica gel eluting with chloroform and purified by preparative thin-layer chromatography (n-hexane:ethyl acetate=1:1, v/v) to give methyl (E)-3-[6-(4-bromobutyramido)pyridin-3-yl]acrylate (101 mg).

mp: 155.8–172.7° C. NMR (CDCl$_3$, δ): 2.27 (2H, quint, J=7.5 Hz), 2.62 (2H, t, J=7.5 Hz), 3.53 (2H, t, J=7.5 Hz), 3.81 (3H, s), 6.43 (1H, d, J=16 Hz), 7.64 (1H, d, J=16 Hz), 7.87 (1H, dd, J=2, 8 Hz), 8.12 (1H, br s), 8.23 (1H, d, J=8 Hz), 8.39 (1H, d, J=2 Hz).

(3) To a solution of methyl (E)-3-[6-(4-bromobutyramido)-pyridin-3-yl]acrylate (90 mg) in dimethylformamide was added sodium hydride (6.93 mg) at 0° C. under nitrogen atmosphere, and the mixture was stirred for 1 hour. The reaction mixture was poured into water and extracted with ethyl acetate. The organic layer was washed with water and brine, dried over magnesium sulfate and concentrated in vacuo to give methyl (E)-3-[6-(2-oxopyrrolidin-1-yl)pyridin-3-yl]acrylate (65 mg).

mp: 151–160° C. NMR (CDCl$_3$, δ): 2.16 (2H, quint, J=7.5 Hz), 2.69 (2H, t, J=7.5 Hz), 3.81 (3H, s), 4.11 (2H, t, J=7.5 Hz), 6.43 (1H, d, J=16 Hz), 7.65 (1H, d, J=16 Hz), 7.87 1H, dd, J=2. 8 Hz), 8.44–8.50 (2H, m).

(4) (E)-3-[6-(2-Oxopyrrolidin-1-yl)pyridin-3-yl]acrylic acid was obtained according to a similar manner to that of Preparation 3.

mp: >233° C. (dec.) NMR (CD$_3$OD, δ): 2.14 (2H, quint, J=7.5 Hz), 2.66 (2H, t, J=7.5 Hz), 4.11 (2H, t, J=7.5 Hz), 6.52 (1H, d, J=16 Hz), 7.65 (1H, d, J=16 Hz), 8.06 (1H, d, J=8 Hz), 8.39 (1H, d, J=8 Hz), 8.51 (1H, s-like).

(5) 8-[2,6-Dichloro-3-[N-methyl-N-[(E)-3-[6-(2-oxo-pyrrolidin-1-yl)pyridin-3-yl]acryloylglycyl]-amino]benzyloxy]-2-methylquinoline was obtained according to a similar manner to that of Example 1.

NMR (CDCl$_3$, δ): 2.15 (2H, quint, J=7.5 Hz), 2.69 (2H, t, J=7.5 Hz), 2.74 (3H, s), 3.27 (3H, s), 3.68 (1H, dd, J=4, 18 Hz), 3.95 (1H, dd, J=4, 18 Hz), 4.12 (2H, t, J=7.5 Hz), 5.60–5.71 (2H, m), 6.48 (1H, d, J=16 Hz), 6.66 (1H, t-like), 7.22–7.36 (2H, m), 7.36–7.59 (5H, m), 7.84 (1H, d, J=8 Hz), 8.03 (1H, d, J=8 Hz), 8.39 –8.48 (2H, m).

its dihydrochloride

NMR (DMSO-d$_6$, δ): 2.05 (2H, quint, J=7.5 Hz), 2.59 (2H, t, J=7.5 Hz), 2.91 (3H, s), 3.15 (3H, s), 3.59 (1H, dd, J=4, 16 Hz), 3.89 (1H, dd, J=4, 16 Hz), 4.00 (2H, t, J=7.5 Hz), 5.56–5.72 (2H, m), 6.81 (1H, d, J=16 Hz), 7.39 (1H, d, J=16 Hz), 7.77–8.08 (7H, m), 8.29–8.40 (2H, m), 8.55 (1H, d, J=2Hz), 8.97 (1H, brpeak).

EXAMPLE 41

(1) A mixture of 2-methoxyaniline (10 g), acetic acid (1 ml) and ethyl 2-acetylpropionate (12.3 g) in benzene (30 ml) was refluxed for 24 hours, and then the solvent was removed to give crude ethyl 3-(2-methoxyanilino)-2-methyl-2-butenoate, which was used as a starting compound at the following example without further purification.

(2) A mixture of biphenyl (15 g) and diphenyl ether (15 ml) was heated at 250–270° C., and 3-(2-methoxyanilino)-2-methyl-2-butenoate obtained above was added thereto. The mixture was stirred at the same temperature for 1 hour. During cooling n-hexane (30 ml) was added to the mixture, and the resulting precipitates were collected by filtration. The residue was recrystallized with acetonitrile to give 2,3-dimethyl-4-hydroxy-8-methoxyquinoline (4.49 g).

mp: 299.2° C. NMR (DMSO-d$_6$, δ): 1.95 (2H, s), 2.43 (3H, s), 3.97 (3H, s), 7.13 (1H, d, J=9 Hz), 7.16 (1H, d, J=9 Hz), 7.56–7.66 (1H, m).

(3) To a suspension of 2,3-dimethyl-4-hydroxy-8-methoxyquinoline (3.0 g) in phosphoryl chloride was dropwise added N,N-dimethylaniline (3.58 g) under ice-cooling, and the mixture was stirred for 15 minutes at the same temperature, for 30 minutes at ambient temperature and then for 1 hour at 70° C. The solvent was removed, and saturated sodium bicarbonate solution and 10% solution of methanol in dichloromethan were added to the residue. The organic layer was dried over magnesium sulfate and concentrated. The residue wa purified by flash chromatography (Ethyl acetatein-hexane=1:2 v/v) to give 4-chloro-2,3-dimethyl-8-methoxyquinoline (3.02 g).

mp: 134.4–137.6° C. NMR (CDCl$_3$, δ): 2.55 (3H, s), 2.78 (3H, s), 4.06 (3H, s), 7.02 (1H, d, J=9 Hz), 7.45 (1H, t, J=9 Hz), 7.74 (1H, d, J=9 Hz).

(4) To a solution of 4-chloro-2,3-dimethyl-8-methoxyquinoline (2.5 g) in dichloromethane (5 ml) was added boron tribromide (22.6 ml) under ice-cooling, and the mixture was stirred for 3 hours. The reaction mixture was extracted with 10% solution of methanol in chloroform, and the organic layer was dried over magnesium sulfate and concentrated. The residue was dissolved in acetonitrile under heating, and the mixture was allowed to cool. The resulting precipitates were collected by filtration to give 4-chloro-2,3-dimethyl-8-hydroxyquinoline (1.50 g).

mp: 120.5° C. NMR (CDCl$_3$, δ): 2.54 (3H, s), 2.71 (3H, s), 7.11 (1H, d, J=9 Hz), 7.44 (1H, t, J=9 Hz), 7.59 (1H, d, J=9 Hz).

(5) 4-Chloro-8-[2,6-Dichloro-3-[N-methyl-N-[4-(methylcarbamoyl)cinnamoylglycyl]amino]benzyloxy]-2,3-dimethylquinoline was obtained according to a similar manner to that of Example 9.

NMR (CDCl$_3$, δ): 2.54 (3H, s), 2.72 (3H, s), 2.98 (3H, d, J=5 Hz), 3.24 (3H, s), 3.62 (1H, dd, J=17, 4 Hz), 3.91 (1H, dd, J=17, 5 Hz), 5.60 (1H, d, J=9 Hz), 5.65 (1H, d, J=9 Hz), 6.25 (1H, br q, J=5 Hz), 6.51 (1H, d, J=15 Hz), 6.68 (1H, t, J=5 Hz), 7.24–7.34 (3H, m), 7.43–7.57 (4H, m), 7.57 (1H, d, J=15 Hz), 7.74 (2H, d, J=9 Hz), 7.86 (1H, d, J=9 Hz).

its hydrochloride

NMR (CDCl$_3$—OD, δ): 2.74 (3H, s), 2.99 (3H, s), 3.13 (3H, br s), 3.29 (3H, s), 3.85 (1H, d, J=17 Hz), 4.18 (1H, d, J=17 Hz), 5.59 (1H, d, J=9 Hz), 5.73 (1H, d, J=9 Hz), 6.65 (1H, d, J=15 Hz), 7.40 (1H, d, J=15 Hz), 7.45–7.70 (5H, m), 7.77 (2H, d, J=9 Hz), 7.94 (1H, t, J=9 Hz), 8.08 (1H, d, J=8 Hz).

EXAMPLE 42

(1) Ethyl 3-(2-benzyloxyanilino)-2-butenoate was obtained by reacting 2-benzyloxyaniline with ethyl acetoacetate according to a similar manner to that of Example 41-(1).

NMR (CDCl$_3$, δ): 1.28 (3H, t, J=7 Hz), 1.99 (3H, s), 4.16 (2H, q, J=7.0 Hz), 4.73 (1H, s), 5.11 (2H, s), 6.88–6.99 (2H, m), 7.03–7.15 (2H, m), 7.26–7.40 (2H, m), 7.47 (2H, d, J=8.5 Hz).

(2) 8-Benzyloxy-4-hydroxy-2-methylquinoline was obtained according to a similar manner to that of Example 41-(2).

mp: 155–164° C. NMR (DMSO-d$_6$, δ): 2.40 (3H, s), 5.38 (2H, s), 5.90 (1H, s), 7.13 (1H, t, J=8.5 Hz), 7.22 (1H, d, J=8.5 Hz), 7.28–7.43 (3H, m), 7.53 (2H, d, J=8.5 Hz), 7.57 (1H, d, J=8.5 Hz).

(3) 8-Benzyloxy-4-ethoxycarbonylmethoxy-2-methylquinoline was obtained by reacting 8-benzyloxy-4-hydroxy-2-methylquinoline with ethyl bromoacetate according to a similar manner to that of Preparation 20-(1).

mp: 138–140° C. NMR (CDCl$_3$, δ): 1.31 (3H, t, J=7.5 Hz), 2.74 (3H, s), 4.31 (2H, q, J=7.5 Hz), 4.81 (2H, s), 5.43 (2H, s), 6.53 (1H, s), 7.02 (1H, d, J=8.5 Hz), 7.22–7.40 (4H, m), 7.51 (2H, d, J=8.5 Hz), 7.79 (1H, d, J=8.5 Hz).

(4) A mixture of 8-benzyloxy-4-ethoxycarbonylmethoxy-2-methylquinoline (1.30 g) and palladium on carbon (130 mg) in a mixture of ethanol (8 ml) and dioxane (7 ml) was stirred for 3 hours at ambient temperature under hydrogen atmosphere. The reaction mixture was filtered, and the filtrate was concentrated in vacuo to give 4-ethoxycarbonylmethoxy-8-hydroxy-2-methylquinoline (539 mg).

mp: 97–98° C. NMR (DMSO-d$_6$, δ): 1.23 (3H, t, J=7.5 Hz), 2.60 (3H, s), 4.22 (2H, q, J=7.5 Hz), 5.07 (2H, s), 6.92 (1H, s), 7.04 (1H, d, J=8.5 Hz), 7.34 (1H, t, J=8.5 Hz), 7.52 (1H, d, J=8.5 Hz).

(5) 8-[2,6-Dichloro-3-[N-methyl-N-[4-(methylcarbamoyl)-cinnamoylglycyl]amino]benzyloxy]-4-ethoxycarbonylmethoxy-2-methylquinoline was obtained according to a similar manner to that of Example 9.

mp: 134–147° C. NMR (DMSO-d$_6$, δ): 1.22 (3H, t, J=7.5 Hz), 2.53 (3H, s), 2.79 (3H, d, J=5.5 Hz), 3.15 (3H, s), 3.51 (1H, dd, J=16.5, 5.5 Hz), 3.81 (1H, dd, J=16.5, 5.5 Hz), 4.21 (2H, q, J=7.5 Hz), 5.07 (2H, s), 5.47 (1H, d, J=11.5 Hz), 5.53 (1H, d, J=11.5 Hz), 6.88 (1H, d, J=15 Hz), 6.91 (1H, s), 7.34–7.49 (3H, m), 7.61–7.68 (2H, m), 7.72–7.80 (3H, m), 7.86 (2H, d, J=8.5 Hz), 8.33 (1H, t, J=5.5 Hz), 8.49 (1H, q, J=5.5 Hz).

its hydrochloride mp: 147–158° C. NMR (DMSO-d$_6$, δ): 1.28 (3H, t, J=7.5 Hz), 2.79 (3H, d, J=4.5 Hz), 2.38 (3H, s), 3.15 (3H, s), 3.60 (1H, dd, J=16.5, 4.5 Hz), 3.91 (1H, dd, J=16.5, 4.5 Hz), 4.14 (2H, q, J=7.5 Hz), 5.37 (2H, s), 5.62 (1H, d, J=10.5 Hz), 5.67 (2H, s), 5.62 (1H, d, J=10.5 Hz), 5.67 (1H, d, J=10.5 Hz), 6.89 (1H, d, J=16 Hz), 7.42 (1H, d, 16 Hz), 7.57–7.70 (3H, m), 7.79–8.00 (7H, m), 8.39 (1H, t, J=4.5 Hz), 8.52 (1H, q, J=4.5 Hz).

(6) 4-Carboxymethoxy-8-[2,6-dichloro-3-[N-methyl-N-[4-(methylcarbamoyl)cinnamoylglycyl]amino]benzyloxy]-2-methylquinoline was obtained according to a similar manner to that of Example 3.

mp: 233–257° C. NMR (DMSO-d$_6$, δ): 2.54 (3H, s), 2.78 (3H, d, J=4.5 Hz), 3.17 (3H, s), 3.51 (1H, dd, J=16.5, 4.5 Hz), 3.82 (1H, dd, J=16.5, 4.5 Hz), 4.96 (2H, s), 5.47 (1H, d, J=10 Hz), 5.53 (1H, d, J=10 Hz), 6.89 (1H, d, J=16.5 Hz), 6.93 (1H, s), 7.33–7.50 (3H, m), 7.60–7.70 (2H, m), 7.73–7.81 (3H, m), 7.85 (2H, d, J=8.5 Hz), 8.32 (1H, t, J=4.5 Hz), 8.49 (1H, q, J=4.5 Hz).

(7) 8-[2,6-Dichloro-3-[N-methyl-N-[4-(methylcarbamoyl)-cinnamoylglycyl]amino]benzyloxy]-4-dimethylcarbamoylmethoxy-2-methylquinoline was obtained from 4-carboxymethoxy-8-[2,6-dichloro-3-[N-methyl-N-[4-(methylcarbamoyl) cinnamoylglycyl]-amino] benzyloxy]-2-methylquinoline and dimethylamine hydrochloride according to a similar manner to that of Example 7.

NMR (DMSO-d$_6$, δ): 2.53 (3H, s), 2.76 (3H, d, J=4.5 Hz), 2.86 (3H, s), 3.04 (3H, s), 3.15 (3H, s), 3.50 (1H, dd, J=16.5, 4.5 Hz), 3.80 (1H, dd, J=16.5, 4.5 Hz), 5.10 (2H, s), 5.45 (1H, d, J=9 Hz), 5.51 (1H, d, J=9 Hz), 6.87 (1H, d, J=15 Hz), 6.88 (1H, s), 7.32–7.48 (3H, m), 7.61–7.69 (2H, m), 7.73–7.81 (3H, m), 7.87 (2H, d, J=8.5 Hz), 8.33 (1H, t, J=4.5 Hz), 8.48 (1H, q, J=4.5 Hz).

its hydrochloride mp: 157–172° C. NMR (DMSO-$d_6$, δ): 2.78 (3H, d, J=4.5 Hz), 2.83 (3H, s), 2.90 (3H, s), 3.03 (3H, s), 3.15 (3H, s), 3.60 (1H, dd, J=16.5, 4.5 Hz), 3.91 (1H, dd, J=16.5, 4.5 Hz), 5.49 (2H, s), 5.61 (1H, d, J=11.5 Hz), 5.66 (1H, d, J=11.5 Hz), 6.88 (1H, d, J=16.0 Hz), 7.42 (1H, d, J=16.0 Hz), 7.53 (1H, s), 7.63 (2H, d, J=8.5 Hz), 7.79–7.89 (5H, m), 7.91–7.99 (2H, m), 8.38 (1H, t, J=4.5 Hz), 8.52 (1H, q, J=4.5 Hz).

Preparation 34

(1) 1-(tert-Butyldiphenylsilyloxymethyl)-2,6-dimethyl-3-nitrobenzene was obtained by reacting 2,6-dimethyl-3-nitrobenzyl alcohol with tert-butyldiphenylsilyl chloride according to a similar manner to that of Preparation 18-(1).

NMR (CDCl$_3$, δ): 1.03 (9H, s), 2.20 (3H, s), 2.38 (3H, s), 5.73 (2H, s), 7.06 (1H, d, J=8 Hz), 7.33–7.49 (6H, m), 7.58–7.73 (5H, m).

(2) To a suspension of 1-(tert-butyldiphenylsilyloxymethyl)-2,6-dimethyl-3-nitrobenzene (42 g) and ammonium chloride (4.2 g) in ethanol (378 ml)-water (42 ml) was added iron (7.0 g), and the mixture was refluxed for 6 hours, during which iron (7.0 g) was added thereto twice. Insoluble materials were filtered off, and the filtrate was concentrated. To the residue was added water and extracted with ethyl acetate. The organic layer was washed with water and brine, dried over magnesium sulfate and concentrated to give 3-amino-1-(tert-butyldiphenylsilyloxymethyl)-2,6-dimethylbenzene (42.8 g) as pale yellow oil.

NMR (CDCl$_3$, δ): 1.04 (9H, s), 2.09 (3H, s), 2.11 (3H, s), 3.48 (2H, br s), 4.70 (2H, s), 6.58 (1H, d, J=8 Hz), 6.71 (1H, d, J=8 Hz), 7.33–7.48 (6H, m), 7.66–7.73 (4H, m).

(3) 1-(tert-Butyldiphenylsilyloxymethyl)-2,6-dimethyl-3-(phthalimidoacetylamino)benzene was obtained according to a similar manner to that of Preparation 9.

mp: 207–210° C. NMR (CDCl$_3$, δ): 1.02 (9H, s), 2.12 (3H, s), 2.19 (3H, s), 4.52 (2H, s), 4.70 (2H, s), 6.95 (1H, d, J=8 Hz), 7.25–7.50 (7H, m), 7.63–7.80 (6H, m), 7.86–7.96 (2H, m).

(4) 1-(tert-Butyldiphenylsilyloxymethyl)-2,6-dimethyl-3-[N-methyl-N-(phthalimidoacetyl)amino]benzene was obtained according to a similar manner to that of Preparation 10.

mp: 180–182° C. NMR (CDCl$_3$, δ): 1.04 (9H, s), 2.21 (3H, s), 2.27 (3H, s), 3.17 (3H, s), 3.82 (1H, d, J=17 Hz), 4.12 (1H, d, J=17 Hz), 4.78 (2H, s), 7.09 (1H, d, J=8 Hz), 7.15 (1H, d, J=8 Hz), 7.34–7.49 (6H, m), 7.65–7.73 (6H, m), 7.80–7.88 (2H, m).

(5) 3-(N-Glycyl-N-methylamino)-1-(tert-butyldiphenylsilyloxymethyl)-2,6-dimethylbenzene was obtained according to a similar manner to that of Preparation 11.

NMR (CDCl$_3$, δ): 1.03 (9H, s), 2.02 (3H, s), 2.22 (3H, s), 2.82 (1H, d, J=17 Hz), 3.09 (1H, d, J=17 Hz), 3.15 (3H, s), 4.72 (2H, s), 6.92 (1H, d, J=8 Hz), 7.01 (1H, d, J=8 Hz), 7.32–7.49 (6H, m), 7.62–7.70 (4H, m).

(6) 1-(tert-Butyldiphenylsilyloxymethyl)-2,6-dimethyl-3-[N-methyl-N-[4-(methylcarbamoyl)cinnamoylglycyl]amino]benzene was obtained according to a similar manner to that of Preparation 18-(6).

mp: 204–208° C. NMR (CDCl$_3$, δ): 1.05 (9H, s), 2.05 (3H, s), 2.26 (3H, s), 3.02 (3H, d, J=5Hz), 3.20 (3H, s), 3.52 (1H, dd, J=17, 5 Hz), 3.87 (1H, dd, J=17, 5 Hz), 4.73 (2H, s), 6.16 (1H, br d, J=5 Hz), 6.51 (1H, d, J=15 Hz), 6.69 (1H, br t, J=5 Hz), 6.98 (1H, d, J=8 Hz), 7.06 (1H, d, J=8 Hz), 7.35–7.48 (6H, m), 7.51–7.60 (3H, m), 7.65–7.80 (6H, m).

(7) 2,6-Dimethyl-1-hydroxymethyl-3-[N-methyl-N-[4-(methylcarbamoyl)cinnamoylglycyl]amino]benzene was obtained according to a similar manner to that of Preparation 18-(7).

mp: 261–263° C. NMR (DMSO-$d_6$, δ): 2.27 (3H, s), 2.40 (3H, s), 2.79 (3H, d, J=5 Hz), 3.08 (3H, s), 3.43 (1H, dd, J=17. 5 Hz), 3.65 (1H, dd, J=17. 5 Hz), 4.53 (2H, d, J=5 Hz), 4.88 (1H, t, J=5 Hz), 6.89 (1H, d, J=15 Hz), 7.15 (2H, s), 7.41 (1H, d, J=15 Hz), 7.64 (2H, d, J=8 Hz), 7.85 (2H, d, J=8 Hz), 8.21 (1H, br t, J=5 Hz), 8.48 (1H, br d, J=8 Hz).

(8) To a solution of 2,6-dimethyl-1-hydroxymethyl-3-[N-methyl-N-[4-(methylcarbamoyl) cinnamoylglycyl]amino] benzene (2.00 g) in N,N-dimethylformamide (100 ml) was added methanesulfonyl chloride (784 mg) under ice-cooling, and the mixture was stirred for 2 hours at the same temperature and overnight at ambient temperature. To the mixture was added water and extracted with chloroform. The organic layer was washed with brine, dried over magnesium sulfate and concentrated. The residue was pulverized with diethyl ether to give 1-chloromethyl-2,6-dimethyl-3-[N-[4-(methylcarbamoyl)cinnamoylglycyl]-N-methylamino] benzene (2.00 g) as white powder.

mp: 232° C. NMR (CDCl$_3$, δ): 2.29 (3H, s), 2.46 (3H, s), 3.03 (3H, d, J=5 Hz), 3.24 (3H, s), 3.59 (1H, d, J=17, 5 Hz), 3.82 (1H, dd, J=17, 4 Hz), 4.67 (2H, s), 6.20 (1H, m), 6.50 (1H, d, J=15 Hz), 6.70 (1H, d, J=5 Hz), 7.04 (1H, d, J=9 Hz), 7.14 (1H, d, J=9 Hz), 7.50–7.60 (3H, m), 7.75 (2H, d, J=9 Hz).

Preparation 35

(1) 2,6-Dimethyl-1-hydroxymethyl-3-[N-methyl-N-(phthalimidoacetyl)amino]benzene was obtained from 1-(tert-butyldiphenylsilyloxymethyl)-2,6-dimethyl-3-[N-methyl-N-(phthalimidoacetyl)amino]benzene according to a similar manner to that of Preparation 18-(7).

mp: 241–243° C. NMR (CDCl$_3$, δ): 2.47 (3H, s), 2.48 (3H, s), 3.20 (3H, s), 3.81 (1H, d, J=17 Hz), 4.18 (1H, d, J=17 Hz), 4.83 (2H, s), 7.14 (1H, d, J=8 Hz), 7.19 (1H, d, J=8 Hz), 7.68–7.75 (2H, m), 7.80–7.88 (2H, m).

(2) A mixture of 2,6-dimethyl-1-methanesulfonyloxymethyl-3-[N-methyl-N-(phthalimidoacetyl)amino]benzene and 1-chloromethyl-2,6-dimethyl-3-[N-methyl-N-(phthalimidoacetyl)amino] benzene was obtained according to a similar manner to that of Example 33-(3).

Preparation 36

(1) 1-(tert-Butyldiphenylsilyloxymethyl)-2,4,6-trimethyl-3-nitrobenzene was obtained by reacting 2,4,6-trimethyl-3-nitrobenzyl alcohol with tert-butyldiphenylsilyl chloride according to a similar manner to that of Preparation 18-(1).

mp: 81–83° C. NMR (CDCl$_3$, δ): 1.02 (9H, s), 2.13 (3H, s), 2.18 (3H, s), 2.23 (3H, s), 4.67 (2H, s), 6.88 (1H, s), 7.35–7.48 (6H, m), 7.65 (4H, d, J=8 Hz).

(2) 3-Amino-1-(tert-butyldiphenylsilyloxymethyl)2,4,6-trimethylbenzene was obtained according to a similar manner to that of Preparation 34-(2).

NMR (CDCl$_3$, δ): 1.03 (9H, s), 2.08 (3H, s), 2.13 (3H, s), 2.16 (3H, s), 3.48 (2H, br s), 4.68 (2H, s), 6.72 (1H, s), 7.33–7.47 (6H, m), 7.70 (4H, d, J=8 Hz).

(3) 1-(tert-Butyldiphenylsilyloxymethyl)-3-(phthalimidoacetylamino)-2,4,6-trimethylbenzene was obtained according to a similar manner to that of Preparation 9.

mp: 218–220° C. NMR (CDCl₃, δ): 1.01 (6H, s), 1.04 (3H, s), 2.11 (2H, s), 2.15 (2H, s), 2.18 (2H, s), 2.21 (1H, s), 2.31 (1H, s), 2.39 (1H, s), 3.94 (0.7H, s), 4.5 (1.3 H, s), 4.64 (1.3 H, s), 4.72 (0.7H, s), 6.71 (0.4H, s), 6.86 (0.6H, s), 6.93 (0.6H, s), 6.99 (0.4H, s), 7.32–7.46 (6H, m), 7.83–7.88 (0.6H, m), 7.90–7.94 (1.4H, m).

(4) 1-(tert-Butyldiphenylsilyloxymethyl)-3-[N-methyl-N-(phthalimidoacetyl)amino]-2,4,6-trimethylbenzene was obtained according to a similar manner to that of Preparation 10.

mp: 146.5–149.7° C. NMR (CDCl₃, δ): 1.04 (9H, s), 2.19 (3H, s), 2.23 (3H, s), 2.32 (3H, s), 3.12 (3H, s), 3.85 (1H, d, J=17 Hz), 3.92 (1H, d, J=17 Hz), 4.72 (2H, s), 7.00 (1H, s), 7.33–7.48 (6H, m), 7.63–7.73 (6H, m), 7.80–7.88 (2H, m).

(5) 1-Hydroxymethyl-3-[N-methyl-N-(phthalimidoacetyl)amino]-2,4,6-trimethylbenzene was obtained according to a similar manner to that of Preparation 18-(7).

mp: 254–256° C. NMR (CDCl₃, δ): 2.33 (3H, s), 2.44 (6H, s), 3.26 (3H, s), 3.95 (2H, s), 4.78 (2H, s), 7.05 (1H, s), 7.67–7.74 (2H, m), 7.80–7.88 (2H, m).

(6) A mixture of 1-methanesulfonyloxymethyl-3-[N-methyl-N-(phthalimidoacetyl)amino]-2,4,6-trimethylbenzene and 1-chloromethyl-3-[N-methyl-N-(phthalimidoacetyl)amino]-2,4,6-trimethylbenzene was obtained according to a similar manner to that of Example 33-(3).

Preparation 37

(1) 2,6-Dimethoxy-3-nitrobenzyl alcohol was obtained from 2,6-dimethoxy-3-nitrobenzoic acid according to a similar manner to that of Example 33-(2).

mp: 71–73° C. NMR (CDCl₃, δ): 2.31 (1H, t, J=7.5 Hz), 3.96 (3H, s), 3.98 (3H, s), 4.78 (2H, d, J=7.5 Hz), 6.75 (1H, d, J=8 Hz), 7.99 (1H, d, J=8 Hz).

(2) A mixture of 2,6-dimethoxy-3-nitrobenzyl methanesulfonate and 2,6-dimethoxy-3-nitrobenzyl chloride was obtained according to a similar manner to that of Example 33-(3).

Preparation 38

(1) 1-(tert-Butyldiphenylsilyloxymethyl)-2,6-dimethyl-3-[N-ethyl-N-(phthalimidoacetyl)amino]benzene was obtained by reacting 1-(tert-butyldiphenylsilyloxymethyl)-2,6-dimethyl-3-(phthalimidoacetylamino)benzene with ethyl iodide according to a similar manner to that of Preparation 10.

mp: 146–150° C. NMR (CDCl₃, δ): 1.04 (9H, s), 1.12 (3H, t, J=7.5 Hz), 2.22 (3H, s), 2.28 (3H, s), 3.21 (1H, q, J=7.5 Hz), 3.78 (1H, d, J=17 Hz), 4.01–4.12 (2H, m), 4.78 (2H, s), 7.10 (2H, s), 7.33–7.47 (6H, m), 7.65–7.73 (6H, m), 7.80–7.88 (2H, m).

(2) 2,6-Dimethyl-1-hydroxymethyl-3-[N-ethyl-N-(phthalimidoacetyl)amino]benzene was obtained according to a similar manner to that of Preparation 18-(7).

mp: 205–207° C. NMR (CDCl₃, δ): 1.12 (3H, t, J=7.5 Hz), 1.50 (1H, br s), 2.46 (3H, s), 2.49 (3H, s), 3.24 (1H, m), 3.88 (1H, d, J=17 Hz), 4.03–4.19 (2H, m), 4.73 (2H, br s), 7.15 (2H, s), 7.68–7.75 (2H, m), 7.80–7.88 (2H, m).

(3) A mixture of 2,6-dimethyl-1-methanesulfonyloxymethyl-3-[N-ethyl-N-(phthalimidoacetyl)amino]benzene and 1-chloromethyl-2,6-dimethyl-3-[N-ethyl-N-(phthalimidoacetyl)amino]benzene was obtained according to a similar manner to that of Example 33-(3).

Preparation 39

(1) To a stirred solution of 8-benzyloxy-4-hydroxy-2-methylquinoline (5.00 g) and 2,6-lutidine (3.03 g) and 4-dimethylaminopyridine (230 mg) in dichloromethane (80 ml) was added trifluoromethanesulfonic anhydride (5.85 g) dropwise in an ice bath. The reaction mixture was stirred at the same temperature for half an hour and then at ambient temperature for an hour. The mixture was poured into saturated ammonium chloride (100 ml), extracted with chloroform and dried over anhydrous magnesium sulfate. The solvent was removed in vacuo and the residual solid was crystallized from 90% aqueous acetonitrile (100 ml) and collected to give 8-benzyloxy-2-methyl-4-(trifluoromethanesulfonyloxy)quinoline (6.58 g) as white powder.

mp: 158° C. NMR (CDCl₃, δ): 2.86 (3H, s), 5.46 (2H, s), 7.10 (1H, d, J=7.5 Hz), 7.25–7.60 (8H, m).

(2) A mixture of 8-benzyloxy-2-methyl-4-(trifluoromethanesulfonyloxy)quinoline (300 mg), vinyltributyltin (263 mg), tetrakis(triphenylphosphine)palladium (0) (43.6 mg) and lithium chloride (96 mg) in 1,4-dioxane (6 ml) was refluxed for three hours and then left at ambient temperature overnight. The mixture was diluted with ethyl acetate and was added silica gel (70–230 mesh, 5 g) and stirred at ambient temperature for half an hour. The silica gel was removed by filtration and the filtrate was concentrated in vacuo. The residue was chromatographed on a silica gel column eluting with ethyl acetate-n-hexane (1:4, V/V) to give a solid. This solid was crystallized from diisopropyl ether to give 8-benzyloxy-2-methyl-4-vinylquinoline (110 mg) as pale yellow solid.

mp: 114.2° C. NMR (CDCl₃, δ): 2.80 (3H, s), 5.45 (2H, s), 5.60 (1H, d, J=10 Hz), 5.91 (1H, d, J=16 Hz), 6.98 (1H, d, J=7.5 Hz), 7.20–7.40 (5H, m), 7.44–7.53 (2H, m), 7.59 (1H, d, J=7.5 Hz).

(3) To a stirred solution of 8-benzyloxy-2-methyl-4-vinylquinoline (200 mg) in 1,4-dioxane-water (3:1, V/V, 1 ml) was added catalytic amount of osmium tetroxide in tert-butanol in an ice bath. Sodium periodate (342 mg) was added to the reaction mixture portionwise and the resulting suspension was vigorously stirred overnight at ambient temperature. The mixture was extracted with ethyl acetate and washed with water and brine. The organic layer was dried over anhydrous magnesium sulfate and concentrated in vacuo to give a brown oil. This was purified by a silica gel column eluting with ethyl acetate-n-hexane (1:3, V/V) to give 8-benzyloxy-4-formyl-2-methylquinoline as a yellow solid (123 mg).

mp: 129.1° C. NMR (CDCl₃, δ): 2.90 (3H, s), 5.46 (2H, s), 7.10 (1H, d, J=7.5 Hz), 7.24–7.40 (3H, m), 7.41–7.55 (3H, m), 7.71 (1H, s), 8.46 (1H, d, J=8.0 Hz), 10.49 (1H, s).

(4) To a stirred solution of sodium dihydrogenphosphate dihydrate (788 mg) and 2-methyl-2-butene (885 mg) in tert-butanol (12 ml) and water (3 ml) was added 8-benzyloxy-4-formyl-2-methylquinoline (700 mg) and sodium chloride (79% purity, 457 mg) successively at ambient temperature. After being stirred for one and half an hour, the reaction was quenched with water (12 ml), then the pH of the mixture was adjusted to about 3–4 by addition of 1N hydrochloric acid. The mixture was extracted with chloroform and dried over anhydrous magnesium sulfate. The organic phase was concentrated in vacuo and the residual solid was triturated with diethyl ether to give 8-benzyloxy-4-carboxy-2-methylquinoline (729 mg, 98.5%) as a pale yellow powder.

mp: 241.3° C. NMR (CDCl₃, δ): 2.82 (3H, s), 5.41 (2H, s), 7.07 (1H, d, J=7.5 Hz), 7.24–7.53 (6H, m), 7.84 (1H, s), 8.26 (1H, d, J=7.5 Hz).

(5) To a stirred mixture of 8-benzyloxy-4-carboxy-2-methylquinoline (700 mg), potassium carbonate (659 mg) and N,N-dimethylformamide (0.3 ml) was dropwise added ethyl iodide (409 mg) under ice-cooling and the mixture was stirred for 30 minutes at the same temperature and for 1 hour at ambient temperature. To the mixture was added water and extracted with ethyl acetate. The organic layer was washed with water and brine, dried over magnesium sulfate, dried over magnesium sulfate. The solvent was removed, and the residue was crystallized from diisopropyl ether to give 8-benzyloxy-4-ethoxycarbonyl-2-methylquinoline (686 mg) as solid.

mp: 134.5° C. NMR (CDCl₃, δ): 1.46 (3H, t, J=7.5 Hz), 2.85 (3H, s), 4.48 (2H, q, J=7.5 Hz), 5.45 (2H, s), 7.04 (1H, d, J=7.5 Hz), 7.26–7.43 (4H, m), 7.46–7.55 (2H, m), 7.79 (1H, s), 8.19 (1H, d, J=7.5 Hz).

(6) A mixture of 8-benzyloxy-4-ethoxycarbonyl-2-methylquinoline (663 mg) and palladium(II) hydroxide (60 mg) in a mixture of ethanol (6 ml) and dioxane (6 ml) was stirred for 3 hours at ambient temperature under hydrogen atmosphere. The reaction mixture was filtered, and the filtrate was concentrated. The residue was pulverized with n-hexane to give 4-ethoxycarbonyl-8-hydroxy-2-methylquinoline (370 mg) as pale yellow solid.

mp: 71.8° C. NMR (CDCl₃, δ): 1.46 (3H, t, J=7.5 Hz), 2.77 (3H, s), 4.49 (2H, q, J=7.5 Hz), 7.16 (1H, d, J=7.5 Hz), 7.46 (1H, t, J=7.5 Hz), 7.83 (1H, s), 8.11 (1H, d, J=7.5 Hz), 8.35 (1H, br s).

Preparation 40

A mixture of 8-benzyloxy-2-methyl-4-vinylquinoline (200 mg) and palladium(II) hydroxide (40 mg) in a mixture of ethanol (1.5 ml) and dioxane (1.5 ml) was stirred for 9 hours at ambient temperature under hydrogen atmosphere. The reaction mixture was filtered, and the filtrate was concentrated. The residue was purified by flash chromatography (Ethyl acetate:n-hexane=1:2, V/V) to give 4-ethyl-8-hydroxy-2-methylquinoline (66 mg) as brown oil.

NMR (CDCl₃, δ): 1.36 (3H, t, J=7.5 Hz), 2.68 (3H, s), 3.04 (2H, q, J=7.5 Hz), 7.10 (1H, d, J=9 Hz), 7.15 (1H, s), 7.36 (1H, t, J=9 Hz), 7.44 (1H, d, J=7.5 Hz).

Preparation 41

(1) To a suspension of 8-benzyloxy-4-formyl-2-methylquinoline (300 mg) in a mixture of methanol (3 ml) and tetrahydrofuran (2 ml) was added sodium borohydride (20.6 mg) portionwise in an ice bath. The suspension was stirred for half an hour, then quenched with saturated sodium chloride. The mixture was extracted with chloroform and the organic layer was dried over anhydrous magnesium sulfate. After being concentrated in vacuo the residue was chromatographed on silica gel eluting with ethyl acetate-n-hexane to give an amorphous solid which was solidified with diisopropyl ether to afford 8-benzyloxy-4-hydroxymethyl-2-methylquinoline (250 mg) as a colorless solid.

mp: 137.0–140.7° C. NMR (CDCl₃, δ): 2.79 (3H, s), 5.12 (2H, br s), 5.45 (2H, s), 6.99 (1H, d, J=8 Hz), 7.21–7.45 (6H, m), 7.53 (2H, d, J=9 Hz).

(2) 4-Hydroxymethyl-8-hydroxy-2-methylquinoline was obtained according to a similar manner to that of Preparation 39-(6).

NMR (CDCl₃—CD₃OD, δ): 2.71 (3H, s), 5.10 (2H, s), 7.11 (1H, d, J=8 Hz), 7.29–7.43 (2H, m), 7.51 (1H, s).

Preparation 42

(1) To a solution of 8-benzyloxy-4-hydroxymethyl-2-methylquinoline (148 mg) in N,N-dimethylformamide (1.5 ml) was added sodium hydroxide (60% in oil, 23.3 mg) under ice-cooling, and the mixture was stirred for 15 minutes at the same temperature. To the mixture was added methyl iodide (82.7 mg) under ice-cooling, and the mixture was stirred for 15 minutes at the same temperature and then overnight at ambient temperature. To the mixture was added saturated sodium bicarbonate solution, and the mixture was extracted with ethyl acetate. The organic layer was washed with water twice, dired over magnesium sulfate and concentrated in vacuo. The residue was purified by flash chromatography (Ethyl acetate:n-hexane=1:3, V/V) to give 8-benzyloxy-4-methoxymethyl-2-methylquinoline (123 mg) as pale yellow solid.

mp: 73.7–76.3° C. NMR (CDCl₃, δ): 2.80 (3H, s), 3.51 (3H, s), 4.86 (2H, s), 5.45 (2H, s), 6.99 (1H, d, J=9 Hz), 7.24–7.54 (8H, m).

(2) 8-Hydroxy-4-methoxymethyl-2-methylquinoline was obtained according to a similar manner to that of Preparation 39-(6).

NMR (CDCl₃, δ): 2.70 (3H, s), 3.53 (3H, s), 4.86 (2H, s), 7.12 (1H, d, J=8 Hz), 7.29–7.44 (3H, m).

Preparation 43

A mixture of 2-hydroxyaniline (2 g), crotonoylbenzene (8.03 g) and concentrated hydrochloric acid (8 ml) was refluxed for 24 hours. The mixture was neutralized with concentrated ammonia water under ice-cooling, and extracted with chloroform. The organic layer was washed with brine, dried over magnesium sulfate and concentrated in vacuo. The residue was purified according to a conventional manner to give 8-hydroxy-2-methyl-4-phenylquinoline (2.4 g) as an oil.

NMR (CDCl₃, δ): 2.75 (3H, s), 7.14 (1H, m), 7.27–7.36 (2H, m), 7.40–7.61 (6H, m), 7.95 (1H, d, J=8 Hz).

Preparation 44

The following compounds were obtained according to a similar manner to that of Preparation 27-(5).

(1) 6-Hydroxymethyl-3,4-dihydro-2(1H)-quinoline (from methyl 2,3-dihydro-2(1H)-quinolinone-6-carboxylate)

mp: 148–173° C. NMR (CDCl₃, δ): 2.61 (2H, t, J=7.5 Hz), 2.96 (2H, t, J=7.5 Hz), 4.61 (2H, s), 6.74 (1H, d, J=8 Hz), 7.14–7.22 (2H, m).

(2) 5-Hydroxymethyl-2-[(E)-2-(4-pyridyl)vinyl]pyridine (from methyl 2-[(E)-2-(4-pyridyl)vinyl]pyridine-5-carboxylate)

mp: >198.9° C. NMR (CDCl₃, δ): 4.73 (2H, s), 7.34 (1H, d, J=16 Hz), 7.40–7.49 (3H, m), 7.53 (1H, d, J=16 Hz), 8.53–8.65 (3H, m).

Preparation 45

(1) To a solution of methyl 3,4-dihydro-2(1H)-quinolinone-6-carboxylate (500 mg) in tetrahydrofuran was dropwise added 2M solution of borane-methyl sulfide complex in tetrahydrofuran (2.5 ml) under ice-cooling, and the mixture was refluxed for 45 minutes. After cooling, methanol (1 ml) was dropwise added thereto, and the mixture was stirred for 1 hour. The solvent was removed, and ethyl acetate and water were added to the residue. The organic layer was washed with water, saturated sodium bicarbonate solution and brine, dried over magnesium sulfate and concentrated in vacuo. The residue was pulverized with diisopropyl ether-n-hexane to give methyl 1,2,3,4-tetrahydroquinoline-6-carboxylate (385 mg) as solid.

mp: 75–84° C. NMR (CDCl$_3$, δ): 2.93 (2H, quint, J=7 Hz), 2.76 (2H, t, J=7 Hz), 3.33 (2H, t, J=7 Hz), 3.83 (3H, s), 4.29 (1H, br s), 6.39 (2H, d, J=8 Hz), 7.59–7.68 (2H, m).

(2) 6-Hydroxymethyl-1,2,3,4-tetrahydroquinoline was obtained according to a similar manner to that of Preparation 27-(5).

NMR (CDCl$_3$, δ): 1.53 (1H, t, J=6 Hz), 1.90 (2H, quint, J=7 Hz), 2.73 (2H, t, J=7 Hz), 3.28 (2H, t, J=7 Hz), 4.49 (2H, d, J=6 Hz), 6.44 (1H, d, J=8 Hz), 6.90–7.00 (2H, m).

(3) To a solution of 6-hydroxymethyl-1,2,3,4-tetrahydroquinoline (314 mg) in methanol (4 ml) was dropwise added acetic anhydride (589 mg) under ice-cooling, and the mixture was stirred for 1 hour at the same temperature. The solvent was removed in vacuo, and ethyl acetate and saturated sodium bicarbonate solution was added to the residue. The organic layer was washed with water and brine, dried and concentrated in vacuo. The residue was purified by preparative thin-layer chromatography (n-hexane:ethyl acetate=1:2, V/V) to give 1-acetyl-6-hydroxymethyl-1,2,3,4-tetrahydroquinoline (227 mg) as powder.

mp: 95–106° C. NMR (CDCl$_3$, δ): 1.70 (1H, t-like), 1.96 (2H, quint, J=7 Hz), 2.24 (3H, s), 2.75 (2H, t, J=7 Hz), 3.80 (2H, t, J=7 Hz), 4.67 (2H, d, J=6 Hz), 6.96–7.36 (3H, m).

Preparation 46

(1) A mixture of 3-methoxy-4-nitrobenzyl alcohol (1.0 g) and 10% palladium on carbon (100 mg) in methanol was stirred for 2 hours under 3 atmospheric pressure of hydrogen. After filtration, the filtrate was concentrated in vacuo to give 4-amino-3-methoxybenzyl alcohol (910 mg) as an oil.

NMR (CDCl$_3$, δ): 3.77 (2H, br s), 3.84 (3H, s), 4.56 (2H, s), 6.66 (1H, d, J=8 Hz), 6.76 (1H, d, J=8 Hz), 6.81 (1H, s).

(2) To a solution of 4-amino-3-methoxybenzyl alcohol (900 mg) in methanol was added acetic anhydride (1.8 g) under ice cooling, and the mixture was stirred for 1 hour at the same temperature. After evaporation, the residue was dissolved in ethyl acetate, and the solution was washed with sodium bicarbonate solution, water and brine, dried over magnesium sulfate and concentrated in vacuo to give 4-acetamido-3-methoxybenzyl alcohol (840 mg) as solid.

mp: 104° C. NMR (CDCl$_3$, δ): 1.69 (1H, t, J=5 Hz), 2.20 (3H, s), 3.90 (3H, s), 4.65 (2H, d, J=5 Hz), 6.88–6.97 (2H, m), 7.74 (1H, br s), 8.32 (1H, d, J=8 Hz).

Preparation 47

The following compounds were obtained according to a similar manner to that of Preparation 32-(7).

(1) 6-Formyl-3,4-dihydro-2(1H)-quinoline mp: 207° C. NMR (CDCl$_3$, δ): 2.70 (2H, t, J=7.5 Hz), 3.07 (2H, t, J=7.5 Hz), 6.90 (1H, d, J=8 Hz), 7.68–7.75 (2H, m), 9.89 (1H, s).

(2) 1-Acetyl-6-formyl-1,2,3,4-tetrahydroquinoline

NMR (CDCl$_3$, δ): 2.01 (2H, quint, J=7 Hz), 2.29 (3H, s), 2.82 (2H, t, J=7 Hz), 3.81 (2H, t, J=7 Hz), 7.46–7.60 (1H, brpeak), 7.65–7.74 (2H, m), 9.93 (1H, s).

(3) 4-Acetamido-3-methoxybenzaldehyde mp: 145° C. NMR (CDCl$_3$, δ): 2.25 (3H, s), 3.97 (3H, s), 7.41 (1H, d, J=2 Hz), 7.48 (1H, dd, J=2, 8 Hz), 7.99 (1H, br s), 8.59 (1H, d, J=8 Hz), 9.88 (1H, s).

(4) 5-Formyl-2-[(E)-2-(4-pyridyl)vinyl]pyridine mp: 131–136° C. NMR (CDCl$_3$, δ): 7.40 (1H, d, J=16 Hz), 7.47 (2H, d, J=6 Hz), 7.56 (1H, d, J=8 Hz), 7.78 (1H, d, J=16 Hz), 8.19 (1H, dd, J=2, 8 Hz), 8.65 (2H, d, J=6 Hz), 9.07 (1H, d, J=2 Hz), 10.12 (1H, s).

(5) 5-Formyl-2-[(E)-2-(3-pyridyl)vinyl]pyridine (from 5-hydroxymethyl-2-[(E)-2-(3-pyridyl)vinyl]pyridine)

NMR (CDCl$_3$, δ): 7.29 (1H, d, J=16 Hz), 7.35 (1H, dd, J=5, 8 Hz), 7.54 (1H, d, J=8 Hz), 7.85 (1H, d, J=16 Hz), 7.93 (1H, ddd, J=2, 8 Hz), 8.18 (1H, dd, J=2, 8 Hz), 8.58 (1H, d, J=5 Hz), 8.83 (1H, d, J=2 Hz), 9.06 (1H, d, J=2 Hz), 10.10 (1H, s).

Preparation 48

The following compounds were obtained according to a similar manner to that of Preparation 1.

(1) Methyl (E)-3-(2-oxo-1,2,3,4-tetrahydroquinolin-6-yl)acrylate

NMR (CDCl$_3$, δ): 2.66 (2H, t, J=7.5 Hz), 3.00 (2H, t, J=7.5 Hz), 3.80 (3H, s), 6.35 (1H, d, J=16 Hz), 6.75 (1H, d, J=8 Hz), 7.31–7.39 (2H, m), 7.80 (1H, br s).

(2) Methyl (E)-3-(1-acetyl-1,2,3,4-tetrahydroquinolin-6-yl)acrylate

NMR (CDCl$_3$, δ): 1.97 (2H, quint, J=7 Hz), 2.25 (3H, s), 2.75 (2H, t, J=7 Hz), 3.79 (2H, t, J=7 Hz), 3.80 (3H, s), 6.38 (1H, d, J=16 Hz), 7.27–7.33 (4H, m).

(3) Methyl 4-acetamido-3-methoxycinnamate mp: 137° C. NMR (CDCl$_3$, δ): 2.21 (3H, s), 3.80 (3H, s), 3.93 (3H, s), 6.36 (1H, d, J=16 Hz), 7.01 (1H, s), 7.14 (1H, d, J=8 Hz), 7.63 (1H, d, J=16 Hz), 7.83 (1H, br s), 8.40 (1H, d, J=8 Hz).

(4) Methyl (E)-3-(3-quinolyl)acrylate (from 3-quinolinecarbaldehyde)

mp: 122° C. NMR (CDCl$_3$, δ): 3.87 (3H, s), 6.68 (1H, d, J=16 Hz), 7.60 (1H, t, J=8 Hz), 7.78 (1H, t, J=8 Hz), 7.81–7.90 (2H, m), 8.12 (1H, d, J=8 Hz), 8.25 (1H, d, J=2 Hz), 9.10 (1H, d, J=2 Hz).

(5) Methyl (E)-3-[6-[(E)-2-(4-pyridyl)vinyl]pyridin-3-yl]acrylate mp: >143.2° C. NMR (CDCl$_3$, δ): 3.83 (3H, s), 6.53 (1H, d, J=16 Hz), 7.34 (1H, d, J=16 Hz), 7.40–7.47 (3H, m), 7.64 (1H, d, J=16 Hz), 7.70 (1H, d, J=16 Hz), 7.87 (1H, d, J=8 Hz), 8.63 (2H, d, J=6 Hz), 8.75 (1H, d, J=2 Hz).

(6) Methyl (E)-3-[6-[(E)-2-(2-pyridyl)vinyl]pyridin-3-yl]acrylate (from 5-formyl-2-[(E)-2-(2-pyridyl)vinyl]-pyridine)

NMR (CDCl$_3$, δ): 3.83 (3H, s), 6.52 (1H, d, J=16 Hz), 7.22 (1H, dd, J=5, 8 Hz), 7.45 (2H, d, J=8 Hz), 7.65–7.77 (4H, m), 7.84 (1H, dd, J=2, 8 Hz), 8.64 (1H, d, J=5 Hz), 8.75 (1H, d, J=2 Hz).

(7) Methyl (E)-3-[6-[(E)-2-(3-pyridyl)vinyl]pyridin-3-yl]acrylate

NMR (CDCl$_3$, δ): 3.82 (3H, s), 6.51 (1H, d, J=16 Hz), 7.23 (1H, d, J=16 Hz), 7.32 (1H, dd, J=5, 8 Hz), 7.41 (1H, d, J=8 Hz), 7.60 (1H, d, J=16 Hz), 7.61 (1H, d, J=16 Hz), 7.85 (1H, dd, J=2, 8 Hz), 7.90 (1H, ddd, J=2, 2, 8 Hz), 8.54 (1H, d, J=5 Hz), 8.73 (1H, d, J=2 Hz), 8.81 (1H, d, J=2 Hz).

Preparation 49

The following compounds were obtained according to a similar manner to that of Preparation 1.

(1) (E)-3-(2-Oxo-1,2,3,4-tetrahydroquinolin-6-yl)acrylic acid mp: >250° C. NMR (DMSO-$d_6$, δ): 2.46 (2H, t, J=7.5 Hz), 2.90 (2H, t, J=7.5 Hz), 6.40 (1H, d, J=16 Hz), 6.86 (1H, d, J=8 Hz), 7.41–7.57 (3H, m).

(2) (E)-3-(1-Acetyl-1,2,3,4-tetrahydroquinolin-6-yl) acrylic acid

NMR (DMSO-$d_6$, δ): 1.85 (2H, quint, J=7 Hz), 2.17 (3H, s), 2.73 (2H, t, J=7 Hz), 3.68 (2H, t, J=7 Hz), 6.46 (1H, d, J=16 Hz), 7.41–7.63 (4H, m).

(3) 4-Acetamido-3-methoxycinnamic acid mp: 221.5–230° C. NMR (DMSO-$d_6$, δ): 2.10 (3H, s), 3.89 (3H, s), 6.52 (1H, d, J=16 Hz), 7.20 (1H, d, J=8 Hz), 7.38 (1H, s-like), 7.53 (1H, d, J=16 Hz), 8.07 (1H, d, J=8 Hz), 9.26 (1H, s).

(4) (E)-3-(3-Quinolyl)acrylic acid

NMR (DMSO-$d_6$, δ): 6.85 (1H, d, J=16 Hz), 7.66 (1H, t, J=8 Hz), 7.72–7.86 (2H, m), 7.96–8.06 (2H, m), 8.69 (1H, d, J=2 Hz), 9.23 (1H, d, J=2 Hz).

(5) (E)-3-[6-[(E)-2-(4-Pyridyl)vinyl]pyridin-3-yl]acrylic acid mp: >250° C. NMR (DMSO-$d_6$, δ): 6.71 (1H, d, J=16 Hz), 7.56–7.77 (6H, m), 8.20 (1H, dd, J=2, 8 Hz), 8.59 (2H, d, J=6 Hz), 8.88 (1H, d, J=2 Hz).

(6) (E)-3-[6-[(E)-2-(2-Pyridyl)vinyl]pyridin-3-yl]acrylic acid

NMR (DMSO-$d_6$, δ): 6.70 (1H, d, J=16 Hz), 7.33 (1H, dd, J=5, 8 Hz), 7.59–7.72 (3H, m), 7.78 (1H, d, J=2 Hz), 7.83 (2H, ddd, J=2, 8, 8 Hz), 8.19 (1H, dd, J=2, 8 Hz), 8.62 (1H, d, J=5 Hz), 8.88 (1H, d, J=2 Hz).

(7) (E)-3-[6-[(E)-2-(3-Pyridyl)vinyl]pyridin-3-yl]acrylic acid

NMR (DMSO-$d_6$, δ): 6.69 (1H, d, J=17 Hz), 7.43 (1H, dd, J=5, 8 Hz), 7.49 1H, d, J=16 Hz), 7.60 (1H, d, J=8 Hz), 7.64 (1H, d, J=16 Hz), 7.78 (1H, d, J=17 Hz), 8.09–8.22 (2H, m), 8.50 (1H, d, J=5 Hz), 8.85 (1H, s-like).

EXAMPLE 43

(1) 2,4-Dimethyl-8-[2,6-dimethyl-3-[N-(phthalimidoacetyl)-N-methylamino]benzyloxy]quinoline was obtained by reacting 8-hydroxy-2,4-dimethylquinoline with a mixture of 2,6-dimethyl-1-methanesulfonyloxymethyl-3-[N-methyl-N-(phthalimidoacetyl)amino]benzene and 1-chloromethyl-2,6-dimethyl-3-[N-methyl-N-(phthalimidoacetyl)amino]benzene according to a similar manner to that of Preparation 6.

mp: 123–125° C. NMR (CDCl$_3$, δ): 2.50 (3H, s), 2.58 (3H, s), 2.65 (3H, s), 2.68 (3H, s), 3.22 (3H, s), 3.94 (1H, d, J=17 Hz), 4.19 (1H, d, J=17 Hz), 5.38 (1H, d, J=10 Hz), 5.42 (1H, d, J=10 Hz), 7.15 (1H, br s), 7.19–7.28 (3H, m), 7.42 (1H, t, J=8 Hz), 7.61 (1H, d, J=8 Hz), 7.67–7.74 (2H, m), 7.80–7.88 (2H, m).

(2) 8-[3-(N-Glycyl-N-methylamino)-2,6-dimethylbenzyloxy]-2,4-dimethylquinoline was obtained according to a similar manner to that of Preparation 11.

mp: 145–148° C. NMR (CDCl$_3$, δ): 2.32 (3H, s), 2.52 (3H, s), 2.65 (3H, s), 2.68 (3H, s), 2.93 (1H, d, J=17 Hz), 3.15 (1H, d, J=17 Hz), 3.21 (3H, s), 5.34 (2H, s), 7.02 (1H, d, J=8 Hz), 7.10–7.18 (2H, m), 7.22 (1H, d, J=8 Hz), 7.42 (1H, t, J=8 Hz), 7.61 (1H, d, J=8 Hz).

(3) 2,4-Dimethyl-8-[2,6-dimethyl-3-[N-methyl-N-[N'-[3-[(4-pyridyl)carbamoyl]phenyl]ureidoacetyl]amino]benzyloxy]-quinoline was obtained by reacting 8-[3-(N-glycyl-N-methylamino)2,6-dimethylbenzyloxy]-2,4-dimethylquinoline with phenyl 3-[(4-pyridyl)carbamoyl]phenylcarbamate according to a similar manner to that of Example 19.

NMR (CDCl$_3$, δ): 2.32 (3H, s), 2.53 (3H, s), 2.64 (3H, s), 2.68 (3H, s), 3.23 (3H, s), 3.93 (2H, br s), 5.09 (1H, br d, J=10 Hz), 5.25 (1H, d, J=10 Hz), 6.66 (1H, br s), 6.72 (1H, br s), 6.98–7.08 (3H, m), 7.15 (1H, br s), 7.20 (1H, br d, J=8 Hz), 7.29 (1H, gr d, J=8 Hz), 7.46–7.55(2H, m), 7.65 (1H, d, J=8 Hz), 7.90 (2H, d, J=7.5 Hz), 8.43 (2H, d, J=7.5 Hz), 8.51 (1H, br s), 9.75 (1H, br s).

its dihydrochloride

NMR (CDCl$_3$—CD$_3$OD, δ): 2.32 (3H, s), 2.47 (3H, s), 2.93 (6H, br s), 3.27 (3H, s), 3.80 (2H, br s), 5.39 (1H, br d, J=10 Hz), 5.50 (1H, br d, J=10 Hz), 7.19–7.30 (3H, m), 7.53 (1H, br d, J=8 Hz), 7.63 (2H, br d, J=8 Hz), 7.71 (1H, br s), 7.78–7.89 (2H, m), 7.91 (1H, br s), 8.42–8.52 (4H, m).

EXAMPLE 44

(1) 2-Methyl-8-[2-methyl-3-nitrobenzyloxy]quinoline was obtained according to a similar manner to that of Preparation 6.

mp: 184–188° C. NMR (CDCl$_3$, δ): 2.56 (3H, s), 2.80 (3H, s), 5.48 (2H, s), 7.00 (1H, d, J=8 Hz), 7.28–7.44 (4H, m), 7.74 (1H, d, J=8 Hz), 7.82 (1H, d, J=8 Hz), 8.04 (1H, d, J=8 Hz), (2) 8-[3-Amino-2-methylbenzyloxy]-2-methylquinoline was obtained according to a similar manner to that of Preparation 8.

mp: 223–227° C. NMR (CDCl$_3$, δ): 2.23 (3H, s), 2.79 (3H, s), 3.66 (2H, br s), 5.41 (2H, s), 6.68 (1H, br d, J=8 Hz), 6.92–7.05 (3H, m), 7.24–7.38 (3H, m), 8.00 (1H, d, J=8 Hz), (3) 2-Methyl-8-[2-methyl-3-(phthalimidoacetylamino)-benzyloxy]quinoline was obtained according to a similar manner to that of Preparation 9.

mp: 283–285° C. NMR (DMSO-$d_6$, δ): 2.27 (3H, s), 2.65 (3H, s), 4.48 (2H, s), 5.30 (2H, s), 7.20 (1H, t, J=8 Hz), 7.26–7.34 (4H, m), 7.85–7.98 (4H, m), 8.20 (1H, d, J=8 Hz), 9.85 (1H, br s).

(4) 2-Methyl-8-[2-methyl-3-[N-(phthalimidoacetyl)-N-methylamino]benzyloxy]quinoline was obtained according to a similar manner to that of Preparation 10.

mp: 158–161° C. NMR (CDCl$_3$, δ): 2.47 (3H, s), 2.80 (3H, s), 3.26 (3H, s), 3.92 (1H, d, J=17 Hz), 4.19 (1H, d, J=17 Hz), 5.46 (2H, s), 7.06 (1H, br d, J=8 Hz), 7.23–7.42 (5H, m), 7.65–7.75 (3H, m), 7.81–7.89 (2H, m), 8.03 (1H, d, J=8 Hz).

(5) 8-[3-(N-Glycyl-N-methylamino)-2-methylbenzyloxy]-2-methylquinoline was obtained according to a similar manner to that of Preparation 11. NMR (CDCl$_3$, δ): 2.29 (3H, s), 2.80 (3H, s), 2.90 (1H, d, J=17 Hz), 3.13 (1H, d, J=17 Hz), 3.24 (3H, s), 5.40 (2H, s), 7.01 (1H, br d, J=8 Hz), 7.09 (1H, br d, J=8 Hz), 7.21–7.43 (4H, m), 7.60 (1H, br d, J=8 Hz), 8.03 (1H, d, J=8 Hz).

EXAMPLE 45

(1) 2,4-Dimethyl-8-[3-[N-(phthalimidoacetyl)-N-methylamino]-2,4,6-trimethylbenzyloxy]quinoline was obtained by reacting 8-hydroxy-2,4-dimethylquinoline with a mixture of 1-methanesulfonyloxymethyo-3-[N-methyl-N-

(phthalimidoacetyl)-amino]-2,4,6-trimethylbenzene and 1-chloromethyl-3-[N-methyl-N-(phthalimidoacetyl)amino]-2,4,6-trimethylbenzene according to a similar manner to that of Preparation 6.

mp: 204–206° C. NMR (CDCl$_3$, δ): 2.37 (3H, s), 2.47 (3H, s), 2.51 (3H, s), 2.64 (3H, s), 2.68 (3H, s), 3.18 (3H, s), 3.98 (2H, s), 5.32 (1H, d, J=10 Hz), 5.39 (1H, d, J=10 Hz), 7.10 (1H, s), 7.15 (1H, s), 7.14 (1H, d, J=8 Hz), 7.41 (1H, t, J=8 Hz), 7.60 (1H, d, J=8 Hz), 7.68–7.74 (2H, m), 7.81–7.89 (2H, m).

(2) 8-[3-(N-Glycyl-N-methylamino)-2,4,6-trimethylbenzyloxy]-2,4-dimethylquinoline was obtained according to a similar manner to that of Preparation 11.

NMR (CDCl$_3$, δ): 2.18 (3H, s), 2.29 (3H, s), 2.49 (3H, s), 2.65 (3H, s), 2.68 (3H, s), 2.95 (2H, s), 3.16 (3H, s), 5.31 (2H, s), 7.02 (1H, s), 7.13 (1H, s), 7.21 (1H, d, J=8 Hz), 7.41 (1H, t, J=8 Hz), 7.60 (1H, d, J=8 Hz).

EXAMPLE 46

(1) 8-[2,6-Dimethoxy-3-nitrobenzyloxy]-2-methylquinoline was obtained by reacting 8-hydroxy-2-methylquinoline with a mixture of 2,6-dimethoxy-3-nitrobenzyl methanesulfonate and 2,6-dimethoxy-3-nitrobenzyl chloride according to a similar manner to that of Preparation 6.

mp: 192–196° C. NMR (CDCl$_3$, δ): 2.68 (3H, s), 3.91 (3H, s), 4.08 (3H, s), 5.40 (2H, s), 6.78 (1H, d, J=8 Hz), 7.22–7.31 (2H, m), 7.37–7.46 (2H, m), 8.00 (1H, d, J=8 Hz), 8.09 (1H, d, J=8 Hz).

(2) To a mixture of 8-[2,6-dimethoxy-3-nitrobenzyloxy]-2-methylquinoline (2.28 g), ferrric chloride (68 mg), carbon (68 mg) and methanol (34 ml) was added hydrazine monohydrate (1.25 ml) at 60° C., and the mixture was refluxed for 4 hours. Ferric chloride (68 mg), carbon (68 mg), hydrazine monohydrate (1.25 ml) and methanol (10 ml) was further added, and the mixture was refluxed overnight. Insoluble materials were filtered off, and the filtrate was concentrated. The residue was dissolved in chloroform, and the solution was washed with saturated sodium bicarbonate solution, water and brine, dried over magnesium sulfate and concentrated. The residue was purified by silica gel column chromatography (chloroform-methanol) and crystallized with methanol to give 8-[3-amino-2,6-dimethoxybenzyloxy]-2-methylquinoline (1.33 g) as pale brown crystals.

mp: 208–210° C. NMR (CDCl$_3$, δ): 2.27 (3H, s), 2.37 (3H, s), 2.72 (3H, s), 3.57 (2H, br s), 5.32 (2H, s), 6.67 (1H, d, J=8 Hz), 6.91 (1H, d, J=8 Hz), 7.18–7.31 (2H, m), 7.36–7.42 (2H, m), 8.00 (1H, d, J=8 Hz).

(3) 8-[2,6-Dimethoxy-3-(phthalimidoacetylamino)benzyloxy]-2-methylquinoline was obtained according to a similar manner to that of Preparation 9.

mp: 229–231° C. NMR (CDCl$_3$, δ): 2.70 (3H, s), 3.79 (3H, s), 3.94 (3H, s), 4.55 (2H, s), 5.36 (2H, s), 6.66 (1H, d, J=8Hz), 7.22–7.30 (2H, m), 7.32–7.42 (2H, m), 7.71–7.79 (2H, m), 7.86–7.92 (2H, m), 7.99 (1H, d, J=8Hz), 8.08 (1H, br s), 8.19 (1H, d, J=8Hz).

(4) 8-[2,6-Dimethoxy-3-[N-(phthalimidoacetyl)-N-methylamino]benzyloxy]-2-methylquinoline was obtained according to a similar manner to that of Preparation 10.

mp: 184–185° C.

NMR (CDCl$_3$, δ): 2.70 (3H, s), 3.29 (3H, s), 3.90 (3H, s), 4.01 (3H, s), 4.22 (1H, d, J=17Hz), 4.32 (1H, d, J=17Hz), 5.44 (2H, s), 6.79 (1H, d, J=8Hz), 7.24–7.44 (5H, m), 7.69–7.75 (2H, m), 7.81–7.89 (2H, m), 8.00 (1H, d, J=8Hz).

(5) 8-[3-(N-Glycyl-N-methylamino)-2,6-dimethoxybenzyloxy]-2-methylquinoline was obtained according to a similar manner to that of Preparation 11.

NMR (CDCl$_3$, δ): 2.69 (3H, s), 3.10 (1H, d, J=17Hz), 3.22 (1H, d, J=17Hz), 3.30 (3H, s), 3.85 (6H, s), 5.33 (1H, d, J=10Hz), 5.44 (1H, d, J=10Hz), 6.72 (1H, d, J=8Hz), 7.12 (1H, d, J=8Hz), 7.21–7.45 (4H, m), 8.00 (1H, d, J=8Hz).

EXAMPLE 47

(1) 2,4-Dimethyl-8-[2,6-dimethyl-3-[N-ethyl-N-(phthalimidoacetyl)amino]benzyloxy]quinoline was obtained by reacting 8-hydroxy-2,4-dimethylquinoline with a mixture of 2,6-dimethyl-1-methanesulfonyloxymethyl-3-[N-ethyl-N-(phthalimidoacetyl)amino]benzene and 1-chloromethyl-2,6-dimethyl-3-[N-ethyl-N-(phthalimidoacetyl)amino]benzene according to a similar manner to that of Preparation 6.

NMR (CDCl$_3$, δ): 1.15 (3H, t, J=7.5Hz), 2.50 (3H, s), 2.58 (3H, s), 2.65 (3H, s), 2.68 (3H, s), 3.28 (1H, m), 3.90 (1H, d, J=17Hz), 4.05–4.19 (2H, m), 5.40 (2H, s), 7.14 (1H, br s), 7.20 (2H, s), 7.25 (1H, d, J=8Hz), 7.42 (1H, t, J=8Hz), 7.61 (1H, d, J=8Hz), 7.67–7.73 (2H, m), 7.80–7.88 (2H, m).

(2) 8-[3-(N-Glycyl-N-ethylamino)-2,6-dimethylbenzyloxy]-2,4-dimethylquinoline was obtained according to a similar manner to that of Preparation 11.

NMR (CDCl$_3$, δ): 1.15 (3H, t, J=7.5Hz), 2.32 (3H, s), 2.52 (3H, s), 2.65 (3H, s), 2.67 (3H, s), 2.89 (1H, d, J=17Hz), 3.11 (1H, d, J=17Hz), 3.25 (1H, m), 4.14 (1H, m), 5.35 (2H, s), 6.99 (1H, d, J=8Hz), 7.10–7.17 (2H, m), 7.22 (1H, d, J=8Hz), 7.42 (1H, t, J=8Hz), 7.61 (1H, d, J=8Hz).

EXAMPLE 48

(1) 8-[2,6-Dimethyl-3-[N-(phthalimidoacetyl)-N-methylamino]benzyloxy]-2-methylquinoxaline was obtained by reacting 8-hydroxy-2-methylquinoxaline with a mixture of 2,6-dimethyl-1-methanesulfonyloxymethyl-3-[N-methyl-N-(phthalimidoacetyl)amino]benzene and 1-chloromethyl-2,6-dimethyl-3-[N-methyl-N-(phthalimidoacetyl)amino]benzene according to a similar manner to that of Preparation 6.

mp: 124–127° C.

NMR (CDCl$_3$, δ): 2.50 (3H, s), 2.54 (3H, s), 2.76 (3H, s), 3.22 (3H, s), 3.96 (1H, d, J=17Hz), 4.20 (1H, d, J=17Hz), 5.37 (1H, d, J=10Hz), 7.20–7.35 (3H, m), 7.61–7.77 (4H, m), 7.81–7.89 (2H, m), 8.74 (1H, s).

(2) 8-[3-(N-Glycyl-N-methylamino)-2,6-dimethylbenzyloxy]-2-methylquinoxaline was obtained according to a similar manner to that of Preparation 11.

NMR (CDCl$_3$, δ): 2.32 (3H, s), 2.51 (3H, s), 2.78 (3H, s), 2.68 (3H, s), 2.93 (1H, d, J=17Hz), 3.16 (1H, d, J=17Hz), 3.22 (3H, s), 5.34 (2H, s), 7.06 (1H, d, J=8Hz), 7.16 (1H, d, J=8Hz), 7.29 (1H, d, J=8Hz), 7.65 (1H, t, J=8Hz), 7.76 (1H, d, J=8Hz), 8.74 (1H, s).

EXAMPLE 49

The following compounds were obtained according to a similar manner to that of Example 9.

(1) 8-[2,6-Dichloro-3-[N-methyl-N-[4-(methylcarbamoyl)cinnamoylclycyl]amino]benzyloxy]-2,4-dimethylquinoline NMR (CDCl$_3$, δ): 2.65 (3H, s), 3.00 (3H, d, J=5Hz), 3.26 (3H, s), 3.66 (1H, dd, J=17, 4Hz), 3.93 (1H, dd, J=17, 5Hz), 5.61 (1H, d, J=10Hz), 5.66 (1H, d, J=10Hz), 6.32 (1H, br d, J=5Hz), 6.52 (1h, d, J=15Hz), 6.72 (1H, br s), 7.14 (1H, s), 7.22–7.32 (2H, m), 7.39–7.66 (6H, m), 7.74 (2H, d, J=8Hz).

its hydrochloride

NMR (CDCl$_3$-CD$_3$OD, δ): 2.95 (3H, s), 2.99 (3H, s), 3.07 (3H, br s), 3.28 (3H, s), 3.89 (1H, d, J=17Hz), 4.20 (1H, d,

J=17Hz), 5.58 (1H, d, J=10Hz), 5.67 (1H, d, J=10Hz), 6.68 (1H, d, J=15Hz), 7.35 (1H, d, J=15Hz), 7.40–7.62 (5H, m), 7.67–7.76 (3H, m), 7.79–7.90 (2H, m).

(2) 8-[2,6-Dichloro-3-[N-methyl-N-[4-(methylcarbamoyl)cinnamoylglycyl]amino]benzyloxy]-2,3-dimethylquinoline NMR (CDCl$_3$, δ): 2.43 (3H, s), 2.66 (3H, s), 3.00 (3H, d, J=5Hz), 3.27 (3H, s), 3.65 (1H, dd, J=17, 4Hz), 3.94 (1H, dd, J=17, 5Hz), 5.63 (2H, s), 6.27 (1H, br d, J=5Hz), 6.52 (1H, d, J=15Hz), 6.69 (1H, br s), 7.17–7.32 (2H, m), 7.36–7.41 (2H, m), 7.45–7.62 (4H, m), 7.74 (2H, d, J=8Hz), 7.81 (1H, br s).

it hydrochloride

NMR (CDCl$_3$-CD$_3$OD, δ): 2.63 (3H, br s), 3.00 (3H, s), 3.10 (3H, br s), 3.29 (3H, s), 3.89 (1H, d, J=17Hz), 4.22 (1H, d, J=17Hz), 5.60 (1H, d, J=10Hz), 5.69 (1H, d, J=10Hz), 6.69 (1H, d, J=15Hz), 7.34–7.61 (7H, m), 7.67–7.89 (3H, m), 8.63 (1H, br s).

(3) 8-[2,6-Dichloro-3-[N-methyl-N-[4-(methylcarbamoyl)cinnamoylglycyl]amino]benzyloxy]-2,3-dimethyl-4-ethoxyquinoline NMR (CDCl$_3$, δ): 1.52 (3H, t, J=7.5Hz), 2.35 (3H, s), 2.65 (3H, s), 3.00 (3H, d, J=5Hz), 3.27 (3H, s), 3.66 (1H, dd, J=17, 4Hz), 3.94 (1H, dd, J=17, 5Hz), 4.09 (2H, q, J=7.5Hz), 5.62 (2H, s), 6.28 (1H, br d, J=5Hz), 6.52 (1H, d, J=15Hz), 6.71 (1H, br t, J=5Hz), 7.19 (1H, d, J=8Hz), 7.30 (1H, d, J=8Hz), 7.39 (1H, t, J=8Hz), 7.45–7.62 (4H, m), 7.69 (1H, d, J=8Hz), 7.74 (2H, d, J=8Hz).

its hydrochloride

NMR (CDCl$_3$-CD$_3$OD, δ): 1.61 (3H, t, J=7.5Hz), 2.41–2.51 (3H, overlapped with H$_2$O), 2.98 (3H, s), 3.01 (3H, s), 3.28 (3H, s), 3.86 (1H, d, J=17Hz), 4.26 (1H, d, J=17Hz), 4.42 (2H, q, J=7.5Hz), 5.54 (1H, d, J=10Hz), 5.68 (1H, d, J=10Hz), 6.68 (1H, d, J=15Hz), 7.38 (1H, d, J=15Hz), 7.48–7.62 (5H, m), 7.73–7.90 (4H, m).

(4) 8-[2,6-Dimethyl-3-[N-[4-(methylcarbamoyl)cinnamoylglycyl]-N-methylamino]benzyloxy]-4-ethoxycarbonyl-2-methylquinoline NMR (CDCl$_3$-CD$_3$OD, δ): 1.47 (3H, t, J=7.5Hz), 2.35 (3H, s), 2.52 (3H, s), 2.77 (3H, s), 3.00 (3H, d, J=5Hz), 3.25 (3H, s), 3.62 (1H, dd, J=17 and 5Hz), 3.86 (1H, dd, J=17, 4Hz), 4.00 (2H, q, J=7.5Hz), 5.34 (2H, s), 6.20 (1H, br q, J=5Hz), 6.52 (1H, d, J=17Hz), 6.71 (1H, br t, J=5Hz), 7.06 (1H, d, J=8Hz), 7.16 (1H, d, J=8Hz), 7.20 (1H, d, J=8Hz), 7.48–7.62 (4H, m), 7.70–7.80 (3H, m), 8.31 (1H, d, J=8Hz).

its hydrochloride

NMR (CDCl$_3$-CD$_3$OD, δ): 1.51 (3H, t, J=7.5Hz), 2.32 (3H, s), 2.49 (3H, s), 2.97 (3H, s), 3.17 (3H, s), 3.27 (3H, s), 3.81 (2H, s), 4.60 (2H, q, J=7.5Hz), 5.41 (1H, d, J=9Hz), 5.51 (1H, d, J=9Hz), 6.60 (1H, d, J=15Hz), 7.24 (2H, s), 7.46 (1H, d, J=15Hz), 7.53 (2H, d, J=8Hz), 7.70 (1H, d, J=8Hz), 7.80 (2H, d, J=8Hz), 7.92 (1H, t, J=8Hz), 8.20 (1H, s), 8.42 (1H, d, J=8Hz).

(5) 8-[2,6-Dimethyl-3-[N-[4-(methylcarbamoyl)cinnamoylglycyl]-N-methylamino]benzyloxy]-4-ethyl-2-methylquinoline NMR (CDCl$_3$, δ): 1.39 (3H, t, J=7.5Hz), 2.36 (3H, s), 2.52 (3H, s), 2.67 (3H, s), 2.98 (3H, d, J=7.5Hz), 3.06 (2H, q, J=7.5Hz), 3.25 (3H, s), 3.62 (1H, dd, J=17, 5Hz), 3.86 (1H, dd, J=17, 4Hz), 5.33 (2H, s), 6.25 (1H, br q, J=7.5Hz), 6.51 (1H, d, J=17Hz), 6.72 (1H, t, J=5Hz), 7.04 (1H, d, J=8Hz), 7.12–7.18 (2H, m), 7.24 (1H, d, J=8Hz), 7.44 (1H, t, J=8Hz), 7.51 (2H, d, J=9Hz), 7.55 (1H, d, J=17Hz), 7.66 (1H, d, J=8Hz), 7.74 (2H, d, J=9Hz).

its hydrochloride

NMR (CDCl$_3$-CD$_3$OD, δ): 1.50 (3H, t, J=7.5Hz), 2.30 (3H, s), 2.48 (3H, s), 2.98 (3H, s), 3.05 (3H, br d), 3.28 (3H, s), 3.34 (2H, q, J=7.5Hz), 3.80 (1H, d, J=15Hz), 3.86 (1H, d, J=15Hz), 5.39 (1H, d, J=9Hz), 5.50 (1H, d, J=9Hz), 6.63 (1H, d, J=17Hz), 7.20–7.28 (2H, m), 7.45 (1H, d, J=17Hz), 7.53 (2H, d, J=9Hz), 7.61–7.76 (2H, m), 7.81 (2H, d, J=9Hz), 7.84–7.95 (2H, m).

(6) 8-[2,6-Dimethyl-3-[N-[4-(methylcarbamoyl)cinnamoylglycyl]-N-methylamino]benzyloxy]-4-hydroxymethyl-2-methylquinoline NMR (CDCl$_3$-CD$_3$OD, δ): 2.32 (3H, s), 2.50 (3H, s), 2.66 (3H, s), 2.96 (3H, s), 3.24 (3H, s), 3.65 (1H, d, J=17Hz), 3.92 (1H, d, J=17Hz), 5.10 (1H, d, J=9Hz), 5.16 (1H, d, J=9Hz), 5.31 (2H, s), 6.56 (1H, d, J=16Hz), 7.13 (1H, d, J=7.5Hz), 7.20 (1H, d, J=7.5Hz), 7.26 (1H, d, J=8Hz), 7.39–7.58 (6H, m), 7.64 (2H, d, J=9Hz).

its hydrochloride

NMR (CDCl$_3$-CD$_3$OD, δ): 2.20 (3H, s), 2.50 (3H, s), 2.97 (3H, s), 3.04 (3H, s), 3.28 (3H, s), 3.74 (1H, d, J=17Hz), 3.91 (1H, d, J=17Hz), 5.34 (2H, s), 5.37 (1H, d, J=9Hz), 5.51 (1H, d, J=9Hz), 6.66 (1H, d, J=15Hz), 7.25 (1H, d, J=8Hz), 7.30 (1H, d, J=8Hz), 7.48 (1H, d, J=15Hz), 7.52–7.62 (2H, m), 7.67–7.93 (2H, m), 8.15 (1H, s).

(7) 8-[2,6-Dimethyl-3-[N-[4-(methylcarbamoyl)cinnamoylglycyl]-N-methylamino]benzyloxy]-4-methoxymethyl-2-methylquinoline NMR (CDCl$_3$, δ): 2.35 (3H, s), 2.52 (3H, s), 2.70 (3H, s), 2.98 (3H, d, J=5Hz), 3.24 (3H, s), 3.51 (3H, s), 3.62 (1H, dd, J=17, 5Hz), 3.86 (1H, dd, J=17, 4Hz), 4.87 (2H, s), 5.34 (2H, s), 6.24 (1H, br q, J=5Hz), 6.50 (1H, d, J=15Hz), 6.73 (1H, m), 7.05 (1H, d, J=8Hz), 7.15 (1H, d, J=8Hz), 7.22–7.29 (1H, m), 7.38 (1H, s), 7.45 (1H, t, J=8Hz), 7.49–7.60 (4H, m), 7.74 (2H, d, J=9Hz).

its hydrochloride

NMR (CDCl$_3$-CD$_3$OD, δ): 2.30 (3H, s), 2.49 (3H, s), 2.96 (3H, s), 3.08 (3H, s), 3.28 (3H, s), 3.66 (3H, s), 3.80 (1H, d, J=17Hz), 3.86 (1H, d, J=17Hz), 5.13 (2H, s), 5.49 (1H, d, J=9Hz), 5.50 (1H, d, J=9Hz), 6.62 (1H, d, J=15Hz), 7.24 (2H, s), 7.44 (1H, d, J=15Hz), 7.51 (2H, d, J=9Hz), 7.66–7.74 (2H, m), 7.80 (2H, d, J=9Hz), 7.90 (1H, d, J=9Hz), 7.99 (1H, s).

(8) 8-[2,6-Dimethyl-3-[N-[4-(methylcarbamoyl)cinnamoylglycyl]-N-methylamino]benzyloxy]-2-methyl-4-phenylquinoline NMR (CDCl$_3$, δ): 2.39 (3H, s), 2.55 (3H, s), 2.74 (3H, s), 2.99 (3H, d, J=5Hz), 3.26 (3H, s), 3.64 (1H, dd, J=17, 4Hz), 3.88 (1H, dd, J=17, 5Hz), 5.37 (2H, s), 6.25 (1H, br q, J=5Hz), 6.50 (1H, d, J=15Hz), 6.73 (1H, br t, J=5Hz), 7.07 (1H, d, J=7.5Hz), 7.16 (1H, d, J=7.5Hz), 7.20–7.30 (3H, m), 7.38 (1H, t, J=7.5Hz), 7.44–7.60 (8H, m), 7.74 (2H, d, J=9Hz).

its hydrochloride

NMR (CDCl$_3$-CD$_3$OD, δ): 2.32 (3H, s), 2.50 (3H, s), 2.96 (3H, s), 3.12 (3H, s), 3.29 (3H, s), 3.80 (1H, d, J=17Hz), 3.87 (1H, d, J=17Hz), 5.42 (1H, d, J=9Hz), 5.55 (1H, d, J=9Hz), 6.64 (1H, d, J=15Hz), 7.33 (1H, s), 7.40–7.88 (15H, m).

(9) 8-[2,6-Dimethyl-3-[N-methyl-N-[4-(methylcarbamoyl)cinnamoylclycyl]amino]benzyloxy]-2-methylquinoxaline NMR (CDCl$_3$, δ): 2.34 (3H, s), 2.51 (3H, s), 2.77 (3H, s), 3.02 (3H, d, J=5Hz), 3.27 (3H, s), 3.65 (1H, dd, J=17, 4Hz), 3.88 (1H, dd, J=17, 5Hz), 5.35 (2H, s), 6.17 (1H, br d, J=5Hz), 6.53 (1H, d, J=15Hz), 6.71 (1H, br t, J=5Hz), 7.09 (1H, d, J=8Hz), 7.19 (1H, d, J=8Hz), 7.30 (1H, d, J=8Hz), 7.51–7.61 (3H, m), 7.67 (1H, t, J=8Hz), 7.72–7.79 (3H, m), 8.75 (1H, s).

(10) 8-[3-[N-[(E)-3-(6-Acetylaminopyridin-3-yl)acryloylglycyl]-N-methylamino]-2,6-dimethylbenzyloxy]-2-methylquinoxaline NMR (CDCl$_3$, δ): 2.22 (3H, s), 2.35 (3H, s), 2.51 (3H, s), 2.77 (3H, s), 3.27 (3H, s), 3.64 (1H, dd, J=17, 5Hz), 3.87 (1H, dd, J=17, 5Hz), 5.35 (2H, s), 6.47 (1H, d, J=15Hz), 6.71 (1H, br t, J=5Hz), 7.10 (1H, d, J=8Hz), 7.19 (1H, d, J=8Hz), 7.31 (1H, d, J=8Hz), 7.51 (1H, d, J=15Hz), 7.67 (1H, t, J=8Hz), 7.76 (1H, d, J=8Hz), 7.85 (1H, d, J=8Hz), 8.07 (1H, br s), 7.21 (1H, br d, J=8Hz), 8.36 (1H, br s), 8.74 (1H, s).

EXAMPLE 50

The following compounds were obtained according to a similar manner to that of Example 1.

(1) 8-[2,6-Dichloro-3-[N-methyl-[(E)-3-(2-oxo-1,2,3,4-tetrahydroquinolin-6-yl)acryloylglycyl]amino]benzyloxy]-2-methylquinoline NMR (CDCl$_3$, δ): 2.63 (2H, t, J=7.5Hz), 2.72 (3H, s), 2.97 (2H, t, J=7.5Hz), 3.26 (3H, s), 3.64 (1H, dd, J=4, 18Hz), 3.94 (1H, dd, J=4, 18Hz), 5.60–5.66 (2H, m), 6.39 (1H, d, J=16Hz), 6.60 (1H, t-like), 6.71 (1H, d, J=8Hz), 7.18–7.54 (9H, m), 7.71 (1H, br s), 8.02 (1H, d, J=8Hz).

its hydrochloride

NMR (DMSO-d$_6$, δ): 2.48 (2H, t, J=7.5Hz), 2.90 (2H, t, J=7.5Hz), 2.92 (3H, s), 3.15 (3H, s), 3.58 (1H, dd, J=4, 16Hz), 3.87 (1H, dd, J=4, 16Hz), 5.56–5.70 (2H, m), 6.65 (1H, d, J=16Hz), 6.87 (1H, d, J=8Hz), 7.29 (1H, d, J=16Hz), 7.31–7.42 (2H, m), 7.75–8.00 (6H, m), 8.21 (1H, t-like) 8.96 (1H, brpeak), 10.26 (1H, s).

(2) 8-[3-[N-[(E)-3-(1-Acetyl-1,2,3,4-tetrahydroquinolin-6-yl)acryloylglycyl]-N-methylamino]-2,6-dichlorobenzyloxy]-2-methylquinoline NMR (CDCl$_3$, δ): 1.97 (2H, quint, J=7Hz), 2.24 (3H, s), 2.68–2.77 (5H, m), 3.26 (3H, s), 3.64 (1H, dd, J=4, 16Hz), 3.78 (2H, t, J=7Hz), 3.94 (1H, dd, J=4, 16Hz), 5.59–5.70 (2H, m), 6.42 (1H, d, J=16Hz), 6.60 (1H, t-like), 7.21–7.36 (6H, m), 7.36–7.56 (6H, m), 8.03 (8H, d).

its hydrochloride

NMR (DMSO-d$_6$, δ): 1.86 (2H, quint, J=7Hz), 2.19 (3H, s), 2.72 (2H, t, J=7Hz), 2.91 (3H, s), 3.15 (3H, s), 3.59 (1H, dd, J=4, 16Hz), 3.67 (2H, t, J=7Hz), 3.89 (2H, t, J=7Hz), 5.57–5.77 (2H, m), 6.73 (1H, d, J=16Hz), 7.27–7.43 (2H, m), 7.50–7.61 (1H, brpeak), 7.77–8.00 (7H, m), 8.27 (1H, t, J=6Hz), 8.90–9.03 (1H, m).

(3) 8-[3-[N-(4-Acetamido-3-methoxycinnamoylglycyl)-N-methylamino]-2,6-dichlorobenzyloxy]-2-methylquinoline NMR (CDCl$_3$, δ): 2.20 (3H, s), 2.73 (3H, s), 3.26 (3H, s), 3.84–4.00 (4H, m), 5.60–5.71 (2H, m), 6.40 (1H, d, J=16Hz), 6.60 (1H, brpeak), 6.98 (1H, s-like), 7.12 (1H, d, J=8Hz), 7.20–7.34 (3H, m), 7.34–7.55 (4H, m), 7.81 (1H, br s), 8.02 (1H, d, J=8Hz), 8.37 (1H, d, J=8Hz).

its hydrochloride

NMR (DMSO-d$_6$, δ): 2.09 (3H, s), 2.89 (3H, s), 3.15 (3H, s), 3.86 (3H, s), 5.56–5.69 (2H, m), 6.75 (1H, d, J=16Hz), 7.10 (1H, d, J=8Hz), 7.21 (1H, s-like), 7.32 (1H, d, J=16Hz), 7.72–7.96 (6H, m), 8.03 (1H, d, J=8Hz), 8.20 (1H, t-like), 8.93 (1H, brpeak), 9.23 (1H, s-like).

(4) 8-[2,6-Dichloro-3-[N-methyl-N-(3-methyl-4-nitrocinnamoylglycyl)amino]benzyloxy]-2-methylquinoline NMR (CDCl$_3$, δ): 2.59 (3H, s), 2.72 (3H, s), 3.25 (3H, s), 3.68 (1H, dd, J=4, 16Hz), 3.94 (1H, dd, J=4, 16Hz), 5.60–5.70 (2H, m), 6.58 (1H, d, J=16Hz), 6.71 (1H, t-like), 7.22–7.33 (3H, m), 7.35–7.51 (5H, m), 7.55 (1H, d, J=16Hz) 7.98 (1H, d, J=8Hz), 8.03 (1H, d, J=8Hz).

(5) 8-[2,6-Dichloro-3-[N-methyl-N-[(E)-3-(3-quinolyl) acryloylglycyl]amino]benzyloxy]-2-methylquinoline NMR (DMSO-d$_6$, δ): 2.73 (3H, s), 3.28 (3H, s), 3.72 (1H, dd, J=5, 16Hz), 3.96 (1H, dd, J=5, 16Hz), 5.59–5.71 (2H, m), 6.66–6.80 (2H, m), 7.21–7.36 (3H, m), 7.36–7.61 (4H, m), 7.67–7.86 (3H, m), 8.02 (1H, d, J=8Hz), 8.09 (1H, d, J=8Hz), 8.20 (1H, s-like), 9.07 (1H, d, J=2Hz).

its dihydrochloride

NMR (DMSO-d$_6$, δ): 2.91 (3H, s), 3.17 (3H, s), 3.62 (1H, dd, J=5, 17Hz), 3.92 (1H, dd, J=5, 17Hz), 5.62 (1H, d, J=10Hz), 5.69 (1H, d, J=10Hz), 7.13 (1H, d, J=16Hz), 7.63 (1H, d, J=16Hz), 7.69–8.01 (8H, m), 8.07–8.17 (2H, m), 8.45 (1H, t, J=6Hz), 8.74 (1H, s-like), 8.90–9.02 (1H, m), 9.24 (1H, s-like).

(6) 8-[2,6-Dichloro-3-[N-methyl-N-[(E)-3-[6-[(E)-2-(4-pyridyl)vinyl]pyridin-3-yl]acryloylglycyl]amino] benzyloxy]-2-methylquinoline NMR (CDCl$_3$, δ): 2.74 (3H, s), 3.28 (3H, s), 3.68 (1H, dd, J=4, 16Hz), 3.95 (1H, dd, J=4, 16Hz), 5.61–5.71 (2H, m), 6.58 (1H, d, J=16Hz), 6.72 (1H, t-like), 7.23–7.66 (12H, m), 7.82 (1H, dd, J=2, 8Hz), 8.03 (1H, d, J=8Hz), 8.62 (2H, d, J=6Hz), 8.73 (1H, d, J=2Hz).

its hydrochloride

NMR (DMSO-d$_6$, δ): 2.90 (3H, s), 3.15 (3H, s), 3.59 (1H, dd, J=4, 16Hz), 3.60 (1H, dd, J=4, 16Hz), 5.58–5.70 (2H, m), 7.01 (1H, d, J=16Hz), 7.48 (1H, d, J=16Hz), 7.68–7.98 (8H, m), 8.05 (1H, d, J=16Hz), 8.12 (1H, dd, J=2, 8Hz), 8.31 (2H, d, J=6Hz), 8.44 (1H, t-like), 8.85–8.93 (3H, m), 8.69 (1H, brpeak).

(7) 8-[2,6-Dimethyl-3-[N-methyl-N-[4-(2-oxopyrrolidin-1-yl)cinnamoylglycyl]amino]benzyloxy]-2-methylquinoline NMR (CDCl$_3$, δ): 2.11–2.25 (2H, m), 2.38 (3H, s), 2.54 (3H, s), 2.63 (2H, t, J=7.5Hz), 2.74 (3H, s), 3.27 (3H, s), 3.63 (1H, dd, J=17, 4Hz), 3.82–3.94 (3H, m), 5.38 (2H, s), 6.42 (1H, d, J=15Hz), 6.67 (1H, br s), 7.08 (1H, d, J=8Hz), 7.18 (1H, d, J=8Hz), 7.23–7.32 (2H, m), 7.40–7.59 (5H, m), 7.67 (2H, d, J=8Hz), 8.04 (1H, d, J=8Hz).

its hydrochloride

NMR (CDCl$_3$-CD$_3$OD, δ): 2.12–2.26 (2H, m), 2.32 (3H, s), 2.50 (3H, s), 3.65 (2H, t, J=7.5Hz), 3.19 (3H, br s), 3.30 (3H, s), 3.80–3.93 (4H, m), 5.42 (1H, br d, J=10Hz), 5.51 (1H, br d, J=10Hz), 6.50 (1H, d, J=15Hz), 7.20 (1H, d, J=8Hz), 7.26 (1H, d, J=8Hz), 7.45–7.53 (3H, m), 7.59–7.68 (3H, m), 7.77–7.94 (3H, m), 8.90 (1H, br d, J=8Hz).

(8) 8-[3-[N-(4-Acetamido-3-methylcinnamoylglycyl)-N-methylamino]-2,6-dimethylbenzyloxy]-2-methylquinoline NMR (CDCl$_3$, δ): 2.22 (3H, br s), 2.29 (3H, s), 2.54 (3H, s), 2.74 (3H, s), 3.27 (3H, s), 3.63 (1H, dd, J=17, 5Hz), 3.89 (1H, dd, J=17, 5Hz), 5.37 (2H, s), 6.41 (1H, d, J=15Hz), 6.67 (1H, br s), 7.02 (1H, br s), 7.09 (1H, d, J=8Hz), 7.19 (1H, d, J=8Hz), 7.23–7.55 (7H, m), 7.93 (1H, br s), 8.05 (1H, d, J=8Hz).

its hydrochloride

NMR (CDCl$_3$-CD$_3$OD, δ): 2.24–2.38 (9H, overlapped with H$_2$O), 2.50 (3H, s), 3.13 (3H, br s), 3.28 (3H, s), 3.78 (1H, br d, J=17Hz), 3.87 (1H, br d, J=17Hz), 5.41 (1H, d, J=10Hz), 5.50 (1H, d, J=10Hz), 6.45 (1H, d, J=15Hz), 7.19–7.30 (4H, m), 7.39 (1H, d, J=15Hz), 7.64 (1H, d, J=8Hz), 7.70 (1H, d, J=8Hz), 7.76–7.93 (3H, m), 7.93 (1H, br d, J=8Hz), 8.05 (1H, d, J=8Hz).

(9) 8-[3-[N-(4-Acetamido-3-methoxycinnamoylglycyl)-N-methylamino]-2,6-dimethylbenzyloxy]-2-methylquinoline NMR (CDCl$_3$, δ): 2.21 (3H, s), 2.38 (3H, s), 2.53 (3H, s), 2.72 (3H, s), 3.25 (3H, s), 3.62 (1H, dd, J=17, 5Hz), 3.82–3.93 (4H, m), 5.37 (2H, s), 6.40 (1H, d, J=15Hz), 6.65 (1H, br s), 6.98 (1H, br s), 7.04–7.20 (3H, m), 7.22–7.32 (2H, m), 7.40–7.54 (3H, m), 7.81 (1H, br s), 8.02 (1H, d, J=8Hz), 8.38 (1H, br d, J=8Hz).

its hydrochloride

NMR (CDCl$_3$-CD$_3$OD, δ): 2.21 (3H, s), 2.26–2.45 (3H, overlapped with H$_2$O), 2.50 (3H, s), 3.18 (3H, br s), 3.29

(3H, s), 3.82 (2H, br s), 3.95 (3H, s), 5.38–5.55 (2H, m), 6.49 (1H, br d, J=15Hz), 7.00–7.10 (2H, m), 7.20–7.32 (2H, m), 7.46 (1H, br d, J=15Hz), 7.64 (1H, br s), 7.75–7.97 (3H, m), 8.29 (1H, d, J=8Hz), 8.90 (1H, br s).

(10) 8-[3-[N-(4-Acetamido-3-methoxycinnamoylglycyl)-N-methylamino]-2,6-dimethylbenzyloxy]-2,4-dimethylquinoline NMR (CDCl$_3$, δ): 2.20 (3H, s), 2.35 (3H, s), 2.50 (3H, s), 2.64 (3H, s), 2.66 (3H, s), 3.24 (3H, s), 3.60 (1H, dd, J=17, 5Hz), 3.82–3.92 (4H, m), 5.33 (2H, s), 6.39 (1H, d, J=15Hz), 6.64 (1H, br t, J=5Hz), 6.98 (1H, br s), 7.03–7.26 (5H, m), 7.40–7.52 (2H, m), 7.61 (1H, d, J=8Hz), 7.80 (1H, br s), 8.36 (1H, d, J=8Hz).

its hydrochloride

NMR (CDCl$_3$-CD$_3$OD, δ): 2.21 (3H, s), 2.33 (3H, s), 2.49 (3H, s), 2.95 (3H, s), 3.12 (3H, s), 3.29 (3H, s), 3.82 (2H, br s), 3.93 (3H, s), 5.42 (1H, d, J=10Hz), 5.50 (1H, d, J=10Hz), 6.50 (1H, d, J=15Hz), 7.01–7.08 (2H, m), 7.20 (1H, d, J=8Hz), 7.26 (1H, d, J=8Hz), 7.45 (1H, d, J=15Hz), 7.61 (1H, br d, J=8Hz), 7.70 (1H, br s), 7.78–7.92 (2H, m), 8.28 (1H, d, J=8Hz).

(11) 2,4-Dimethyl-8-[2,6-dimethyl-3-[N-[4-(dimethylcarbamoyl)cinnamoylglycyl]-N-methylamino]benzyloxy]quinoline NMR (CDCl$_3$, δ): 2.37 (3H, s), 2.52 (3H, s), 2.65 (3H, s), 2.67 (3H, s), 2.99 (3H, br s), 3.11 (3H, br s), 3.26 (3H, s), 3.63 (1H, dd, J=17, 5Hz), 3.89 (1H, dd, J=17, 5Hz), 5.33 (2H, s), 6.50 (1H, d, J=15Hz), 6.71 (1H, br s), 7.07 (1H, d, J=8Hz), 7.11–7.28 (3H, m), 7.37–7.64 (7H, m).

its hydrochloride

NMR (CDCl$_3$-CD$_3$OD, δ): 2.24 (3H, s), 2.50 (3H, s), 2.94 (3H, s), 3.06 (6H, br s), 3.14 (3H, s), 3.30 (3H, s), 3.84 (2H, br s), 5.42 (1H, d, J=10Hz), 5.50 (1H, d, J=10Hz), 6.61 (1H, d, J=15Hz), 7.21 (1H, d, J=8Hz), 7.26 (1H, d, J=8Hz), 7.40 (2H, br d, J=8Hz), 7.49–7.58 (3H, m), 7.61 (1H, br d, J=8Hz), 7.70 (1H, br s), 7.78–7.90 (2H, m).

(12) 2,4-Dimethyl-8-[2,6-dimethyl-3-[N-methyl-N-[4-(2-oxopyrrolidin-1-yl)cinnamoylglycyl]amino]benzyloxy]quinoline NMR (CDCl$_3$, δ): 2.11–2.23 (2H, m), 2.37 (3H, s), 2.53 (3H, s), 2.59≧2.70 (8H, m), 3.26 (3H, s), 3.61 (1H, dd, J=17, 4Hz), 3.83–3.93 (3H, m), 5.35 (2H, s), 6.42 (1H, d, J=15Hz), 6.65 (1H, br s), 7.07 (1H, d, J=8Hz), 7.14–7.19 (2H, m), 7.22–7.28 (1H, overlapped with CDCl$_3$), 7.41–7.57 (4H, m), 7.60–7.67 (3H, m).

its hydrochloride

NMR (CDCl$_3$-CD$_3$OD, δ): 2.13–2.26 (2H, m), 2.32 (3H, s), 2.49 (3H, s), 2.63 (2H, d, J=7.5Hz), 2.95 (3H, s), 3.11 (3H, s), 3.29 (3H, s), 3.81 (2H, s), 3.89 (2H, d, J=7.5Hz), 5.42 (1H, d, J=10Hz), 5.50 (1H, d, J=10Hz), 6.50 (1H, d, J=15Hz), 7.20 (1H, br d, J=8Hz), 7.26 (1H, br d, J=8Hz), 7.44–7.52 (3H, m), 7.59–7.66 (3H, m), 7.70 (1H, br s), 7.79–7.90 (2H, m).

(13) 2,4-Dimethyl-8-[2,6-dimethyl-3-[N-methyl-N-[4-(propionamido)cinnamoylglycyl]amino]benzyloxy]quinoline NMR (CDCl3, δ): 1.22 (3H, t, J=7.5Hz), 2.31—2.42 (5H, m), 2.51 (3H, s), 2.66 (6H, s), 3.24 (3H, s), 3.61 (1H, dd, J=17, 5Hz), 3.86 (1H, dd, J=17, 5Hz), 5.32 (2H, s), 6.39 (1H, d, J=15Hz), 6.64 (1H, br t, J=5Hz), 7.05 (1H, d, J=8Hz), 7.14 (2H, d, J=8Hz), 7.25 (1H, d, J=8Hz), 7.40–7.56 (7H, m), 7.62 (1H, d, J=8Hz).

its hydrochloride

NMR (CDCl$_3$-CD$_3$OD, δ): 1.20 (3H, t, J=7.5Hz), 2.31 (3H, s), 2.40–2.50 (5H, m), 2.93 (3H, s), 3.05 (3H, br s), 3.27 (3H, s), 3.85 (2H, br s), 5.40 (1H, br d, J=10Hz), 5.48 (1H, br d, J=10Hz), 6.42 (1H, br d, J=15Hz), 7.18–7.39 (3H, m), 7.58–7.65 (3H, m), 7.69 (1H, br s), 7.76–7.89 (2H, m).

(14) 2,4-Dimethyl-8-[2,6-dimethyl-3-[N-methyl-N-[4-(methylcarbamoyl)cinnamoylglycyl]amino]benzyloxy]quinoline NMR (CDCl$_3$, δ): 2.36 (3H, s), 2.52 (3H, s), 2.65 (6H, s), 3.01 (3H, d, J=5Hz), 3.26 (3H, s), 3.63 (1H, dd, J=4, 17Hz), 3.88 (1H, dd, J=4, 17Hz), 5.35 (2H, s), 6.21 (1H, q-like), 6.53 (1H, d, J=16Hz), 6.72 (1H, t-like), 7.07 (1H, d, J=8Hz), 7.12–7.19 (2H, m), 7.22–7.29 (1H, m), 7.46 (1H, t, J=8Hz), 7.50–7.65 (4H, m), 7.75 (2H, d, J=8Hz).

its hydrochloride

NMR (DMSO-d$_6$, δ): 2.27 (3H, s), 2.47 (3H, s), 2.79 (3H, d, J=4Hz), 2.90 (6H, s), 3.12 (3H, s), 3.57 (1H, dd, J=4, 16Hz), 3.63–3.85 (1H, m), 5.41–5.55 (2H, m), 6.90 (1H, d, J=16Hz), 7.28–7.44 (3H, m), 7.63 (2H, d, J=8Hz), 7.82–8.00 (6H, m), 8.28 (1H, t-like), 8.50 (1H, q-like).

(15) 8-[3-[N-(4-Acetamido-3-methylcinnamoylglycyl)-N-methylamino]-2,6-dimethylbenzyloxy]-2,4-dimethylquinoline NMR (CDCl$_3$, δ): 2.22 (3H, s), 2.26 (3H, s), 2.35 (3H, s), 2.52 (3H, s), 2.65 (3H, s), 2.67 (3H, s), 3.25 (3H, s), 3.61 (1H, dd, J=4, 18Hz), 3.87 (1H, dd, J=4, 18Hz), 5.35 (2H, s), 6.40 (1H, d, J=16Hz), 6.64 (1H, brpeak), 6.99 (1H, brpeak), 7.06 (1H, d, J=8Hz), 7.11–7.19 (2H, m), 7.22–7.28 (1, m), 7.28–7.40 (2H, m), 7.40–7.54 (2H, m), 7.62 (1H, d, J=8Hz), 7.93 (1H, br d, J=8Hz).

its hydrochloride

NMR (DMSO-d$_6$, δ): 2.07 (3H, s), 2.21 (3H, s), 2.29 (3H, s), 2.46 (3H, s), 2.90 (6H, s), 3.11 (3H, s), 3.54 (1H, dd, J=4, 18Hz), 3.70 (1H, dd, J=4, 18Hz), 5.43–5.55 (2H, m), 6.73 (1H, d, J=16Hz), 7.22–7.42 (5H, m), 7.54 (1H, d, J=8Hz), 7.86–8.00 (4H, m), 8.18 (1H, t, J=6Hz), 9.36 (1H, s).

(16) 8-[3-[N-[(E)-3-(1-Acetyl-1,2,3,4-tetrahydroquinolin-6-yl)acryloylglycyl]-N-methylamino]-2,6-dimethylbenzyloxy]-2,4-dimethylquinoline NMR (CDCl$_3$, δ): 1.96 (2H, quint, J=7Hz), 2.25 (3H, s), 2.36 (3H, s), 2.53 (3H, s), 2.65 (3H, s), 2.68 (3H, s), 2.74 (2H, t, J=7Hz), 3.25 (3H, s), 3.61 (1H, dd, J=4, 18Hz), 3.77 (2H, t, J=7Hz), 3.88 (1H, dd, J=4, 18Hz), 5.34 (2H, s), 6.42 (1H, d, J=16Hz), 6.65 (1H, t-like), 7.07 (1H, d, J=8Hz), 7.13–7.20 (2H, m), 7.21–7.35 (4H, m), 7.41–7.56 (2H, m), 7.63 (1H, d, J=8Hz).

its hydrochloride

NMR (DMSO-d$_6$, δ): 1.84 (2H, quint), 2.16 (3H, s), 2.25 (3H, s), 2.45 (3H, s), 2.70 (2H, t, J=7Hz), 2.87 (6H, s), 3.53 (1H, dd, J=4, 16Hz), 3.61–3.73 (3H, m), 5.41–5.53 (2H, m), 6.73 (1H, d, J=16Hz), 7.23–7.38 (5H, m), 7.46–7.59 (1H, brpeak), 7.84–7.98 (4H, m), 8.16 (1H, t, J=6Hz).

(17) 2,4-Dimethyl-8-[2,6-dimethyl-3-[N-[4-(ethylcarbamoyl)cinnamoylglycyl]-N-methylamino]benzyloxy]quinoline NMR (CDCl$_3$, δ): 1.25 (3H, t, J=7.5Hz), 2.36 (3H, s), 2.52 (3H, s), 2.65 (3H, s), 2.66 (3H, s), 3.26 (3H, s), 3.50 (2H, quint, J=7.5Hz), 3.62 (1H, dd, J=4, 18Hz), 3.87 (1H, dd, J=4, 18Hz), 5.34 (2H, s), 6.09 (1H, t-like), 6.53 (1H, d, J=16Hz), 6.71 (1H, t-like), 7.06 (1H, d, J=8Hz), 7.11–7.18 (2H, m), 7.22–7.27 (1H, m), 7.45 (1H, t, J=8Hz), 7.50–7.64 (4H, m), 7.74 (2H, d, J=8Hz).

its hydrochloride

NMR (DMSO-d$_6$, δ): 1.11 (3H, t, J=7.5Hz), 2.28 (3H, s), 2.46 (3H, s), 2.88 (6H, s), 3.12 (3H, s), 3.28 (2H, quint, J=7.5Hz), 3.56 (1H, dd, J=4, 18Hz), 3.73 (1H, dd, J=4, 18Hz), 5.43–5.55 (2H, m), 6.90 (1H, d, J=16Hz), 7.31 (1H, d, J=8Hz), 7.35–7.44 (2H, m), 7.63 (2H, d, J=8Hz), 7.82–8.00 (6H, m), 8.28 (1H, t-like), 8.52 (1H, t-like).

(18) 2,4-Dimethyl-8-[2,6-dimethyl-3-[N-methyl-N-[4-(isonicotinamido)cinnamoylglycyl]amino]benzyloxy]quinoline NMR (CDCl$_3$, δ): 2.26 (3H, s), 2.42 (3H, s), 2.59 (3H, s), 2.66 (3H, s), 3.19 (3H, s), 3.59 (1H, dd, J=4, 18Hz), 3.80 (1H, dd, J=4, 18Hz), 5.30 (2H, s), 6.40 (1H, d, J=16Hz), 7.00 (1H, d, J=8Hz), 7.07 (1H, d, J=8Hz), 7.14 (1H, s), 7.26 (1H, d, J=8Hz), 7.40–7.53 (4H, m), 7.59–7.60 (3H, m), 7.75 (2H, d, J=5Hz), 8.67–8.75 (3H, m).

its dihydrochloride

NMR (DMSO-d$_6$, δ): 2.28 (3H, s), 2.45 (3H, s), 2.88 (6H, s), 3.11 (3H, s), 3.55 (1H, dd, J=4, 16Hz), 5.42–5.55 (2H, m), 6.75 (1H, d, J=16Hz), 7.28–7.43 (3H, m), 7.59 (2H, d, J=8Hz), 7.81–7.99 (6H, m), 7.99–8.06 (2H, m), 8.21 (1H, t-like), 8.87 (2H, d, J=5Hz), 10.82 (1H, s).

(19) 2,4-Dimethyl-8-[2,6-dimethyl-3-[N-[(E)-3-(6-ethoxycarbonylpyridin-3-yl)acryloylglycyl]-N-methylamino]benzyloxy]quinoline NMR (CDCl$_3$, δ): 1.46 (3H, t, J=7.5Hz), 2.37 (3H, s), 2.53 (3H, s), 2.65 (3H, s), 2.68 (3H, s), 3.27 (3H, s), 3.62 (1H, dd, J=17, 5Hz), 3.90 (1H, dd, J=17, 5Hz), 4.49 (2H, q, J=7.5Hz), 5.35 (2H, s), 6.62 (1H, d, J=15Hz), 6.79 (1H, br t, J=5Hz), 7.07 (1H, d, J=8Hz), 7.13–7.20 (2H, m), 7.22–7.28 (2H, m), 7.44 (1H, t, J=8Hz), 7.54–7.66 (3H, m), 7.91 (1H, dd, J=8, 3Hz), 8.12 (1H, d, J=8Hz), 8.84 (1H, br s).

(20) 8-[3-[N-[(E)-3-(6-Acetamidopyridin-3-yl)acryloylglycyl]-N-methylamino]-2,6-dimethylbenzyloxy]-2,4-dimethylquinoline NMR (CDCl$_3$, δ): 2.20 (3H, s), 2.36 (3H, s), 2.52 (3H, s), 2.66 (3H, s), 2.69 (3H, s), 3.25 (3H, s), 3.63 (1H, dd, J=4, 18Hz), 3.88 (1H, dd, J=4, 18Hz), 5.33 (2H, s), 6.45 (1H, d, J=16Hz), 6.72 (1H, t-like), 7.07 (1H, d, J=8Hz), 7.12–7.19 (2H, m), 7.22–7.26 (1H, m), 7.40–7.56 (2H, m), 7.62 (1H, d, J=8Hz), 7.81 (1H, dd, J=2, 8Hz), 8.07 (1H, s), 8.20 (1H, d, J=8Hz), 8.34 (1H, d, J=2Hz).

its hydrochloride

NMR (DMSO-d$_6$, δ): 2.11 (3H, s), 2.28 (3H, s), 2.46 (3H, s), 2.89 (6H, s), 3.11 (3H, s), 3.54 (1H, dd, J=4, 16Hz), 3.71 (1H, dd, J=4, 16Hz), 5.42–5.55 (2H, m), 6.81 (1H, d, J=16Hz), 7.29–7.42 (3H, m), 7.86–8.04 (5H, m), 8.11 (1H, d, J=8Hz), 8.23 (1H, t-like), 8.48 (1H, d-like).

(21) 8-[3-[N-[(E)-3-(6-Aminopyridin-3-yl)acryloylglycyl]-N-methylamino]-2,6-dimethylbenyloxy]-2,4-dimethylquinoline NMR (CDCl$_3$, δ): 2.33 (3H, s), 2.52 (3H, s), 2.65 (3H, s), 2.67 (3H, s), 3.25 (3H, s), 3.61 (1H, dd, J=4, 18Hz), 3.86 (1H, dd, J=4, 18Hz), 4.66 (2H, br s), 5.33 (2H, s), 6.29 (1H, d, J16Hz), 6.48 (1H, d, J=8Hz), 6.59 (1H, t-like, 7.05 (1H, d, J=8Hz), 7.10–7.19 (2H, m), 7.21–7.28 (1H, m), 7.40–7.50 (2H, m), 7.56–7.65 (2H, m), 8.17 (1H, d, J=2Hz).

(22) 2,4-Dimethyl-8-[2,6-3-[N-methyl-N-[(E)-3-[6-[(E)-2-(4-pyridyl)vinyl]pyridin-3-yl]acryloylglycyl]amino]benzyloxy]quinoline NMR (CDCl$_3$, δ): 2.36 (3H, s), 2.53 (3H, s), 2.65 (3H, s), 2.68 (3H, s), 3.25 (3H, s), 3.64 (1H, dd, J=4, 18Hz), 3.90 (1H, dd, J=4, 18Hz), 5.35 (2H, s), 6.56 (1H, d, J=16Hz), 6.73 (1H, t-like), 7.07 (1H, d, J=8Hz), 7.12–7.20 (2H, m), 7.20–7.32 (1H, m), 7.32–7.50 (6H, m), 7.53–7.65 (2H, m), 7.82 (1H, dd, J=2, 8Hz), 8.61 (1H, d, J=6Hz), 8.73 (1H, d, J=2Hz).

its trihydrochloride

NMR (DMSO-d$_6$, δ): 2.27 (3H, s), 2.45 (3H, s), 2.89 (6H, s), 3.11 (3H, s), 3.56 (1H, dd, J=4, 16Hz), 3.75 (1H, dd, J=4, 16Hz), 5.44–5.55 (2H, m), 7.02 (1H, d, J=16Hz), 7.29–7.41 (2H, m), 7.45 (1H, d, J=16Hz), 7.75 (1H, d, J=8Hz), 7.86–8.14 (8H, m), 8.25–8.40 (3H, m), 8.85–8.93 (3H, m).

(23) 2,4-Dimethyl-8-[2,6-dimethyl-3-[N-methyl-N-[(E)-3-[6-[(E)-2-(2-pyridyl)vinyl]pyridin-3-yl]acryloylglycyl]amino]benzyloxy]quinoline NMR (CDCl$_3$, δ): 2.37 (3H, s), 2.53 (3H, s), 2.65 (3H, s), 2.66 (3H, s), 3.27 (3H, s), 3.64 (1H, dd, J=4, 18Hz), 3.89 (1H, dd, J=4, 18Hz), 5.35 (2H, s), 6.55 (1H, d, J=16Hz), 6.75 (1H, t-like), 7.08 (1H, d, J=8Hz), 7.13–7.28 (4H, m), 7.37–7.75 (8H, m), 7.80 (1H, dd, J=2, 8Hz), 8.65 (1H, d, J=5Hz), 8.73 (1H, d, J=2Hz).

its trihydrochloride

NMR (DMSO-d$_6$, δ): 2.28 (3H, s), 2.46 (3H, s), 2.91 (6H, s), 3.12 (3H, s), 3.57 (1H, dd, J=4, 16Hz), 3.75 (1H, dd, J=4, 16Hz), 5.44–5.55 (2H, m), 7.02 (1H, d, J=16Hz), 7.31 (1H, d, J=8Hz), 7.39 (1H, d, J=8Hz), 7.46 (1H, d, J=16Hz), 7.71 (1H, dd, J=5, 8Hz), 7.79 (1H, d, J=8Hz), 7.89–8.06 (6H, m), 8.12–8.21 (2H, m), 8.26–8.40 (2H, m), 8.77 (1H, d, J=5Hz), 8.49 (1H, s-like).

(24) 2,4-Dimethyl-8-[2,6-dimethyl-3-[N-methyl-N-[(E)-3-[6-[(E)-2-(3-pyridyl)vinyl]pyridin-3-yl]acryloylglycyl]amino]benzyloxy]quinoline NMR (CDCl$_3$, δ): 2.37 (3H, s), 2.54 (3H, s), 2.65 (3H, s), 2.68 (3H, s), 3.27 (3H, s), 3.64 (1H, dd, J=4, 18Hz), 3.89 (1H, dd, J=4, 18Hz), 5.35 (2H, s), 6.55 (1H, d, J=16Hz), 6.73 (1H, t-like), 7.06 (1H, d, J=8Hz), 7.12–7.27 (4H, m), 7.31 (1H, dd, J=5, 8Hz), 7.39 (1H, t, J=8Hz), 7.45 (1H, d, J=8Hz), 7.52–7.71 (3H, m), 7.80 (1H, dd, J=2, 8Hz), 7.89 (1H, ddd, J=2, 2, 8Hz), 8.53 (1Hz, d, J=5Hz), 8.70 (1H, d, J=2Hz), 8.80 (1H, d, J=2Hz).

its trihydrochloride

NMR (DMSO-d$_6$, δ): 2.27 (3H, s), 2.46 (3H, s), 2.89 (6H, s), 3.12 (3H, s), 3.55 (1H, dd, J=4, 16Hz), 3.74 (1H, dd, J=4, 16Hz), 5.43–5.56 (2H, m), 6.99 (1H, d, J=16Hz), 7.29–7.50 (3H, m), 7.64–7.76 (2H, m), 7.82–8.00 (6H, m), 8.09 (1H, d, J=8Hz), 8.32 (1H, t-like), 8.20 (1H, dd, J=2, 8Hz), 8.76 (1H, d, J=5Hz), 8.83 (1H, s-like), 9.13 (1H, s-like).

(25) 2-Methyl-8-[2-methyl-3-[N-methyl-N-[4-(methylcarbamoyl)cinnamoylglycyl]amino]benzyloxy]quinoline NMR (CDCl$_3$, δ): 2.32 (3H, s), 2.79 (3H, s), 3.02 (3H, d, J=5Hz), 3.28 (3H, s), 3.67 (1H, dd, J=17, 5Hz), 3.88 (1H, dd, J=17, 4Hz), 5.38 (1H, d, J=10Hz), 5.46 (1H, d, J=10Hz), 6.18 (1H, br d, J=5Hz), 6.52 (1H, d, J=15Hz), 6.70 (1H, br s), 7.06 (1H, dd, J=8, 3Hz), 7.12 (1H, br d, J=8Hz), 7.24–7.43 (4H, m), 7.50–7.66 (4H, m), 7.75 (2H, d, J=8Hz), 8.04 (1H, d, J=8Hz).

(26) 2,4-Dimethyl-8-[3-[N-methyl-N-[4-(methylcarbamoyl)cinnamoylglycyl]amino]-2,4,6-trimethylbenzyloxy]quinoline mp: 213–215° C.

NMR (CDCl$_3$, δ): 2.20 (3H, s), 2.32 (3H, s), 2.48 (3H, s), 2.65 (3H, s), 2.67 (3H, s), 3.02 (3H, d, J=5Hz), 3.21 (3H, s), 3.57–3.78 (2H, m), 5.30 (2H, s), 6.22 (1H, br d, J=5Hz), 6.53 (1H, d, J=15Hz), 6.72 (2H, br t, J=5Hz), 7.05 (1H, s), 7.15 (1H, s), 7.21–7.28 (1H, overlapped with H$_2$O), 7.44 (1H, t, J=8Hz), 7.50–7.65 (4H, m), 7.75 (2H, d, J=8Hz).

its hydrochloride

NMR (CDCl$_3$-CD$_3$OD, δ): 2.28 (3H, s), 2.30 (3H, br s), 2.43 (3H, s), 2.93 (3H, s), 2.99 (3H, s), 3.08 (3H, br s), 3.22 (3H, s), 3.70 (1H, br d, J=17Hz), 3.88 (1H, br d, J=17Hz), 5.38 (1H, br d, J=10Hz), 5.45 (1H, d, J=10Hz), 6.63 (1H, br d, J=15Hz), 7.11 (1H, s), 7.40–7.52 (3H, m), 7.60 (1H, br d, J=8Hz), 7.69–7.89 (5H, m).

(27) 8-[2,6-Dimethoxy-3-[N-methyl-N-[4-(methylcarbamoyl)cinnamoylglycyl]amino]benzyloxy]-2-methylquinoline NMR (CDCl$_3$, δ): 2.26 (3H, s), 2.99 (3H, d, J=5Hz), 3.32 (3H, s), 3.82–3.92 (7H, m), 3.98 (1H, dd, J=17, 5Hz), 5.31 (1H, d, J=10Hz), 5.47 (1H, d, J=10Hz), 6.28 (1H, br d, J=5Hz), 6.51 (1H, d, J=15Hz), 6.70 (1H, br t, J=5Hz), 6.75 (1H, d, J=8Hz), 7.19 (1H, d, J=8Hz), 7.22–7.59 (7H, m), 7.74 (2H, d, J=8Hz), 7.99 (1H, d, J=8Hz).

its hydrochloride

NMR (CDCl$_3$-CD$_3$OD, δ): 3.00 (3H, s), 3.12 (3H, s), 3.37 (3H, s), 3.79 (3H, s), 3.84 (3H, s), 3.96 (1H, d, J=17Hz), 4.18 (1H, d, J=17Hz), 5.33 (1H, d, J=10Hz), 5.54 (1H, d, J=10Hz), 6.63 (1H, d, J=15Hz), 6.82 (1H, d, J=8Hz), 7.39 (2H, d, J=8Hz), 7.48–7.91 (8H, m), 8.83 (1H, d, J=8Hz).

(28) 2,4-Dimethyl-8-[2,6-dimethyl-3-[N-ethyl-N-[4-(methylcarbamoyl)cinnamoylglycyl]amino]benzyloxy]quinoline NMR (CDCl$_3$, δ): 1.18 (3H, t, J=7.5Hz), 2.35 (3H, s), 2.54 (3H, s), 2.66 (6H, s), 3.01 (3H, d, J=5Hz), 3.29 (1H, m), 3.60 (1H, dd, J=17, 5Hz), 3.86 (1H, dd, J=17, 5Hz), 4.19 (1H, m), 5.32 (1H, d, J=10Hz), 5.38 (1H, d, J=10Hz), 6.20 (1H, br d, J=5Hz), 6.52 (1H, d, J=15Hz), 6.76 (1H, br t, J=5Hz), 7.04 (1H, d, J=8Hz), 7.13–7.20 (2H, m), 7.22–7.30 (1H, overlapped with H$_2$O), 7.46 (1H, t, 8Hz), 7.50–7.65 (4H, m), 7.75 (2H, d, J=8Hz).

its hydrochloride

NMR (CDCl$_3$-CD$_3$OD, δ): 1.18 (3H, t, J=7.5Hz), 2.32 (3H, s), 2.48 (3H, s), 2.95 (3H, s), 2.99 (3H, s), 3.07 (3H, s), 3.43 (1H, m), 3.80 (2H, br s), 4.09 (1H, m), 5.40 (1H, d, J=10Hz), 5.50 (1H, d, J=10Hz), 6.60 (1H, d, J=15Hz), 7.17–7.28 (2H, m), 7.40–7.53 (3H, m), 7.62 (1H, d, J=8Hz), 7.71–7.90 (6H, m).

(29) 2,4-Dimethyl-8-[2,6-dimethyl-3-[N-methyl-N-[3-[4-[(2-pyridylmethyl)carbamoyl]phenyl]propionylglycyl]amino]benzyloxy]quinoline NMR (CDCl$_3$, δ): 2.32 (3H, s), 2.48–2.57 (5H, m), 2.65 (3H, s), 2.67 (3H, s), 2.99 (2H, t, J=7.5Hz), 3.45 (1H, dd, J=4, 18Hz), 3.72 (1H, dd, J=4, 18Hz), 4.75 (2H, d, J=5Hz), 5.33 (2H, s), 6.43 (1H, t-like), 7.02 (1H, d, J=8Hz), 7.11–7.34 (7H, m), 7.44 (1H, t, J=8Hz), 7.50 (1H, t-like), 7.59–7.71 (2H, m), 7.77 (2H, d, J=8Hz), 8.55 (1H, d, J=5Hz).

its dihydrochloride

NMR (DMSO-d$_6$, δ): 2.23 (3H, s), 2.38–2.52 (3H, m), 2.78–2.94 (8H, m), 3.09 (3H, s), 3.40 (1H, dd, J=4, 16Hz), 3.58 (1H, dd, J=4, 16Hz), 4.75 (2H, d, J=6Hz), 5.42–5.53 (2H, m), 7.26–7.37 (4H, m), 7.71–7.99 (8H, m), 8.06 (1H, t-like), 8.29–8.37 (1H, m), 8.76 (1H, d, J=5Hz), 9.35 (1H, t-like).

(30) 8-[2,6-Dimethyl-3-[N-methyl-N-[4-(2-oxopyrrolidin-1-yl)cinnamoylglycyl]amino]benzyloxy]-2-methylquinoxaline NMR (CDCl$_3$, δ): 2.11–2.23 (2H, m), 2.34 (3H, s), 2.50 (3H, s), 2.62 (2H, t, J=7.5Hz), 2.77 (3H, s), 3.26 (3H, s), 3.64 (1H, dd, J=17, 5Hz), 3.81–3.91 (3H, m), 5.35 (2H, s), 6.42 (1H, d, J=15Hz), 6.64 (1H, br s), 7.10 (1H, d, J=8Hz), 7.19 (1H, d, J=8Hz), 7.30 (1H, d, J=8Hz), 7.48–7.57 (3H, m), 7.62–7.70 (3H, m), 7.75 (1H, d, J=8Hz), 8.74 (1H, s).

(31) 8-[2,6-Dimethyl-3-[N-methyl-N-[4-(propionamido)cinnamoylglycyl]amino]benzyloxy]-2-methylquinoxaline NMR (CDCl$_3$, δ): 1.24 (3H, t, J=7.5Hz), 2.34 (3H, s), 2.39 (2H, q, J=7.5Hz), 2.77 (3H, s), 3.27 (3H, s), 3.63 (1H, dd, J=17, 5Hz), 3.87 (1H, dd, J=17, 4Hz), 5.32 (2H, s), 6.40 (1H, d, J=15Hz), 6.63 (1H, br t, J=5Hz), 7.09 (1H, d, J=8Hz), 7.18 (1H, d, J=8Hz), 7.29–7.33 (2H, m), 7.42–7.57 (5H, m), 7.68 (1H, t, J=8Hz), 7.75 (1H, d, J=8Hz), 8.73 (1H, br s).

(32) 8-[2,6-Dimethyl-3-[N-[4-(dimethylcarbamoyl)cinnamoylglycyl]-N-methylamino]benzyloxy]-2-methylquinoxaline NMR (CDCl$_3$, δ): 2.31 (3H, s), 2.50 (3H, s), 2.73 (3H, s), 2.98 (3H, br s), 3.11 (3H, br s), 3.26 (3H, s), 3.63 (1H, dd, J=4, 18Hz), 3.87 (1H, dd, J=4, 18Hz), 5.34 (2H, s), 6.50 (1H, d, J=16Hz), 6.68 (1H, t-like), 7.08 (1H, d, J=8Hz), 7.18 (1H, d, J=8Hz), 7.30 (1H, d, J=8Hz), 7.41 (2H, d, J=8Hz), 7.48–7.60 (3H, m), 7.65 (1H, t, J=8Hz), 7.75 (1H, d, J=8Hz), 8.73 (1H, s).

(33) 8-[2,6-Dimethyl-3-[N-[4-(ethylcarbamoyl)cinnamoylglycyl]-N-methylamino]benzyloxy]-2-methylquinoxaline NMR (CDCl$_3$, δ): 1.25 (3H, t, J=7.5Hz), 2.34 (3H, s), 2.51 (3H, s), 2.76 (3H, s), 3.27 (3H, s), 3.45–3.56 (2H, m), 3.63 (1H, dd, J=17, 5Hz), 3.88 (1H, dd, J=17, 4Hz), 5.35 (2H, s), 6.09 (1H, br t, J=7Hz), 6.52 (1H, d, J=15Hz), 6.71 (1H, br t, J=5Hz), 7.10 (1H, d, J=8Hz), 7.18 (1H, d, J=8Hz), 7.30 (1H, d, J=8Hz), 7.51–7.61 (3H, m), 7.66 (1H, t, J=8Hz), 7.72–7.79 (3H, m), 8.74 (1H, br s).

(34) 8-[2,6-Dimethyl-3-[N-[(E)-3-(6-ethoxycarbonylpyridin-3-yl)acryloylglycyl]-N-methylamino]benzyloxy]-2-methylquinoxaline NMR (CDCl$_3$, δ): 1.45 (3H, t, J=7.5Hz), 2.33 (3H, s), 2.51 (3H, s), 2.77 (3H, s), 3.27 (3H, s), 3.64 (1H, dd, J=17, 5Hz), 3.89 (1H, dd, J=17, 4Hz), 4.49 (2H, q, J=7.5Hz), 5.35 (2H, s), 6.63 (1H, d, J=15Hz), 6.78 (1H, br t, J=5Hz), 7.10 (1H, d, J=8Hz), 7.20 (1H, d, J=8Hz), 7.31 (1H, d, J=8Hz), 7.60 (1H, d, J=15Hz), 7.67 (1H, t, J=8Hz), 7.76 (1H, d, J=8Hz), 7.92 (1H, dd, J=8, 3Hz), 8.14 (1H, d, J=8Hz), 8.74 (1H, br s), 8.85 (1H, d, J=3Hz).

(35) 8-[3-[N-[(E)-3-(6-Aminopyridin-3-yl)acryloylglycyl]-N-methylamino]-2,6-dimethylbenzyloxy]-2-methylquinoxaline NMR (CDCl$_3$, δ): 2.33 (3H, s), 2.50 (3H, s), 2.85 (3H, s), 3.25 (3H, s), 3.63 (1H, dd, J=4, 18Hz), 3.85 (1H, dd, J=4, 18Hz), 4.69 (2H, s), 5.33 (2H, s), 6.30 (1H, d, J=16Hz), 6.49 (1H, d, J=8Hz), 6.61 (1H, t-like), 7.10 (1H, d, J=8Hz), 7.18 (1H, d, J=8Hz), 7.31 (1H, d, J=8Hz), 7.47 (1H, d, J=16Hz), 7.57–7.71 (2H, m), 7.75 (1H, d, J=8Hz), 8.17 (1H, s-like), 8.74 (1H, s-like).

EXAMPLE 51

8-[3-[N-(4-Amino-3-methylcinnamoylglycyl)-N-methylamino]-2,6-dichlorobenzyloxy]-2-methylquinoline was obtained from 8-[2,6-dichloro-3-[N-methyl-N-(3-methyl-4-nitrocinnamoylglycyl)amino]benzyloxy]-2-methylquinoline according to a similar manner to that of Preparation 15-(1).

NMR (CDCl$_3$, δ): 2.16 (3H, s), 2.73 (3H, s), 3.26 (3H, s), 3.61 (1H, dd, J=4, 16Hz), 3.82 (2H, br s), 3.93 (1H, dd, J=4, 16Hz), 5.60–5.70 (2H, m), 6.27 (1H, d, J=16Hz), 6.48 (1H, t-like), 6.64 (1H, d, J=8Hz), 7.17–7.35 (5H, m), 7.35–7.51 (4H, m), 8.02 (1H, d, J=8Hz).

EXAMPLE 52

To a solution of 8-[3-[N-(4-amino-3-methylcinnamoylglycyl)-N-methylamino]-2,6-dichlorobenzyloxy]-2-methylquinoline (200 mg) and triethylamine (35.9 mg) in dichloromethane was dropwise added isobutyryl chloride (41.6 mg) at 0° C. under nitrogen atmosphere, and the mixture was stirred for 30 minutes at the same temperature. The mixture was concentrated, and the residue was dissolved in methanol (3 ml). To the solution was added saturated sodium bicarbonate solution (1 ml), and the mixture was stirred for 2 hours at ambient temperature and concentrated. To the residue were added ethyl acetate and water, and the organic layer was washed with water, saturated sodium bicarbonate solution and brine, dried and concentrated. The residue was purified by preparative thin-layer chromatography (dichloromethane:methanol=15:1, V/V) to give 8-[2,6-dichloro-3-[N-methyl-N-(4-isobutyramido-3-methylcinnamoylglycyl)amino]benzyloxy]-2-methylquinoline (195 mg) as an amorphous powder.

NMR (CDCl$_3$, δ): 1.28 (6H, d, J=7.5Hz), 2.25 (3H, s), 2.56 (1H, m), 2.72 (3H, s), 3.26 (3H, s), 3.63 (1H, dd, J=4,

18Hz), 3.93 (1H, dd, J=4, 18Hz), 5.62 (1H, d, J=10Hz), 5.68 (1H, d, J=10Hz), 6.41 (1H, d, J=16Hz), 6.58 (1H, t-like), 7.02 (1H, br s), 7.23–7.55 (9H, m), 7.95–8.07 (2H, m).

its hydrochloride

NMR (DMSO-d$_6$, δ): 1.10 (6H, d, J=7Hz), 2.21 (3H, s), 2.69 (1H, m), 2.89 (3H, s), 3.15 (3H, s), 3.58 (1H, dd, J=4, 16Hz), 3.88 (1H, dd, J=4, 16Hz), 5.57–5.69 (2H, m), 6.72 (1H, d, J=16Hz), 7.26–7.52 (4H, m), 7.77–7.99 (6H, m), 8.26 (1H, t, J=6Hz), 8.95 (1H, br s), 9.27 (1H, s).

The following compounds were obtained according to a similar manner to that of Example 52.

(1) 8-[2,6-Dichloro-3-[N-methyl-N-[3-methyl-4-(isonicotinamido)cinnamoylglycyl]amino]benzyloxy]-2-methylquinoline NMR (CDCl$_3$, δ): 2.33 (3H, s), 2.72 (3H, s), 3.25 (3H, s), 3.63 (1H, dd, J=4, 18Hz), 3.93 (1H, dd, J=4, 18Hz), 5.58–5.68 (2H, m), 6.43 (1H, d, J=16Hz), 6.61 (1H, t-like), 7.21–7.33 (3H, m), 7.33–7.57 (6H, m), 7.70 (2H, d, J=6Hz), 7.77 (1H, s), 7.96–8.05 (2H, m), 8.80 (2H, d, J=6Hz).

its dihydrochloride

NMR (DMSO-d$_6$, δ): 2.28 (3H, s), 2.93 (3H, s), 3.16 (3H, s), 3.60 (1H, dd, J=4, 16Hz), 3.90 (1H, dd, J=4, 16Hz), 5.59–5.70 (2H, m), 6.79 (1H, d, J=16Hz), 7.37 (1H, d, J=16Hz), 7.41–7.53 (3H, m), 7.79–7.99 (6H, m), 8.01 (2H, d, J=6Hz), 8.31 (1H, t, J=6Hz), 8.91 (2H, d, J=6Hz), 8.98 (1H, d, J=8Hz), 10.44 (1H, s).

(2) 2,4-Dimethyl-8-[2,6-dimethyl-3-[N-methyl-N-[(E)-3-(6-propionamidopyridin-3-yl)acryloylglycyl]amino]benzyloxy]quinoline NMR (CDCl$_3$, δ): 1.25 (3H, t, J=7.5Hz), 2.36 (3H, s), 2.44 (2H, q, J=7.5Hz), 2.65 (3H, s), 2.66 (3H, s), 3.25 (3H, s), 3.63 (1H, dd, J=4, 18Hz), 3.88 (1H, dd, J=4, 18Hz), 5.35 (2H, s), 6.55 (1H, d, J=16Hz), 6.70 (1H, t-like), 7.06 (1H, d, J=8Hz), 7.12–7.19 (2H, m), 7.21–7.28 (1H, m), 7.45 (1H, t, J=8Hz), 7.51 (1H, d, J=16Hz), 7.82 (1H, dd, J=2, 8Hz), 7.98 (1H, s), 8.22 (1H, d, J=8Hz), 8.44 (1H, d, J=2Hz).

its dihydrochloride

NMR (DMSO-d$_6$, δ); 1.07 (3H, t, J=7.5Hz), 2.26 (3H, s), 2.42 (2H, q, J=7.5Hz), 2.46 (3H, s), 2.90 (6H, s), 3.11 (3H, s), 3.54 (1H, dd, J=4, 16Hz), 3.71 (1H, dd, J=4, 16Hz), 5.54–5.55 (2H, m), 6.81 (1H, d, J=16Hz), 7.28–7.41 (3H, m), 7.89–8.06 (6H, m), 8.13 (1H, d, J=8Hz), 8.23 (1H, t-like), 8.48 (1H, d, J=2Hz).

(3) 2,4-Dimethyl-8-[2,6-dimethyl-3-[N-methyl-N-[(E)-3-[6-(2-methylpyridine-3-carboxamido)pyridin-3-yl]acryloylglycyl]amino]benzyloxy]quinoline NMR (CDCl$_3$, δ): 2.37 (3H, s), 2.53 (3H, s), 2.65 (3H, s), 2.67 (3H, s), 2.75 (3H, s), 3.25 (3H, s), 3.63 (1H, dd, J=4, 18Hz), 3.89 (1H, dd, J=4, 18Hz), 5.35 (2H, s), 6.49 (1H, d, J=16Hz), 6.73 (1H, t-like), 7.07 (1H, d, J=8Hz), 7.13–7.20 (2H, m), 7.20–7.27 (2H, m), 7.45 (1H, t, J=8Hz), 7.52 (1H, d, J=16Hz), 7.62 (1H, d, J=8Hz), 7.83 (1H, d, J=8Hz), 7.90 (1H, dd, J=2, 8Hz), 8.31–8.39 (2H, m), 8.40 (1H, s), 8.63 (1H, d, J=6Hz).

its trihydrochloride

NMR (DMSO-d$_6$, δ): 2.27 (3H, s), 2.47 (3H, s), 2.75 (3H, s), 2.90 (6H, s), 3.12 (3H, s), 3.55 (1H, dd, J=4, 16Hz), 3.73 (1H, dd, J=4, 16Hz), 5.43–5.56 (2H, m), 6.88 (1H, d, J=16Hz), 7.28–7.45 (3H, m), 7.81 (1H, dd, J=6, 8Hz), 7.89–8.00 (4H, m), 8.10 (1H, dd, J=2, 8Hz), 8.20–8.31 (2H, m), 8.46 (1H, d, J=8Hz), 8.56 (1H, d, J=2Hz), 8.80 (1H, d, J=6Hz), 11.44 (1H, s).

(4) 2,4-Dimethyl-8-[2,6-dimethyl-3-[N-methyl-N-[(E)-3-[6-(4-pyridylacetamido)pyridin-3-yl]acryloylglycyl]amino]benzyloxy]quinoline NMR (CDCl$_3$, δ): 2.35 (3H, s), 2.51 (3H, s), 2.65 (3H, s), 2.67 (3H, s), 3.25 (3H, s), 3.62 (1H, dd, J=4, 18Hz), 3.74 (2H, s), 3.87 (1H, dd, J=4, 18Hz), 5.33 (2H, s), 6.45 (1H, d, J=16Hz), 6.74 (1H, t-like), 7.06 (1H, d, J=8Hz), 7.12–7.19 (2H, m), 7.22–7.30 (3H, m), 7.44 (1H, t, J=8Hz), 7.50 (1H, d, J=16Hz), 7.62 (1H, d, J=8Hz), 7.80–7.86 (1H, m), 8.08 (1H, s), 8.18 (1H, d, J=8Hz), 8.33 (1H, d, J=2Hz), 8.62 (2H, d, J=7Hz).

its trihydrochloride

NMR (DMSO-d$_6$, δ): 2.26 (3H, s), 2.45 (3H, s), 2.89 (6H, s), 3.11 (3H, s), 3.47–3.59 (1H, m), 3.66–3.77 (1H, m), 4.17 (2H, s), 5.42–5.55 (2H, m), 6.83 (1H, d, J=16Hz), 7.27–7.41 (3H, m), 7.85–8.10 (8H, m), 8.22 (1H, t-like), 8.51 (1H, s-like), 8.86 (2H, d, J=6Hz).

(5) 8-[2,6-Dimethyl-3-[N-methyl-N-[(E)-3-[6-(2-methylpyridine-3-carboxamido)pyridin-3-yl]acryloylglycyl]amino]benzyloxy]-2-methylquinoxaline NMR (CDCl$_3$, δ): 2.33 (3H, s), 2.50 (3H, s), 2.75 (6H, s), 3.25 (3H, s), 3.63 (1H, dd, J=4, 18Hz), 3.87 (1H, dd, J=4, 18Hz), 5.34 (2H, s), 6.48 (1H, d, J=16Hz), 6.72 (1H, t-like), 7.09 (1H, d, J=8Hz), 7.14–7.17 (2H, m), 7.31 (1H, d, J=8Hz), 7.54 (1H, d, J=16Hz), 7.67 (1H, t, J=8Hz), 7.75 (1H, d, J=8Hz), 7.83 (1H, d, J=8Hz), 7.92 (1H, dd, J=2, 8Hz), 8.32–8.44 (3H, m), 8.64 (1H, d, J=5Hz), 8.74 (1H, s).

EXAMPLE 54

To a solution of 8-[3-[N-(4-amino-3-methylcinnamoylglycyl)-N-methylamino]-2,6-dichlorobenzyloxy]-2-methylquinoline (200 mg) and triethylamine (35.9 mg) in dichloromethane was dropwise added methanesulfonyl chloride (0.03 ml) at 0° C. under nitrogen atmosphere, and the mixture was stirred for 1 hour at the same temperature. Methanesulfonyl chloride (0.03 ml) and triethylamine (36 mg) were further added thereto, and the mixture was stirred for 1 hour at the same temperature. The solvent was removed in vacuo, and the residue was dissolved in methanol. To the solution was added 1N sodium hydroxide solution (0.5 ml), and the mixture was stirred for 3 hours at ambient temperature and concentrated. To the residue were added dichloromethane and water, the organic layer was washed with water, saturated sodium bicarbonate solution and brine, dried and concentrated in vacuo. The residue was purified by preparative thin-layer chromatography (dichloromethane:methanol=15:1, V/V) to give 8-[2,6-dichloro-3-[N-(4-methanesulfonamido-3-methylcinnamoylglycyl)-N-methylamino]benzyloxy]-2-methylquinoline (185 mg) as an amorphous powder.

NMR (CDCl$_3$, δ): 2.29 (3H, s), 2.73 (3H, s), 3.05 (3H, s), 3.26 (3H, s), 3.64 (1H, dd, J=4, 18Hz), 3.95 (1H, dd, J=4, 18Hz), 5.65 (2H, s-like), 6.27 (1H, s), 6.43 (1H, d, J=16Hz), 6.62 (1H, t-like), 7.22–7.57 (10H, m), 8.03 (1H, d, J=8Hz).

its hydrochloride

NMR (DMSO-d$_6$, δ): 2.30 (3H, s), 2.88 (3H, s), 3.02 (3H, s), 3.58 (1H, dd, J=4, 16Hz), 5.56–5.69 (2H, m), 6.75 (1H, d, J=16Hz), 7.28–7.47 (4H, m), 7.75–7.97 (6H, m), 8.29 (1H, t, J=6Hz), 8.91 (1H, br s), 9.19 (1H, s).

EXAMPLE 55

2,4-Dimethyl-8-[2,6-dimethyl-3-[N-[(E)-3-(6-methanesulfonamidopyridin-3-yl)acryloylglycyl]-N-methylamino]benzyloxy]quinoline was obtained according to a similar manner to that of Example 54.

NMR (CDCl$_3$, δ): 2.35 (3H, s), 2.51 (3H, s), 2.62 (3H, s), 2.64 (3H, s), 3.19 (3H, s), 3.25 (3H, s), 3.62 (1H, dd, J=4, 16Hz), 3.87 (1H, dd, J=4, 16Hz), 5.33 (2H, s), 6.41 (1H, d, J=16Hz), 6.73 (1H, t-like), 7.06 (1H, d, J=8Hz), 7.10–7.27 (5H, m), 7.38–7.50 (2H, m), 7.62 (1H, d, J=8Hz), 7.80 (1H, d, J=8Hz), 8.29 (1H, d, J=2Hz).

its dihydrochloride

NMR (DMSO-d$_6$, δ): 2.27 (3H, s), 2.46 (3H, s), 2.89 (6H, s), 3.11 (3H, s), 3.29 (3H, s), 3.53 (1H, dd, J=4, 16Hz), 3.71 (1H, dd, J=4, 16Hz), 5.43–5.55 (2H, m), 6.75 (1H, d, J=16Hz), 7.02 (1H, d, J=8Hz), 7.27–7.40 (3H, m), 7.86–8.00 (5H, m), 8.23 (1H, t-like), 8.40 (1H, s-like).

EXAMPLE 56

To a solution of 8-[3-[N-(4-amino-3-methylcinnamoylglycyl)-N-methylamino]-2,6-dichlorobenzyloxy]-2-methylquinoline (200 mg) and triethylamine (35.9 mg) in dichloromethane was dropwise added methyl isocyanate (0.023 ml) at 0° C. under nitrogen atmosphere, and the mixture was stirred for 1 hour at the same temperature and for 2 hours at ambient temperature. Methyl isocyanate (0.03 ml) was further added thereto, and the mixture was stirred overnight at ambient temperature. The mixture was partitioned between dichloromethane and water, the organic layer was washed with water, saturated sodium bicarbonate solution and brine, dried and concentrated in vacuo. The residue was purified by preparative thin-layer chromatography (dichloromethane:methanol= 15:1, V/V) to give 8-[2,6-dichloro-3-[N-methyl-N-[3-methyl-4-(N'-methylureido)cinnamoylglycyl]amino] benzyloxy]-2-methylquinoline (150 mg) as an amorphous powder.

NMR (CDCl$_3$, δ): 2.07 (3H, s), 2.69 (3H, s), 2.78 (3H, d, J=5Hz), 3.24 (3H, s), 3.63 (1H, dd, J=4, 18Hz), 3.90 (1H, dd, J=4, 18Hz), 5.31 (1H, q-like), 5.61 (2H, s-like), 6.38 (1H, d, J=16Hz), 6.50 (1H, s), 6.64 (1H, t-like), 7.21–7.35 (5H, m), 7.39–7.51 (4H, m), 7.69 (1H, d, J=8Hz), 8.05 (1H, d, J=8Hz).
its hydrochloride NMR (DMSO-d$_6$, δ): 2.20 (3H, s), 2.66 (3H, s), 2.92 (3H, s), 3.15 (3H, s), 3.58 (1H, dd, J=4, 16Hz), 3.88 (1H, dd, J=4, 16Hz), 5.57–5.69 (2H, m), 6.63 (1H, d, J=16Hz), 7.21–7.34 (3H, m), 7.78–8.00 (8H, m), 8.19 (1H, t-like), 9.00 (1H, brpeak).

EXAMPLE 57

2,4-Dimethyl-8-[2,6-dimethyl-3-[N-[(E)-3-[6-(N'-ethylureido)pyridin-3-yl]acryloylglycyl]-N-methylamino] benzyloxy]quinoline was obtained according to a similar manner to that of Example 56.

NMR (CDCl$_3$, δ): 1.25 (3H, t, J=7.5Hz), 2.36 (3H, s), 2.52 (3H, s), 2.65 (3H, s), 2.66 (3H, s), 3.25 (3H, s), 3.42 (2H, quint, J=7.5Hz), 3.64 (1H, dd, J=4, 18Hz), 3.88 (1H, dd, J=4, 18Hz), 5.35 (2H, s), 6.40 (1H, d, J=16Hz), 6.70–6.78 (2H, m), 7.07 (1H, d, J=8Hz), 7.13–7.19 (2H, m), 7.22–7.27 (1H, m), 7.40–7.52 (2H, m), 7.63 (1H, d, J=8Hz), 7.73 (1H, d, J=8Hz), 7.86 (1H, s), 8.25 (1H, d, J=2Hz), 9.15 (1H, brpeak).
its dihydrochloride NMR (DMSO-d$_6$, δ): 1.09 (3H, t, J=7.5Hz), 2.27 (3H, s), 2.45 (3H, s), 2.88 (1H, s, J=6Hz), 3.11 (3H, s), 3.13–3.25 (2H, m), 3.54 (1H, dd, J=4, 17Hz), 3.71 (1H, dd, J=4, 17Hz), 5.42–5.56 (2H, m), 6.74 (1H, d, J=16Hz), 7.27–7.40 (3H, m), 7.46 (1H, d, J=8Hz), 7.85–8.02 (6H, m), 8.20 (1H, t, J=6Hz), 8.33 (1H, d, J=2Hz), 9.72 (1H, br s).

EXAMPLE 58

(1) 8-[3-[N-[4-(4-Bromobutyramido)-3-methylcinnamoylglycyl]-N-methylamino]-2,6-dichlorobenzyloxy]-2-methylquinoline was obtained from 8-[3-[N-(4-amino-3-methylcinnamoylglycyl)-N-methylamino]-2,6-dichlorobenzyloxy]-2-methylquinoline and 4-bromobutyric acid according to a similar manner to that of Example 5.

NMR (CDCl$_3$, δ): 2.14–2.30 (5H, m), 2.61 (2H, t, J=7Hz), 2.73 (3H, s), 3.26 (3H, s), 3.59–3.71 (3H, m), 3.94 (1H, dd, J=4, 18Hz), 5.60–5.70 (2H, m), 6.41 (1H, d, J=16Hz), 6.60 (1H, brpeak), 7.07 (1H, br s), 7.21–7.55 (9H, m), 7.95 (1H, d-like), 8.03 (1H, d, J=8Hz).

(2) To a solution of 8-[3-[N-[4-(4-bromobutyramido)-3-methylcinnamoylglycyl]-N-methylamino]-2,6-dichlorobenzyloxy]-2-methylquinoline (110 mg) in N,N-dimethylformamide was added potassium carbonate (64 mg) and the mixture was stirred for 2 hours at 50° C. The mixture was poured into water and extracted with ethyl acetate. The organic layer was washed with water and brine, dried and concentrated in vacuo. The residue was purified by preparative thin-layer chromatography (dichloromethane-methanol) to give 8-[2,6-dichloro-3-[N-methyl-N-[3-methyl-4-(2-oxopyrrolidin-1-yl)cinnamoylglycyl]amino]benzyloxy]-2-methylquinoline (72 mg) as an amorphous powder.

NMR (CDCl$_3$, δ): 2.15–2.29 (5H, m), 2.58 (2H, t, J=7.5Hz), 2.73 (3H, s), 3.26 (3H, s), 3.64 (1H, dd, J=4, 18Hz), 3.73 (2H, t, J=7.5Hz), 3.93 (1H, dd, J=4, 18Hz), 5.60–5.70 (2H, m), 6.43 (1H, d, J=16Hz), 6.63 (1H, brpeak), 7.21–7.58 (9H, m), 8.02 (1H, d, J=8Hz).
its hydrochloride NMR (DMSO-d$_6$, δ): 2.05–2.18 (5H, m), 2.41 (2H, t, J=7.5Hz), 2.90 (3H, s), 3.15 (3H, s), 3.58 (1H, dd, J=4, 16Hz), 3.68 (2H, t, J=7.5Hz), 3.90 (1H, dd, J=4, 16Hz), 5.58–5.69 (2H, m), 6.79 (1H, d, J=16Hz), 7.26 (1H, d, J=8Hz), 7.35 (1H, d, J=16Hz), 7.39–7.50 (2H, m), 7.77–7.98 (6H, m), 8.30 (1H, t-like), 7.96 (1H, brpeak).

EXAMPLE 59

The following compounds were obtained according to a similar manner to that of Example 58-(1) and (2).

(1) 2,4-Dimethyl-8-[2,6-dimethyl-3-[N-methyl-N-[(E)-3-[6-(2-oxopyrrolidin-1-yl)pyridin-3-yl]acryloylglycyl] amino]benzyloxy]quinoline NMR (CDCl$_3$, δ): 2.15 (2H, quint, J=7.5Hz), 2.36 (3H, s), 2.53 (3H, s), 2.61–2.72 (8H, m), 3.25 (3H, s), 3.63 (1H, dd, J=4, 18Hz), 3.87 (1H, dd, J=4, 18Hz), 4.11 (1H, t, J=7.5Hz), 5.35 (2H, s), 6.46 (1H, d, J=16Hz), 6.69 (1H, t-like), 7.07 (1H, d, J=8Hz), 7.13–7.19 (2H, m), 7.23–7.28 (1H, m), 7.45 (1H, t, J=8Hz), 7.52 (1H, d, J=16Hz), 7.63 (1H, d, J=8Hz), 7.82 (1H, dd, J=2, 8Hz), 8.38–8.45 (2H, m).
its dihydrochloride NMR (DMSO-d$_6$, δ): 2.05 (2H, quint, J=7.5Hz), 2.28 (3H, s), 2.47 (3H, s), 2.59 (2H, t, J=7.5Hz), 2.90 (6H, s), 3.11 (3H, s), 3.54 (1H, dd, J=4, 16Hz), 3.72 (1H, dd, J=4, 16Hz), 4.00 (2H, t, J=7.5Hz), 5.43–5.56 (2H, m), 6.82 (1H, d, J=16Hz), 7.27–7.41 (3H, m), 7.86–8.05 (5H, m), 8.25 (1H, t-like), 8.34 (1H, d, J=8Hz), 8.53 (1H, d-like).

(2) 8-[2,6-Dimethyl-3-[N-methyl-N-[(E)-3-[6-(2-oxopyrrolidin- 1-yl)pyridin-3-yl]acryloylglycyl]amino] benzyloxy]-2-methylquinoxaline NMR (CDCl$_3$, δ): 2.14 (2H, quint, J=7.5Hz), 2.34 (3H, s), 2.51 (3H, s), 2.68 (2H, t, J=7.5Hz), 2.76 (3H, s), 3.25 (3H, s), 3.63 (1H, dd, J=4, 18Hz), 3.87 (1H, dd, J=4, 18Hz), 4.11 (2H, t, J=7.5Hz), 5.34 (2H, s), 6.46 (1H, d, J=16Hz), 6.67 (1H, t-like), 7.10 (1H, d, J=8Hz), 7.19 (1H, d, J=8Hz), 7.30 (1H, d, J=8Hz), 7.53 (1H, d, J=16Hz), 7.67 (1H, t, J=8Hz), 7.75 (1H, d, J=8Hz), 7.84 (1H, dd-like, J=8Hz), 8.41–8.46 (2H, m), 8.74 (1H, s).

EXAMPLE 60

The following compounds were obtained according to a similar manner to that of Example 3.

(1) 8-[3-[N-[(E)-3-(6-Carboxypyridin-3-yl) acryloylglycyl]-N-methylamino]-2,6-dimethylbenzyloxy]-2,4-dimethylquinoline NMR (DMSO-$d_6$, δ): 2.30 (3H, s), 2.42 (3H, s), 2.51 (3H, s), 2.59 (3H, s), 3.09 (3H, s), 3.49 (1H, dd, J=17, 5Hz), 3.68 (1H, dd, J=17, 5Hz), 5.28 (2H, br s), 7.00 (1H, d, J=15Hz), 7.20–7.31 (3H, m), 7.39 (1H, d, J=8Hz), 7.42–7.60 (3H, m), 7.61 (1H, d, J=8Hz), 8.03 (1H, d, J=8Hz), 8.11 (1H, dd, J=8, 2Hz), 8.31 (1H, br t, J=8Hz), 8.85 (1H, br s).

(2) 8-[3-[N-[(E)-3-(6-Carboxypyridin-3-yl) acryloylglycyl]-N-methylamino]-2,6-dimethylbenzyloxy]-2-methylquinoxaline NMR (CDCl$_3$, δ): 2.36 (3H, s), 2.51 (3H, s), 2.78 (3H, s), 3.28 (3H, s), 3.66 (1H, dd, J=17, 5Hz), 3.90 (1H, dd, J=17, 5Hz), 5.35 (2H, s), 6.68 (1H, d, J=15Hz), 6.83 (1H, br t, J=5Hz), 7.10 (1H, d, J=8Hz), 7.20 (1H, d, J=8Hz), 7.31 (1H, d, J=8Hz), 7.58–7.70 (2H, m), 7.77 (1H, d, J=8Hz), 8.02 (1H, dd, J=8, 2Hz), 8.21 (1H, d, J=8Hz), 8.70 (1H, br d, J=2Hz), 8.75 (1H, s).

EXAMPLE 61

The following compounds were obtained according to a similar manner to that of Example 7.

(1) 2,4-Dimethyl-8-[2,6-dimethyl-3-[N-methyl-N-[(E)-3-[6-(4-pyridylcarbamoyl)pyridin-3-yl]acryloylglycyl]amino] benzyloxy]quinoline NMR (CDCl$_3$, δ): 2.39 (3H, s), 2.55 (3H, s), 2.66 (3H, s), 2.68 (3H, s), 3.28 (3H, s), 3.67 (1H, dd, J=17, 5Hz), 3.91 (1H, dd, J=17, 4Hz), 5.36 (2H, s), 6.67 (1H, d, J=15Hz), 6.82 (1H, br s), 7.08 (1H, br d, J=8Hz), 7.13–7.30 (4H, m), 7.45 (1H, t, J=8Hz), 7.60–7.68 (2H, m), 7.71 (2H, d, J=7Hz), 8.01 (1H, br d, J=8Hz), 8.29 (1H, d, J=8Hz), 8.58 (2H, d, J=7Hz), 8.70 (1H, br s).

its trihydrochloride

NMR (CDCl$_3$-CD$_3$OD, δ): 2.36 (3H, s), 2.49 (3H, s), 2.97 (3H, s), 3.12 (3H, br s), 3.30 (3H, s), 3.84 (1H, br d, J=17Hz), 3.95 (1H, br d, J=17Hz), 5.39 (1H, br d, J=10Hz), 5.49 (1H, br d, J=10Hz), 6.91 (1H, br d, J=15Hz), 7.22–7.31 (2H, m), 7.52 (1H, br d, J=15Hz), 7.62 (1H, br d, J=8Hz), 7.74 (1H, br s), 7.80–7.90 (2H, m), 8.16 (1H, br s), 8.37 (1H, br s), 8.42–8.51 (2H, m), 8.61–8.70 (2H, m), 8.95 (1H, br s).

(2) 2,4-Dimethyl-8-[2,6-dimethyl-3-[N-methyl-N-[(E)-3-[6-[(2-pyridylmethyl)carbamoyl]pyridin-3-yl] acryloylglycyl]amino]benzyloxy]quinoline NMR (CDCl$_3$, δ): 2.38 (3H, s), 2.53 (3H, s), 2.65 (3H, s), 2.67 (3H, s), 3.27 (3H, s), 3.64 (1H, dd, J=17, 5Hz), 3.90 (1H, dd, J=17, 4Hz), 4.80 (2H, d, J=7Hz), 5.35 (2H, s), 6.61 (1H, d, J=15Hz), 6.78 (1H, br t, J=5Hz), 7.08 (1H, d, J=8Hz), 7.13–7.28 (4H, m), 7.34 (1H, br d, J=8Hz), 7.45 (1H, t, J=8Hz), 7.57–7.70 (3H, m), 7.94 (1H, dd, J=8, 2Hz), 8.20 (1H, d, J=8Hz), 8.60 (1H, br d, J=7Hz), 8.68 (1H, d, J=2Hz), 8.89 (1H, br t, J=7Hz).

its trihydrochloride

NMR (CDCl$_3$-CD$_3$OD, δ): 2.32 (3H, s), 2.46 (3H, s), 2.97 (3H, s), 3.10 (3H, br s), 3.26 (3H, s), 3.84 (1H, d, J=17Hz), 3.92 (1H, d, J=17Hz), 5.16 (2H, s), 5.39 (1H, br d, J=10Hz), 5.49 (1H, br d, J=10Hz), 6.99 (1H, br d, J=15Hz), 7.19–7.28 (2H, m), 7.50 (1H, br d, J=15Hz), 7.61 (1H, br d, J=8Hz), 7.72–7.92 (4H, m), 8.15 (1H, br d, J=8Hz), 8.34–8.58 (3H, m), 8.78 (1H, br d, J=7Hz), 9.07 (1H, br s).

(3) 2,4-Dimethyl-8-[2,6-dimethyl-3-[N-methyl-N-[(E)-3-[6-(methylcarbamoyl)pyridin-3-yl]acryloylglycyl]amino] benzyloxy]quinoline NMR (CDCl$_3$, δ): 2.37 (3H, s), 2.53 (3H, s), 2.65 (3H, s), 2.68 (3H, s), 3.04 (3H, d, J=5Hz), 3.27 (3H, s), 3.64 (1H, dd, J=17, 5Hz), 3.90 (1H, dd, J=17, 5Hz), 5.34 (2H, s), 6.61 (1H, d, J=15Hz), 6.79 (1H, br t, J=5Hz), 7.08 (1H, d, J=8Hz), 7.15–7.20 (2H, m), 7.25 (1H, d, J=8Hz), 7.45 (1H, t, J=8Hz), 7.56–7.66 (2H, m), 7.90–8.00 (2H, m), 8.19 (1H, d, J=8Hz), 8.61 (1H, d, J=2Hz).

its dihydrochloride

NMR (CDCl$_3$-CD$_3$OD, δ): 2.31 (3H, s), 2.40 (3H, s), 2.97 (3H, s), 3.06 (3H, s), 3.11 (3H, br s), 3.28 (3H, s), 3.88 (1H, d, J=17Hz), 4.06 (1H, d, J=17 Hz), 5.34 (1H, d, J=10 Hz), 5.46 (1H, d, J=10 Hz), 7.10 (1H, br d, J=15 Hz), 7.19–7.32 (2H, m), 7.49 (1H, br d, J=15 Hz), 7.60 (1H, br d, J=8 Hz), 7.72–7.89 (3H, m, 8.74 (1H, br d, J=8 Hz), 8.88 (1H, br d, J=8 Hz),9.42 (1H, br s).

(4) 8-[2, 6-Dimethyl-3-[N-methyl-N-[(E)-3-[6-(methylcarbamoyl)pyridin-3-yl]acryloylglycyl]amino]-benzyloxy]-2-methylquinoxaline NMR (CDCl$_3$, δ): 2.34 (3H, s), 2.52 (3H, s), 2.77 (3H, s), 3.04 (3H, d, J=5 Hz), 3.28 (3H, s), 3.64 (1H, dd, J=17, 5 Hz), 3.89 (1H, dd, J=17, 5 Hz), 5.34 (2H, s), 6.61 (1H, d, J=15 Hz), 6.76 (1H, br t, J=5 Hz), 7.10 (1H, d, J=8 Hz), 7.19 (1H, d, J=8 Hz), 7.31 (1H, d, J=8 Hz), 7.60 (1H, d, J=15 Hz),7.67 (1H, t, J=8 Hz),7.75 (1H, d, J=8 Hz), 7.91–8.00 (2H, m), 8.20 (1H, d, J=8 Hz), 8.61 (1H, d, J=2 Hz), 8.73 (1H, s),

EXAMPLE 62

(1) 4-carboxy-8-[2,6-dimethyl-3-[N-[4-(methylcarbamoyl)-cinnamoylglycyl]-N-methylamino] benzyloxyl]-2-methylquinoline was obtained from 8-[2,6-dimethyl-3-[N-[4-(methylcarbamoyl)-cinnamoylglycyl]-N-methylamino]benzyloxy]-4-ethoxycarbonyl-2-methylquinoline according to a similar manner to that of Example 3.

mp: 178.2–184.2° C.

NMR (DMSO-$d_6$, δ): 2.30 (3H, s), 2.45 (3H, s), 2.70 3H, s), 2.76 (3H, d, J=5 Hz), 3.10 (3H, s), 3.50 (1H, dd, J=17, 5 Hz), 3.69 (1H, dd, J=17, 4 Hz), 5.34 (2H, s), 6.87 (1H, d, J=15 Hz), 7.27 (1H, d, J=8 Hz), 7.34 (1h, d, J=8 Hz), 7.40 (1H, d, J=15 Hz), 7.53–7.71 (4H, m, 7.80–8.04 (3H, m, 8.18 (1H, d, J=8 Hz), 8.27 (1H, br t, J=5 Hz), 8.52 (1H, br q, J=5 Hz), (2) 8-[2,6-Dimethyl-3-[N-[4-(methylcarbamoyl)-cinnamoylglycyl]-N-methylamino]benzyloxy]-2-methyl-4-(methylcarbamoyl)quinoline was obtained from 4-carboxy-8-[2,6-dimethyl-3-[N-[4-(methylcarbamoyl) cinnamoylglycyl]-N-methylamino]benzyloxy]-2-methylquinoline and methylamine hydrochloride according to a similar manner to that of Example 7.

NMR (CDCl$_3$, δ): 2.36 (3H, s), 2.52 (3H, s), 2.64 (3H, s), 2.99 (3H, d, J=5 Hz), 3.06 (3H, d, J=5 Hz), 323 (3H, s), 3.47 (1H, dd, J=17, 5 Hz), 3.79 (1H, dd, J=17, 4 Hz), 5.36 (2H, s), 6.27 (1H, br q, J=5 Hz), 6.50 (1H, d, J=15 Hz), 6.58 (1H, br q, J=5 Hz), 671–6.80 (1H, m), 7.04 (1H, d, J=9 Hz), 7.15 (1H, d, J=9 Hz), 7.21–7.30 (2H, m), 7.50–7.60 (3H, m), 7.51 (1H, d, J=15 Hz), 7.67 (1H, d, J=9 Hz), 7.75 (1H, d, J=8 Hz).

its hydrochloride

NMR (CDCl$_3$—CD$_3$OD, δ): 2.30 (3H, s), 2.50 (3H, s), 2.96 (3H, s), 3.06 (3.06 (3H, s), 3.08 (3H, s), 3.28 (3H, s), 3.74 (1H, d, J=17 Hz), 3.89 (1H, d, J=17 Hz), 5.36 (1H, d, J=9 Hz), 5.49 (1H, d, J=9 Hz), 6.60 (1H, d, J=15 Hz), 7.20–7.31 (2H, m), 7.49 (1H, d, J=15 Hz), 7.55 (2H, d, J=9 Hz), 7.65 (1H, d, J=8 Hz), 7.78 (2H, d, J=9 Hz), 7.85 (1H, t, J=8 Hz), 8.00 (1H, s), 8.05 (1H, d, J=8 Hz).

EXAMPLE 63

A misture of 3-[(Z)-2-(4-methylcarbamoylphenyl)vinyl]-benzoic acid (281 mg) and thionyl chloride (10 ml) was refluxed for 2 hours and then the mixture was concentrated in vacuo. The residue was dissolved in dichloromethane (10 ml), and thriethylamine (0.3 ml) and 8-[2,6-dichloro-3-(methylamino)benzyloxy]-2-methylquinoline (347 mg) were added thereto with stirring under ice-bath cooling. The mixture was stirred for 12 hours at ambient temperature. Chloroform and brine were added thereto, and the organic layer was dried over magnesium sulfate and concentrated in vacuo. The residue was prufied by flash chromatograph (chloroform-methanol) to give 8-[2,6-dichloro-3-[N-methyl-N-[3-[(Z)-2-(4-methylcarbamoylphenyl)vinyl] benzoyl]amino]benzyloxy]-2-methylquinoline (110 mg) as an amorphous powder.

NMR (CDCl$_3$, δ): 2.73 (3H, s), 3.02 (3H, d, J=6 Hz), 3.40 (3H, s), 5.48 (1H, d, J=10 Hz), 5.54 (1H, d, J=10 Hz), 6.23 (1H, br s), 6.98–7.63 (14H), 7.70 (1H, d, J=8 Hz), 8.02 (1H, d, J=8 Hz),

EXAMPLE 64

8-[2,6-Dichloro-3-[N-methyl-N-[3-[(E)-2-(4-methylcarbamoylphenyl)vinyl]benzoyl]amino]benzyloxy]-2-methylquinoline was obtained from 3-[(E)-2-(4-methylcarbamoylpheny)vinyl]benzoic acid and 8-[2,6-dichloro-3-(methylamino)benzyloxy]-2-methylquinoline according to a similar manner to that of Example 63.

NMR (CDCl$_3$, δ): 2.65 (2.4H, s), 2.69 (0.6H, s), 2.78 (3H, d, J=6 Hz), 3.29 (2.4H br s), 3.40 (0.6H, br s), 5.58 (2H, br s), 6.41 (0.4H, br s), 6.58 (1.6H, br s), 6.98–7.73 (15H), 8.03 (1H, d, J=8 Hz),

Preparation 50

The mixture of 4-chloro-8-hydroxy-2-methylquinoline 600 mg), piperidine (6.13 ml) and tetrabutylammonium iodide (10 mg) was refluxed for 18 hours. The cooled reaction mixture was concentrated in vacuo and to the residue was added chloroform and aqueous sodium bicarbonate solution. The organic layer was dried over magnesium sulfate and evaporated in vacuo. The residue was recrystallized from n-hexane to give 8-hydroxy-2-methyl-4-piperidinoquinoline (712 mg) as pale brown crystals.

mp: 115–118° C.

NMR (CDCl$_3$, δ): 1.63–1.74 (2H, m), 1.79–1.89 (4H, m), 2.64 (3H, s), 3.15–3.22 (4H, m), 6.70 (1H, s), 7.06 (1H, d, J=8 Hz), 7.28 (1H, t, J=8 Hz), 7.39 (1H, d, J=8 Hz).

Preparation 51

The following compounds were obtained according to a similar manner to that of Prepartion 6.

(1) 8-[2,6-Dichloro-3-[N-methyl-N-(phthalimidoacetyl) amino]-benzyloxy]-4-dimethylamino-2-methylquinoline NMR CDCl$_3$, δ): 2.66 (3H, s), 2.96 (3H, s), 3.21 (3H, s), 4.07 (2H, s), 5.63 (1H, d, J=10 Hz), 5.71 (1H, d, J=10 Hz), 6.99 (1H, s), 7.20 (1H, d, J=8 Hz), 7.30 (1H, d, J=8 Hz), 7.46 (1H, d, J=8 Hz), 7.53 (1H, d, J=8 Hz), 7.65–7.75 (3H, m), 7.82–7.90 (2H, m).

(2) 8-[2,6-Dichloro-3-(N-phthalimidoacetyl-N-methylamino)-benzyloxy]-2-methyl-4-piperidinoquinoline mp: 223–226° C.

NMR (CDCl$_3$, δ) 1.59–1.72 (2H, m), 1.78–1.88 (4H, m), 2.65 (3H, s), 3.07–3.19 (4H, m), 3.22 (3H, s, 4.08 (2H, s), 5.64 (1H, d, J=10 Hz), 5.71 (1H, d, J=10 Hz), 6.73 (1H, s), 7.20 (1H, br d, J=8 Hz), 7.30 (1H, t, J=8 Hz), 7.46 (1H, d, J=8 Hz), 7.51 (1H, d, J=8 Hz), 7.64 (1H, br d, J=8 Hz), 7.70–7.76 (2H, m, 7.82–7.89 (2H, m).

(3) 8-[2,6-Dichlor-3-(N-phthalimidoacetyl-N-methylamino)benzyloxy]-2-methyl-4-morpholinoquinoline NMR (CDCl$_3$, δ) 2.69 (3H, s), 3.19 (4H, t, J=6 Hz), 3.21 (3H, s), 3.96 (4H, t, J=5 Hz), 4.06 (2H, s), 5.65 (1H, d, J=10 Hz), 5.72 (1H, d, J=10 Hz), 6.76 (1H, s), 7.22 (1H, d, J=8 Hz), 7.32 (1H, t, J=8 Hz), 7.47 (1H, d, J=8 Hz), 7.53 (1H, d, J=8 Hz), 7.66 (1H, d, J=8 Hz), 7.72 (2H, dd, J=8, 2 Hz), 7.84 (2H, dd, J=8, 2 Hz).

Preparation 52 the following compounds were contained according to a similar manner to that of Preparation 11.

(1) 8-[3-(N-Glycyl-N-methylamino)-2,6-dichlorobenzyloxy]-4-dimethylamino-2methylquinoline NMR (CDCl$_3$, δ): 2.66 (3H, s), 2.91–3.13 (8H, m), 3.21 (3H, s, 5.61 (2H, s, 6.70 (1H, s), 7.12–7.36 (3H, m), 7.45 (1H, d, J=8 Hz), 7.70 (1H, d, J=8 Hz).

(2) 8-[3-(N-Glycyl-N-methylamino)-2,6-dichlorobenzyloxy]-2-methyl-4-piperidinoquinoline NMR (CDCl$_3$, δ): 1.57–1.90 (6H, m, 2.65 (3H, s), 2.97 (1H, d, J=17 Hz), 3.02–3.18 (4H, m), 3.2 (3H),s, 5.60 (2H, s), 6.72 (1H, s), 7.15 (1H, br d, J=8 Hz), 7.19–7.34 (2H, m), 7.43 (1H, d, J=8 Hz), 7.64 (1H, br d, J=8 Hz).

(3) 8-[3-Glycyl-N-methylamino)-2,6-dichlorobenzyloxy]-2-methyl-4-morpholinoquinoline NMR (CDCl$_3$, δ): 2.69 (3H, s), 2.8 (1H, d, J=17 Hz), 3.09 (1H, d, J=17 Hz), 3.13–3.22 (4H), 3.20 (3H, s), 3.92–4.00 (4H), 5.62 (2H, s), 6.77 (1H, s, 716–7.26 (2H), 7.33 (1H, t, J=8 Hz), 7.44 (1H, d, J=8 Hz), 7.66 (1H, d, J=8 Hz).

Preparation 53

The following compounds were obtained according to a similar manner to that of Preparqtion 2.

(1) Methyl 4-[N-(2-dimethylaminoethyl)carbamoyl] cinnamate ms 104–106° C.

NMR (CDCl$_3$, δ): 2.27 (6H, s), 2.51 (2H, t, J=7 Hz), 3.51 (2H, br q, J=7 Hz), 3.81 (3H, s), 6.49 (1H, d, J=15 Hz), 6.85 (1H, br s), 7.58 (2H, br d, J=8 Hz), 7.70 (1H, d, J=15 Hz), 7.81 (2H, br d, J=8 Hz).

(2) Methyl 4-[N-(2-dimethylaminoethyl)-N-methylcarbamoyl]-cinnamate

NMR (CDCl$_3$, δ): 2.09 (3H, br s), 2.31 (3H, br s), 2.36–2.64 (2H, m), 2.94–3.14 (3H, m), 3.32 (1H, br s), 3.65 (1H, br s), 3.80 (3H, s), 6.47 (1H, d, J=15 Hz), 7.42 (2H, br d, J=8 Hz), 7.55 (2H, br d, J=8 Hz), 7.69 (1H, d, J=15 Hz).

Preparation 54

The following compounds were obtained according to a similar manner to that of Preparation 3.

(1) 4-[N-(2-Dimethylaminoethyl)carbamoyl]cinnamic acid mp:219–223° C.

NMR (DMSO-d$_6$, δ): 2.33 (6H, s), 2.62 (2H, br t, J=7 Hz), 3.43 (2H, br q, J=7 Hz), 6.59 (1H, d, J=15 Hz), 7.57 (1H, d, J=15 Hz), 7.75 (2H, d, J=8 Hz), 7.86 (2H, d, J=8 Hz), 8.54 (1H, br t, J=7 Hz).

(2) 4-[N-(2-Dimethylaminoethyl)-N-methylcarbamoyl] cinnamic acid mp: 171–174° C.

NMR (DMSO-d$_6$, δ): 1.98 (3H, br s), 2.28–2.60 (5H, m), 2.84–3.00 (4H, m), 3.07–3.75 (1H, overlapped with H$_2$O), 6.59 (1H, d, J=15 Hz), 7.40 (2H, d, J=8 Hz), 7.61 (1H, d, J=15 Hz), 7.74 (2H, d, J=8 Hz).

Preparation 55

The following compounds were obtained according to a similar manner to that of Preparation 46-(1).

(1) N-(3-Aminobenzoyl)methanesulfonamide (from N-(3-nitrobenzoyl)methanesulfonamide)

mp: 153–155 °C.

NMR (DMSO-$d_6$, δ): 3.32 (3H, s), 6.78 (1H, dd, J=8, 2 Hz), 7.01–7.17 (3H, m).

(2) N-(3-Aminobenzoyl)-4-methylbenzenesulfonamide (from N-(3-nitrobenzoyl)-4-methylbenzenesulfonamide)

NMR (DMSO-$d_6$, δ): 2.39 (3H, s), 6.74 (1H, br dd, J=8, 2 Hz), 6.92–6.99 (2H, m), 7.08 (1H, t, J=8 Hz), 7.41 (2H, d, J=8 Hz), 7.84 (2H, d, J=8 Hz).

Preparation 56

To a solution of N-(3-aminobenzoyl)methanesulfonamide (400 mg) in dioxane (4 ml) and 1N sodium hydroxide solution (3.73 ml) was added phenyl chloroformate (351 mg) under ice-cooling, and the mixture was stirred for 2.5 hours at ambient temperature. Water was added thereto, the mixture was adjusted pH 3 with hydrochloric acid. The mixture was extracted with chloroform-methanol, and the extract was dried over magnesium sulfate and concentrated in vacuo to give phenyl 3-(methanesulfonylaminocarbonyl)phenylcarbamate (600 mg) as colorless crystals.

mp: 201–202° C.

NMR (DMSO-$d_6$, δ): 3.22 (3H, s), 7.22–7.30 (3H, m), 7.47–7.57 (3H, m), 7.62 (1H, d, J=8 Hz), 7.70 (1H, br d, J=8 Hz), 8.07 (1H, br s).

Preparation 57

Phenyl 3-(4-methylbenzenesulfonylaminocarbonyl)-phenylcarbamate was obtained according to a similar manner to that of Preparation 55.

NMR (CDCl$_3$, δ): 2.38 (3H, br s), 7.11–7.43 (10H, m), 7.51 (1H, br d, J=8 Hz), 7.66 (1H, br d, J=8 Hz), 7.87 (1H, br s), 7.99 (2H, br d, J=8 Hz).

Preparation 58

(1) A mixture of 2-hydroxypryidine (2.40 g), ethyl 4-iodobenzoate (6.97 g), potassium carbonate (3.83 g) and copper (253 mg) in N,N-dimethylformamide (12 ml) was stirred for 4 hours at 175° C. under nitrogen atmosphere. Insoluble material was filtered off, and the filtrate was concentrated in vacuo. To the residue was added ethyl acetate and 1N hydrochloric acid, the organic layer was washed with water, saturated sodium bicarbonate solution and brine, dried over magnesium sulfate and concentrated in vacuo to give ethyl 4-(2-oxo-1,2-dihydropyridin-1yl)benzoate (2.18 g) as brown powder.

NMR (CDCl$_3$, δ): 1.40 (3H, t, J=7.0 Hz), 4.40 (2H, q, J=7.0 Hz), 6.26 (1H, t, J=7.5 Hz), 6.67 (1H, d, J=7.5 Hz), 7.32 (1H, d, J=7.5 Hz), 7.41 (1H, t, J=7.5 Hz), 7.47 (2H, d, J=8.5 Hz), 8.17 (2 H, d, J=8.5 Hz).

(2) 4-(2Oxo-1,2-dihydropyridin-1-yl) benzyl alcohol was obtained according to a similar manner to that of Preparation 27-(5).

NMR (CDCl$_3$, 67 ): 4.71 (2H, s), 6.23 (1H, t, J=7.5 Hz), 6.66 (1H, d, J=7.5 Hz), 7.29–7.51 (2H, m), 7.33 (2H, d, J=8.5 Hz), 7.46 (2H, d, J=8.5 Hz).

(3) 4-(2-Oxo-1,2-dihydropyridin-1-yl) benzaldehyde was obtained according to a similar manner to that of Preparation 32-(7).

NMR (CDCl$_3$, δ): 6.31 (1H, t, J=7.5 Hz), 6.68 (1H, d, J=7.5 Hz), 7.33 (1H, d, J=7.5 Hz), 7.42 (1H, t, J=7.5 Hz), 7.61 (2H, d, J=8.5 Hz), 8.03 (2H, d, J=8.5 Hz), 10.08 (1H, s).

(4) 4-(2-Oxo-1,2-dihydropyridin-1-yl) cinnamic acid was obtained according to a similar manner to that of Preparation 4.

mp: 279–282° C.

NMR (CDCl$_3$—CD$_3$OD, δ): 6.37 (1H, t, J=7.5 Hz), 6.47 (1H, d, J=16.0 Hz), 6.68 (1H, d, J=7.5 Hz), 7.33–7.54 (4H, m), 7.67 (2H, d, J=8.85 Hz), 7.71 (1H, d, J=16.0 Hz).

EXAMPLE 65

(1) 8-Hydroxy-2methyl-4-(pyrrolidin-1-yl)quinoline was obtained from 4-chloro-8-hydroxy-2-methylquinoline and pyrrolidine according to a similar manner to that of Preparation 16.

m;: 135–137° C.

NMR (CDCl$_3$, δ): 1.99–2.10 (4H, m), 2.56 (3H, s), 3.65–3.76 (4H, m), 6.32 (1H, s), 7.03 (1H, d, J=7.5 Hz), 7.16 (1H, t, J=7.5 Hz), 7.65 (1H, d, J=7.5 Hz).

(2) 8-[2,6-Dichloro-3-[N-methyl-N-[4-methylcarbamoyl)-cinnamoylglycyl]amino]benzyloxy]-2-methyl-4-(pyrrolidin-1-yl)quinoline was obtained according to a similar manner to that of Example 9.

NMR (CDCl$_3$, δ): 1.98–2.06 (4H, m), 2.54 (3H, s), 2.99 (3H, d, J=5 Hz), 3.24 (3H, s), 3.59–3.72 (5H, m), 3.93 (1H, dd, J=17, 5 Hz), 5.56 (1H, d, J=10 Hz), 5.60 (1H, d, J=10 Hz), 6.33–6.41 (2H, m), 6.52 (1H, d, J=15 Hz), 6.85 (1H, br s), 7.11–7.30 (3H, m), 7.41–7.50 (3H, m), 7.55 (1H, d, J=15 Hz), 7.71 (2H, br d, J=8 Hz), 7.84 (1H, br d, J=8 Hz).
its dihydrochloride mp: 203–206° C.

NMR (CDCl$_3$—CD$_3$OD, δ): 2.14–2.26 (4H, m), 2.67 (3H, s), 2.99 (3H, s), 3.29 (3H, s), 3.87 (1H, d, J=17 Hz), 3.89–4.08 (4H, m), 4.13 (1H, d, J=17 Hz), 5.48 (1H, d, J=10 Hz), 5.65 (1H, d, J=10 Hz), 6.51 (1H, s), 6.62 (1H, d, J=15 Hz), 7.33–7.64 (7H, m), 7.81 (2H, d, J=8 Hz), 8.02 (1H, d, J=8 Hz).

EXAMPLE 66

(1) 8-Hydroxy-2-methyl-4-(4-methylpiperazin-1-yl)quinoline hydrochloride was obtained from 4-chloro-8-hydroxy-2-methylquinoline and 1-methylpiperazine according to a similar manner to that of Preparation 16.

mp: >300° C.

NMR (DMSO-$d_6$, δ): 2.66 (3H, s), 2.46 (3H, br s), 3.10–3.60 (8H, overlapped with H$_2$O), 7.01–7.11 (2H, m), 7.30–7.42 (2H, m).

(b 2) 8-[2,6-Dichloro-3-[N-methyl-N-[4-(methylcarbamoyl)-cinnamoylglycyl]amino]benzyloxy]-2-methyl-4-(4-methylpiperazin-1-yl)quinoline was obtained according to a similar manner to that of Example 9.

NMR (CDCl$_3$, δ): 2.42 (3H, s), 2.66 (3H, s), 2.67–2.75 (4H, m), 3.01 (3H, d, J=5 Hz), 3.19–3.29 (7H, m), 3.68 (1H, dd, J=17, 4 Hz), 3.94 (1H, dd, J=17, 5 Hz), 5.59 (1H, d, J=10 Hz), 5.65 (1H, d, J=10 Hz), 6.25 (1H, br d, J=5 Hz), 6.53 (1H, d, J=15 Hz), 6.70–6.79 (2H, m), 7.18–7.68 (8H, m), 7.75 (2H, br d, J=7.5 Hz).
its trihydrochloride NMR (CDCl$_3$—CD$_3$OD, δ): 2.84 (3H, br s), 2.99 (3H, s), 3.04 (3H, br s), 3.30 (3H, s), 3.50–3.59 (2H, m), 3.86–4.02 (4H, m), 4.19–4.29 (4H, m), 5.50 (1H, d, J=10 Hz), 5.68 (1H, d, J=10 Hz), 6.59 (1H, d, J=15 Hz), 7.37–7.81 (11H, m).

EXAMPLE 67

(1) 4-Hexamethyleneimino-8-hydroxy-2-methylquinoline was obtained from 4-chloro-8-hydroxy-2- methylquinoline and hexamethyleneimine according to a similar manner to that of Preparation 16.

NMR (CDCl₃, δ): 1.70–1.80 (4H, m), 1.87–1.99 (4H, m), 2.59 (3H, s), 3.49–3.58 (4H, m), 6.63 (1H, s), 7.03 (1H, d, J=8 Hz), 7.21 (1H, t, J=8 Hz), 7.46 (1H, d, J=8 Hz).

(2) 4-Hexamethyleneimino-8-[2,6-dichloro-3-[N-methyl-N-[4-(methylcarbamoyl)cinnamoylglycyl]amino]benzyloxy]-2-methylquinoline was obtained according to a similar manner to that of Example 9.

NMR (CDCl₃, δ): 1.59–1.80 (4H, m), 1.86–1.97 (4H, m), 2.60 (3H, br s), 2.99 (3H, d, J=5 Hz), 3.24 (3H, s), 3.43–3.53 (4H, m), 3.70 (1H, dd, J=17, 4 Hz), 3.95 (1H, dd, J=17, 5 Hz), 5.57 (2H, s), 6.35 (1H, br s), 6.54 (1H, d, J=15 Hz), 6.70 (1H, br s), 7.19 (1H, br d, J=8 Hz), 7.27–7.35 (2H, m), 7.41–7.50 (3H, m), 7.54 (1H, d, J=15 Hz), 7.67–7.75 (3H, m).

its dihydrochloride

NMR (CDCl₃—CD₃OD, δ): 1.69–1.79 (4H, m), 2.00–2.11 (4H, m), 2.69 (3H, s), 2.99 (3H, s), 3.28 (3H, s), 3.86 (1H, d, J=17 Hz), 3.90–4.00 (4H, m), 4.24 (1H, br d, J=17 Hz), 5.46 (1H, d, J=10 Hz), 5.62 (1H, d, J=10 Hz), 6.65(1H, d, J=15 Hz), 6.69 (1H, br s), 7.33 (1H, d, J=15 Hz), 7.42 (1H, br d, J=8 Hz), 7.48–7.61 (5H, m), 7.76–7.84 (3H, m).

EXAMPLE 68

The following compounds were obtained according to a similar manner to that of Example 1.

(1) 8-[2,6-Dichloro-3-[N-[4-(dimethylcarbamoyl)-cinnamoylglycyl]-N-methylamino]benzyloxy]-4-dimethylamino-2-methylquinoline NMR (CDCl₃, δ): 2.69 (3H, br s), 2.92–3.15 (12H, m), 3.28 (3H, s), 3.70 (1H, br d, J=17 Hz), 3.98 (1H, br d, J=17 Hz), 5.62 (2H, br s), 6.53 (1H, br d, J=15 Hz), 6.69 (1H, s), 7.18–7.60 (10H, m), 7.71 (1H, br d, J=8 Hz)

its dihydrochloride

NMR (CDCl₃—CD₃OD, δ): 2.78 (3H, br s), 2.95–3.15 (6H, m), 3.28 (3H, s), 3.49 (6H, s), 3.85 (1H, d, J=17 Hz), 4.09 (1H, d, J=17 Hz), 5.50 (1H, d, J=10 Hz), 5.61 (1H, d, J=10 Hz), 6.64 (1H, d, J=15 Hz), 6.71 (1H, br s), 7.32–7.61 (9H, m), 7.79 (1H, br d, J=8 Hz).

(2) 8-[2,6-Dichloro-3-[N-methyl-N-[4-[N-(2-pyridylmethyl)-carbamoyl]cinnamoylglycyl]amino]benzyloxy]-4-dimethylamino-2-methylquinoline NMR (CDCl₃, δ): 2.67 (3H, s), 3.05 (6H, s), 3.27 (3H, s), 3.66–3.77 (1H, m), 3.91–4.05 (1H, m), 4.76 (2H, d, J=6 Hz), 5.61 (2H, s), 6.57 (1H, d, J=16 Hz), 6.67 (1H, s), 7.16–7.74 (13H, m), 7.78–7.85 (2H, m), 8.53–8.60 (1H, m).

its trihydrochloride

NMR (DMSO-d₆, δ): 2.63 (3H, s), 3.13 (3H, s), 3.42 (6H, s), 3.57 (1H, dd, J=4, 16 Hz), 3.90 (1H, dd, J=4, 16 Hz), 4.74 (2H, d, J=6 Hz), 5.50–5.63 (2H, m), 6.85–6.97 (2H, m), 7.43 (1H, d, J=16 Hz), 7.59 (1H, t, J=8 Hz), 7.64–7.90 (7H, m), 7.90–8.03 (3H, m), 8.23 (1H, t, J=8 Hz), 8.40 (1H, t, J=6 Hz), 8.71 (1H, d, J=6 Hz), 9.43 (1H, t, J=8 Hz), 12.75 (1H, s).

(3) 8-[2,6-Dichloro-3-[N-[4-[N-(2-dimethylaminoethyl)-carbamoyl]cinnamoylglycyl]-N-methylamino]benzyloxy]-4-dimethylamino-2-methylquinoline NMR (CDCl₃, δ): 2.30 (6H, s), 2.56 (1H, br t, J=7 Hz), 2.65 (3H, s), 3.00 (6H, s), 3.26 (3H, s), 3.54 (1H, br q, J=7 Hz), 3.69 (1H, dd, J=17, 4 Hz), 3.95 (1H, dd, J=17, 5 Hz), 5.59 (1H, d, J=10 Hz), 5.64 (1H, d, J=10 Hz), 6.53 (1H, d, J=15 Hz), 6.69 (1H, s), 6.78 (1H, br s), 6.98 (1H, br s), 7.20 (1H, br d, J=8 Hz), 7.28–7.38 (2H, m), 7.45–7.55 (3H, m), 7.58 (1H, d, J=15 Hz), 7.70 (1H, br d, J=8 Hz), 7.80 (2H, br d, J=8 Hz).

its trihydrochloride

NMR (CDCl₃—CD₃OD, δ): 2.72 (3H, s), 2.95 (6H, s), 3.00 (6H, s), 3.27 (3H, s), 3.39–3.51 (8H, m), 3.82–3.92 (3H, m), 4.15 (1H, d, J=17 Hz), 5.48 (1H, d, J=10 Hz), 5.62 (1H, d, J=10 Hz), 6.62 (1H, d, J=15 Hz), 6.70 (1H, s), 7.33 (1H, d, J=15 Hz), 7.40–761 (6H, m), 7.80 (1H, br d, J=8 Hz), 7.96 (2H, br d, J=8 Hz).

(4) 8-[2,6-Dichloro-3-[N-[4-[N-(2-dimethylaminoethyl)-N-methylcarbamoyl]cinnamoylglycyl]-N-methylamino]-benzyloxy]-4-dimethylamino-2-methylquinoline NMR (CDCl₃, δ): 2.09 (3H, br s), 2.24–2.46 (4H, m), 2.53–2.70 (4H, m), 2.91–3.13 (9H, m), 3.26 (3H, s), 3.34 (1H, m), 3.60–3.73 (2H, m), 3.96 (1H, dd, J=17, 5 Hz), 5.60 (1H, d, J=10 Hz), 5.65 (1H, d, J=10 Hz), 6.50 (1H, d, J=15 Hz), 6.69 (1H, s), 6.73 (1H, br s), 7.20 (1H, d, J=8 Hz), 7.28–7.60 (9H, m), 7.70 (1H, br d, J=8 Hz), its trihydrochloride NMR (CDCl₃—CD₃OD, δ): 2.74 (3H, br s), 2.97 (6H, br s), 3.10 (3H, br s), 3.28 (3H, br s), 3.38–3.52 (8H, m), 3.88 (1H, br d, J=17 Hz), 3.95–4.02 (2H, m), 4.15 (1H, d, J=17 Hz), 5.49 (1H, d, J=10 Hz), 5.62 (1H, d, J=10 Hz), 6.67 (1H, d, J=15 Hz), 6.72 (1H, br s), 7.31–7.62 (9h, m), 7.79 (1h, br d, J=8 Hz).

(5) 8-[2,6-Dichloro-3-[N-methyl-N-[4-(4-pyridylcarbamoyl)-cinnamoylglycyl]amino]benzyloxy]-4-dimethylamino-2-methylquinoline NMR (CDCl₃, δ): 2.45 (3H, s), 3.01 (6H, s), 3.15 (3H, s), 3.61 (1H, dd, J=4, 16 Hz), 3.81 (1H, dd, J=4, 16 Hz), 5.51 (2h, s), 6.48 (1h, D, J=16 Hz), 6.63 (1H, s), 6.87 (1H, br peak), 7.13–7.40 (6H, m), 7.46 (1H, d, J=16 Hz), 7.64–7.76 (3H, m), 7.90 (2H, d, J=8 Hz), 8.43 (2H, d, J=6 Hz), 9.65 (1H, s), its trihydrochloride NMR (DMSO-d₆, δ) 2.65 (3H, s), 3.15 (3H, s), 3.42 (6H, s), 3.60 (1H, dd, J=4, 16 Hz), 3.93 (1H, dd, J=4, 16 Hz), 5.51–5.63 (2H, m), 6.92 (1H, s), 6.97 (1H, d, J=16 Hz), 7.49 (1H, d, J=16 Hz), 7.55–7.63 (1H, m), 7.72–7.85 (5H, m), 7.95 (1H, d, J=8 Hz), 8.13 (2H, d, J=8 Hz), 8.35–8.50 (3H, m), 8.77 (2H, d, J=6 Hz), 11.76 (1H, s).

(6) 8-[2,6-Dichloro-3-[N-[3-methoxy-4-(methylcarbamoyl)-cinnamoylglycyl]-N-methylamino]benzyloxy]-4-dimethylamino-2-methylquinoline NMR (CDCl₃, δ): 2.67 (3H, s), 2.93–3.14 (9H, m), 3.25 (3H, s), 3.66–3.78 (1H, m), 3.89–4.02 (4H, m), 5.55–5.66 (2H, m), 6.52–6.63 (1H, m), 6.68 (1H, s), 7.04 (1H, s), 7.11–7.42 (5H, m), 7.46 (1H, d, J=8 Hz), 7.52 (1H, d, J=16 Hz), 7.70 (1H, d, J=8 Hz), 7.74–7.83 (1H, m), 8.09–8.20 (1H, br peak, its dihydrochloride NMR (DMSO-d₆, δ): 2.61 (3H, s), 2.79 (3H, s), 3.14 (3H, s), 3.40 (6H, s), 3.47–3.65 (1H, m), 3.80–3.96 (4H, m), 5.50–5.63 (2H, m), 6.83–6.97 (2H, m), 7.21 (1H, d, J=8 Hz), 7.31 (1H, s), 7.41 (1H, d, J=16 Hz), 7.53–7.83 (1H, m), 7.67–7.87 (4H, m), 7.93 (1H, d, J=8 Hz), 8.14 (1H, q-like), 8.31 (1H, t-like).

(7) 8-[2,6-Dichloro-3-[N-methyl-N-[3-[4-[N-(2-pyridylmethyl)carbamoyl]phenyl]propionylglycyl]amino]-benzyloxy]-4-dimethylamine-2-methylquinoline NMR (CDCl₃, δ): 2.52 (2H, br t, J=7.5 Hz), 2.65 (3H, s), 2.92–3.06 (8H, m), 3.22 (3H, s), 3.49 (1H, br d, J=17 Hz), 3.80 (1H, dd, J=17, 4 Hz), 4.74 (2H, d, J=5 Hz), 5.60 (2H, s), 6.68 (1H, br s), 7.17–7.36 (8H, m), 7.43–7.55 (2H, m), 7.63–7.80 (4H, m), 8.56 (1H, br d, J=5 Hz), its trihydrochloride NMR (CDCl₃—CD₃OD, δ): 2.50–2.63 (4H, m), 2.90 (1H m), 3.25 (3H, s), 3.51 (6H, s), 3.69 (1H, d, J=17 Hz), 3.78 (1H, d, J=17 Hz), 4.99 (2H, s), 5.48 (1H, d, J=10 Hz), 5.63

(1H, d, J=10 Hz), 6.80 (1H, br s), 7.18 (2H, d, J=8 Hz), 7.40–7.61 (4H, m), 7.79–7.90 (4H, m), 8.11 (1H, br d, J=8 Hz), 8.39 (1H, br t, J=8 Hz), 8.73 (1H, br d, J=5 Hz).

(8) 8-[2,6-Dichloro-3-[N-methyl-N-[4-methanesulfonamido)-cinnamoylglycyl]amino]benzyloxy]-4-dimethylamino-2-methylquinoline NMR (CDCl$_3$, δ): 2.64 (3H, s), 3.01 (6H, s), 3.26 (3H, s), 3.68 (1H, dd, J=4, 18 Hz), 3.95 (1H, dd, J=4, 18 Hz), 5.53–5.64 (2H, m), 6.41 (1H, d, J=16 Hz), 6.67 (1H, s), 6.81 (1H, br peak), 7.11–7.38 (6H, m), 7.38–7.53 (4H, m), 7.70 (1H, d, J=8 Hz), its dihydrochloride NMR (DMSO-d$_6$, δ): 2.62 (3H, s), 3.03 (3H, s), 3.13 (3H, s), 3.41 (6H, s), 3.55 (1H, dd, J=4, 18 Hz), 3.90 (1H, dd, J=4, 18 Hz), 5.53 (1H, d, J=10 Hz), 5.59 (1H, d, J=10 Hz), 6.68 (1H, d, J=16 Hz), 6.92 (1H, s), 7.23 (2H, d, J=8 Hz), 7.32 (1h, d, J=16 Hz), 7.52 (2H, d, J=8 Hz), 7.58 (1H, t, J=8 Hz), 7.72–7.83 (3H, m), 7.94 (1H, d, J=8 Hz), 8.29 (1H, t-like), 10.03 (1H, s).

(9) 8-[2,6-Dichloro-3-[N-methyl-N-[4-(isonicotinamido)-cinnamoylglycyl]amino]benzyloxyl]-2-methyl-4-dimethylaminoquinoline NMR (CDCl$_3$—CD$_3$OD, δ): 2.58 (3H, s), 3.04 (6H, br), 3.25 (3H, s), 3.39 (1H, m), 3.69 (2H, m), 4.00 (1H, d, J=15 Hz), 5.54 (2H, m), 6.48 (1H, d, J=15 Hz), 6.69 (1H, s), 7.20 (1H, d, J=8 Hz), 7.36–7.52 (6H, m), 7.70 (3H, m), 7.83 (2H, d, J=8 Hz), 8.70 (2H, d, J=8 Hz), its trihydrochloride NMR (CDCl$_3$—CD$_3$OD, δ): 2.70 (3H, s), 3.29 (3H, s), 3.52 (6H, s), 3.88–4.04 (4H, m), 5.49 (1H, d, J=15 Hz), 5.68 (1H, d, J=15 Hz), 6.51 (1H, d, J=15 Hz), 6.70 (1H, s), 7.36–7.64 (7H, m), 7.84 (1H, d, J=8 Hz), 7.92 (2H, d, J=8 Hz), 8.66 (2H, d, J=8 Hz), 8.99 (2H, d, J=8 Hz).

(10) 8-[2,6-Dichloro-3-[-methyl-N-[4-(2-oxopyrrolidin-1-yl)cinnamoylglycyl]amino]benzyloxy]-4-dimethylamino-2-methylquinoline NMR (CDCl$_3$, δ): 2.10–2.23 (2H, m, 2.61 (2H, t, J=7.5 Hz), 2.67 (3H, s), 3.03 (6H, s), 3.26 (3H, s), 3.63–3.75 (1H, m), 3.86 (2H, t, J=7.5 Hz), 3.90–4.02 (1H, m), 5.60 (2H, s), 6.45 (1H, d, J=16 Hz), 6.67 (1H, s), 7.16–7.28 (2H, m), 7.28–7.41 (2H, m), 7.41–7.56 (4H, m), 7.62 (2H, d, J=8 Hz), 7.70 (1H, d, J=8 Hz), its dihydrochloride NMR (DMSO-d$_6$, δ): 2.00–2.13 (2H, m), 2.62 (3H, s), 3.13 (3H, s), 3.41 (6H, s), 3.46–3.61 (1H, m), 3.80–3.97 (3H, m), 5.53 (1H, d, J=10 Hz), 5.60 (1H, d, J=10 Hz), 6.71 (1H, d, J=16 Hz), 6.92 (1H, s), 7.33 (1H, d, J=16 Hz), 7.52–7.63 (2H, m), 7.67–7.86 (5H, m), 7.93 (1H, d, J=8 Hz), 8.30 (1H, t, J=6 Hz), 12.75 (1H, s).

(11) 8-[2,6-Dichloro-3-[N-[4-[N-(2-methoxyacetyl)-N-(3-pyridylmethyl)amino]cinnamoylglycyl]-N-methylaminol]-benzyloxy]-2-methyl-4-dimethylaminoquinoline NMR (CDCl$_3$, δ): 2.68 (3H, s), 3.07 (6H, s), 3.26 (3H, s), 3.36 (3H, s), 3.63–4.00 (2H, m), 3.78 (2H, s), 4.88 (2H, s), 5.59 (2H, s), 6.50 (1H, d, J=15 Hz), 6.67 (1H, s), 6.93 (2H, d, J=8 Hz), 7.20 (2H, m), 7.30 (2H, m), 7.41–7.52 (4H, m), 7.63 (1H, d, J=8 Hz), 7.68 (1H, d, J=8 Hz), 8.34 (1H, br), 8.50 (1H, d, J=7 Hz), its trihydrochloride NMR (CDCl$_3$—CD$_3$OD, δ): 2.70 (3H, br), 3.28 (3H, s), 3.36 (3H, s), 3.53 (6H, br), 3.83–4.10 (2H, m), 3.88 (2H, br), 5.09 (2H, br), 5.49 (1H, d, J=15 Hz), 5.68 (1H, d, J=15 Hz), 6.63–6.79 (2H, m), 7.17 (2H, br), 7.40 (1H, m), 7.48 (1H, d, J=8 Hz), 7.58 (4H, br), 7.83 (1H, d, J=8 Hz), 8.04 (1H, br), 8.57 (1H, br, 8.75 (1H, br), 8.80 (1H, br).

(12) 8-[3-[N-(4-Acetamido-3-methylcinnamoylglycyl)-N-methylamino]-2,6-dichlorobenzyloxy]-2-methyl-4-dimethylaminoquinoline NMR (CDCl$_3$, δ): 2.20 (3H, s), 2.27 (3H, s), 2.65 (3H, s), 3.00 (6H, s), 3.25 (3H, s), 3.65 (1H, dd, J=7, 15 Hz), 3.94 (1H, dd, J=7, 15 Hz), 5.61 (2H, m), 6.40 (1H, d, J=15 Hz), 6.68 (2H, s), 7.06 (1H, br), 7.20 (1H, d, J=8 Hz), 7.27–7.36 (4H, m), 7.44–7.52 (2H, m), 7.69 (1H, d, J=8 Hz), 7.90 (1H, d, J=8 Hz), its dihydrochloride NMR (CDCl$_3$—CD$_3$OD, δ): 2.22 (3H, s), 2.28 (3H, s), 2.70 (3H, s), 3.28 (3H, s), 3.49 (6H, s), 3.91 (2H, m), 5.48 (1H, d, J=8 Hz), 5.67 (1H, d, J=8 Hz), 6.47 (1H, d, J=15 Hz), 6.70 (1H, s), 7.27–7.38 (3H, m), 7.47–7.63 (6H, m), 7.83 (1H, d, J=8 Hz).

(13) 8-[3-[N-[(E)-3-(1-Acetyl-1,2,3,4-tetrahydroquinolin-6-yl)acryloxylglycyl]-N-methylamino]-2,6-dichlorobenzyloxy]-4-dimethylamino-2-methylquinoline NMR (CDCl$_3$, δ): 1.96 (2H, quint, J=7 Hz), 2.26 (3H, s), 2.68 (3H, s), 2.72 (2H, t, J=7 Hz), 3.02 (6H, s), 3.27 (3H, s), 3.67 (1H, dd, J=4, 18 Hz), 3.77 (2H, t, J=7 Hz), 3.95 (1H, dd, J=5, 18 Hz), 5.55–5.67 (2H, m), 6.45 (1H, d, J=16 Hz), 6.69 (1H, s), 6.80 (1H, br peak), 7.22 (1H, d, J=8 Hz), 7.25–7.39 (5H, m), 7.47 (1H, d, J=8 Hz), 7.52 (1H, d, J=16 Hz), 7.70 (1H, d, J=8 Hz), its dihydrochloride NMR (DMSO-d$_6$, δ): 1.87 (2H, quint, J=7 Hz), 2.20 (3H, s), 2.63 (3H, s), 2.72 (2H, t, J=7 Hz), 3.15 (3H, s), 3.42 (6H, s), 3.51–3.81 (3H, m), 3.91 (1H, dd, J=5, 16 Hz), 5.52–5.63 (2H, m), 6.72 (1H, d, J=16 Hz), 6.93 (1H, s), 7.26–7.41 (3H, m), 7.50–7.65 (2H, m), 7.75 (1H, d, J=8 Hz), 7.81 (2H, s-like), 7.94 (1H, d, J=8 Hz), 8.27 (1H, t-like).

(14) 8-[2,6-Dichloro-3-[N-[(E)-3-(6-ethoxycarbonylpyridin-3-yl)acryloylglycyl]-N-methylaamino]benzyloxy]-4-dimethylamine-2-methylquinoline NMR (CDCl$_3$, δ): 1.45 (1H, t, J=7.5 Hz), 2.62 (3H, s), 3.00 (6H, br s), 3.28 (3H, s), 3.72 (1H, br dd, J=17, 4 Hz), 3.95 (1H, br dd, J=17, 5 Hz), 4.49 (2H, q, J=7.5 Hz), 5.60 (1H, d, J=10 Hz), 5.65 (1H, d, J=10 Hz), 6.63–6.72 (2H, m), 6.88 (1H, br s), 7.20 (1H, br d, J=8 Hz), 7.29–7.38 (2H, m), 7.48 (1H, d, J=8 Hz), 7.60 (1H, d, J=15 Hz), 7.70 (1H, d, J=8 Hz), 7.90 (1H, dd, J=8, 2 Hz), 8.10 (1H, br d, J=8 Hz), 8.83 (1H, hr s).

(15) 8-[3-[N-[(E)-3-(6-Aminopyridin-3-yl)acryloylglycyl]-N-methylamino]-2,6-dichlorobenzyloxy]-4-dimethylamino-2-methylquinoline NMR (CDCl$_3$, δ): 2.63 (3H, s), 2.98 (6H, s), 3.24 (3H, s), 3.64 (1H, dd, J=4, 17 Hz), 3.93 (1H, dd, J=4, 17 Hz), 4.67 (2H, s), 5.55–5.67 (2H, m), 6.29 (1H, d, J=16 Hz), 6.46 (1H, d, J=8 Hz), 6.55 (1H, t-like), 6.69 (1H, s), 7.18 (1H, d, J=8 Hz), 7.22–7.36 (2H, m), 7.40–7.50 (2H, m), 7.58 (1H, d, J=8 Hz), 7.69 (1H, d, J=8 Hz), 8.16 (1H, s).

(16) 8-[2,6-Dichloro-3-[N-methyl-N-[(E)-3-[6-[(E)-2-(pyridin-4-yl)vinyl]pyridin-3yl]acryloylglycyl]amino]benzyloxy]-4-dimethylamino-2-methylquinoline NMR (CDCl$_3$, δ): 2.67 (3H, s), 3.03 (6H, s), 3.27 (3H, s), 3.66–3.80 (1H, m), 3.91–4.05 (1H, m), 5.56–5.68 (2H, m), 6.61 (1H, d, J=16 Hz), 6.70 (1H, s), 7.15–7.66 (11H, m), 7.66–7.777 (1H, m), 7.77–7.85 (1H, m), 8.61 (2H, d, J=6 Hz), 8.69–8.75 (1H, m), its tetrahydrochloride NMR (DMSO-d$_6$, δ): 2.63 (3H, s), 3.15 (3H, s), 3.43 (6H, s), 3.91 (1H, dd, J=4, 18 Hz), 5.51–5.64 (2H, m), 6.93 (1H, s), 7.00 (1H, d, J=16 Hz), 7.47 (1H, d, J=16 Hz), 7.59 (1H, t, J=8 Hz), 7.73–8.15 (8H, m), 8.29 (2H, d, J=6 Hz), 8.44 (1H, t-like), 8.85–8.93 (3H, m).

(17) 8-[2,6-Dichloro-3-[N-[4-(dimethylcarbamoyl)-cinnamoylglycyl]-N-methylamino]benzyloxyl]-2-methyl-4-piperidinoquinoline NMR (CDCl₃, δ): 1.60–1.75 (2H, overlapped with H₂O), 1.79–1.90 (4H, m), 2.68 (3H, br s), 2.98 (3H, br s), 3.06–3.29 (10H, m), 3.70 (1H, br d, J=17 Hz), 3.97 (1H, br d, J=17 Hz), 5.60 (2H, br s), 6.52 (1H, hr d, J=15 Hz), 6.71 (1H, s), 7.20 (1H, br d, J=8 Hz), 7.27–7.60 (9H, m), 7.62 (1H, br d, J=8 Hz), its dihydrochloride NMR (CDCl₃—CD₃OD, δ): 1.82–1.94 (6H, m), 2.84 (3H, br s), 3.00 (3H, br s), 3.10 (3H, br s), 3.39 (3H, s), 3.67–3.76 (4H, m), 3.89 (1H, br d, J=17 Hz), 4.12 (1H, br d, J=17 Hz), 5.51 (1H, d, J=10 Hz), 5.61 (1H, d, J=10 Hz), 6.68 (1H, d, J=15 Hz), 6.84 (1H, br s), 7.32–7.61 (10H, m).

(18) 8-[2,6-Dichloro-3[N-methyl-N-[4-[N-(2-pyridylmethyl-carbamoyl]cinnamoylglycyl]amino]benzyloxy]-2methyl-4-piperidinoquinoline NMR (CDCl₃, δ): 1.24 (2H, t, J=7 Hz), 1.80 (4H, br), 2.66 (3H, s), 3.17 (4H, br), 3.25 (3H, s), 3.70 (1H, m), 3.96 (1H, dd, J=7, 15 Hz), 4.75 (2H, d, J=7 Hz), 5.58 (2H, m), 6.55 (1H, d, J=15 Hz), 6.72 (1H, s), 7.20 (2H, m), 7.29–7.38 (3H, m), 7.44–7.77 (7H, m), 7.80–7.91 (2H, m), 8.55 (1H, d, J=7 Hz), ps its trihydrochloride NMR (CD₃OD, δ): 1.67 (6H, br), 2.49 (3H, s), 3.07 (3H, s), 3.58 (4H, br), 360–3.83 (2H, m), 4.65 (2H, br (overlap)), 5.42 (1H, d, J=8 Hz), 5.50 (1H, d, J=8 Hz), 6.58 (1H, d, J=15 Hz), 6.83 (1H, s), 7.31 (1H, d, J=15 Hz), 7.40–7.58 (6H, m), 7.19–7.83 (4H, m), 8.30 (2H, m), 8.52 (2H, br).

(19) 8-[2,6-Dichloro-3-[N-[3-methoxy-4-(methylcarbamoyl)-cinnamoylglycyl]-N-methylamino]benzyloxy]-2-methyl-4-piperidinoquinoline NMR (CDCl₃, δ): 1.57–1.74 (2H, overlapped with H₂O), 1.79–1.90 (4H, m), 2.65 (3H, br s), 3.00 (3H, d, J=5 Hz), 3.19–3.22 (4H, m), 3.26 (3H, s), 3.70 (1H, br d, J=17 Hz), 3.90–4.01 (5H, m), 5.58 (1H, d, J=10 Hz), 5.64 (1H, d, J=10 Hz), 6.57 (1H, br d, J=15 Hz), 6.70–6.80 (2H, m), 7.04 (1H, br s), 7.16–7.39 (4H, m), 7.48 (1H, d, J=8 Hz), 7.52 (1H, br d, J=15 Hz), 7.64 (1H, br d, J=8 Hz), 7.79 (1H, br d, J=5 Hz), 8.19 (1H, br s), its dihydrochloride NMR (CDCl₃—CD₃Od, δ): 1.81–1.95 (6H, m), 2.82 (3H, br s), 3.00 (3H, s), 3.28 (3H, s), 3.69–3.78 (4H, m), 3.88 (1H, br d, J=17 Hz), 4.04 (3H, s), 4.20 (1H, br d, J=17 Hz), 5.50 (1H, br d, J=10 Hz), 5.61 (1H, br d, J=10Hz), 6.73–6.86 (2H, m), 7.04 (1H, d, J=8 Hz), 7.21 (1H, br s), 7.33–7.61 (6H, m), 8.01 (1H, br d, J=8 Hz).

(20) 8-[2,6-Dichloro-3-[-methyl-N-[4-(isonicotinamido)-cinnamoylglycyl]amino]benzyloxy]-2-methyl-4-piperidinoquinoline NMR (CDCl₃, δ): 1.58–1.90 (6H, m), 2.51 (3H, br s), 3.14–3.27 (7H, m), 3.62 (1H, br d, J=17 Hz), 3.89 (1H, br dd, J=17, 5 Hz), 5.52 (2H, s), 6.41 (1H, d, J=15 Hz), 6.70 (1H, s), 7.18–7.31 (4H, m), 7.37–7.44 (3H, m, 7.49 (1H, br d, J=15 Hz), 7.64 (1H, br d, J=18 Hz), 7.72 (2H, d, J=8 Hz), 7.78 (2H, d, J=5 Hz), 8.63 (2H, d, J=5 Hz), 9.35 (1H, br s), its trihydrochloride NMR (CDCl₃—CD₃OD, δ): 1.81–1.96 (6H, m), 2.76 (3H, br s), 3.28 (3H, s), 3.70–3.80 (4H, m), 3.88 (1H, br d, J=17 Hz), 4.11 (1H, br d, J=17 Hz), 5.48 (1H, d, J=10 Hz), 5.66 (1H, d, J=10 Hz), 6.50 (1H, br d, J=15 Hz), 6.86 (1H, br s), 7.24–7.63 (8H, m), 7.92 (2H, br d, J=8 Hz), 8.70 (2H, d, J=5 Hz), 8.95 (2H, d, J=5 Hz).

(21) 8-[2,6-Dichloro-3-[N-methyl-N-[4-(2-oxopyrrolidin-1-yl)cinnamoylglycyl]amino]benzyloxy]-2-methyl-4-piperidinoquinoline NMR (CDCl₃, δ): 1.25 (2H, t, J=7 Hz), 1.84 (4H, br), 2.15 (2H, m), 2.60 (2H, t, J=7 Hz), 2.65 (3H, s), 3.16 (4H, br), 3.27 (3H, s), 3.65 (1H, dd, J=7, 15 Hz, 3.87 (2H, t, J=7 Hz), 3.93 (1H, dd, J=7, 15 Hz, 5.60 (2H, m), 6.44 (1H, d, J=15 Hz), 6.72 (1H, s), 6.80(1H, br), 7.18 (1H, d, J=8 Hz), 7.30–7.37 (2H, m), 7.46–7.66 (7H, m), its dihydrochloride NMR (CD₃OD, δ): 1.84 (6H, br), 2.19 (2H, m), 2.58–2.66 (2H, m), 2.69 (3H, s), 3.27 (3H, s), 3.79 (4H, br, 3.85–4.03 (2H, m), 5.60 (1H, d, J=8 Hz), 5.72 (1H, d, J=8 Hz), 6.60 (1H, d, J=15 Hz), 7.06 (1H, s, 7.46 (1H, d, J=15 Hz), 7.54 (2H, m), 7.62–7.75 (7H, m).

(22) 8-[3-[N-[(E)-3-(1-Acetyl-1,2,3,4-tetrahydroquinolin-6-yl)acryloxyglycyl]-N-methylamino]-2,6-dichlorobenzyloxy]-2-methyl-4-piperidinoquinoline and its dihydrochloride

(23) 8-[2,6-Dichloro-3-[N-[(E)-3-(6-ethoxycarbonylpyridin-3-yl)acryloxylglycyl]-N-methylamino]benzylox]-2-methyl-4-piperidinoquinoline NMR (CDCl₃, δ): 1.43 (1H, t, J=7.5 Hz), 1.59–1.74 (2H, overlapped with H₂O), 1.78–1.90 (4H, m), 2.65 (3H, br s), 3.09–3.22 (4H, m), 3.27 (3H, s), 3.74 (1H, br d, J=17 Hz), 3.97 (1H, br d, J=17 Hz), 4.48 (2H, q, J=7.5 Hz), 5.60 (1H, s), 6.64–6.75 (2H, m), 6.89 (1H, br s), 7.16–7.40 (3H, m), 7.47 (1H, br d, J=8 Hz), 7.52–7.67 (2H, m), 7.90 (1H, br d, J=8 Hz), 8.08 (1H, br d, J=8 Hz), 8.70 (1H, br s).

(24) 8-[3-[N-[(E)-3-[6-(Acetamido)pyridin-3-yl]-acryloylglycyl]-N-methylamino-2,6-dichlorobenzyloxy]-2-methyl-4-piperidinoquinoline NMR (CDCl₃, δ): 1.10–1.26 (2H, m), 1.82 (4H, br), 2.19 (3H, s), 2.63 (3H, s), 3.15 (4H, br), 3.24 (3H, s), 3.68 (1H, dd, J=7, 15 Hz), 3.94 (1H, dd, J=7, 15 Hz), 5.60 (2H, m), 6.47 (1H, d, J=15 Hz), 6.72 (1 H, s), 6.83 (1H, br), 7.18 (1H, d, J=8 Hz), 7.27–7.39 (2H, m), 7.46 (1H, d, J=8 Hz), 7.52 (1H, d, J=15 Hz), 7.63 (1H, d, J=8Hz), 7.80 (1H, dd, J=4, 8 Hz), 8.17 (1H, d, J=8 Hz), 8.26 (1H, br), 8.32 (1H, s).

(25) 8-[3-[N-[(E)-3-(6-Aminopyridin-3-yl)acryloxylglycyl]-N-methylamino]-2,6-dichlorobenzyloxy]-2-methyl-4-piperidinoquinoline NMR (CDCl₃, δ): 1.55–1.72 (2H, m), 1.77–1.88 (4H, m), 2.64 (3H, s), 3.07–3.18 (4H, m), 3.24 (3H, s) 3.64 (1H, dd, J=4, 18 Hz), 3.93 (1H, dd, J=4, 18 Hz), 4.66 (2H, s), 5.57 (1H, d, J=10 Hz), 5.63 (1H, d, J=10 Hz), 6.29 (1H, d, J=15 Hz), 6.47(1H, d, J=8 Hz), 6.59 (1H, t-like), 6.73 (1H, s), 7.18 (1H, d, J=8 Hz), 7.23–7.37 (2H, m), 7.40–7.50 (2H, m), 7.59 (1H, dd, J=2, 8 Hz), 7.64 (1H, d, J=8 Hz), 8.16 (1H, d, J=2 Hz).

(26) 8-[2,6-Dichloro-3-[N-[4-(dimethylcarbamoyl)-cinnamoylglycyl]--methylamino]benzyloxyl]-2-methyl-4-morpholinoquinoline NMR (CDCl₃, δ) 2.69 (3H, s, 2.99 (3H, br s), 3.11 (3H, br s), 3.17–3.24 (4H, m), 3.28 (3H, s), 3.67 (1H, br dd, J=17, 4 Hz), 3.90–4.01 (5H, m), 5.60 (1H, d, J=10 Hz), 5.65 (1H, d, J=10 Hz), 6.50 (1H, d, J=15 Hz, 6.69 (1H, br s), 6.78 (1H, s), 7.19–7.53 (8 H, m), 7.58 (1H, d, J=15 Hz), 7.68 (1H, br d, J8 Hz), its dihydrochloride NMR (CDCl₃—CD₃OD, δ: 2.91 (3H, s, 2.97–3.14 (6H, m), 3.29 (3H, s, 3.72–3.81 (4H, m), 3.88 (1H, br d, J=17 Hz), 3.96–4.05 (5H, m), 5.53 (1H, d, J=10 Hz), 5.64 (1H, d, J=10 Hz), 6.65 (1H, d, J=15 Hz), 7.06 (1H, br s), 7.37 (2H, d, J=8 Hz), 7.42–7.68 (8H, m).

(27) 8-[2,6-Dichloro-3-[N-methyl-N-[4-[N-(2-pyridylmethyl)-carbamoyl]cinnamoylglycyl]amino]benzyloxy]-2-methyl-4-morpholinoquinoline NMR (CDCl₃, δ): 2.68 (3H, s), 3.22 (4H, m), 3.28 (3H, s, 3.64–3.77 (2H, m), 3.95 (4H, m), 4.74 (2H, d, J=7 Hz), 5.60 (2H, m), 6.54 (1H, d, J=15 Hz), 6.78 (1H, s, 7.00 (1H, br), 7.20–7.25 (2H, m), 7.29–7.42 (3H, m), 7.45–7.73 (7H, m), 7.76–7.90 (2H, m)

its trihydrochloride

(28) 8-[2,6-Dichloro-3-[N-[3-methoxy-4-(methylcarbamoyl)-cinnamoylglycyl]-N-methylamino]benzyloxy]-2-methyl-4-morpholinoquinoline NMR (CDCl$_3$, δ): 2.67 (3H, br s), 3.00 (3H, d, J=5 Hz), 3.16–3.22 (4H, m), 3.27 (3H, s), 3.69(1H, br dd, J=17, 4 Hz), 3.89–4.01 (7H, m), 5.59 (1H, d, J=10 Hz), 5.64 (1H, d, J=10 Hz), 6.55 (1H, d, J=15 Hz), 6.72 (1H, br s), 6.78 (1H, s), 7.21 (1H, br d, J=8 Hz), 7.30 (1H, d, J=8 Hz), 7.37 (1H, t, J=8 Hz), 7.48 (1H, d, J=8 Hz), 7.53 (1H, d, J=15 Hz, 7.66 (1H, br d, J=8 Hz), 7.79 (1H, br d, J=5 Hz), 8.20 (1H, d, J=8 Hz), its dihydrochloride NMR (CDCl$_3$—CD$_3$OD, δ): 2.90 (3H, br s), 2.99 (3H, s), 3.28 (3H, s), 3.73–3.81 (4H, m), 3.87 (1H, d, J=17 Hz), 3.97–4.07 (7H, m), 4.15 (1H, d, J=17 Hz, 5.52 (1H, d, J=10 Hz), 5.62 (1H, d, J=10 Hz), 6.76 (1H, d, J=15 Hz), 7.00–7.09 (2H, m), 7.18 (1H, s), 7.37–7.68 (6H, m), 7.98 (2H, d, J=8 Hz).

(29) 8-[2,6-Dichloro-3-[N-methyl-N-[4-isonicotinamido)-cinnamoylglycyl]amino]benzyloxy]-2-methyl-4-morpholinoquinoline NMR (CDCl$_3$, δ): 2.52 (3H, br s), 3.13–3.25 (7H, m), 3.60 (1H, dd, J=17, 4 Hz), 3.85 (1H, dd, J=17, 5 Hz), 3.93–4.02 (4H, m), 5.56 (2H, s), 6.40 (1H, d, J=15 Hz), 6.63 (1H, br s), 6.72 (1H, s), 7.17–7.34 (3H, m), 7.38–7.47 (3H, m), 7.50 (1H, d, J=15 Hz), 7.63–7.77 (5H, m), 8.66 (2H, br d, J=8 Hz), 9.11 (1H, br s), its trihydrochloride NMR (CDCl$_3$—CD$_3$OD, δ): 2.83 (3H, br s), 3.28 (3H, s), 3.70–3.87 (5H, m), 3.92–4.03 (4H, m), 4.16 (1H, br d, J=17 Hz), 5.48 (1H, br d, J=10 Hz), 5.67 (1H, br d, J=10 Hz), 6.54 (1H, br s), 7.07 (1H, br s), 7.24–7.68 (8H, m), 7.89–7.99 (2H, m), 8.71–8.93 (4H, m),

(30) 8-[2,6-Dichloro-3-[N-methyl-N-[4-(2-oxopyrrolidin-1-yl)cinnamoylglycyl]amino]benzyloxy]-2-methyl-4-morpholinoquinoline NMR (CDCl$_3$, δ): 2.18 (2H, m), 2.62 (2H, t, J=7 Hz), 2.67 (3H, s), 3.22 (4H, br), 3.26 (3H, s), 3.60–3.73 (2H, m), 3.87 (2H, m), 3.96 (4H, m), 5.60 (2H, m), 6.40 (1H, d, J=15 Hz), 6.76 (2H, br), 7.19 (1H, d, J=8 Hz), 7.29–7.38 (2H, m), 7.46–7.50 (4H, m), 7.59–7.68 (3H, m), its dihydrochloride NMR (CD$_3$OD, δ): 2.19 (2H, m), 2.61 (2H, t, J=7 Hz), 2.74 (3H, s), 3.28 (3H, s), 3.79 (4H, m), 3.88–3.98 (8H, m), 5.63 (1H, d, J=8 Hz), 5.72 (1H, d, J=8 Hz), 6.60 (1H, d, J=15 Hz), 7.12 (1H, s), 7.44 (1H, d, J=15 Hz), 7.54 (2H, d, J=8 Hz), 7.60–7.78 (7H, m).

(31) 8-[3-[N-[(E)-3-(1-Acetyl-1,2,3,4-tetrahydroquinolin-6-yl)acryloxylglycyl]-N-methylamino]-2,6-dichlorobenzyloxy]-2-methyl-4-morpholinoquinoline and its dihyrdrochloride

(32) 8-[2,6-Dichloro-3-[N-[(E)-3-(6-ethoxycarbonylpyridin-3-yl)acryloylglycyl]-N-methylamino]benzyloxy]-2-methyl-4-morpholinoquinoline NMR (CDCl$_3$, δ): 1.45 (1H, t, J=7.5 Hz), 2.66 (3H, s), 3.17–3.25 (4H, m), 3.29 (3H, s), 3.73 (1H, br dd, J=17, 4 Hz), 3.90–4.02 (5H, m), 4.50 (2H, q, J=7.5 Hz), 5.60 (1H, d, J=10 Hz), 5.66 (1H, d, J=10 Hz), 6.67 (1H, d, J=15 Hz), 6.78 (1H, s), 6.83 (1H, br s), 720–7.28 (1H, overlapped with CDCl$_3$), 7.31 (1H, d, J=8 Hz), 7.39 (1H, t, J=8 Hz), 7.60 (1H, d, J=15 Hz), 7.68 (1H, br d, J=8 Hz), 7.91 (1H, br d, J=8 Hz), 8.11 (1H, br d, J=8 Hz), 8.73 (1H, br s).

(33) 8-[3-[N-[(E)-3-[6-(Acetamido)pyridin-3yl]-acryloylglycyl]-N-methylamino]-2,6-dichlorobenzyloxy]-2-methyl-4-morpholinoquinoline NMR (CDCl$_3$, δ): 2.21 (3H, s), 2.67 (3H, s), 3.15–3.23 (4H, m), 3.36 (3H, s), 3.70 (1H, dd, J=17, 4 Hz), 3.88–4.01 (5H, m), 5.58 (1H, d, J=10 Hz), 5.63 (1H, d, J=10 Hz), 6.47 (1H, d, J=15 Hz), 6.39–6.79 (2H, m), 7.19–7.28 (1H, overlapped with CDCl$_3$), 7.30 (1H, d, J=8 Hz), 7.37 (1H, t, J=8 Hz), 7.47 (1H, d, J=8 Hz), 7.51 (1H, d, J=15 Hz), 7.65 (1H, d, J=8 Hz), 7.80 (1H, br d, J=8 Hz), 8.09 (1H, br s), 8.19 (1H, br, d, J=8 Hz), 8.33 (1H, br s).

(34) 8-[3-[N-[(E)-3-(6-Aminopyridin-3yl)acryloxylglycyl]-N-methylamino]-2,6-dichlorobenzyloxy]-2-methyl-4-morpholinoquinoline NMR (CDCl$_3$, δ): 2.67 (3H, s), 3.19 (4H, m), 3.28 (3H, s), 3.73 (2H, m), 3.98 (4H, m), 4.71 (2H, br), 5.61 (2H, m), 6.29 (1H, d, J=15 Hz), 6.47 (1H, d, J=8 Hz), 6.60 (1H, m), 6.77 (1H, s), 7.21 (1H, m), 728–7.39 (2H, m), 7.43–7.49 (2H, m), 7.60 (1H, d, J=8 Hz), 7.66 (1H, d, J=8 Hz), 8.18 (1H, s).

(35) 8-[2,6-Dichloro-3-[N-methyl-N-[4-[(E)-2-(pyridin-4-yl)vinyl]cinnamoylglycyl]amino]benzyloxy]-2-methylquinoline NMR (CDCl$_3$, δ): 2.73 (3H, s), 3.28 (3H, s), 3.67 (1H dd, J=17, 4 Hz), 3.96 (1H, d, J=14, 5 Hz), 5.64 (2H, s), 6.50 (1H, d, J=15 Hz), 6.67 (1H, br s), 7.04 (1H, d, J=16 Hz), 7.23–7.61 (14H, m), 8.02 (1H, d, J=8 Hz), 8.59 (2H, d, J=7 Hz), its dihydrochloride NMR (CDCl$_3$—CD$_3$OD, δ): 3.23 (3H, br s), 3.31 (3H, s, 3.91 (1H, d, J=17 Hz), 4.09 (1H, d, J=17 Hz), 5.62 (1H, d, J=10 Hz), 5.70 (1H, d, J=10 Hz), 6.68 (1H, br d, J=15 Hz), 7.14 (1H, br d, J=15 Hz), 7.43 (1H, br d, J=15 Hz), 7.50–7.64 (8H, m), 7.77 (1H, d, J=8 Hz), 7.82–7.98 (4H, m), 8.64–8.73 (2H, m), 8.82 (1H, br d, J=8 Hz).

(36) 8-[2,6-Dichloro-3-[N-[3-methoxy-4-(methylcarbamoyl)-cinnamoylglycyl]N--methylamino]benzyloxy]-2-methylquinoline NMR (CDCl$_3$, δ): 2.72 (3H, s), 3.01 (3H, d, J=5 Hz), 3.28 (3H, s), 3.68 (1H, dd, J=4, 18 Hz), 3.89–4.02 (4H, m), 5.60–5.70 (2H, m), 6.55 (1H, d, J=16 Hz), 6.70 (1H, t-like), 7.04 (1H, s-like), 7.18–7.36 (5H, m), 7.38–7.60 (3H, m), 7.78 (1H, q-like), 8.03 (1H, d, J=8 Hz), 8.21 (1H, d, J=8 Hz), its hydrochloride NMR (DMSO-d$_6$, δ): 2.79 (3H, d, J=5 Hz), 2.92 (3H, s), 3.16 (3H, s), 3.60 (1H, dd, J=4, 16 Hz), 3.83–3.96 (4H, m), 5.58–5.71 (2H, m), 6.93 (1H, d, J=16 Hz), 7.23 (1H, d, J=8 Hz), 7.30–7.46 (2H, m), 7.73–8.01 (7H, m), 8.16 (1H, q-like), 8.32 (1H, t-like 8.94–9.06 (1H, br peak).

(37) 8-[2,6-Dichloro-3-[N-methyl-N-[4-(2-oxo-1,2-dihydropyridin-1-yl)cinnamoylglycyl]amino]benzyloxy]-2-methylquinoline mp 160.5–172° C.

NMR (CDCl$_3$, δ): 2.73 (3H, s), 3.26 (3H, s), 3.64 (1H, dd, J=17.5, 4.0 Hz), 3.94 (1H, dd, J=17.5, 5.5 Hz), 5.63 (1H, d, J=11.5 Hz), 5.68 (1H, d, J=11.5 Hz), 6.23 (1H, t, J=7.5 Hz), 6.50 (1H, d, J=16.0 Hz), 6.66 (1H, d, J=7.5 Hz), 6.67 (1H, m, 7.22–7.34 (4H, m), 7.36–7.52 (6H, m, 7.60 (1H, d, J=16.0 Hz), 7.61 (2H, d, J=8.5 Hz), 8.01 (1H, d, J=7.5 Hz).

(38) 8-[2,6-Dimethyl-3-[N-methyl-N-[(E)-3-[6-[(E)-2-(pyridin-4-yl)vinyl]pyridin-3-yl]acryloylglycyl]amino]benzyloxy]-2-methylquinoline NMR (CDCl$_3$, δ): 2.36 (3H, s), 2.53 (3H, s), 2.73 (3H, s), 3.27 (3H, s), 3.66 (1H, dd, J=4, 18 Hz), 3.90 (1H, dd, J=4, 18 Hz), 5.37 (2H, s), 6.56 (1H, d, J=16 Hz), 6.75 (1H, t-like), 7.09 (1H, d, J=8 Hz), 7.19 (1H, d, J=8 Hz), 7.22–7.33 (2H, m), 7.33–7.48 (6H, m), 7.53–7.67 (2H, m), 7.81 (1H, d, J=8 Hz), 8.04 (1H, d, J=8 Hz), 8.62 (2H, d, J=5 Hz), 8.74 (1H, s-like), its trihydrochloride NMR (DMSO-d₆, δ): 2.30 (3H, s), 2.47 (3H, s), 2.84 (3H, s), 3.12 (3H, s), 3.55 (1H, dd, J=4, 16 Hz), 3.74 (1H, dd, J=4, 16 Hz), 5.44 (2H, s), 7.01 (1H, d, J=16 Hz), 7.30 (1H, d, J=8 Hz), 7.38 (1H, d, J=8 Hz), 7.47 (1H, d, J=16 Hz), 7.70–7.95 (6H, m), 8.02 (1H, d, J=8 Hz), 8.11 (1H, dd, J=2, 8 Hz), 8.23–8.29 (2H, m), 8.35 (1H, t-like, 8.76–8.91 (4H, m.

(39) 8-[3-[N-[(E)-3-(6-Aminopyridin-3-yl)acryloxylglycyl]-N-methylamino]-2,6-dimethylbenzyloxy]-2-methylquinoline NMR (CDCl₃, δ): 2.36 (3H, s), 2.53 (3H, s), 2.73 (3H, s), 3.26 (3H, s), 3.62 (1H, dd, J=4, 18 Hz), 3.87 (1H, dd, J=4, 18 Hz), 4.68 (2H, br s), 5.35 (2H, s), 6.30 (1H, d, J=16 Hz), 6.49 (1H, d, J=8 Hz), 6.60 (1H, t-like), 7.06 (1H, d, J=8 Hz), 7.17 (1H, d, J=8 Hz), 7.22–7.33 (2H, m), 7.40–7.50 (3H, m), 7.60 (1H, dd, J=2, 8 Hz), 8.03 (1H, d, J=8 Hz), 8.17 (1H, d, J=2 Hz).

(40) 8-[2,6-Dimethyl-3-[N-[(E)-3-[6-ethoxycarbonylpyridin-3-yl)acryloylglycyl]-N-methylamino]benzyloxy]-2-methylquinoline NMR (CDCl₃, δ): 1.45 (3H, t, J=7.5 Hz), 2.38 (3H, s), 2.53 (3H, s), 2.72 (3H, s), 3.26 (3H, s), 3.64 (1H, dd, J=4, 18 Hz), 3.90 (1H, dd, J=4, 18 Hz), 4.49 (2H, q, J=7.5 Hz), 5.36 (2H, s), 6.64 (1H, d, J=16 Hz), 6.78 (1H, t-like), 7.08 (1H, d, J=8 Hz), 7.18 (1H, d, J=8 Hz), 7.23–7.33 (2H, m), 7.39–7.49 (2H, m), 7.61 (1H, d, J=16 Hz), 7.92 (1H, dd, J=2, 8 Hz), 8.03 (1H, d, J=8 Hz), 8.13 (1H, d, J=8 Hz), 8.84 (1H, d, J=2 Hz).

(41) 8-[2,6-Dichloro-3[N-methyl-N-[4-(4-pyridylcarbamoyl)-cinnamoylglycyl]amino]benzyloxy]-2-methyl-4-piperidinoquinoline NMR (CDCl₃, δ): 1.65–1.76 (2H, m), 1.79–1.90 (4H, m), 2.54 (3H, br s), 3.18 (3H, s), 3.20–3.30 (4H, m), 3.64 (1H, br dd, J=17, 4 Hz), 3.91 (1H, br d, J=17 Hz), 5.52 (2H, s), 6.51 (1H, d, J=15 Hz), 6.71 (1H, s), 7.21–7.45 (7H, m), 7.64 (1H, br d, J=8 Hz), 7.75 (2H, br d, J=7 Hz), 7.90 (2H, d, J=8 Hz), 8.45 (2H, d, J=7 Hz), 9.59 (1H, br s),
its trihydrochloride NMR (CDCl₃—CD₃OD, δ): 1.78–2.04 (6H, m), 2.78 (3H, br s), 3.29 (3H, s), 3.62–4.00 (5H, m), 4.21 (1H, br s), 5.49 (1H, d, J=10 Hz), 5.66 (1H, d, J=10 Hz), 6.60 (1H, br s), 6.87 (1H, br s), 7.22–7.70 (8H, m), 8.06–8.20 (2H, m), 8.41–8.55 (2H, m), 8.60–8.77 (2H, m).

(42) 8-[2,6-Dichloro-3-[N-methyl-N-[4-(4-pyridylcarbamoyl)-cinnamoylglycyl]amino]benzyloxy]-2-methyl-4-morpholinoquinoline NMR (CDCl₃, δ): 2.55 (5H, s), 3.17–3.24 (7H, m), 3.62 (1H, dd, J=17, 4 Hz), 3.85 (1H, dd, J=17, 5 Hz), 3.95–4.01 (4H, m), 5.57 (2H, s), 6.50 (1H, d, J=15 Hz), 6.70–6.76 (2H, m), 7.20–7.28 (2H, m), 7.33–7.56 (5H, m), 7.61–7.71 (3H, m), 7.89 (2H, d, J=8Hz), 8.49 (2H, d, J=7 Hz), 8.99 (1H, br s),
its trihydrochloride NMR (CDCl₃—CD₃OD, δ): 2.87 (3H, br s), 3.29 (3H, s), 3.68–4.25 (10H, m), 5.50 (1H, br d, J=10 Hz), 5.69 (1H, br d, J=10 Hz), 6.61 (1H, br s), 7.07 (1H, br s), 7.28–7.74 (8H, m), 8.01–8.16 (2H, m), 8.45–8.70 (4H, m).

EXAMPLE 69

The following compounds were obtained according to a similar manner to that of Example 3.

(1) 8-[3-[N-[(E)-3-(6-Carboxypyridin-3-yl)acryloylglycyl]-N-methylamino]-2,6-dichlorobenzyloxy]-4-dimethylamino-2-methylquinoline NMR (DMSO-d₆, δ): 2.60 (3H, s), 3.13 (3H, s), 3.20–3.42 (6H, overlapped with H₂O), 3.58 (1H, br dd, J=17, 4 Hz), 3.90 (1H, br dd, J=17, 5 Hz), 5.51 (1H, d, J=10 Hz), 5.58 (1H, d, J=10 Hz), 6.90 (1H, br s), 7.01 (1H, d, J=15 Hz), 7.44–7.93 (6H, m), 8.07 (1H, d, J=8 Hz), 8.14 (1H, br d, J=8 Hz), 8.45 (1H, br t, J=5 Hz), 8.88 (1H, br s).

(2) 8-[3-[N-[(E)-3-(6-Carboxypyridin-3-yl)acryloylglycyl]-N-methylamino]-2,6-dichlorobenzyloxy]-2-methyl-4-piperidinoquinoline NMR (DMSO-d₆, δ): 1.59–1.83 (6H, m), 2.55 (3H, br s), 3.00–3.60 (8H, overlapped with H₂O), 3.86 (1H, br d, J=17, 4 Hz), 5.50 (2H, br s), 6.87–7.08 (2H, m), 7.30–7.67 (4H, m), 7.79 (2H, s), 8.03–8.51 (4H, m), 8.59 (0.5H, br s), 8.89 (0.5H, br s).

(3) 8-[3-[N-[(E)-3-(6-Carboxypyridin-3-yl)acryloylglycyl]-N-methylamino]-2,6-dichlorobenzyloxy]-2-methyl-4-morpholinoquinoline NMR (CDCl₃—CD₃OD, δ): 2.67 (3H, br s), 3.25 (3H, s), 3.30–3.45 (4H, m), 3.77 (1H, br d, J=17 Hz), 3.92–4.11 (5H, m), 5.45–5.62 (2H, m), 6.64–7.00 (2H, m), 7.14–7.68 (6H, m), 7.90 (1H, br d, J=8 Hz), 8.04 (1H, br s), 8.70 (1H, br s).

(4) 8-[3-[N-[(E)-3-(6-Carboxypyridin-3-yl)acryloylglycyl]-N-methylamino]-2,6-dimethylbenzyloxy]-2-methylquinoline NMR (DMSO-d₆, δ): 2.33 (3H, s), 2.46 (3H, s), 2.61 (3H, s), 3.13 (3H, s), 3.51 (1H, dd, J=5, 16 Hz), 3.71 (1H, dd, J=5, 16 Hz), 5.25–5.37 (2H, m), 7.00 (1H, d, J=16 Hz), 7.25 (1H, d, J=8 Hz), 7.37 (1H, d, J=8 Hz), 7.37–7.57 (5H, m), 8.00 (1H, d, J=8 Hz), 8.08 (1H, d, J=8 Hz), 8.21 (1H, d, J=8 Hz), 8.33 (1H, t-like, 8.78 (1H, s-like).

EXAMPLE 70

The following compounds were obtained according to a similar manner to that of Example 7.

(1) 8-[2,6-Dichloro-3-[N-methyl-N-[(E)-3-[6-(methylcarbamoyl)pyridin-3-yl]acryloxylglycyl]amino]-benzyloxy]-2methyl-4-dimethylaminoquinoline NMR (CDCl₃, δ): 2.62 (3H, s), 2.98 (6H, s), 3.04 (3H, d, J=7 Hz), 3.26 (3H, s), 3.74 (1H, dd, J=7, 15 Hz), 3.95 (1H, dd, J=7, 15 Hz), 5.58 (2H, m), 6.59–6.68 (2H, m), 6.94 (1H, br), 7.19 (1H, d, J=8 Hz), 7.28–7.36 (2H, m), 7.48 (1H, d, J=8 Hz), 7.58 (1H, d, J=15 Hz), 7.70 (1H, d, J=8 Hz), 7.84–8.01 (2H, m), 8.08 (1H, d, J=10 Hz), 8.56 (1H, s),
its trihydrochloride NMR (CDCl₃—CD₃OD, δ): 2.74 (3H, s), 3.07 (3H, s), 3.28 (3H, br), 3.51 (6H, s), 3.87 (1H, d, J=15 Hz), 4.30 (1H, d, J=15 Hz), 5.45 (1H, d, J=8 Hz), 5.65 (1H, d, J=8 Hz), 6.77 (1H, br), 6.98 (1H, d, J=15 Hz), 7.37–7.47 (2H, m), 7.51–7.64 (3H, m), 7.81 (1H, d, J=8 Hz), 8.49 (1H, br), 8.64 (1H, br), 9.23 (1H, br).

(2) 8-[2,6-Dichloro-3-[N-[(E)-3-[6-(dimethylcarbamoyl)-pyridin-3-yl]acryloylglycyl]-N-methylamino]benzyloxy]-4-dimethylamino-2-methylquinoline NMR (CDCl₃, δ): 2.66 (3H, br s), 3.03 (6H, br s), 3.13 (3H, s), 3.26 (3H, s), 3.75 (1H, br d, J=18 Hz), 3.98 (1H, br d, J=18 Hz), 5.54–5.65 (2H, m), 6.58–6.71 (2H, m), 7.15–7.41 (4H, m), 7.48 (1H, d, J=8 Hz), 7.51–7.64 (2H, m), 7.70 (1H, d, J=8 Hz), 7.89 (1H, dd, J=2, 8 Hz), 8.64 (1H, s),
its trihydrochloride NMR (DMSO-D₆, δ): 2.63 (3H, s), 2.95 (3H, s), 3.01 (3H, s), 3.14 (3H, s), 3.42 (6H, s), 3.59 (1H, dd, J=4, 16 Hz), 3.92 (1H, dd, J=4, 16 Hz), 5.53 (1H, d, J=10 Hz), 5.60 (1H, d, J=10 Hz), 690–7.00 (2H, m), 7.45 (1H, d, J=16 Hz), 7.53–7.65 (2H, m), 7.72–7.89 (3H, m), 7.95 (1H, d, J=8 Hz), 8.09 (1H, d, J=8 Hz), 8.43 (1H, t-like), 8.75 (1H, s).

(3) 8-[2,6-Dichloro-3-[N-methyl-N-[(E)-3-[6-(2-pyridylmethylcarbamoyl)pyridin-3-yl]acryloylglycyl]-amino]benzyloxy]-4-dimethylamino-2-methylquinoline NMR (CDCl$_3$, δ): 2.65 (3H, br s), 3.00 (6H, br s), 3.26 (3H, s), 3.73 (1H, br d, J=17 Hz), 3.97 (1H, br d, J=17 Hz), 4.79 (2H, d, J=5 Hz), 5.60 (2H, br s), 6.67 (1H, br s), 6.85 (1H, broad), 7.17–7.36 (5H, m), 7.46 (1H, d, J=8 Hz), 7.59 (1H, d, J=15 Hz), 7.62–7.72 (3H, m), 7.90 (1H, br d, J=8 Hz), 8.15 (1H, m), 8.57–8.65 (2H, m), 8.88 (1H, m),
its tetrahydrochloride NMR (CDCl$_3$—CD$_3$OD, δ): 2.62–2.88 (3H, overlapped with H$_2$O), 3.27 (3H, s), 3.50 (6H, s), 3.87 (1H, d, J=17 Hz), 4.25 (1H, d, J=17 Hz), 5.12 (2H, br s), 5.46 (1H, d, J=10 Hz), 5.62 (1H, d, J=10 Hz), 6.74 (1H, br s), 6.95 (1H, br d, J=15 Hz), 7.37–7.65 (5H, m, 7.81 (1H, br d, J=8 Hz), 7.89 (1H, br t, J=7 Hz), 8.11 (1H, br d, J=8 Hz), 8.27 (1H, m), 8.34 (1H, m, 8.44 (1H, br t, J=8 Hz), 8.78 (1H, br d, J=5 Hz), 8.92 (1H, m).

(4) 8-[2,6-Dichloro-3-[N-methyl-N-[(E)-3-[6-[N-(4-pyridyl)carbamoyl]pyridin-3-yl]acryloylglycyl]amino]-benzyloxy]-2-methyl-4-dimethylaminoquinoline NMR (CDCl$_3$, δ): 2.63 (3H, s), 3.00 (6H, s), 3.28 (3H, s), 3.79 (1H, dd, J=7, 15 Hz), 3.99 (1H, dd, J=7, 15 Hz), 5.60 (2H, m), 6.68 (1H, s), 6.73 (1H, d, J=15 Hz), 7.19–7.28 (3H, m), 7.31–7.42 (2H, m), 7.48 (1H, d, J=8 Hz), 7.62 (1H, d, J=15 Hz), 7.66–7.75 (3H, m), 7.95 (1H, dd, J=4, 8 Hz), 8.17 (1H, d, J=8 Hz), 8.57 (2H, d, J=8 Hz), 8.62 (1H, s),
its tetrahydrochloride NMR (CD$_3$OD, δ): 2.68 (3H, s), 3.28 (3H, s), 3.49 (6H, s), 3.82 (1H, d, J=15 Hz), 4.02 (1H, d, J=15 Hz), 5.65 (1H, d, J=8 Hz), 5.71 (1H, d, J=8 Hz), 6.87 (1H, s), 6.97 (1H, d, J=15 Hz), 7.54–7.71 (6H, m), 7.97 (1H, d, J=8 Hz), 8.28 (2H, m), 8.53 (2H, d, J=8 Hz), 8.70 (2H, d, J=8 Hz), 8.91 (1H, s).

(5) 8-[2,6-Dichloro-3-[N-methyl-N-[(E)-3-[6-(2-pyridylmethylcarbamoyl)pyridin-3-yl ]-acryloylglycyl]-amino]benzyloxy]-2-methyl-4-piperidinoquinoline NMR (CDCl$_3$, δ): 1.59–1.74 (2H, overlapped with H$_2$O), 1.79–1.89 (4H, m), 2.63 (3H, br s), 309–3.20 (4H, m), 3.26 (3H, s), 3.73 (1H, br d, J=17 Hz), 3.95 (1H, br d, J=17 Hz), 4.79 (2H, d, J=5 Hz), 5.60 (2H, s), 6.63 (1H, br d, J=15 Hz), 6.72 (1H, br s), 6.85 (1H, br s), 7.17–7.39 (5H, m), 7.48 (1H, d, J=8 Hz), 7.56–7.71 (3H, m), 7.91 (1H, br d, J=8 Hz), 8.16 (1H, br d, J=8 Hz), 8.61 (1H, d, J=5 Hz), 8.65 (1H, br s), 8.89 (1H, br t, J=5 Hz),
its tetrahydrochloride NMR (CDCl$_3$—CD$_3$OD, δ): 1.81–1.98 (6H, m), 2.80 (3H, br s), 3.27 (3H, s), 3.69–3.79 (4H, m), 3.89 (1H, br d, J=17 Hz), 4.40 (1H, br d, J=17 Hz), 5.16 (2H, br s), 5.48 (1H, br d, J=10 Hz), 5.63 (1H, br d, J=10 Hz), 6.89 (1H, br s), 7.04 (1H, br d, J=15 Hz), 7.33–7.70 (6H, m), 7.89 (1H, br s), 8.15 (1H, br s), 8.39–8.50 (2H, m), 8.53 (1H, br s), 8.79 (1H, br s), 9.04 (1H, br s).

(6) 8-[2,6-Dichloro-3-[N-methyl-N-[(E)-3-[6-(2-pyridylmethylcarbamoyl)pyridin-3-yl]acryloylglycyl]-amino]benzyloxy]-2-methyl-4-morpholinoquinoline and its tetrahydrochloride (7) 8-[2,6-Dimethyl-3-[N-methyl-N-[E)-3-[6-(methylcarbamoyl)pyridin-3-yl]acryloylglycyl]-amino]benzyloxy]-2-methylquinoline NMR (CDCl$_3$, δ) 2.37 (3H, s), 2.53 (3H, s), 2.74 (3H, s), 3.05 (3H, d, J=5 Hz), 3.27 (3H, s), 3.64 (1H, dd, J=4, 16 Hz), 3.90 (1H, dd, J=4, 16 Hz), 5.36 (2H, s), 6.61 (1H, d, J=16 Hz), 6.77 (1H, t-like), 7.07 (1H, d, J=8 Hz), 7.18 (1H, d, J=8 Hz), 7.22–7.33 (2H, m, 7.40–7.49 (2H, m), 7.60 (1H, d, J=16 Hz), 7.90–8.00 (2H, m), 8.03 (1H, d, J=8 Hz), 8.20 (1H, d, J=8 Hz), 8.63 (1H, d, J=2 Hz),
sits dihyrochloride NMR (DMSO-d$_6$, δ): 2.29 (3H, s), 2.48 (3H, s), 2.82 (3H, d, J=5 Hz), 2.92 (3H, s), 3.13 (3H, s), 3.55 (1H, dd, J=4, 16 Hz), 3.75 (1H, dd, J=4, 16 Hz), 5.41–5.54 (2H, m), 7.05 (1H, d, J=16 Hz), 7.31 (1H, d, J=8 Hz), 7.39 (1H, d, J=8 Hz), 7.49 (1H, d, J=16 Hz), 7.81–8.00 (4H, m), 8.05 (1H, d, J=8 Hz), 8.15 (1H, dd, J=2, 8 Hz), 8.35 (1H, t-like, 8.74–8.84 (2H, m), 8.98 (1H, br peak).

(8) 8-[2,6-Dichloro-3-[N-methyl-N-[(E)-3-[6-(methylcarbamoyl)pyridin-3yl]acryloylglycyl]amino]-benzyloxy]-2-methyl-4-piperidinoquinoline NMR (CDCl$_3$, δ): 1.69 (2H, br s), 1.84 (4H, br s), 2.63 (3H, s), 3.05 (3H, d, J=5 Hz), 3.18 (4H, br s), 3.26 (3H, s), 3.72 (1H, dd, J=17, 4 Hz), 3.96 (1H, dd, J=17, 4 Hz), 5.59 (2H, s), 6.65 (1H, d, J=16 Hz), 6.72 (1H, s), 7.00–7.70 (7H), 783–8.21 (3H), 8.58 (1H, s),
its trihydrochloride NMR (CD$_3$OD, δ): 1.87 (6H, br s), 2.71 (3H, s), 2.98 (3H, s), 3.27 (3H, s), 3.78 (4H, br s), 3.82 (1H, d, J=17 Hz), 4.02 (1H, d, J=17 Hz), 5.64 (1H, d, J=11 Hz), 5.72 (1H, d, J=11 Hz), 6.82–8.30 (10H), 8.79 (1H, br s).

(9) 8-[2,6-Dichloro-3-[N-methyl-N-[(E)-3-[6-(methylcarbamoyl)pyridin-3-yl]acryloylglycyl]amino]-benzyloxy]-2-methyl-4-morpholinoquinoline NMR (CDCl$_3$, δ): 2.67 (3H, s), 3.04 (3H, d, J=5 Hz), 3.18–3.24 (4H, m), 3.28 (3H, s), 3.70 (1H, br dd, J=17, 4 Hz), 3.90–4.01 (5H, m), 5.60 (1H, d, J=10 Hz), 5.67 (1H, d, J=10 Hz), 6.62 (1H, br d, J=15 Hz), 6.78 (2H, s), 7.22 (1H, br d, J=8 Hz), 7.30 (1H, d, J=8 Hz), 7.38 (1H, t, J=8 Hz), 7.49 (1H, d, J=8 Hz), 7.60 (1H, d, J=15 Hz), 7.67 (1H, br d, J=8 Hz), 7.90–8.00 (2H, m), 8.18 (1H, d, J=8 Hz), 8.61 (1H, br s),
its trihydrochloride NNR (CDCl$_3$–CD$_3$OD, δ) 2.86 (3H, br s), 3.07 (3H, s), 3.29 (3H, s), 3.73–3.90 (5H, m), 3.98–4.06 (4H, m), 4.48 (1H, br d, J=17 Hz), 5.44 (1H, d, J=10 Hz), 5.63 (1H, d, J=10 Hz), 6.99–7.09 (2H, m), 7.30–7.69 (6H, m), 8.68–8.80 (2H, m), 9.44 (1H, br s).

EXAMPLE 71

The following compounds were obtained according to a similar manner to that of Example 5.

(1) 8-[2,6-Dichloro-3-[N-methyl-N-[(E)-3-[6-4-pyridylacetamido)pyridin-3yl]acryloylglycyl]amino]-benzyloxy]-4-dimethylamino-2methylquinoline NMR (CDCl$_3$, δ): 2.66 (3H, s), 3.02 (6H, s), 3.26 (3H, s), 3.63–379 (3 H, m), 3.96 (1 H, br d, J=18 Hz), 6.55–6.67 (2 H, m), 6.49 (1 H, d, J=16 Hz), 6.68 (1 H, s), 7.16–7.40 (6 H, m), 7.40–7.55 (2 H, m), 7.71 (1 H, d, J=8 Hz), 7.82 (1 H, d, J=8 Hz), 8.10–8.21 (2 H, m), 8.32 (1 H, s-like), 8.62 (2 H, d, J=6 Hz).

(2) 8-[2,6-Dichloro-3-[N-methyl-N-[(E)-3-[6-(2-methylnicotinamido)pyridin-3-yl]acryloylglycyl]amino] benzyloxy]-4-dimethylamino-2-methylquinoline NMR (CDCl$_3$, δ): 2.64 (3 H, s), 2.77 (3 H, s), 2.99 (6 H, s), 3.27 (3 H, s), 3.64–3.77 (1 H, m), 3.94 (1 H, dd, J=4, 18 Hz), 5.56–5.67 (2 H, m), 6.51 (1 H, d, J=16 Hz), 6.69 (1 H, s), 6.76 (1 H, br peak), 7.15–7.38 (4 H, m), 7.45–7.48 (2 H, m), 7.66–7.74 (1 H, m), 7.83 (1 H, d, J=8 Hz), 7.80 (1 H, d, J=8 Hz), 8.30–8.40 (3 H, m), 8.64 (1 H, d, J=6 Hz).

(3) 8-[2,6-Dichloro-3-[N-methyl-N-[(E)-3-[6-(isonicotinamido)pyridin-3-yl]acryloylglycyl]amino] benzyloxy]-4-dimethylamino-2-methylquinoline NMR (CDCl$_3$, δ): 2.66 (3 H, s), 3.04 (6 H, s), 3.27 (3 H, s), 3.76 (1 H, br d, J=18 Hz), 3.98 (1 H, br d, J=18 Hz), 5.60 (2 H, s), 6.65 (1 H, d, J=16 Hz), 6.69 (1 H, s), 7.17–7.42 (4 H, m), 7.48 (1 H, d, J=8 Hz), 7.54 (1 H, d, J=16 Hz), 7.71 (1 H, d, J=8 Hz), 7.78 (2 H, d, J=6 Hz), 7.90 (1 H, dd, J=2, 8 Hz), 8.33 (1 H, d, J=8 Hz), 8.41 (1 H, d, J=2 Hz), 8.76 (1 H, s), 8.84 (2 H, d, J=6 Hz).

(4) 8-[2,6-Dichloro-3-[N-methyl-N-[(E)-3-[6-(4-pyridylacetamido)pyridin-3-yl]acryloylglycyl]amino]benzyloxy]-2-methyl-4-piperidinoquinoline NMR (CDCl₃, δ): 2.61–2.90 (6 H, m), 2.68 (3 H, br s), 3.20 (4 H, br peak), 3.25 (3 H, s), 3.65–3.80 (3 H, m), 3.98 (1 H, br d, J=18 Hz), 5.59 (2 H, s), 6.52 (1 H, d, J=16 Hz), 6.72 (1 H, s), 7.21 (1 H, d, J=8 Hz), 7.25–7.41 (5 H, m), 7.45 (1 H, d, J=8 Hz), 7.49 (1 H, d, J=16 Hz), 7.63 (1 H, d, J=8 Hz), 7.81 (1 H, dd, J=2, 8 Hz), 8.04–8.19 (1 H, m), 8.23–8.33 (2 H, m), 8.61 (2 H, d, J=6 Hz).

(5) 8-[2,6-Dichloro-3-[N-methyl-N-[(E)-3-[6-(4-pyridylacetamido)pyridin-3-yl]acryloylglycyl]amino]benzyloxy]-2-methyl-4-morpholinoquinoline NMR (CDCl₃, δ): 2.67 (3 H, s), 3.22 (4 H, br), 3.27 (3 H, s), 3.66–3.76 (4 H, m), 3.98 (4 H, m), 5.68 (2 H, m), 6.47 (1 H, d, J=15 Hz), 6.78 (1 H, s), 6.94 (1 H, br), 7.22 (1 H, d, J=8 Hz), 7.28–7.50 (6 H, m), 7.66 (1 H, d, J=8 Hz), 7.79 (1 H, dd, J=4, 8 Hz), 8.16 (1 H, d, J=8 Hz), 8.30 (1 H, br), 8.60 (2 H, d, J=7 Hz), 8.68 (1 H, s).

EXAMPLE 72

The folloiwng compounds were obtained according to a similar manner to that of Example 19.

(1) 8-[2,6-Dichloro-3-[N-methyl-N-[N'-[3-[N-(4-pyridyl)carbamoyl]phenyl]ureidoacetyl]amino]benzyloxy]-2-methyl-4-dimethylaminoquinoline NMR (CDCl₃, δ): 2.50 (3 H, s), 3.01 (6 H, s), 3.19 (3 H, s), 3.92 (2 H, m), 5.40 (2 H, m), 6.32 (1 H, br), 6.65 (1 H, s), 7.03 (1 H, m), 7.14 (2 H, m), 7.28–7.42 (4 H, m), 7.64 (1 H, m), 7.70 (1 H, d, J=8 Hz), 7.78 (2 H, m), 8.40–8.52 (2 H, m), 8.69 (1 H, br), 9.47 (1 H, br).
its trihydrochloride NMR (CD₃OD, δ): 2.41 (3 H, s), 3.07 (3 H, s), 3.27 (6 H, s), 3.42–3.70 (2 H, m), 5.40 (1 H, s), 7.18–7.48 (9 H, m), 7.72 (1 H, d, J=8 Hz), 7.86 (1 H, m), 8.10–8.20 (3 H, m), 8.44 (2 H, m).

(2) 8-[2,6-Dichloro-3-[N-methyl-N-[N'-[3-nitrophenyl)ureidoacetyl]amino]benzyloxy]-4-dimethylamino-2-methylquinoline NMR (CDCl₃, δ): 2.44 (3 H, s), 3.06 (6 H, s), 3.23 (3 H, s), 3.77 (1 H, dd, J=3, 18 Mz), 4.70 (1 H, dd, J=10, 18 Hz), 5.32 (1 H, d, J=10 Hz), 5.44–5.53 (1 H, m), 5.56 (1 H, d, J=10 Hz), 7.68 (1 H, s), 7.10–7.21 (2 H, m), 7.21–7.29 (1 H, m), 7.29–7.48 (3 H, m), 7.63–7.74 (2 H, m), 8.20 (1 H, s), 9.90 (1 H, s).

(3) 8-[2,6-Dichloro-3-[N-methyl-N-[N'-[3-[(E)-2-(pyridin-4-yl)vinyl]phenyl]ureidoacetyl]amino]benzyloxy]-2-methyl-4-dimethylaminoquinoline NMR (CDCl₃, δ): 2.48 (3 H, s), 3.04 (6 H, s), 3.22 (3 H, s), 3.65–3.87 (2 H, m), 5.41 (1 H, d, J=8 Hz), 5.61 (1 H, d, J=8 Hz), 5.63 (1 H, br), 6.68–6.80 (2 H, m), 7.00–7.22 (7 H, m), 7.29–7.36 (2 H, m), 7.45 (1 H, t, J=8 Hz), 7.57 (1 H, s), 7.70 (1 H, d, J=8 Hz), 8.52 (2 H, d, J=7 Hz), 8.86 (1 H, br).
its trihydrochloride NMR (CD₃OD, δ): 2.57 (3 H, s), 3.27 (3 H, s), 3.46 (6 H, s), 3.70 (1 H, d, J=15 Hz), 3.90 (1 H, d, J=15 Hz), 5.63 (1 H, d, J=8 Hz), 5.76 (1 H, d, J=8 Hz), 6.75 (1 H, m), 6.80 (1 H, s), 7.15 (1 H, m), 7.30–7.45 (4 H, m), 7.58 (1 H, m), 7.66–7.99 (6 H, m), 8.12 (2 H, d, J=8 Hz), 8.68 (2 H, d, J=8 Hz).

(4) 8-[2,6-Dichloro-3-[N-methyl-N-[N'-[3-[N-(4-pyridyl)-carbamoyl]phenyl]ureidoacetyl]amino]benzyloxy]-2-methyl-4-piperidinoquinoline NMR (CDCl₃, δ): 1.65–1.90 (6 H, m), 2.54 (3 H, s), 3.11–3.29 (7 H, m), 4.00 (2 H, br s), 5.49 (2 H, br s), 6.32 (1 H, br s), 6.70 (1 H, br s), 7.06 (1 H, t, J=8 Hz), 7.19 (2 H, br d, J=8 Hz), 7.23–7.48 (5 H, m), 7.63 (1 H, br d, J=8 Hz), 7.75 (2 H, br d, J=6 Hz), 8.49 (2 H, br d, J=6 Hz), 8.88 (1 H, br s), 9.35 (1 H, br s).
its trihydrochloride NMR (CDCl₃—CD₃OD, δ): 1.81–1.94 (6 H, m), 2.57 (3 H, br s), 3.24 (3 H, s), 3.67–3.77 (4 H, m), 3.82 (1 H, br d, J=17 Hz), 4.19 (1 H, br d, J=17 Hz), 5.48 (1 H, d, J=10 Hz), 5.67 (1 H, d, J=10 Hz), 6.73 (1 H, br s), 7.18 (1 H, br t, J=8 Hz), 7.39–7.65 (7 H, m), 7.92 (1 H, br s), 8.45–8.54 (4 H, m).

(5) 8-[2,6-Dichloro-3-[N-methyl-N-[N'-[3-[N-(4-pyridyl)carbamoyl]phenyl]ureidoacetyl]amino]benzyloxy]-2-methyl-4-morpholinoquinoline NMR (CDCl₃, δ): 2.59 (3 H, s), 3.17–3.26 (7 H, m), 3.91–4.01 (4 H, m), 5.41 (1 H, d, J=10 Hz), 5.49 (1 H, d, J=10 Hz), 6.45 (1 H, br s), 6.76 (1 H, s), 7.00–7.10 (2 H, m), 7.19 (1 H, br d, J=8 Hz), 7.22–7.48 (5 H, m), 7.68 (1 H, br d, J=8 Hz), 7.82 (2 H, br d, J=7 Hz), 8.51 (2 H, br d, J=7 Hz), 8.58 (1 H, br s), 9.51 (1 H, br s).
its trihydrochloride NMR (CDCl₃—CD₃OD, δ): 2.66 (3 H, s), 3.25 (3 H, s), 3.68–4.07 (9 H, m), 4.19 (1 H, br s), 5.49 (1 H, d, J=7.5 Hz), 5.69 (1 H, d, J=7.5 Hz), 6.92 (1 H, br s), 7.16 (1 H, br s), 7.41–7.40 (7 H, m), 7.91 (1 H, br s), 8.40–8.59 (4 H, m).

(6) 8-[2,6-Dichloro-3-[N-methyl-N-[N'-[4-[N-(4-pyridylmethyl)carbamoyl]phenyl]ureidoacetyl]amino]benzyloxy]-2-methylquinoline NMR (CDCl₃, δ): 2.56 (3 H, s), 3.17 (3 H, br), 3.49–3.82 (2 H, m), 4.54 (2 H, br), 5.47 (1 H, d, J=8 Hz), 5.57 (1 H, m), 7.15 (2 H, br), 7.23–7.33 (5 H, m), 7.46 (2 H, br), 7.60 (2 H, d, J=8 Hz), 8.08 (1 H, m), 8.46 (2 H, br), 8.93 (1 H, br).
its dihydrochloride NMR (CD₃OD, δ): 3.00 (3 H, s), 3.28 (3 H, s), 3.80 (2 H, m), 4.84 (2 H, br), 5.70 (1 H, d, J=8 Hz), 5.84 (1 H, d, J=8 Hz), 7.49 (2 H, d, J=8 Hz), 7.73 (2 H, d, J=4 Hz), 7.84 (2 H, m), 7.91 (4 H, m), 8.04 (2 H, d, J=8 Hz), 8.78 (2 H, d, J=8 Hz), 9.03 (1 H, m).

(7) 8-[2,6-Dichloro-3-[N-[N'-[3-(methanesulfonylaminocarbonyl)phenyl]ureidoacetyl]-N-methylamino]benzyloxy]-2-methylquinoline mp: 239–242° C.

NMR (CDCl₃—CD₃OD, δ): 2.64 (3 H, s), 3.22 (3 H, s), 3.28 (3 H, s), 3.79 (1 H, br d, J=17 Hz), 3.90 (1 H, br d, J=17 Hz), 5.52 (1 H, d, J=10 Hz), 5.60 (1 H, d, J=10 Hz), 7.13–7.19 (2 H, m), 7.22–7.60 (7 H, m), 7.81 (1 H, br s), 8.09 (1 H, d, J=8 Hz).

(8) 8-[2,6-Dichloro-3-[N-[N'-[3-(4-methylbenzenesulfonylaminocarbonyl)phenyl]ureidoacetyl]-N-methylamino]benzyloxy]-2-methylquinoline mp: 235–240°C.

NMR (CDCl₃—CD₃OD, δ): 2.37 (3 H, s), 2.61 (3 H, s), 3.21 (3 H, s), 3.80 (1 H, br d, J=17 Hz), 3.90 (1 H, br d, J=17 Hz), 5.51 (1 H, d, J=10 Hz), 5.69 (1 H, d, J=10 Hz), 6.99–7.13 (2 H, m), 7.18–7.49 (9 H, m), 7.70 (1 H, br s), 7.97 (2 H, d, J=8 Hz), 8.05 (1 H, d, J=8 Hz).

(9) 8-[2,6-Dichloro-3-[N-[N'-[3-[(E)-2-(pyridin-4-yl)vinyl]phenyl]ureidoacetyl]amino]benzyloxy]-2-methylquinoline NMR (CDCl₃, δ): 2.62 (3 H, s), 3.22 (3 H, s), 3.63–3.88 (2 H, m), 5.49 (1 H, d, J=8 Hz), 5.63 (1 H, d, J=8 Hz), 5.67 (1 H, br), 6.78–6.88 (2 H, m), 7.03–7.25 (7 H, m), 7.33 (2 H, m), 7.48 (1 H, m), 7.59 (1 H, br), 8.02 (1 H, br), 8.08 (1 H, d, J=8 Hz), 8.41 (1 H, br), 8.51 (2 H, d, J=7 Hz).
its dihydrochloride NMR (CD₃OD, δ): 2.93 (3 H, s), 3.28 (3 H, s), 3.77 (1 H, d, J=15 Hz), 3.89 (1 H, d, J=15 Hz), 5.65 (1 H, m), 5.72 (1

H, d, J=8 Hz), 5.84(1 H, d, J=8 Hz), 7.29–7.40 (3 H, m), 7.59–8.00 (9 H, m), 8.13 (2 H, d, J=8 Hz), 8.69 (2 H, d, J=8 Hz), 9.00 (2 H, m).

(10) 8-[2,6-Dichloro-3-[N-[N'-[3[(Z)-2-(pyridin-4-yl) vinyl]phenyl]ureidoacetyl]amino]benzyloxy]-2-methylquinoline NMR (CDCl₃, δ): 2.61 (3 H, s), 3.17 (3 H, s), 3.76 (1 H, dd, J=4, 16 Hz), 4.01 (1 H, dd, J=5, 16 Hz), 5.47 (1 H, d, J=10 Hz), 5.60 (1 H, d, J=10 Hz), 5.73 (1 H, t-like), 6.35 (1 h, d, J=11 Hz), 6.64 (1 H, d, J=11 Hz), 6.74 (1 H, d, J=8 Hz), 6.94–7.19 (5 H, m), 7.19–7.37 (4 H, m), 7.37–7.51 (2 H, m), 8.05 (1 H, d, J=8 Hz), 8.23–8.58 (3 H, m).

(11) 8-[2,6-Dichloro-3-[N-[N'-[3-[2-(pyridin-4-yl)ethyl] phenyl]ureidoacetyl]amino]benzyloxy]-2-methylquinoline NMR (CDCl₃, δ): 2.61 (3 H, s), 2.66–2.80 (4 H, m), 3.22 (3 H, s), 3.80 (1 H, dd, J=4, 17 Hz), 4.23 (1 H, dd, J=5, 17 Hz), 5.47 (1 H, d, J=10 Hz), 6.71 (1 H, d, J=8 Hz), 6.90–7.13 (4 H, m), 7.19 (1 H, s-like), 7.21–7.35 (4 H, m), 7.42–7.50 (2 H, m), 8.02 (1 H, s-like), 8.08 (1 H, d, J=8 Hz), 8.43 (2 H, d, J=6 Hz).

its dihydrochloride

NMR (DMSO-d₆, δ): 2.82–2.97 (5 H, m), 3.06–3.21 (5 H, m), 3.40–3.90 (2 H, m, (overlap in H₂O)), 5.61 (2 H, s), 6.48 (1 H, br s), 6.77 (1 H, d, J=8 Hz), 7.11 (1 H, t, J=8 Hz), 7.16–7.31 (2 H, m), 7.67–7.88 (6 H, m), 7.93 (2 H, d, J=6 Hz), 8.75–8.89 (3 H, m), 8.96 (1 H, s).

EXAMPLE 73

(1) 8-[N-tert-Butoxycarbonyl-N-[2,6-dichloro-3-[N-methyl-N-(phthalimidoacetyl)amino]benzyl]amino]-2-methylquinoline was obtained from 8-tert-butoxycarbonylamino-2-methylquinoline and 2,6-dichloro-3-[N-methyl-N-(phthalimidoacetyl)amino]benzyl bromide according to asimilar manner to that of Preparation 6.

NMR (CDCl₃—CD₃OD, δ): 1.24, 1.66 (9 H, s), 2.72, 2.78 (3 H, s), 2.96, 3.04 (3 H, s), 3.16–3.22, 3.56–3.66 (2 H, m), 5.18–5.38, 5.50–5.69 (2 H, m), 6.83–8.08 (11 H, m).

(2) 8-[N-[3-(N-Glycyl-N-methylamino)-2,6-dichlorobenzyl]-N-tert-butoxycarbonylamino]-2-methylquinoline was obtained according to a similar manner to that of Preparation 11.

NMR (CDCl₃, δ): 1.20, 1.63 (3 H, s), 2.14–2.20, 2.59–2.88 (2 H, m), 2.19, 2.23 (3 H, s), 5.07–5.22, 5.54–5.70 (2 H, m), 6.83–7.88, 7.66, 8.00 (7 H, m).

(3) 8-[N-tert-Butoxycarbonyl-N-[2,6-dichloro-3-[N-methyl-N-[4-(methylcarbamoyl)cinnamoylglycyl]amino] benzyl]amino]-2-methylquinoline was obtained according to a similar manner to that of Example 1.

NMR (CDCl₃, δ): 1.24, 1.60 (9 H, s), 2.74 (3 H, s), 3.05 (3 H, s), 3.08 (3 H, s), 2.84, 2.90, 3.80, 3.86 (2 H, m), 5.00–5.16, 5.62–5.72 (2 H, m), 6.16 (1 H, br), 6.48 (1 H, m), 6.56 (1 H, m), 6.60–6.98 (1 H, m), 7.10 (1 H, m), 7.46 (1 H, m), 7.50–7.66 (4 H, m), 7.75 (2 H, m), 7.96 (1 H, m).

(4) To a solution of 8-[N-tert-butoxycarbonyl-N-[2,6-dichloro-3-[N-methyl-N-[4-(methylcarbamoyl) cinnamoylglycyl]amino]benzyl]amino]-2-methylquinoline (32.3 mg) in ethyl acetate (0.5 ml) was added 4N solution of hydrogen chloride in ethyl acetate (0.5 ml) under ice-cooling, and the mixture was stirred for 30 minutes at the same temperature and for 2 hours at ambient temperature. The mixture was concentrated in vacuo to give 8-[2,6-dichloro-3-[N-methyl-N-[4-(methylcarbamoyl) cinnamoylglycyl]amino]benzylamino]-2-methylquinoline dihydrochloride (22.0 mg) as amorphous powder.

NMR (CDCl₃, δ): 3.00 (3 H, s), 3.20 (3 H, s), 3.31 (3 H, s), 3.84–4.06 (2 H, m), 4.71–4.85 (2 H, m), 6.25 (1 H, m), 6.55 (1 H, m), 7.07 (1 H, m), 7.16 (1 H, d, J=8 Hz), 7.27–7.31 (2 H, m), 7.42–7.58 (4 H, m), 7.64–7.74 (3 H, m), 8.57 (1 H, m).

EXAMPLE 74

To a suspension of sodium hydride (60% in oil, 38 mg) in anhydrous dimethylformamide (2.0 ml)was added 8-[2,6-dichloro-3-[N-methyl-N-[4-(methylcarbamoyl) cinnamoylglycyl]amino]benzyloxy]-2-methylquinoline (189 mg) under nitrogen atmosphere in an ice-water bath. After stirring for 40 minutes, methyl iodide (0.06 ml) was added thereto and the mixture was stirred for additional 2 hours. The reaction mixture was partitioned between ethyl acetate and water and organic layer was isolated. The aqueous layer was extracted with ethyl acetate. The combined organic phases were washed with water twice,dried over magnesium sulfate and evaporated in vacuo. The residue was pulverized with diethyl ether to give 8-[2,6-dichloro-3-[N-methyl-N-[N-methyl-N-[4-(dimethylcarbamoyl)cinnamoyl]glycyl]amino]benzyloxy]-2-methylquinoline (160 mg) as a pale yellow powder.

NMR (CDCl₃, δ): 2.72 (3 H, s), 2.98 (3 H, br s), 3.11 (3 H, br s), 3.23 (6 H, s), 3.41 (1 H, d, J=16 Hz), 4.36 (1 H, d, J=16 Hz), 5.66 (2 H, s), 6.97 (1 H, d, J=15 Hz), 7.14–7.59 (10 H), 7.66 (1 H, d, J=15 Hz), 8.03 (1 H, d, J=8 Hz).

EXAMPLE 75

(1) To a mixture of 8-(3-amino-2,6-dichlorobenzyloxy)-2-methylquinoline (1.67 g), triethylamine (0.9 ml) and anhydrous dichloromethane (84 ml) was added 3-methoxycarbonylpropionyl chloride (0.7 ml). After stirring at ambient temperature for 9 hours, triethylamine (1.8 ml) and 3-methoxycarbonylpropionyl chloride (1.4 ml) were added thereto and the mixture was stirred for additional 30 minutes. The reaction mixture was washedwith water and saturated aqueous solution of sodium hydrogen carbonate, dried over magnesium sulfate and evaporated in vacuo. The residue was purified by a silica gel column chromatography eluted with chloroform to give 8-[2,6-dichloro-3-(3-methoxycarbonylpropionylamino)benzyloxy]-2-methylquinoline (2.04 g) as a pale yellow oil.

NMR (CDCl₃, δ): 2.63–3.05 (4 H), 2.74 (3 H, s), 3.69 (3 H, s), 5.68 (2 H, s), 7.18–7.46 (6 H), 8.03 (1 H, d, J=8 Hz), 8.27 (1 H, br s).

(2) To a mixture of 8-[2,6-dichloro-3-(3-methoxycarbonylpropionylamino)benzyloxy]-2-methylquinoline (447 mg), iodomethane (0.1 ml) and dimethylformamide (5.0 ml) was added sodium hydride (60% in oil, 44 mg) under ice-water cooling. After stirring for 2 hours at the same temperature, the reaction mixture was diluted with ethyl acetate and washed with water twice. The organic layer was dried over magnesium sulfate and evaporated in vacuo. The residue was purified by a column chromatography eluted with chloroform to give 8-[2,6-dichloro-3-[N-(3-methyoxycarbonylpropionyl)-N-methylamino]benzyloxy]-2-methylquinoline (310 mg) as a pale yellow oil.

NMR (CDCl₃, δ): 2.15 (1 H, dt, J=16, 7 Hz), 2.30–2.55 (2 H), 2.65–2.78 (1 H), 2.75 (3 H, s), 3.19 (3 H, s), 3.68 (3 H, s), 5.67 (2 H, s), 7.21–7.49 (6 H), 8.03 (1 H, d, J=8 Hz).

(3) To a solution of 8-[2,6-dichloro-3-[N-(3-methoxycarbonylpropionyl)-N-methylamino]benzyloxy]-2-methylquinoline (303 mg) in methanol (3 ml) was added 1N aqueous solution of sodium hydroxide (1.0 ml) at ambient temperature. The mixture was stirred for 1 hour and neutralized to pH 4 with 1N hydrochloric acid. The reaction mixture was diluted with chloroform and washed with water. The aqueous layer was saturated with sodium chloride and extracted with chloroform. The combined organic layers were dried over magnesium sulfate and evaporated in vacuo to give 8-[3-[N-(3-carboxypropionyl)-N-methylamino]-2,6-dichlorobenzyloxy]-2-methylquinoline (242 mg) as an off-white powder.

NMR (CDCl$_3$, δ): 2.32 (1 H, m), 2.53–2.69 (3 H), 2.67 (3 H, s), 3.23 (3 H, s), 5.44 (1 H, d,J=10 Hz), 5.62 (1 H, d, J=10 Hz), 7.18–7.53 (6 H), 8.08 (1 H, d, J=8 Hz).

(4) to amixture of 8-[3-[N-(3-carboxypropionyl)-N-methylamino]-2,6-dichlorobenzyloxy]-2-methylquinoline (139 mg), 3-amino-N-methylbenzamide (51.3 mg) and anhydrous dichloromethane (4 ml) were added 1-ethyl-3-(3-dimethylaminopropyl)carbodiimide hydrochloride (71.5 mg) and 1-hydroxybenzotriazole (54.6 mg). The mixture was stirred for 12 hours at ambient temperature ans washed with water. The organic layer was dried over magnesium sulfate and evaporated in vacuo. The residue was purifed by preparative thin-layer chromatography (chloroform-methanol) followed by pulverization with diethyl ether to give 8-[2,6-dichloro-3-[N-[3-[N-(3-methylcarbamoylphenyl)carbamoyl]propionyl]-N-methylamino]benzyloxy]-2-methylquinoline (103 mg) as an amorphous powder.

NMR (CDCl$_3$, δ): 2.32 (1 H, m), 2.48–2.69 (2 H), 2.72 (3 H, s), 2,82 (1 H, m), 2.97 (3 H, d, J=6 Hz), 3.19 (3 H, s), 5.64 (2 H, s), 6.74 (1 H, br s), 7.20–7.50 (8 H), 7.57–7.67 (2 H), 8.04 (1 H, d, J=8 Hz), 9.17 (1 H, s).

EXAMPLE 76

(1) 8-[3-(N-Acetoxyacetyl-N-methylamino)-2,6-dichlorobenzyloxy]-2-methylquinoline was obtained from 8-hydroxy-2-methylquinoline and 3-(N-acetoxyacetyl-N-methylamino)-2,6-dichlorobenzyl bromide according to a similar manner to that of Example 9.

mp: 104–105° C.

NMR (CDCl$_3$, δ): 2.22 (3 H, s), 2.72 (3 H, s), 3.20 (3 H, s), 4.12 (1 H, d, J=15 Hz), 4.45 (1 H, d, J=15 Hz), 5.62 (1 H, d, J=10 Hz), 5.68 (1 H, d, J=10 Hz), 7.20–7.50 (6 H, m), 8.02 (1 H, d, J=8 Hz).

(2) To a solution of 8-[3-(N-acetoxyacetyl-n-methylamino)-2,6-dichlorobenzyloxy]-2-methylquinoline (640 mg) in methanol (6.4 ml) was added potassium carbonate (395 mg), and the mixture was stireed for 2 hours at ambient temperature. To the mixture was added chloroform and water, the organic layer was washed with water and brine, dried over magnesium sulfate and concentrated in vacuo. The residue was purified by chromatography on silica gel (chloroform:ethyl acetate=3.1, V/V) to give 8-[2,6-dichloro-3-(N-hydroxyacetyl-N-methylamino)benzyloxy]-2-methylquinoline (580 mg) as colorless amorphous.

NMR (CDCl$_3$, δ): 2.74 (3 H, s), 3.20–3.29 (4 H, m), 3.62 (1 H, dd, J=15, 4 Hz), 3.80 (1 H, dd, J=15, 5 Hz), 5.62 (1 H, d, J=10 Hz), 5.69 (1 H, d, J=10 Hz), 7.20–7.50 (6 H, m), 8.02 (1 H, d, J=8 Hz).

(3) To a solution of 8-[2,6-dichloro-3-(N-hydroxyacetyl-N-methylamino)benzyloxy]-2-methylquinoline (200 mg) and triethylamine (99.9 mg) in dry dichloromethane (2 ml) was added methanesulfonyl chloride (62.2 ml) under ice-cooling, and the mixture was stirred for 30 minutes. The mixture was washed with water, saturated sodium bicarbonate solution and brine,dried over magnesium sulfate and concentrated in vacuo to give 8-[2,6-dichloro-3-(N-methanesulfonyloxyacetyl-N-methylamino)benzyloxy]-2-methylquinoline (220 mg) as colorless amorphous.

NMR (CDCl$_3$, δ): 2.73 (3 H, s), 3.22 (3 H, s), 3.24 (3 H, s), 4.30 (1 H, d, J=15 Hz), 4.50 (1 H, d, J=15 Hz), 5.63 (1 H, d, J=10 Hz), 5.69 (1 H, d, J=10 Hz), 7.21–7.53 (6 H, m), 8.03 (1 H, J=8 Hz).

(4) To a mixture of dimethylamine hydrochloride (2.79 g) and triethylamine (6.92 g) in dichloromethane (50 ml) was added 4-bromobenzoyl chloride (5 g) was added slowly under ice-cooling, and the mixture was stirred for 20 minutes at the same temperature and for 2 hours at ambient temperature. The mixture was washed with water, saturated sodium bicarbonate solution and brine, dried over magnesium sulfate and concentrated invacuo to give 4-(dimethylcarbamoyl)-1-bromobenzene (5.20 g) as brown oil.

NMR (CDCl$_3$, δ): 2.97 (3 H, br s), 3.10 (3 H, br s), 7.30 (2 H, d, J=8 Hz), 7.54 (2 H, d, J=8 Hz).

(5) To the mixture of 3-aminophenylboronic acid hemisulfate (4.88 g) in toluene (57 ml) were added tetrakis)(triphenylphosphine)palladium(0) (659 mg), a solution of sodium carbonate (6.04 g) in water (28.5 ml), 4-(dimethylcarbamoyl)-1-bromobenzene (5.2 g) and methanol (14.3 ml) at ambient temperature, and the mixture was heated at 80° C. After 90 minutes, the cooled reaction mixture was extracted with chloroform and the organic layer was washed with aqueous sodium bicarbonate solution and brine. The organic layer was dried over magnesium sulfate and evaporated in vacuo. The residue was recrystallized from n-hexane-ethyl acetate to give 4-(3-aminophenyl)-N,N-dimethylbenzamide (4.7 g) as brown crystals.

mp: 139–141° C.

NMR (CDCl$_3$, δ): 3.04 (3 H, br s), 3.13 (3 H, br s), 3.75 (2 H, br s), 6.69 (1 H, d, J=8 Hz), 6.89 (1 H, s), 6.98 (1 H, d, J=8 Hz), 7.22 (1 H, t, J=8 Hz), 7.47 (2 H, d, J=8 Hz), 7.59 (2 H, d, J=8 Hz).

(6) A mixture of 8-[2,6-dichloro-3-(N-methanesulfonyloxyacetyl-N-methylamino)benzyloxy]-2-methylquinoline (110 mg), 4-(3-aminophenyl)-N,N-dimethylbenzamide (60.2 mg) and potassium carbonate (94.2 mg) in N,N -dimethylformamide (1 ml) was stirred for 12 hours at 60° C., and ethyl acetate and water were added thereto. The organic layer was washed with water and brine, dried over magnesium sulfate and concentrated in vacuo. The residue was purified by preparative thin-layer chromatography (chloroform:methanol=20:1, V/V) to give 8-[2,6-dichloro-3-methylamino]benzyloxy]-2-methylquinoline (30 mg) as colorless amorphous.

NMR (CDCl$_3$, δ): 2.70 (3 H, s), 3.01 (3 H, br s), 3.12 (3 H, br s), 3.27 (3 H, s), 3.51 (1 H, br dd, J=17, 4 Hz), 3.67 (1 H, br dd, J=17, 5 Hz), 4.81 (1 H, br s), 5.66 (1 H, d, J=10 Hz), 5.71 (1 H, d,J=10 Hz), 6.49 (1 H, br dd, J=8, 3 Hz), 6.70 (1 H s), 6.91 (1 H, br d, J=8 Hz), 7.17–7.59 (11 H, m), 8.02 (1 H, d, J=8 Hz).

EXAMPLE 77

The following compounds were obtained according to a similar manner to that of Example 63.

(1) 8-[2,6-Dichloro-3-[N-methyl-N-[3-[4-(methylcarbamoyl)benzyloxy]benzoyl]amino]benzyloxy]-2-methylquinoline NMR (CDCl$_3$, δ): 2.70 (3 H, s), 2.98 (3 H, m), 3.33 (3 H, s), 5.03 (2 H, m), 5.60 (2 H, m), 6.40 (1 H, br), 6.80–8.10 (15 H, m).

(2) 8-[2,6-Dichloro-3-[N-methyl-N-[3-[4-(methylcarbamoyl)phenoxymethyl]benzoyl]amino]benzyloxy]-2-methylquinoline NMR (CDCl$_3$, δ): 2.70 (3 H, s), 2.90 (3 H, m), 3.33 (3 H, s), 5.00 (2 H, m), 5.55 (2 H, m), 6.15 (1 H, br), 6.80–8.10 (15 H, m).

(3) 8-[2,6-Dichloro-3-[N-methyl-N-[3-[2-[4-(methylcarbamoyl)phenyl]ethyl]benzoyl]amino]benzyloxy]-2-methylquinoline NMR (CDCl$_3$, δ): 2.70 (3 H, s), 2.80 (3 H, br), 2.90 (3 H, d, J=7 Hz), 3.33 (3 H, br), 5.60 (2 H, d, J=8 Hz), 6.20 (1 H, br), 6.90–8.10 (15 H, m).

(4) 8-[2,6-Dichloro-3-[N-methyl-N-[6-[(E)-2-(4-methylcarbamoylphenyl)vinyl]pyridin-2-ylcarbonyl]amino]benzyloxy]-2-methylquinoline NMR (CDCl$_3$, δ): 2.69 (3 H, s), 3.02 (3 H, d, J=6 Hz), 3.45 (3 H, s), 5.48 (1 H, d, J=12 Hz), 5.55 (1 H, d, J=12 Hz), 6.25 (1 H, br s), 6.83 (1 H, d, J=15 Hz), 7.02 (1 H, d, J=8 Hz), 7.10–7.73 (14 H), 7.98 (1 H, d, J=8 Hz).

EXAMPLE 78

(1) to asolution of 8-[2,6-dichloro-3-[N-methyl-N-(4-aminocinnamoylglycyl)amino]benzyloxy]-2-methylquinoline (50 mg) in ethanol (2 ml) were added N,N-bis(tert-butoxycarbonyl)-S-methoxyisothiourea (28 mg) and mercury (II) oxide (21 mg) at ambient temperature and stirred for 1 hours at 40° C. The reaction mixture was filtered and the filtrate was evaporated in vacuo. The residue was purified by preparative thin-layer chromatography (8% solution of methanol in chloroform) to give 8-[2,6-dichloro-3-[N-[4-[2,3-bis(tert-butoxycarbonyl)guanidino]-cinnamoylglycyl]-N-methylamino]benzyloxy]-2-methylquinoline (60 mg) as an amorphous powder.

NMR (CDCl$_3$, δ): 1.50 (9 H, s), 1.53 (9 H, s), 2.73 (3 H, s), 3.26 (3 H, s), 3.64 (1 H, dd, J=4, 18 Hz), 3.94 (1 H, dd, J=4, 18 Hz), 5.60–5.71 (2 H, m), 6.40 (1 H, d, J=16 Hz), 6.58 (1 H, t-like), 7.21–7.35 (5 H, m), 7.35–7.60 (6 H, m), 7.64 (2 H, d, J=8 Hz), 8.03 (1 H, d, J=8 Hz).

(2) To a solution of 8-[2,6-dichloro-3-[N-[4-[2,3-bis(tert-butoxycarbonyl)guanidino]cinnamoylglycyl]-N-methylamino]benzyloxy]-2-methylquinoline (51 mg) in ethyl acetate and methanol was added 4N solution of hydrogen chloride in methanol (0.5 ml), and themixture was stirred for 2 days at ambient temperature. The mixture was concentrated in vacuo, and the residuewas dissolved in methaol. The solution was adjusted to pH 7 to 8 with aqueous ammonia and concentrated in vacuo. The residue was purified by preparative thin-layer chromatography (chloroform-methanol-aqueous ammonia) to give 8-[2,6-dichloro-3-[N-(4-guanidinocinnamoylglycyl)-N-methylamino]benzyloxy]-2-methylquinoline (12 mg) as amorphous powder.

NMR (CDCl$_3$—CD$_3$OD, δ): 2.67 (3 H, s), 3.21 (3 H, s), 3.48 (1 H, br d, J=16 Hz), 3.71 (1 H, br d, J=16 Hz), 5.50 (1 H, d, J=10 Hz), 5.65 (1 H, d, J=10 Hz), 6.26 (1 H, d, J=16 Hz), 6.97–7.12 (3 H, m), 7.21–7.36 (4 H, m), 7.42–7.58 (3 H, m), 7.80 (1 H, d, J=8 Hz), 8.08 (1 H, d, J=8 Hz).

EXAMPLE 79

8-[2,6-Dimethyl-3-[N-methyl-N-[(E)-3-[6-(2-oxopyrrolidin-1-yl)pyridin-3-yl]acryloylglycyl]amino]benzyloxy]-2-methylquinoline was obtained according to a similar manner to that of Examples 58-(1) and (2).

NMR (CDCl$_3$, δ): 2.13 (2 H, quint, J=7.5 Hz), 2.36 (3 H, s), 2.52 (3 H, s), 2.68 (2 H, t, J=7.5 Hz), 2.72 (3 H, s), 3.25 (3 H, s), 3.63 (1 H, dd, J=4, 18 Hz), 3.89 (1 H, dd, J=4, 18 Hz), 4.11 (2 H, t, J=7.5 Hz), 5.36 (2 H, s), 6.47 (1 H, d, J=16 Hz), 6.70 (1 H, t-like), 7.06 (1 H, d, J=8 Hz), 7.16 (1 H, d, J=8 Hz), 7.22–7.32 (2 H, m), 7.38–7.48 (2 H, m), 7.53 (1 H, d, J=16 Hz), 7.83 (1 H, dd, J=2, 8 Hz), 8.03 (1 H, d, J=8 Hz), 8.39–8.46 (2H, m).

its dihydrochloride

NMR (DMSO-d$_6$, δ): 2.04 (2 H, quint, J=7.5 Hz), 2.28 (3 H, s), 2.48 (3 H, s), 2.60 (2 H, t, J=7.5 Hz), 2.93 (3 H, s), 3.11 (3 H, s), 3.54 (1 H, dd, J=4, 16 Hz), 3.71 (1 H, dd, J=4, 16 Hz), 4.00 (2 H, t, J=7.5 Hz), 5.41–5.53 (2 H, m), 6.83 (1 H, d, J=16 Hz), 7.28–7.41 (3 H, m), 7.81–8.06 (5 H, m), 8.25 (1 H, t-like), 8.35 (1 H, d, J=8 Hz), 8.54 (1 H, d, J=2 Hz), 8.98 (1 H, br s).

EXAMPLE 80

(1) 4-(Methoxycarbonyl)-N-methylcinnamamide was obtained from 4-methoxycarbonylcinnamicacid and methylamine hydrochloride according to a similar manner to that of Preparation 2.

mp: 180–182° C.

NMR (DMSO-d$_6$, δ): 2.71 (3 H, d, J=4.0 Hz), 3.87 (3 H, s), 6.71 (1 H, d, J=16.5 Hz), 7.47(1 H, d, J=16.5 Hz), 7.70 (2 H, d, J=8.5 Hz), 7.98 (2 H, d, J=8.5 Hz), 8.14 (1 H, q, J=4.0 Hz).

(2) 4-Carboxy-N-methylcinnamamide was obtained according to a similar manner to that of Preparation 3.

mp: 270–273° C.

NMR (DMSO-d$_6$, δ): 2.72(3H, d, J=4.0 Hz), 6.70 (1 H, d, J=16.0 Hz), 7.47 (1 H, d, J=16.0 Hz), 7.69 (2 H, d, J=8.5 Hz), 7.96 (2 H, d, J=8.5 Hz), 8.14 (1 H, q, J=4.0 Hz).

(3) 8-[2,6-Dichloro-3-[N-methyl-N-[4-[(E)-2-(methylcarbamoyl)vinyl]benzoylglycyl]amino]benzyloxy]-2-methylquinoline was obtained according to a similar manner to that of Example 1.

mp: 143–150° C.

NMR (DMSO-d$_6$, δ): 2.61 (3 H, s), 2.73 (3 H, d, J=5.5 Hz), 3.16 (3 H, s), 3.57 (1 H, dd, J=16.5, 5.5 Hz), 3.85 (1 H, dd, J=16.5, 5.5 Hz), 5.50 (2 H, s), 6.70 (1 H, d, J=15.0 Hz), 7.35–7.57 (5 H, m), 7.67 (2 H, d, J=8.5 Hz), 7.79 (2 H, s), 7.87 (2 H, dd, J=8.5, 1.0 Hz), 8.11 (1 H, q, J=5.5 Hz), 8.22 (1 H, d, J=8.5 Hz), 8.72 (1 H, t, J=5.5 Hz).

its hydrochloride mp: 160–168° C.

NMR (DMSO-d$_6$, δ): 2.72 (3 H, d, J=4.0 Hz), 2.89 (3 H, s), 3.16 (3 H, s), 3.46–3.79 (1 H, m), 3.93 (1 H, dd, J=16.5, 5.5 Hz), 5.59 (1 H, d, J=10.5 Hz), 5.65 (1 H, d, J=10.5 Hz), 6.70 (1 H, d, J=16.0 Hz), 7.45 (1 H, d, J=16.0 Hz), 7.64 (2 H, d, J=8.5 Hz), 7.77–7.97 (8 H, m), 8.18 (1 H, q, J=4.0 Hz), 8.76 (1 H, t, J=5.5 Hz), 8.94 (1 H, m).

EXAMPLE 81

8-[2,6-Dichloro-3-[N-[4-[(E)-2-(methoxycarbonyl)vinyl]benzoylglycyl]-N-methylamino]benzyloxy]-2-methylquinoline was obtained from 8-[3-(N-glycyl-N-methylamino)-2,6-dichlorobenzyloxy]-2-methylquinoline and methyl 4-carboxycinnamate according to a similar manner to that of Example 1.

NMR (CDCl$_3$, δ): 2.73 (3 H, s), 3.27 (3 H, s), 3.70 (1 H, dd, J=16.5, 4.5 Hz), 3.81 (3 H, s), 4.00 (1 H, dd, J=16.5, 4.5 Hz), 5.63 (2 H, s), 6.50 (1 H, d, J=16.0 Hz), 7.19 (1 H, t, J=4.5 Hz), 7.23–7.34 (3 H, m), 7.37–7.51 (3 H, m), 7.57 (2 H, d, 8.5 Hz), 7.69 (1 H, d, J=16.0 Hz), 7.82 (2 H, d, J=8.5 Hz), 8.02 (1 H, d, J=8.5 Hz), its hydrochloride mp: 171–175° C.

NMR (DMSO-d$_6$, δ): 2.88 (3 H, s), 3.17 (3 H, s), 3.64 (1 H, dd, J=16.5, 5.5 Hz), 3.76 (3 H, s), 3.92 (1 H, dd, J=16.5, 5.5 Hz), 5.59 (1 H, d, J=11.5 Hz), 5.66 (1 H, d, J=11.5 Hz), 6.76 (1 H, d, J=16.0 Hz), 7.71 (1 H, d, J=16.0 Hz), 7.78–7.97 (10 H, m), 8.82 (1 H, t, J=5.5 Hz), 8.92(1 H, m).

EXAMPLE 82

8-[3-[N-[(E)-3-[6-(Acetamido)pyridin-3-yl] acryloylglycyl]-N-methylamino]-2,6-dichlorobenzyloxy]-2-methyl-4-morpholinoquinoline was obtained from 8-hydroxy-2-methyl-4-morpholinoquinoline was 3-[N-[(E)-3-[6-(acetamido)pyridin-3-yl]acryloylglycyl]-N-methylamino]2,6-dichlorobenzyl chloride according to a similar manner to that of Example 9.

NMR (CDCl$_3$, δ): 2.21 (3 H, s), 2.67 (3 H, s), 3.15–3.23 (4 H, m), 3.36 (3 H, s), 3.70 (1 H, dd, J=17, 4 Hz), 3.88–4.01 (5 H, m), 5.58 (1 H, d, J=10 Hz), 5.63 (1 H, d, J=10 Hz), 6.47 (1 H, d, J=15 Hz), 6.39–6.79 (2 H, m), 7.19–7.28 (1 H, overlapped with CDCl$_3$), 7.30 (1 H, d, J=8 Hz), 7.37 (1 H, t, J=8 Hz), 7.47 (1 H, d, J=8 Hz), 7.51 (1 H, d, J=15 Hz), 7.65 (1 H, d, J=8 Hz), 7.80 (1 H, br d, J=8 Hz), 8.09 (1 H, br s), 8.19 (1 H, br d, J=8 Hz), 8.33 (1 H, br s).

EXAMPLE 83

(1) 8-[N-tert-Butoxycarbonyl-N-[2,6-dichloro-3-[N-methyl-N-[N'-(4-pyridyl)ureidoacetyl]amino]benzyl] amino]-2-methylquinoline was obtained by reacting 8-[N-[3-(N-glycyl-N-methylamino)-2,6-dichlorobenzyl]-N-tert-butoxycarbonylamino]-2-methylquinoline with phenyl 4-pyridylcarbamoate according to a similar manner to that of Example 19.

NMR (CDCl$_3$, δ): 1.21, 1.72 (9 H, s), 2.72 (3 H, s), 3.08, 3.12 (3 H, s), 2.80, 3.26, 3.60–3.80 (2 H, m), 5.03–5.18, 5.58–5.70 (2 H, m), 6.20 (1 H, m), 6.83, 6.95 (1 H, m), 7.18 (4 H, br), 7.36 (1 H, m), 7.60 (1 H, m), 7.90–8.05 (2 H, m), 8.29 (2 H, br).

(2) 8-[2,6-Dichloro-3-[N-methyl-N-[N'-(4-pyridyl) ureidoacetyl]amino]benzylamino]-2-methylquinoline trihydrochloride was obtained according to a similar manner to that of Example 73-(4).

NMR (CDCl$_3$—CD$_3$OD, δ): 2.85 (3 H, s), 3.29 (3 H, s), 3.40, 3.61–3.71, 3.84, 3.90 (2 H, m), 4.86 (2 H, m), 7.13 (1 H, m), 7.28 (1 H, m), 7.46–7.60 (5 H, m), 7.97 (2 H, m), 8.48 (2 H, d, J=8 Hz).

EXAMPLE 84

(1) 8-[2,6-Dichloro-3-[(phthaloyl-DL-alanyl)amino] benzyloxy]-2-methylquinoline was obtained from 8-(3-amino-2,6-dichlorobenzyloxy)-2-methylquinoline and 2-phthalimidopropionyl chloride according to a similar manner to that of Preparation 9.

mp: 98–100° C. (dec.)

NMR (CDCl$_3$, δ): 1.75 (3 H, d, J=6 Hz), 2.72 (3 H, s), 5.14 (1 H, q, J=6 Hz), 5.60 (2 H, s), 7.20 (1 H, d, J=8 Hz), 7.23–7.23 (4 H), 7.76 (2 H, dd, J=8, 2 Hz), 7.89 (2 H, dd, J=8, 2 Hz), 8.00 (1 H, d, J=8 Hz), 8.32–8.39 (2 H).

(2) 8-[2,6-Dichloro-3-[N-methyl-N-(phthaloyl-DL-alanyl)amino]benzyloxy]-2-methylquinoline was obtained according to a similar manner to that of Preparation 10.

mp: 169–171° C.

NMR (CDCl$_3$, δ): 1.56 (0.9 H, d, J=6 Hz), 1.69 (2.1 H, d, J=6 Hz), 2.70 (0.9 H, s), 2.73 (2.1 H, s), 3.21 (3 H, s), 4.77–4.92 (1 H), 5.00 (0.3 H, d, J=10 Hz), 5.28 (0.3 H, d, J=10 Hz), 5.64 (0.7 H, d, J=10 Hz), 5.70 (0.7 H, d, J=10 Hz), 7.00–8.06 (11 H).

(3) 8-[3-(N-DL-Alanyl-N-methylamino)-2,6-dichlorobenzyloxy]-2-methylquinoline was obtained according to a similar manner to that of Preparation 11.

NMR (CDCl$_3$, δ): 1.08–1.16 (3 H), 2.73(0.9 H, s), 2.75 (2.1 H, s), 3.14 (0.7 H, q, J=6 Hz), 3.21 (3 H, s), 3.35 (0.3 H, q, J=6Hz), 5.60–5.72 (0.6 H), 5.66 (1.4 H, s), 7.22–7.51 (6 H), 8.03 (1 H, d, J=8 Hz).

(4) 8-[2,6-Dichloro-3-[N-methyl-N-[4-(methylcarbamoyl)cinnamoyl-DL-alanyl]amino] benzyloxy]-2-methylquinoline was obtained according to a similar manner to that of Example 1.

NMR (CDCl$_3$, δ): 1.20 (1.8 H, d, J=7 Hz), 1.27 (1.2 H, d, J=7 Hz), 2.70 (1.2 H, s), 2.72 (1.8 H, s), 2.95–3.03 (3 H, m), 3.23 (3 H, s), 4.43–4.51 (0.4 H, m), 4.51–4.63 (0.6 H, m), 5.53–5.73(2 H, m), 6.17–6.30 (1 H, m), 6.40–6.70 (2 H, m), 7.18–7.35 (2 H, m), 7.35–7.63 (7 H, m), 7.63–7.80 (2 H, m), 8.02 (1 H, d, J=8 Hz).

EXAMPLE 85

(1) 8-[3-[(3-Bromopropionyl)amino]-2,6-dichlorobenzyloxy]-2-methylquinoline was obtained from 8-(3-amino-2,6-dichlorobenzyloxy)-2-methylquinoline and 3-bromopropionyl chloride according to a similar manner to that of Preparation 9.

NMR (CDCl$_3$, δ): 2.70 (3 H, s), 2.99 (0.4 H, t, J=6 Hz), 3.11 (1.6 H, t, J=6 Hz), 3.68 (1.6 H, t, J=6 Hz), 3.86 (0.4 H, t, J=6 Hz), 5.53 (2 H, br s), 7.20–7.48 (6 H), 8.00–8.09 (1 H), 8.30–8.50 (1 H), (2) To asolution of 8-[3-[(3-bromopropionyl)amino]-2,6-dichlorobanzyloxy]-2-methylquinoline (2.08 g), in anhydrous dimethylformamide (21 ml) was added potassium phthalimide (905 mg) and the mixture was stirred at 100° C. for 1.5 hours. To this reaction mixture were added ethyl acetate (105 ml) and water (105 ml) and the mixture was stirred for 1 hour under ice-water cooling. The precipitate was collected by filtration ans washed with ethyl acetate and water to give 8-[2,6-dichloro-3-[(3-phthalimidopropionyl) amino]benzyloxy]-2-methylquinoline (1.49 g) as a grey powder.

NMR (CDCl$_3$, δ): 2.70 (3 H, s), 2.90 (2 H, t, J=6 Hz), 4.12 (2 H, t, J=6 Hz), 5.53 (2 H, s), 7.18–7.45 (6 H), 7.72 (2 H, dd, J=8, 2 Hz), 7.86 (2 H, dd, J=8, 2 Hz), 8.03 (1 H, d, J=8 Hz), 8.15–8.22 (1 H).

(3) 8-[2,6-Dichloro-3-[N-methyl-N-(3-phthalimidopropionyl)amino]benzyloxy]-2-methylquinoline was obtained according to a similar manner to that of Preparation 10.

mp: 176–177° C.

NMR (CDCl$_3$, δ): 2.25–2.52 (2 H), 2.70 (3 H, s), 3.18 (3 H, s), 3.86–4.04 (2 H), 5.61 (2 H, s), 7.20–7.46 (6 H), 7.68 (2 H, dd, J=8, 2 Hz), 7.80 (2 H, dd, J=8, 2 Hz), 8.00 (1 H, d, J=8 Hz).

(4) 8-[3-[N-(3-Aminopropionyl)-N-methylamino]-2,6-dichlorobenzyloxy]-2-methylquinoline was obtained according to a similar manner to that of Preparation 11.

NMR (CDCl$_3$, δ): 1.96–2.21 (2 H, m), 2.73 (3 H, s), 2.81–2.98 (2 H, m), 3.18 (3 H, s), 5.64 (2 H, s), 7.20–7.33 (3 H, m), 7.33–7.50 (3 H, m), 8.02 (1 H, d, J=8 Hz).

(5) 8-[2,6-Dichloro-3-[N-methyl-N-[3-[4-(methylcarbamoyl)cinnamoylamino]propionyl]amino] benzyloxy]-2-methylquinoline was obtained according to a similar manner to that of Example 1.

NMR (CDCl$_3$, δ): 2.03–2.18 (1 H, m), 2.18–2.33 (1 H, m), 2.67 (3 H, s), 2.98 (3 H, d, J=6 Hz), 3.17 (3 H, s), 3.51–3.64 (2 H, m), 5.62 (2 H, s), 6.32–6.42 (1 H, m), 6.42 (1 H, d, J=15 Hz), 6.73 (1 H, t-like), 7.17–7.31 (3 H, m), 7.34–7.51 (5 H, m), 7.55 (1 H, d, J=15 Hz), 7.73 (2 H, d, J=8 Hz), 8.01 (1 H, d, J=8 Hz).

(6) 8-[2,6-Dichloro-3-[N-[3-[N'-[3-(4-pyridylcarbamoyl) phenyl]ureido]propionyl]-N-methylamino]benzyloxy]-2-methylquinoline was obtained according to a similar manner to that of Example 19.

NMR (CDCl₃, δ): 2.23–2.33 (1 H, m), 2.33–2.45 (1 H, m), 2.53 (3 H, s), 3.10 (3 H, s), 3.21–3.41 (1 H, m), 3.41–3.57 (1 H, m), 5.46 (1 h, d, J=10 Hz), 5.57 (1 H, d, J=10 Hz), 5.82 (1 H, br peak), 7.03–7.17 (1 H, m), 7.17–7.34 (4 H, m), 7.43–7.52 (3 H, m), 7.67 (2 H, d, J=6 Hz), 7.79 (1 H, br s), 8.08 (1 H, d, J=8 Hz), 8.45 (2 H, d, J=6 Hz), 8.53 (1 H, br s), 9.37 (1 H, br s).

EXAMPLE 86

8-[3-[N-[N'-(3-Aminophenyl)ureidoacetyl]-N-methylamino]-2,6-dichlorobenzyloxy]-4-dimethylamino-2-methylquinoline was obtained from 8-[2,6-dichloro-3-[N-methyl-[N-[N'-(3-nitrophenyl)ureidoacetyl]amino] benzyloxy]-4-dimethylamino-2-methylquinoline according to a similar manner to that of Preparation 15.

NMR (CDCl₃, δ): 2.48 (3 H, s), 3.10 (6 H, br peak), 3.20 (3 H, s), 5.43 (1 H, d, J=10 Hz), 5.61 (1 H, d, J=10 Hz), 6.22 (1 H, d, J=8 Hz), 6.49 (1 H, d, J=8 Hz), 6.61 (1 H, s-like), 6.75–6.88 (2 H, m), 7.15–7.47 (7 H, m), 7.63–7.71 (2 H, m).

EXAMPLE 87

8-[2,6-Dichloro-3-[N-[N'-(3-isonicontinamidophenyl) ureidoacetyl]-N-methylamino]benzyloxy]-4-dimethylamino-2-methylquinoline was obtained from 8-[3-[N-[N'-(3-aminophenyl)ureidoacetyl]-N-methylamino]-2,6-dichlorobenzyloxy]-4-dimethylamino-2-methylquinoline and isonicotinoyl chloride hydrochloride according to a similar manner to that of Example 52.

NMR (CDCl₃, δ): 2.43 (3 H, s), 3.03 (6 H, s), 3.11 (3 H, s), 3.74–4.08 (2 H, m), 5.43 (1 H, d, J=10 Hz), 5.53 (1 H, d, J=10 Hz), 6.61 (1 H, s), 6.89 (1 H, br peak), 7.03 (1 H, t-like), 7.08–7.33 (4 H, m), 7.40 (1 H, t, J=8 Hz), 7.44–7.55 (1 H, m), 7.55–7.88 (5 H, m), 8.65 (2 H, d, J=6 Hz), 8.90 (1 H, br s).

its trihydrochloride

NMR (DMSO₆, δ): 2.65 (3 H, s), 3.14 (3 H, s), 3.41 (6 H, s), 3.75 (1 H, br d, J=18 Hz), 5.56 (2 H, s), 6.48 (1 H, br s), 6.91 (1 H, s), 7.18–7.25 (2 H, m), d, J=8 Hz), 7.81 (2 H, s-like), 7.88 (1 H, s-like), 7.93 (1 H, d, J=8 Hz), 8.03 (2 H, d, J=6 Hz), 8.88 (2 H, d, J=6 Hz), 9.08 (1 H, s), 10.61 (1 H, s).

EXAMPLE 88

8-[2,6-Dichloro-3-[N-methyl-N-[N'-[4-[N-(4-pyridyl) carbamoyl]phenyl]ureidoacetyl]amino]benzyloxy]-2-methylquinoline and its dihydrochloride was obtained from 8-[2,6-dichloro-3-[N-methyl-N-[N'-(4-carboxyphenyl) ureidoacetyl]amino]benzyloxy]-2-methylquinoline and 4-aminopyridine according to a similar manner to that of Example 7.

EXAMPLE 89

8-[2,6-Dichloro-3-[N-methyl-N-[N'-[4-[N-(4-pyridylmethyl)carbamoyl]phenyl]ureidoacetyl]amino] benzyloxy]-2-methylquinoline was obtained from 8-[2,6-dichloro-3-[N-methyl-N-[N'-(4-carboxyphenyl) ureidoacetyl]amino]benzyloxy]-2-methylquinoline and 4-aminomethylpyridine according to a similar manner to that of Example 7.

NMR (CDCl₃, δ): 2.56 (3 H, s), 3.17 (3 H, br), 3.49–3.82 (2 H, m), 4.54 (2 H, br), 5.47 (1 H, d, J=8 Hz), 5.57 (1 H, m), 7.15 (2 H, br), 7.23–7.33 (5 H, m), 7.46 (2 H, br), 7.60 (2 H, d, J=8 Hz), 8.08 (1 H, m), 8.46 (2 H, br), 8.93 (1 H, br).

its dihydrochloride

NMR (CD₃OD, δ): 3.00 (3 H, s), 3.28 (3 H, s), 3.80 (2 H, m), 4.84 (2 H, br), 5.70 (1 H, d, J=8 Hz), 5.84 (1 H, d, J=8 Hz), 7.49 (2 H, d, J=8 Hz), 7.73 (2 H, d, J=4 Hz), 7.84 (2 H, m), 7.81 (4 H, m), 8.04 (2 H, d J=8 Hz), 8.78 (2 H, d, J=8 Hz), 9.03 (1 H, m).

EXAMPLE 90

(1) To a suspension of 2-amino-3-benzyloxypyridine (5.01 g) in polyphosphoricacid (40 ml) was dropwise added ethyl acetoacetate (6.51 g) at 60° C., and the mixture was warmed at 100° C. for 3 hours. The mixture was poured into ice water, neutralized with sodium hydroxide and extracted with chloroform. The extract was washed with water, dried over magnesium sulfate and concentrated in vacuo. The residue was purified by flash chromatography (methanol-chloroform) to give 9-hydroxy-2-methyl-4H-pyrido[1,2-a] pyrimidin-4-one (880 mg).

mp: 146.3° C.

NMR (CDCl₃, δ): 2.46 (3 H, s), 6.30 (1 H, s), 7.00 (1 H, t, J=8 Hz), 7.13 (1 H, d, J=8 Hz), 8.51 (1 H, d, J=8 Hz).

(2) 9-[2,6-Dimethyl-3-[N-methyl-N-[4 (methylcarbomoyl)cinnamoylglycyl]amino]benzyloxy]-2-methyl-4H-pyrido-[1,2-a]pyrimidin-4-one was obtained according to a similar manner to that of Example 9.

NMR (CDCl₃, δ): 2.31 (3 H, s), 2.45 (3 H, s), 2.49 (3 H, s), 3.00 (3 H, d, J=5 Hz), 3.25 (3 H, s), 3.63 (1 H, dd, J=17, 5 Hz), 3.82 (1 H, dd, J=17, 4 Hz), 5.27 (2 H, s), 6.23 (1 H, br q, J=5 Hz), 6.36 (1 H, s), 6.51 (1 H, d, J=15 Hz), 6.73 (1 H, br t, J=5 Hz), 7.05 (1 H, t, J=8 Hz), 7.10 (1 H, d, J=9 Hz), 7.17 (1 H, d, J=9 Hz), 7.21 (1 H, d, J=8 Hz), 7.51 (2 H, d, J=9 Hz), 7.55 (1 H, d, J=15 Hz), 7.74 (2 H, d, J=9 Hz), 8.74 (1 H, d, J=8 Hz).

We claim:

1. A compound of the formula:

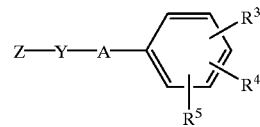

wherein

Z is a group of the formula:

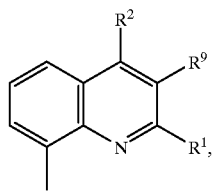

in which

R¹ is lower alkyl,

R² is an N-containing heterocyclic-N-yl group optionally substituted with lower alkyl, R⁹ is hydrogen or lower alkyl, R³ is hydrogen, lower alkyl, lower alkoxy or halogen, R⁴ is lower alkyl, lower alkoxy or halogen,

117

R⁵ is a group of the formula:

in which
R⁶ is hydrogen or lower alkyl, and
R⁷ is hydrogen or a group of the formula:

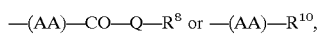

in which
R⁸ is phenylthio, phenyloxy or phenylamino, each of which is optionally substituted with substituent(s) selected from the group consisting of lower alkoxycarbonyl, lower alkylcarbamoyl, lower alkylsulfoylcarbomoyl, tolysulfonylcarbamoyl, pyridylcarbamoyl, pyridyl(lower)alkylcarbamoyl, pyridyl(lower)alkyl, pyridyl(lower)alkenyl, nitro, amino, lower alkanoylamino and pyridylcarbonylamino; heterocyclicthio or heterocyclicamino, each of which is optionally substituted with substituent(s) selected from the group consisting of carboxy, lower alkoxycarbonyl, lower alkylcarbamoyl, lower alkanoylamino, amino and lower alkoxy; halogen; tri(lower)alkylphosphonio; phenyl or naphthyl, each of which is substituted with substituent(s) selected from the group consisting of lower alkyl, lower alkoxy, nitro, carboxy, lower alkoxycarbonyl, lower alkylcarbamoyl, lower alkylamino(lower)alkylcarbamoyl, N-(lower alkylamino(lower)alkyl)-N-(lower alkyl)carbamoyl, pyridylcarbamoyl, pyridyl(lower)alkylcarbamoyl or its oxide, lower alkoxycarbonyl(lower)alkenyl, lower alkylcarbamoyl(lower)alkenyl, pyridyl(lower)alkenyl, carboxy(lower)alkoxy, lower alkoxycarbonyl(lower)alkoxy, lower alkylcarbamoyl(lower)alkoxy, guanidino, amino, lower alkanylamino, halo(lower)alkanoylamino, lower alkylsulfonylamino, pyridylcarbonylamino, lower alkylureido, N-(lower alkoxy(lower)alkanoyl)-N-(pyridyl(lower)alkyl)amino, 2-oxopyrrolidin-1-yl and 2-oxo-1,2-dihydropyridin-1-yl; or pyridyl, quinolyl, indolyl, tetrahydroquinolyl or piperazinyl, each of which is optionally substituted with substituent(s) selected form the group consisting of oxo, lower alkyl, lower alkoxy, nitrophenyl, carboxy, lower alkoxycarbonyl, lower alkanoyl, lower alkylcarbamoyl, pyridylcarbamoyl, pyrazinylcarbamoyl, isoquinolylcarbamoyl, thiazolylcarbamoyl, lower alkyloxazolylcarbamoyl, lower alkylpyrazolylcarbamoyl, lower alkoxypyridylcarbamoyl, pyridyl(lower)alkylcarbamoyl, amino, lower alkanoylamino, pyridylcarbonylamino, pyrazinylcarbonylamino, lower alkylpyridylcarbonylamino, lower alkoxypyridylcarbonylamino, lower alkylthiopyridylcarbonylamino, pyridyl(lower)alkanoylamino, lower alkylpyridyl(lower)alkanoylamino, lower alkylsulfonylamino, lower alkylureido, N-(lower alkanoyl)-N-(lower)alkylamino, lower alkylamino, halogen, pyridyl(lower)alkyl, pyridyl(lower)alkenyl and 2-oxopyrrolidin-1-yl, and
R¹⁰ is lower alkylcarbamoylbiphenyl,
(AA) is amino acid residue, and
Q is lower alkylene, lower alkenylene or single bond,

118

A is lower alkylene, and
Y is O or N—R¹¹, in which R¹¹ is hydrogen or an N-protective group, and pharmaceutically acceptable salts thereof.
2. The compound of claim 1, which is 8-[2,6-dichloro-3-[N-methyl-N-[4-(4-pyridylcarbamoyl)-cinnamoylglycyl]amino]benzyloxy]-2-methyl-4-morpholinoquinoline.
3. The compound of claim 1, wherein R² is morpholino, thiomorpholino, pyrrolidin-1-yl, piperidino, 1,2,3,6-tetrahydropyridin-1-yl, 1,2-dihydropyridin-1-yl or piperazin-1-yl, each of which may be optionally substituted with lower alkyl.
4. A pharmaceutical composition comprising a compound of claim 1, as an active ingredient, in association with a pharmaceutically acceptable, substantially nontoxic carrier or excipeint.
5. A method for the prevention and/or the treatment of bradykinin or its analogues mediated diseases which comprises administering a compound of claim 1 to human being or animals.
6. A compound of the formula:

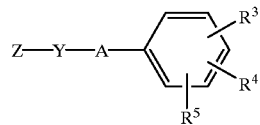

wherein
Z is a group of the formula:

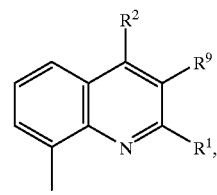

in which
R¹ is lower alkyl,
R² is an N-containing heterocyclic-N-yl group optionally substituted with lower alkyl,
R⁹ is hydrogen or lower alkyl,
R³ is hydrogen, lower alkyl, lower alkoxy or halogen,
R⁴ is lower alkyl, lower alkoxy or halogen,
R⁵ is a group of the formula:

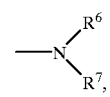

in which
R⁶ is hydrogen or lower alkyl, and
R⁷ is hydrogen or a group of the formula:

in which
R⁸ is phenylthio, phenyloxy or phenylamino, each of which is optionally substituted with substituent(s) selected from the group consisting of lower alkoxycarbonyl, lower alkylcarbamoyl, lower alkylsulfoylcarbomoyl, tolysulfonylcarbamoyl, pyridylcarbamoyl, pyridyl(lower)alkylcarbamoyl, pyridyl(lower)alkyl, pyridyl(lower)alkenyl, nitro, amino, lower alkanoylamino and pyridylcarbonylamino; heterocyclicthio or heterocyclicamino, each of which is optionally substituted with substituent(s) selected from the group consisting of carboxy, lower alkoxycarbonyl, lower alkylcarbamoyl, lower alkanoylamino, amino and lower alkoxy; halogen; tri(lower)alkylphosphonio; phenyl or naphthyl, each of which is substituted with substituent(s) selected from the group consisting of lower alkyl, lower alkoxy, nitro, carboxy, lower alkoxycarbonyl, lower alkylcarbamoyl, lower alkylamino(lower)alkylcarbamoyl, N-(lower alkylamino(lower)alkyl)-N-(lower alkyl)carbamoyl, pyridylcarbamoyl, pyridyl(lower)alkylcarbamoyl or its oxide, lower alkoxycarbonyl(lower)alkenyl, lower alkylcarbamoyl(lower)alkenyl, pyridyl(lower)alkenyl, carboxy(lower)alkoxy, lower alkoxycarbonyl(lower)alkoxy, lower alkylcarbamoyl(lower)alkoxy, guanidino, amino, lower alkanylamino, halo(lower)alkanoylamino, lower alkylsulfonylamino, pyridylcarbonylamino, lower alkylureido, N-(lower alkoxy(lower)alkanoyl)-N-(pyridyl(lower)alkyl)amino, 2-oxopyrrolidin-1-yl and 2-oxo-1,2-dihydropyridin-1-yl; or pyridyl, quinolyl, indolyl, tetrahydroquinolyl or piperazinyl, each of which is optionally substituted with substituent(s) selected form the group consisting of oxo, lower alkyl, lower alkoxy, nitrophenyl, carboxy, lower alkoxycarbonyl, lower alkanoyl, lower alkylcarbamoyl, pyridylcarbamoyl, pyrazinylcarbamoyl, isoquinolylcarbamoyl, thiazolylcarbamoyl, lower alkyloxazolylcarbamoyl, lower alkylpyrazolylcarbamoyl, lower alkoxypyridylcarbamoyl, pyridyl(lower)alkylcarbamoyl, amino, lower alkanoylamino, pyridylcarbonylamino, pyrazinylcarbonylamino, lower alkylpyridylcarbonylamino, lower alkoxypyridylcarbonylamino, lower alkylthiopyridylcarbonylamino, pyridyl(lower)alkanoylamino, lower alkylpyridyl(lower)alkanoylamino, lower alkylsulfonylamino, lower alkylureido, N-(lower alkanoyl)-N-(lower)alkylamino, lower alkylamino, halogen, pyridyl(lower)alkyl, pyridyl(lower)alkenyl and 2-oxopyrrolidin-1-yl, and $R^{10}$ is lower alkylcarbamoylbiphenyl, (AA) is amino acid residue, and Q is lower alkylene, lower alkenylene or single bond, A is lower alkylene, and Y is O or N—$R^{11}$, in which $R^{11}$ is hydrogen or an N-protective group, or its salt, which comprises
a) reaching a compound of the formula:

Z—YH where
Y and z are each as defined above or its salt with a compound of the formula:

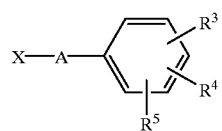

wherein
X is a leaving group, and
$R^3$, $R^4$, $R^5$ and A are each as defined above, or its salt to give a compound of the formula:

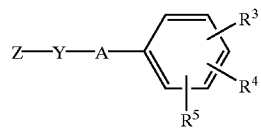

wherein
$R^3$, $R^4$, $R^5$, A, Y, and Z are each as defined above or its salt or
b) reacting a compound of the formula:

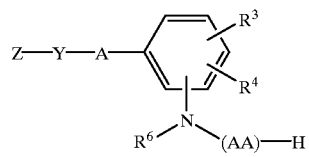

wherein
$R^3$, $R^4$, $R^6$, A, Y, Z and (AA) are each as defined above, or its salt with a compound of the formula:

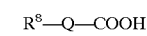

wherein
$R^8$ and Q are each as defined above, or its reactive derivative at the carboxy group or a salt thereof to give a compound of the formula:

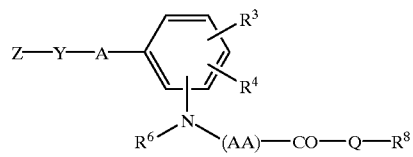

wherein
$R^3$, $R^4$, $R^6$, $R^8$, A, Y, Z, (AA) and Q are each as defined above or its salt, or
c) reacting a compound of the formula:

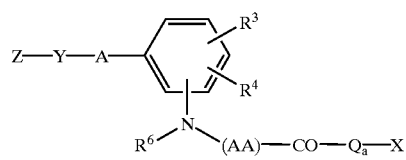

wherein
$Q_a$ is a lower alkylene, and
$R^3$, $R^4$, $R^6$, A, Y, Z, (AA) and X are each as defined above, or its salt with a compound of the formula:

$R^8{}_a$—H wherein $R^8{}_a$ is arylthio optionally substituted with substituent(s) selected from the group consisting of acyl, amino and acylamino; or heterocyclicthio optionally substituted with substituent(s) selected from the group consisting of acyl, acylamino, amino and lower alkoxy; or its salt to give a compound of the formula:

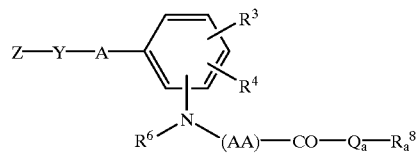

wherein
$R^3$, $R^4$, $R^6$, $R^8{}_a$, A, Y, Z, (AA) and $Q_a$ are each defined above, or its salt.

* * * * *

UNITED STATES PATENT AND TRADEMARK OFFICE
CERTIFICATE OF CORRECTION

PATENT NO. : 5,994,368

DATED : November 30, 1999

INVENTOR(S): Teruo OKU, et al.

It is certified that an error appears in the above-identified patent and that said Letters Patent is hereby corrected as shown below:

On the title page, item [22] should be:

-- [22] PCT Filed: Oct. 25, 1995 --

On the title page, item [86] should be:

--[86] PCT No.: PCT/JP95/02192

§ 371 Date: Apr. 25, 1997

§ 102(e) Date: Apr. 25, 1997

On the title page, item [87] should be:

--[87] PCT Pub. No.: WO 96/13485

PCT Pub. Date: May 9, 1996

Signed and Sealed this

Sixth Day of February, 2001

Attest:

Q. TODD DICKINSON

*Attesting Officer*   *Director of Patents and Trademarks*